(12) United States Patent
Ishiguro et al.

(10) Patent No.: US 9,887,369 B2
(45) Date of Patent: Feb. 6, 2018

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Yoshimi Ishiguro, Kanagawa (JP); Sachiko Kawakami, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 697 days.

(21) Appl. No.: 14/473,314

(22) Filed: Aug. 29, 2014

(65) Prior Publication Data

US 2015/0060824 A1    Mar. 5, 2015

(30) Foreign Application Priority Data

Aug. 30, 2013 (JP) ................. 2013-179360

(51) Int. Cl.

| C07D 403/14 | (2006.01) |
|---|---|
| H01L 51/00 | (2006.01) |
| C07D 405/14 | (2006.01) |
| C07D 409/14 | (2006.01) |
| H01L 51/50 | (2006.01) |

(52) U.S. Cl.
CPC ........ *H01L 51/0072* (2013.01); *C07D 403/14* (2013.01); *C07D 405/14* (2013.01); *C07D 409/14* (2013.01); *H01L 51/0073* (2013.01); *H01L 51/0074* (2013.01); *H01L 51/006* (2013.01); *H01L 51/0059* (2013.01); *H01L 51/0085* (2013.01); *H01L 51/504* (2013.01); *H01L 51/5016* (2013.01); *H01L 51/5072* (2013.01)

(58) Field of Classification Search
CPC .. C07D 403/14; C07D 405/14; C07D 409/14; H01L 51/0072; H01L 51/0073; H01L 51/0074; H01L 51/0059; H01L 51/006; H01L 51/0085; H01L 51/5016; H01L 51/504; H01L 51/5072
USPC ............. 544/343; 546/77; 428/690
See application file for complete search history.

(56) References Cited

U.S. PATENT DOCUMENTS

| 6,723,445 B2 | 4/2004 | Li et al. |
|---|---|---|
| 7,355,340 B2 | 4/2008 | Shitagaki et al. |
| 7,601,435 B2 | 10/2009 | Shitagaki et al. |
| 7,927,720 B2 | 4/2011 | Nomura et al. |
| 7,931,974 B2 | 4/2011 | Egawa et al. |
| 8,084,146 B2 | 12/2011 | Murase et al. |
| 8,119,259 B2 | 2/2012 | Kadoma et al. |
| 8,138,303 B2 | 3/2012 | Chebotareva et al. |
| 8,178,216 B2 | 5/2012 | Nomura et al. |

(Continued)

FOREIGN PATENT DOCUMENTS

| EP | 1 616 864 A1 | 1/2006 |
|---|---|---|
| EP | 1 748 045 A1 | 1/2007 |

(Continued)

OTHER PUBLICATIONS

Goldsmith, C.R. et al., "C—H Bond Activation by a Ferric Methoxide Complex: Modeling the Rate-Determining Step in the Mechanism of Lipdxygenase," Journal of the American Chemical Society, 2002, vol. 124, No. 1, pp. 83-96.

(Continued)

*Primary Examiner* — Deepak Rao
(74) *Attorney, Agent, or Firm* — Husch Blackwell LLP

(57) ABSTRACT

Provided is a novel organic compound that is used as a host material in which a light-emitting substance is dispersed. The organic compound is represented by General Formula (G1). In the formula, A represents a substituted or unsubstituted dibenzofuran-diyl group, a substituted or unsubstituted dibenzothiophene-diyl group, a substituted or unsubstituted N-aryl-9H-carbazole-diyl group, or a substituted or unsubstituted N-alkyl-9H-carbazole-diyl group; $Ar^1$ and $Ar^2$ each independently represent a single-bond or a substituted or unsubstituted arylene group; $R^{11}$ to $R^{19}$ and $R^{21}$ to $R^{29}$ each independently represent hydrogen, an alkyl group having 1 to 6 carbon atoms, or a substituted or unsubstituted aryl group having 6 to 13 carbon atoms; $X^1$ and $X^2$ each independently represent a carbon atom or a nitrogen atom; and the carbon atom is bonded to hydrogen, an alkyl group having 1 to 6 carbon atoms, or a substituted or unsubstituted aryl group having 6 to 13 carbon atoms.

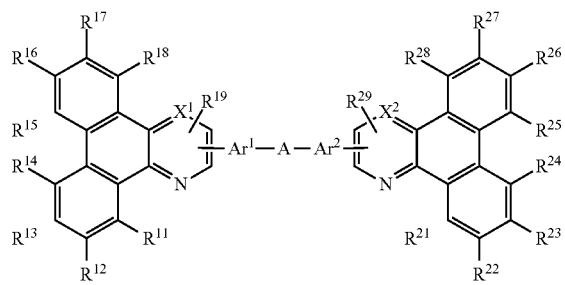

(G1)

26 Claims, 49 Drawing Sheets

(56) References Cited

U.S. PATENT DOCUMENTS

| | | |
|---|---|---|
| 8,231,984 B2 | 7/2012 | Shitagaki et al. |
| 8,252,433 B2 | 8/2012 | Egawa et al. |
| 8,314,101 B2 | 11/2012 | Kadoma et al. |
| 2005/0064237 A1 | 3/2005 | Kato et al. |
| 2009/0026922 A1 | 1/2009 | Iwaki et al. |
| 2009/0072718 A1 | 3/2009 | Nomura et al. |
| 2009/0140641 A1 | 6/2009 | Nomura et al. |
| 2009/0140642 A1 | 6/2009 | Kadoma et al. |
| 2009/0153041 A1 | 6/2009 | Kawakami et al. |
| 2009/0184633 A1 | 7/2009 | Kadoma et al. |
| 2009/0203704 A1 | 8/2009 | Kadoma et al. |
| 2010/0039024 A1 | 2/2010 | Wendeborn et al. |
| 2010/0090588 A1 | 4/2010 | Yokoyama et al. |
| 2010/0109514 A1 | 5/2010 | Schafer et al. |
| 2010/0249349 A1 | 9/2010 | Chebotareva et al. |
| 2010/0289406 A1 | 11/2010 | Ma et al. |
| 2011/0089407 A1 | 4/2011 | Schmidhalter et al. |
| 2011/0210316 A1 | 9/2011 | Kadoma et al. |
| 2012/0138907 A1 | 6/2012 | Murase et al. |
| 2012/0193613 A1 | 8/2012 | Kadoma et al. |
| 2012/0197020 A1 | 8/2012 | Osaka et al. |
| 2012/0286257 A1 | 11/2012 | Shitagaki et al. |
| 2012/0313506 A1 | 12/2012 | Egawa et al. |
| 2013/0048971 A1 | 2/2013 | Kitano et al. |
| 2013/0060033 A1 | 3/2013 | Seo et al. |
| 2013/0075704 A1 | 3/2013 | Takasu et al. |
| 2013/0082591 A1 | 4/2013 | Seo et al. |
| 2013/0112954 A1 | 5/2013 | Osaka et al. |
| 2013/0134395 A1 | 5/2013 | Kitano et al. |
| 2014/0034925 A1 | 2/2014 | Osaka et al. |
| 2014/0124764 A1 | 5/2014 | Kitano et al. |
| 2015/0060818 A1 | 3/2015 | Ishiguro et al. |

FOREIGN PATENT DOCUMENTS

| | | |
|---|---|---|
| EP | 1 905 768 A1 | 4/2008 |
| EP | 1 962 354 A1 | 8/2008 |
| EP | 2 055 704 A1 | 5/2009 |
| EP | 2 065 378 A1 | 6/2009 |
| EP | 2 236 506 A1 | 10/2010 |
| EP | 2 363 398 A1 | 9/2011 |
| EP | 2 450 356 A1 | 5/2012 |
| JP | 09-188874 A | 7/1997 |
| JP | 2007-189001 A | 7/2007 |
| JP | 2013-060413 A | 4/2013 |
| JP | 2013-060414 A | 4/2013 |
| JP | 2013-063963 A | 4/2013 |
| KR | 2011-0042004 A | 4/2011 |
| WO | WO 2003/058667 A1 | 7/2003 |
| WO | WO 2008/119666 A1 | 10/2008 |
| WO | WO 2014/069613 A1 | 5/2014 |

OTHER PUBLICATIONS

Onishi, T. et al., "A Method of Measuring an Energy Level," High Molecular EL Materials—Development of Light-Emitting High Molecular Compounds, Dec. 25, 2004, pp. 64-67, Kyoritsu Shuppan.

Zhang, M. et al., "Highly-Efficient Solution-Processed OLEDs Based on New Bipolar Emitters," Chemical Communications, 2010, vol. 46, pp. 3923-3925.

Wermuth, C.G., "Molecular Variations Based on Isosteric Replacements", *The Practice of Medicinal Chemistry*, 1996, Academic Press, Ltd., pp. 204-237.

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a semiconductor device, a display device, a light-emitting device, a lighting device, a driving method thereof, and a manufacturing method thereof. Specifically, one embodiment of the present invention relates to a novel organic compound and a light-emitting element including the organic compound. One embodiment of the present invention relates to a light-emitting element using organic electroluminescence (EL). One embodiment of the present invention also relates to a light-emitting device, an electronic device, and a lighting device each including the light-emitting element.

2. Description of the Related Art

In recent years, research and development have been extensively conducted on light-emitting elements using electroluminescence. In a basic structure of such a light-emitting element, a light-emitting layer containing a light-emitting substance is interposed between a pair of electrodes. By applying voltage to this element, light emission from the light-emitting substance can be obtained.

Such a light-emitting element is of self-luminous type, and thus has advantages over a liquid crystal display in that visibility of pixels is high, a backlight is not needed, and so on. Therefore, such a light-emitting element is regarded as being suitable as a flat panel display element. Besides, such a light-emitting element has advantages in that it can be manufactured to be thin and lightweight, and has very fast response speed.

Since such light-emitting elements can be formed in a film form, they make it possible to provide emission from a planar surface. Thus, a large-area element having a planar emission surface can be easily formed. This is a feature that is difficult to obtain with point light sources typified by an incandescent lamp and an LED or linear light sources typified by a fluorescent lamp. Therefore, the light-emitting element is very effective for use as a surface light source applicable to lighting and the like.

Such light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of voltage to the light-emitting element causes injection of electrons from a cathode and holes from an anode into the layer containing the organic compound having a light-emitting property and thus current flows. The injected electrons and holes then lead the organic compound to its excited state, whereby light emission is obtained from the excited organic compound.

Note that excited states of the organic compound include a singlet excited state and a triplet excited state. Light emission from the singlet excited state (S*) is called fluorescence, and light emission from the triplet excited state (T*) is called phosphorescence. The statistical generation ratio thereof in the light-emitting element is considered to be S*:T*=1:3.

At room temperature, a compound capable of converting a singlet excited state into luminescence (hereinafter, referred to as a fluorescent compound) generally exhibits only luminescence from the singlet excited state (fluorescence), and luminescence from the triplet excited state (phosphorescence) cannot be observed. Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

In contrast, a compound capable of converting a triplet excited state into luminescence (hereinafter, referred to as a phosphorescent compound) exhibits luminescence from the triplet excited state (phosphorescence). Further, since intersystem crossing (i.e., transition from a singlet excited state to a triplet excited state) easily occurs in a phosphorescent compound, the internal quantum efficiency can be theoretically increased to 100%. That is, higher emission efficiency can be achieved than the case of using a fluorescent compound. For this reason, light-emitting elements using a phosphorescent compound have been under active development recently so that high-efficiency light-emitting elements can be achieved.

When a light-emitting layer of a light-emitting element is formed using the phosphorescent compound described above, in order to suppress concentration quenching or quenching due to triplet-triplet annihilation of the phosphorescent compound, the light-emitting layer is usually formed such that the phosphorescent compound is dispersed in a matrix of another compound. Here, the compound serving as the matrix is called host material, and the compound dispersed in the matrix like the phosphorescent compound is called guest material.

When the phosphorescent compound is used as the guest material, the host material is required to have a higher triplet excitation energy level (difference in energy between the ground state and the triplet excited state, which is also referred to as $T_1$ level) than the phosphorescent compound.

Since the singlet excitation energy level (difference in energy between the ground state and the singlet excited state, which is also referred to as $S_1$ level) is higher than a $T_1$ level, a substance that has a high $T_1$ level also has a high $S_1$ level. Therefore, the above substance that has a high $T_1$ level is also effective in a light-emitting element using a fluorescent compound as a light-emitting substance.

For example, compounds having a dibenzo[f,h]quinoxaline skeleton have been studied as examples of a host material used when a phosphorescent compound is a guest material (see Patent Documents 1 and 2).

REFERENCE

Patent Document

[Patent Document 1] PCT International Publication No. 03/058667

[Patent Document 2] Japanese Published Patent Application No. 2007-189001

SUMMARY OF THE INVENTION

As reported in Patent Document 1 or 2, although host materials of phosphorescent compounds have been developed, there is room for improvement in terms of emission efficiency, reliability, light-emitting characteristics, synthesis efficiency, cost, or the like, and further development is required for obtaining more excellent phosphorescent compounds.

In view of the above problems, an object of one embodiment of the present invention is to provide a novel organic compound. Another object of one embodiment of the present invention is to provide a novel organic compound that can be used in a light-emitting element as a host material of a light-emitting layer in which a light-emitting substance is dispersed. In particular, the object is to provide a novel organic compound that can be suitably used as a host material in the case where a phosphorescent compound is a light-emitting substance. Another object of one embodiment of the present invention is to provide a novel organic compound that has a high electron-transport property and suitably used in an electron-transport layer in a light-emitting element.

Another object of one embodiment of the present invention is to provide a novel light-emitting element. Another object of one embodiment of the present invention is to provide a light-emitting element which is driven at a low voltage and has high current efficiency. Another object of one embodiment of the present invention is to provide a light-emitting element having a long lifetime. Another object of one embodiment of the present invention is to provide a light-emitting device, an electronic device, and a lighting device each having reduced power consumption by using the above light-emitting element.

Note that the description of these objects does not disturb the existence of other objects. In one embodiment of the present invention, there is no need to achieve all the objects. Other objects will be apparent from and can be derived from the description of the specification, the drawings, the claims, and the like.

One embodiment of the present invention is an organic compound represented by General Formula (G1).

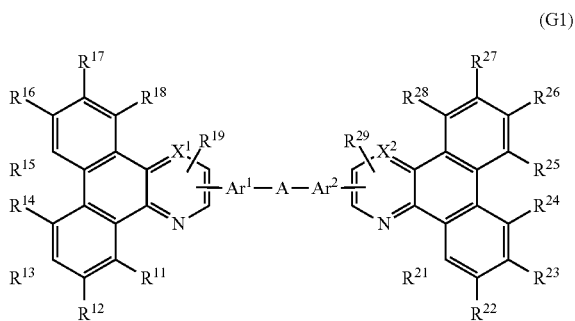

(G1)

In General Formula (G1), A represents a substituted or unsubstituted dibenzofuran-diyl group, a substituted or unsubstituted dibenzothiophene-diyl group, a substituted or unsubstituted N-aryl-9H-carbazole-diyl group, or a substituted or unsubstituted N-alkyl-9H-carbazole-diyl group; $Ar^1$ and $Ar^2$ each independently represent a single-bond or a substituted or unsubstituted arylene group; $R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; $X^1$ and $X^2$ each independently represent a carbon atom or a nitrogen atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms.

Another embodiment of the present invention is an organic compound represented by General Formula (G2).

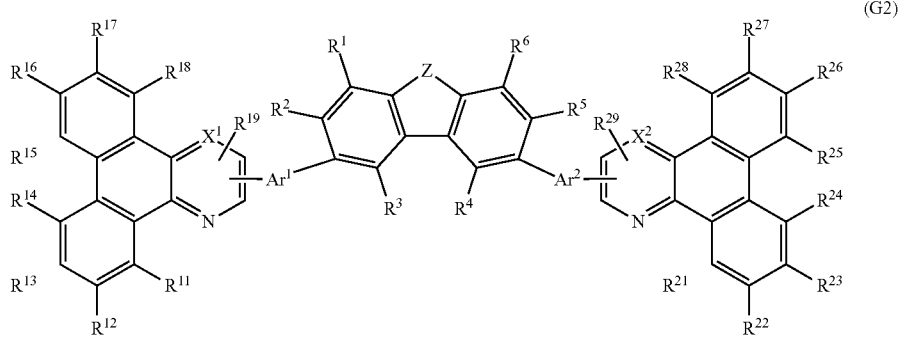

(G2)

In General Formula (G2), $Ar^1$ and $Ar^2$ each independently represent a single-bond or a substituted or unsubstituted arylene group; $R^1$ to $R^6$, $R^{11}$ to $R^{19}$, and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; $X^1$ and $X^2$ each independently represent a carbon atom or a nitrogen atom; the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms; and Z represents an oxygen atom, a sulfur atom, or a nitrogen atom which has, as a substituent, an alkyl group having 1 to 6 carbon atoms, a cycloalkyl group having 3 to 6 carbon atoms, or a substituted or unsubstituted aryl group having 6 to 13 carbon atoms.

In the above structures, it is preferable that $Ar^1$ and $Ar^2$ each independently represent a single-bond or a substituted or unsubstituted phenylene group.

Another embodiment of the present invention is an organic compound represented by any one of Structural Formulae (100), (101), (102), (105), (107), and (183).

(100)
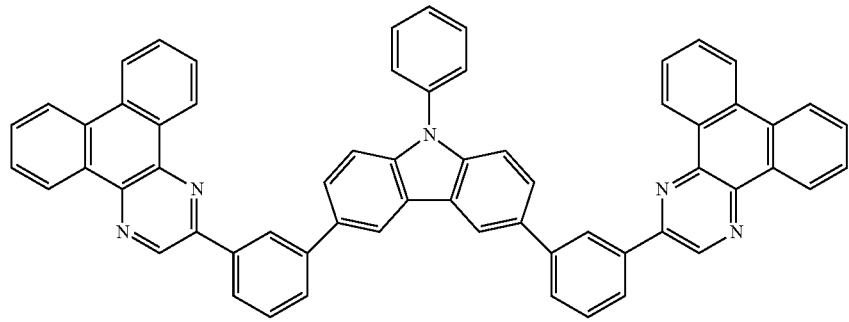
(101)
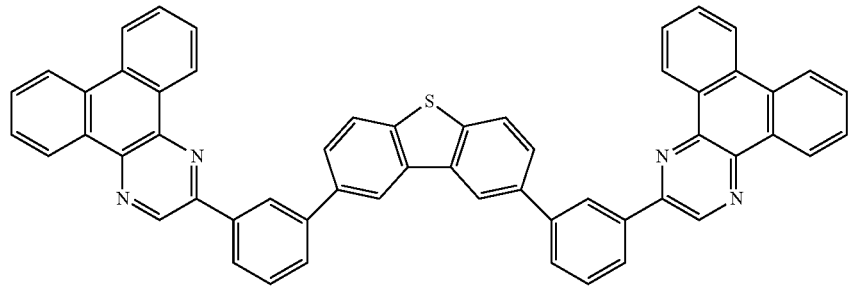
(102)
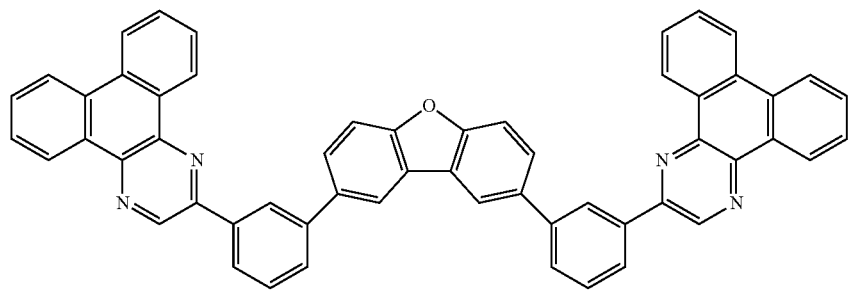
(105)
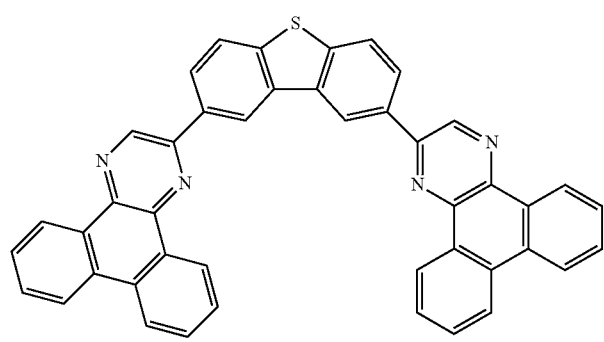
(107)
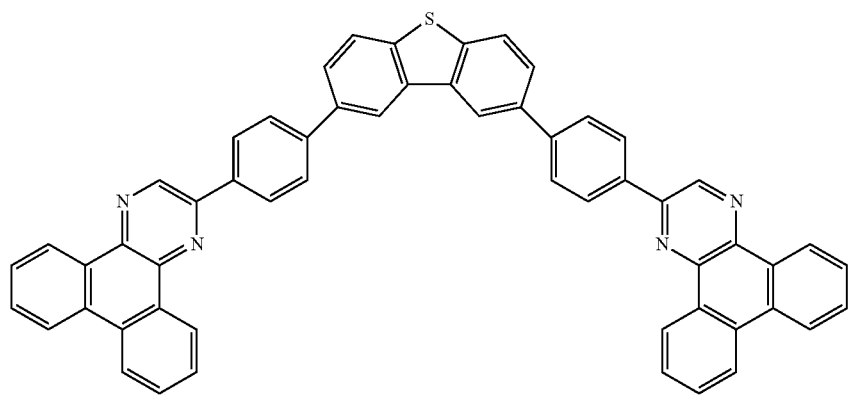

-continued

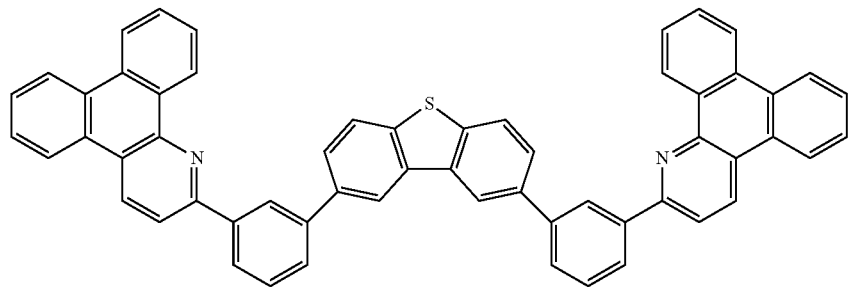

(183)

Another embodiment of the present invention is a light-emitting element including any of the above organic compounds. Another embodiment of the present invention is a light-emitting device including the light-emitting element. Another embodiment of the present invention is an electronic device and a lighting device each including the light-emitting device.

One embodiment of the present invention can provide a novel organic compound that can be used in a light-emitting element as a host material of a light-emitting layer in which a light-emitting substance is dispersed. In particular, a novel organic compound that can be suitably used as a host material in the case where a phosphorescent compound is a light-emitting substance can be provided. Furthermore, a novel organic compound that has a high electron-transport property and suitably used in an electron-transport layer can be provided. Note that effects of one embodiment of the present invention are not limited to the above. Depending on circumstances or conditions, one embodiment of the present invention might produce another effect. Furthermore, depending on circumstances or conditions, one embodiment of the present invention might not produce any of the above effects.

DETAILED DESCRIPTION OF THE INVENTION

Figure 1A:
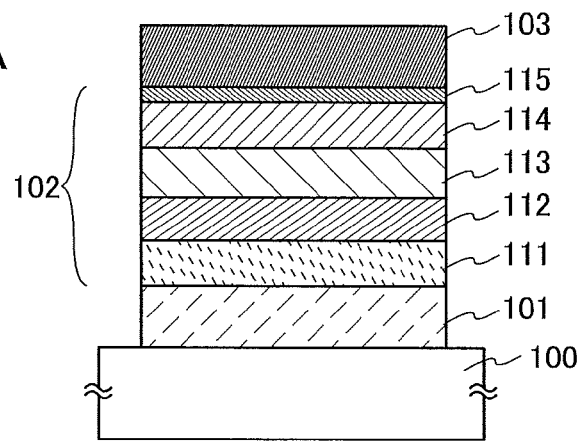
FIGS. 1A to 1C each illustrate a light-emitting element of one embodiment of the present invention.

Embodiments and examples of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention should not be construed as being limited to the descriptions of the embodiments and the examples below.

The light-emitting device in this specification includes, in its category, an image display device that uses a light-emitting element. Further, the category of the light-emitting device includes a module in which a light-emitting element is provided with a connector, an anisotropic conductive film, or a TCP (tape carrier package); a module in which the end of the TCP is provided with a printed wiring board; and a module in which an IC (integrated circuit) is directly mounted on a light-emitting element by a COG (chip on glass) method. Furthermore, the category includes light-emitting devices that are used in lighting devices or the like.

Embodiment 1

In this embodiment, an organic compound of one embodiment of the present invention will be described.

One embodiment of the present invention is an organic compound represented by General Formula (G1).

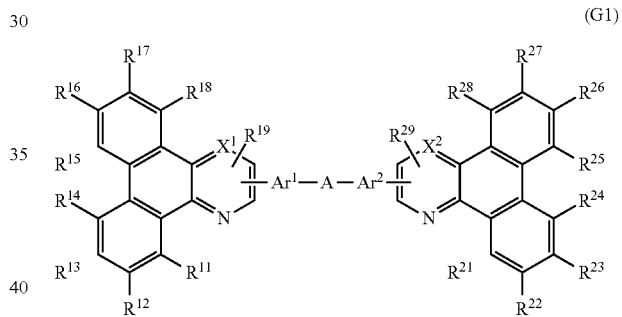

(G1)

In General Formula (G1), A represents a substituted or unsubstituted dibenzofuran-diyl group, a substituted or unsubstituted dibenzothiophene-diyl group, a substituted or unsubstituted N-aryl-9H-carbazole-diyl group, or a substituted or unsubstituted N-alkyl-9H-carbazole-diyl group; $Ar^1$ and $Ar^2$ each independently represent a single-bond or a substituted or unsubstituted arylene group; $R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; $X^1$ and $X^2$ each independently represent a carbon atom or a nitrogen atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms.

Another embodiment of the present invention is an organic compound represented by General Formula (G2).

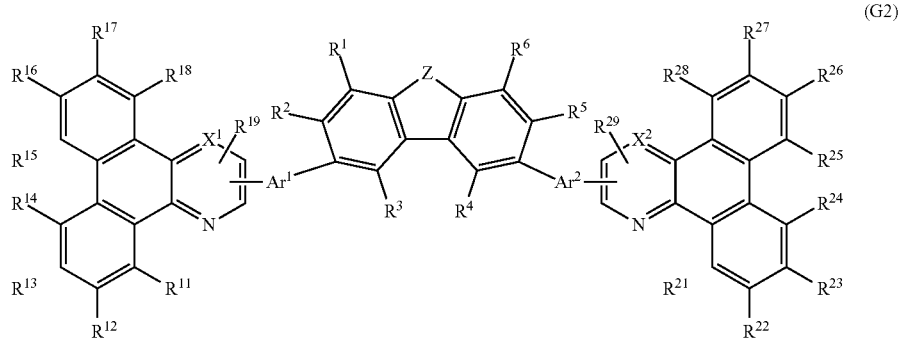

(G2)

In General Formula (G2), $Ar^1$ and $Ar^2$ each independently represent a single-bond or a substituted or unsubstituted arylene group; $R^1$ to $R^6$, $R^{11}$ to $R^{19}$, and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; $X^1$ and $X^2$ each independently represent a carbon atom or a nitrogen atom; the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms; and Z represents an oxygen atom, a sulfur atom, or a nitrogen atom which has, as a substituent, an alkyl group having 1 to 6 carbon atoms, a cycloalkyl group having 3 to 6 carbon atoms, or a substituted or unsubstituted aryl group having 6 to 13 carbon atoms.

In General Formula (G1) and/or General Formula (G2), it is preferable that $Ar^1$ and $Ar^2$ each independently represent a single-bond or a substituted or unsubstituted phenylene group.

In General Formula (G1) and/or General Formula (G2), when $Ar^1$ and $Ar^2$ are each a substituted or unsubstituted arylene group, an example of the arylene group is an arylene group having 6 to 13 carbon atoms. Examples of the arylene group having 6 to 13 carbon atoms include a 1,2-phenylene group, a 1,3-phenylene group, a 1,4-phenylene group, a 1,2-naphthylene group, a 1,4-naphthylene group, a 1,5-naphthylene group, a 2,6-naphthylene group, a 2,8-naphthylene group, a 2,2'-biphenyl-diyl group, a 3,3'-biphenyl-diyl group, a 4,4'-biphenyl-diyl group, a 3,4'-biphenyl-diyl group, a 9H-fluorene-2,7-diyl group, a 9,9-dimethyl-9H-fluorene-2,7-diyl group, a 9,9-dimethyl-9H-fluorene-3,6-diyl group, a 9,9-diphenyl-9H-fluorene-2,7-diyl group, and a 9,9-diphenyl-9H-fluorene-3,6-diyl group. The arylene group may have a substituent.

In General Formula (G1) and/or General Formula (G2), examples of an alkyl group having 1 to 6 carbon atoms or a cycloalkyl group having 3 to 6 carbon atoms include a methyl group, an ethyl group, an n-propyl group, an isopropyl group, a butyl group, a sec-butyl group, an isobutyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a neohexyl group, a cyclohexyl group, a 3-methylpentyl group, a 2-methylpentyl group, a 2-ethylbutyl group, a 1,2-dimethylbutyl group, and a 2,3-dimethylbutyl group. The alkyl group and the cycloalkyl group may have a substituent.

In General Formula (G1) and/or General Formula (G2), as a substituted or unsubstituted aryl group having 6 to 13 carbon atoms, examples of the aryl group include a phenyl group, a 1-naphthyl group, a 2-naphthyl group, an ortho-tolyl group, a meta-tolyl group, a para-tolyl group, an ortho-biphenyl group, a meta-biphenyl group, a para-biphenyl group, a 9,9-dimethyl-9H-fluoren-2-yl group, a 9,9-diphenyl-9H-fluoren-2-yl group, a 9H-fluoren-2-yl group, a para-tert-butylphenyl group, and a mesityl group.

The above substituents are not limited to these examples, and the substituent may further have a substituent.

One embodiment of the present invention is an organic compound represented by any one of Structural Formulae (100), (101), (102), (105), (107), and (183).

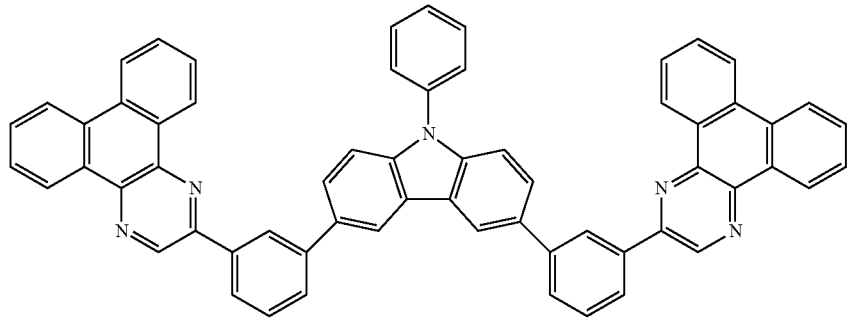

(100)

-continued
(101)
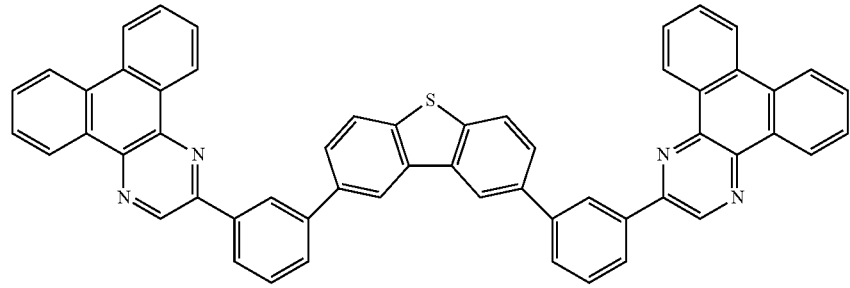
(102)
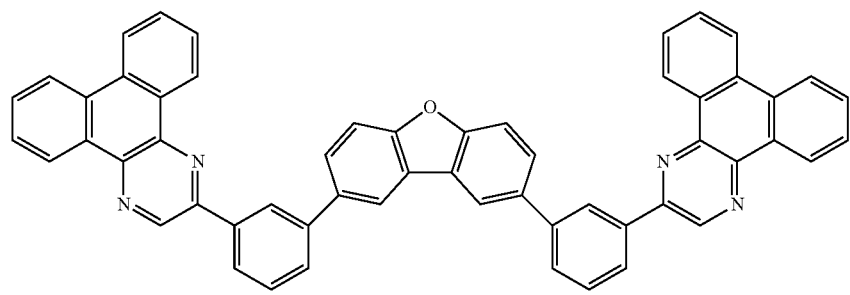
(105)
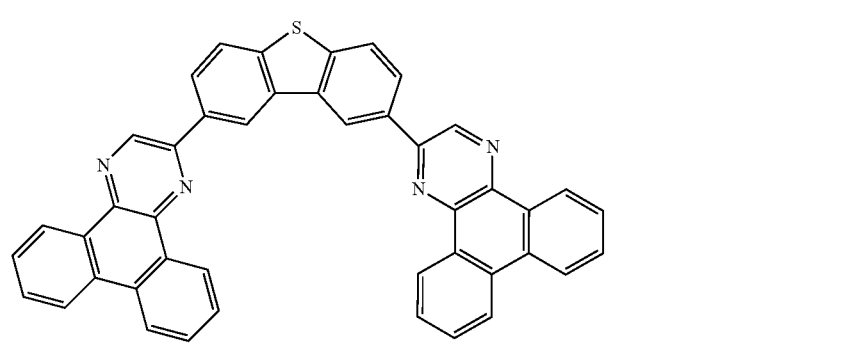
(107)
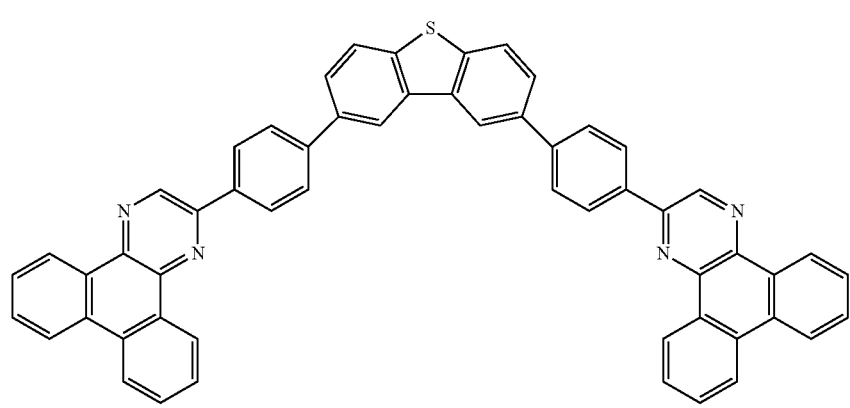
(183)
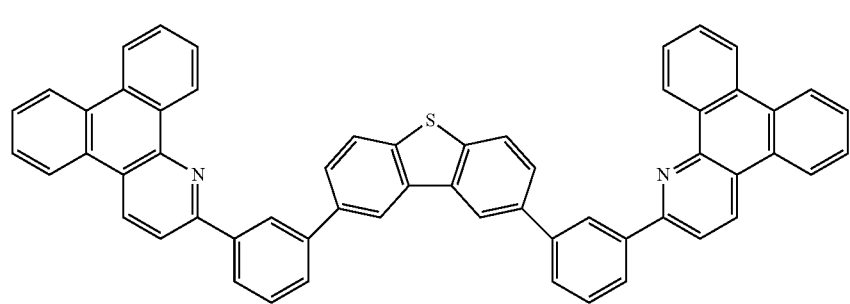

Specific examples of the organic compounds represented by General Formula (G1) and General Formula (G2) include organic compounds represented by Structural Formula (100) to Structural Formula (192). Note that the present invention is not limited thereto.
(100)
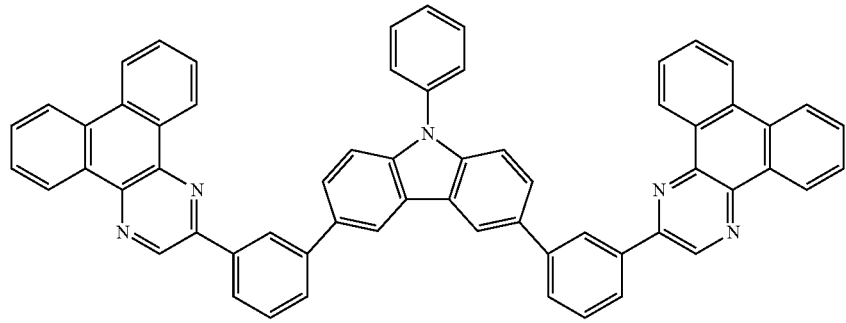
(101)
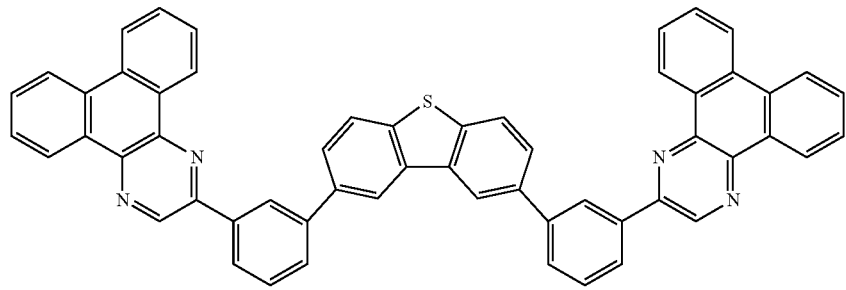
(102)
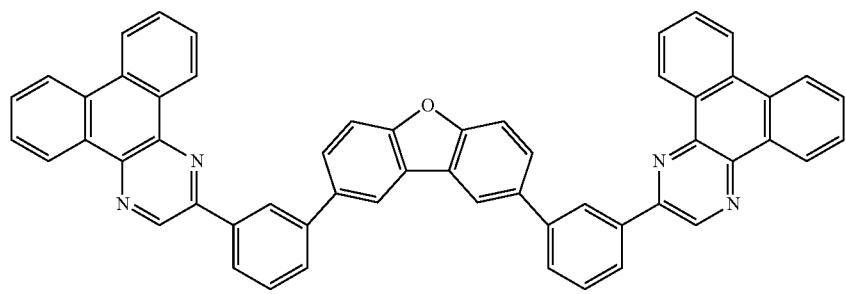
(103)
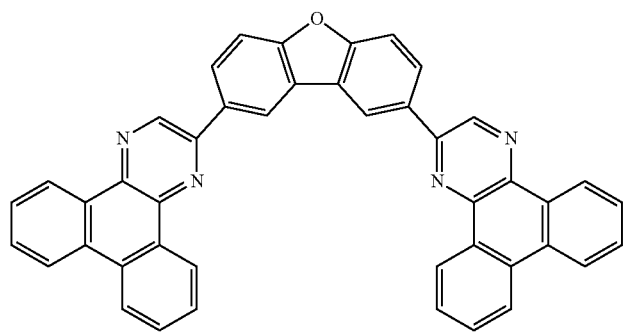

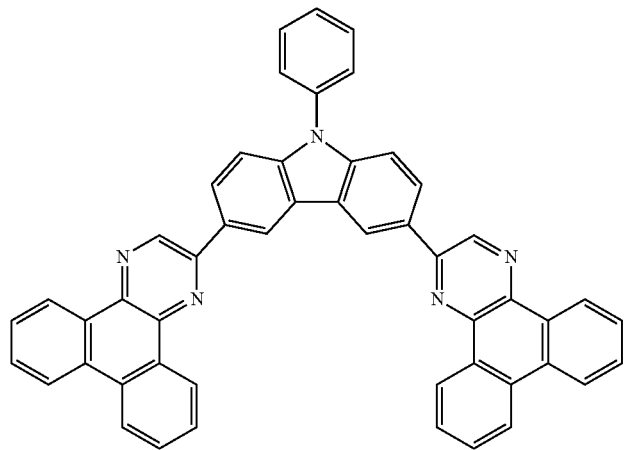
(104)
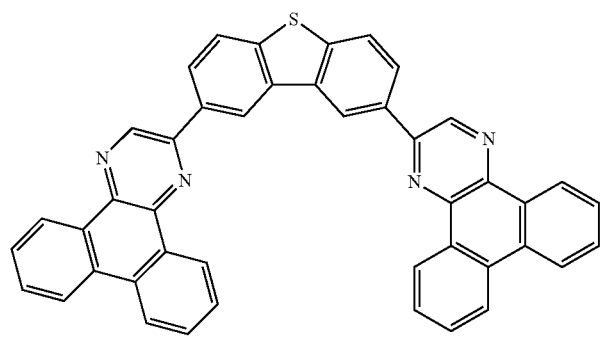
(105)
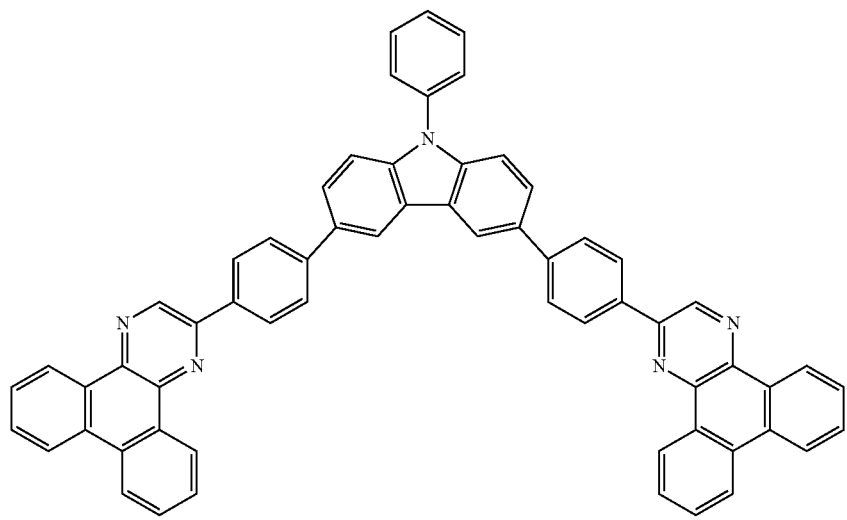
(106)

-continued
(107)
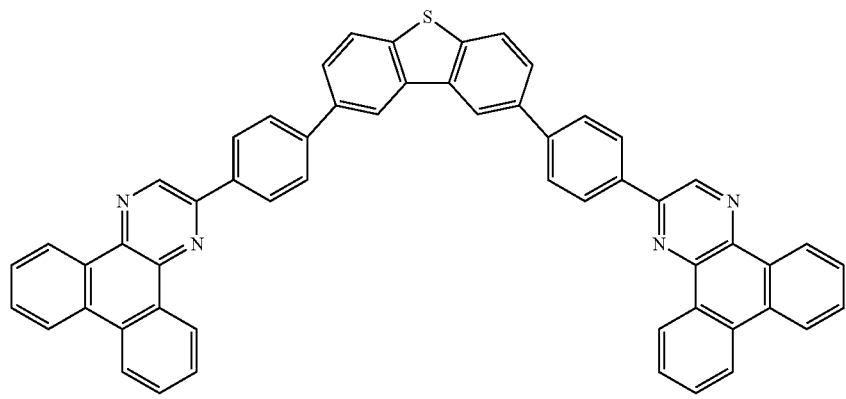
(108)
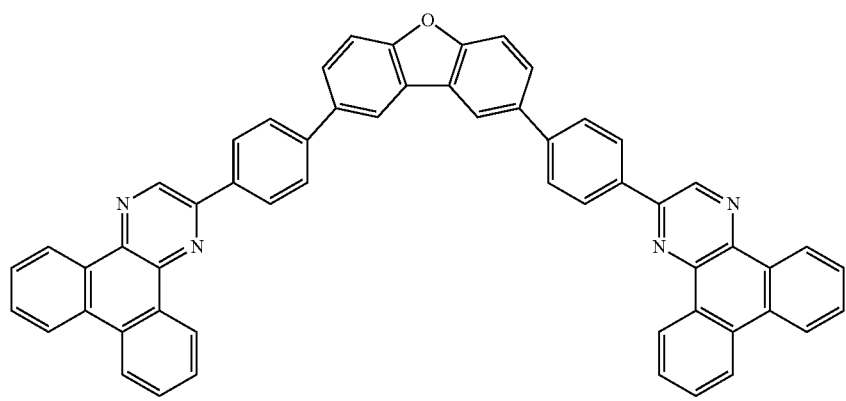
(109)
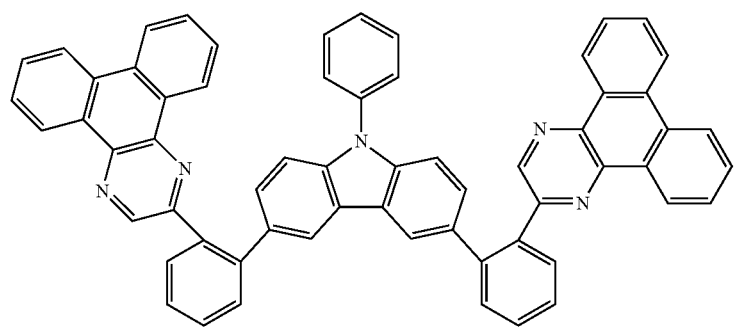
(110)
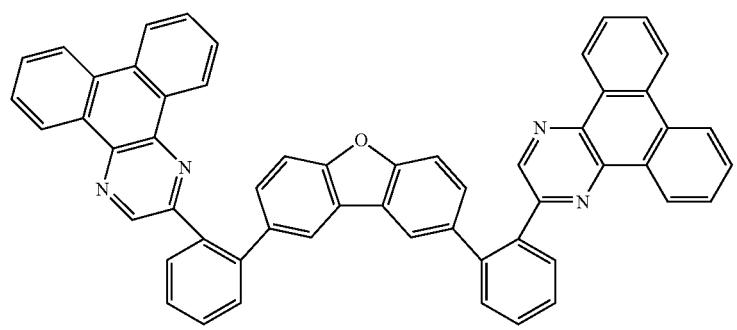

-continued
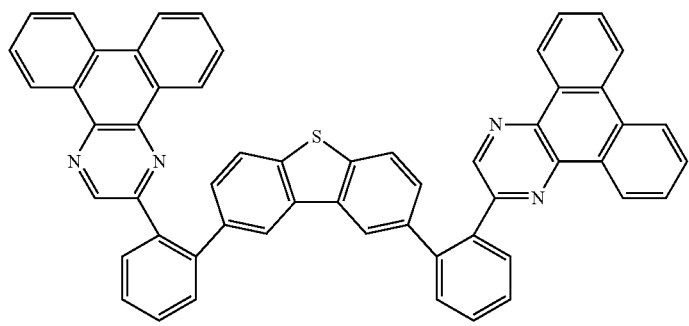
(111)
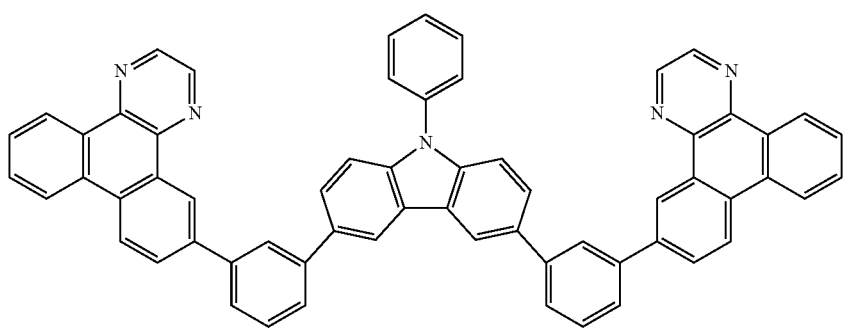
(112)
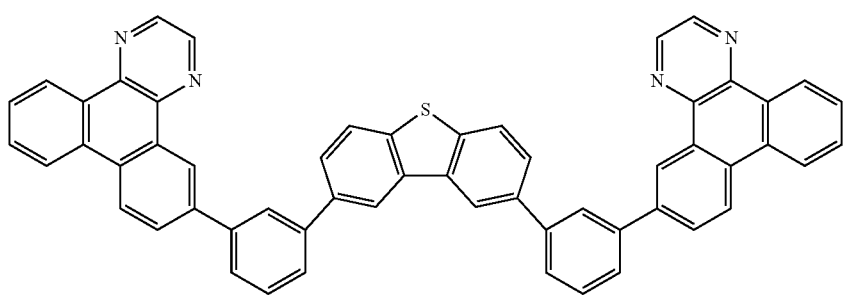
(113)
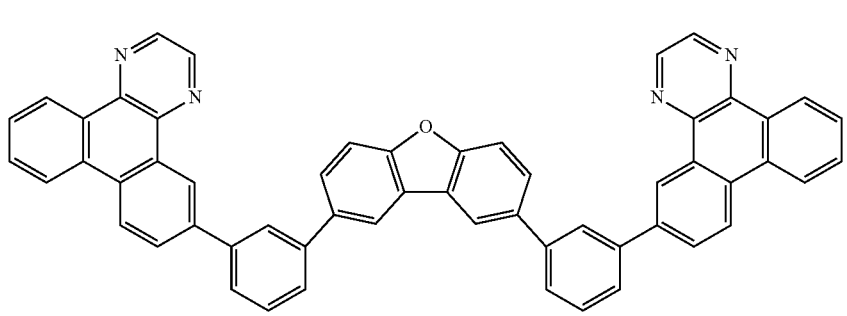
(114)
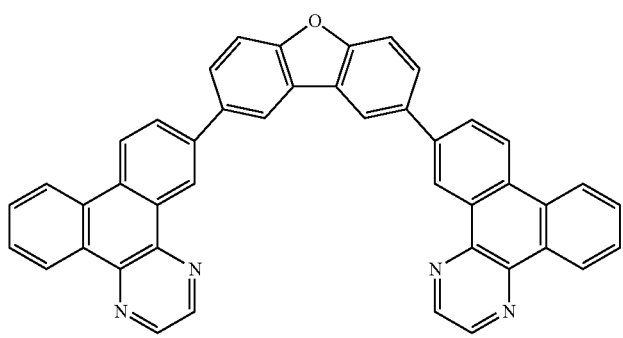
(115)

-continued
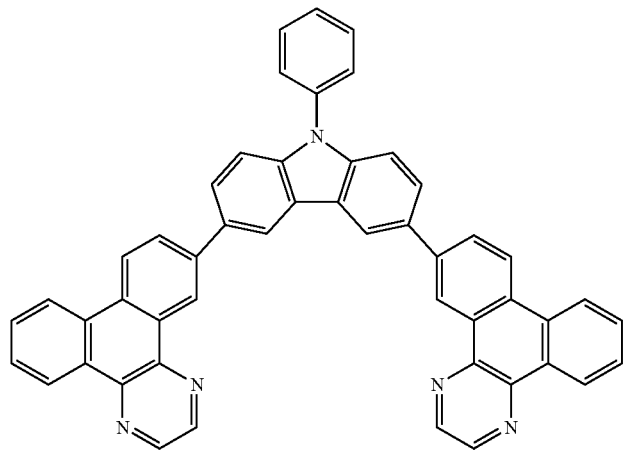
(116)
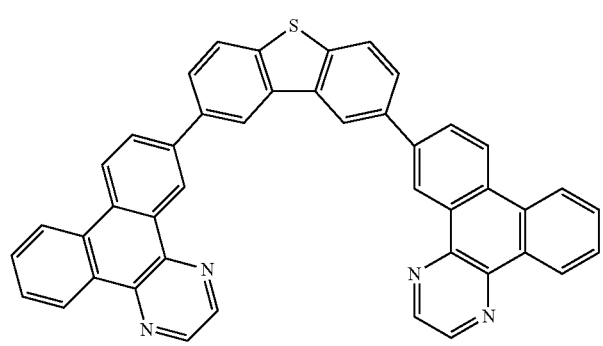
(117)
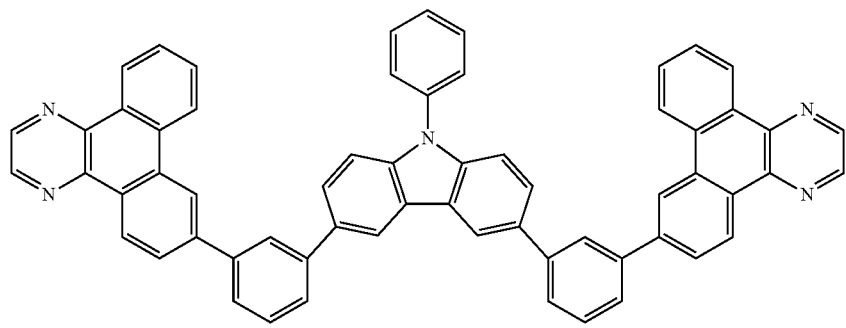
(118)
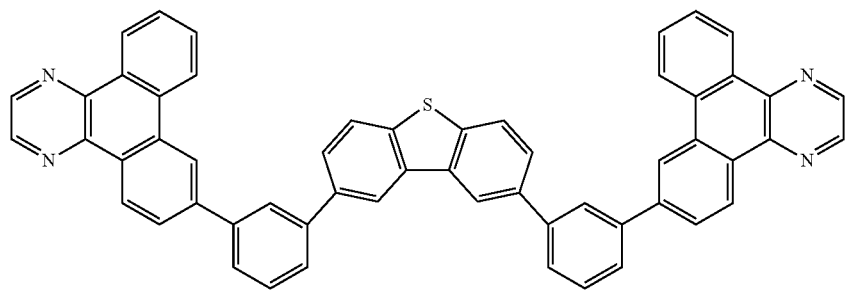
(119)

(120)
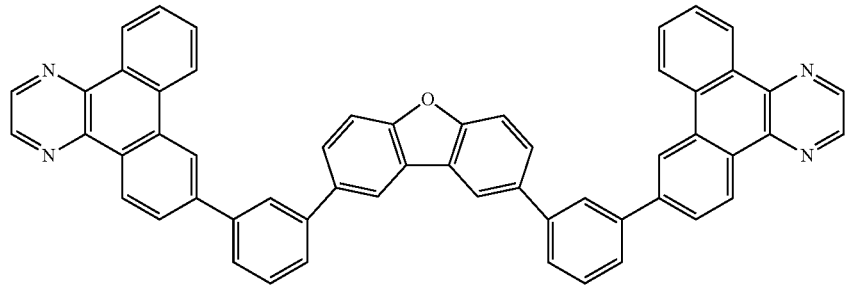
(121)
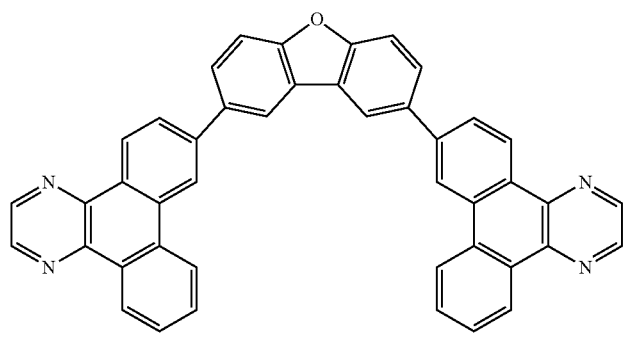
(122)
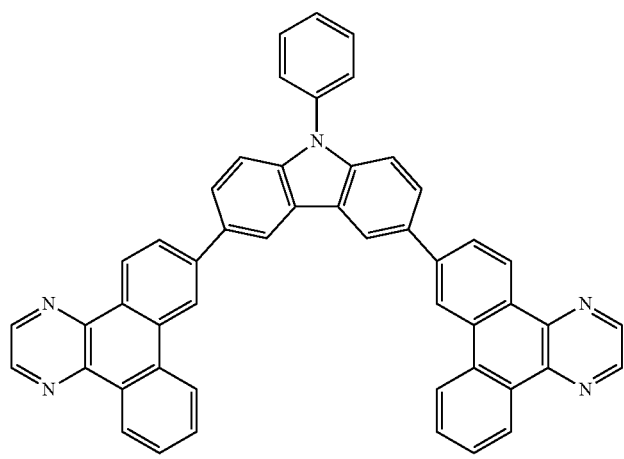
(123)
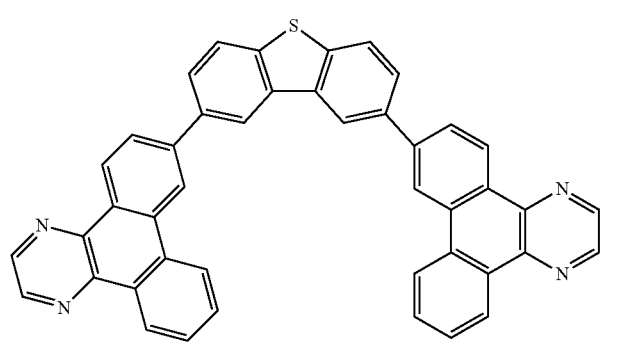

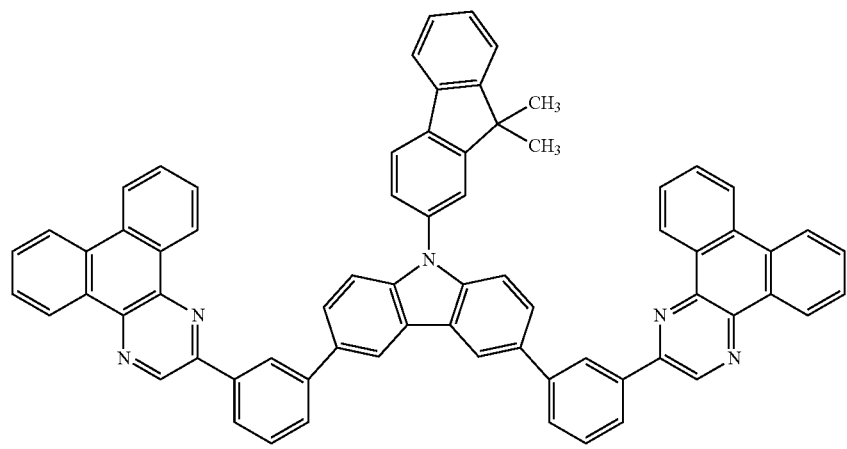
(124)
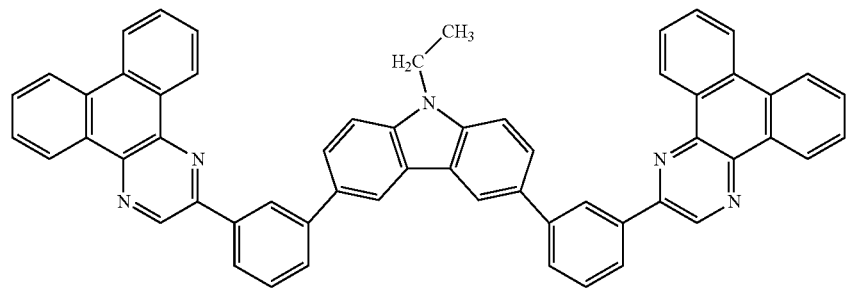
(125)
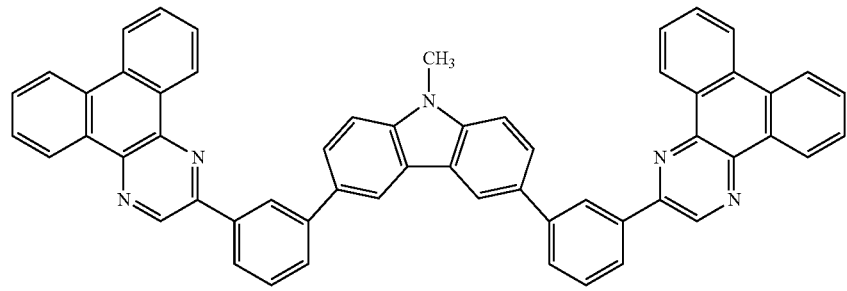
(126)
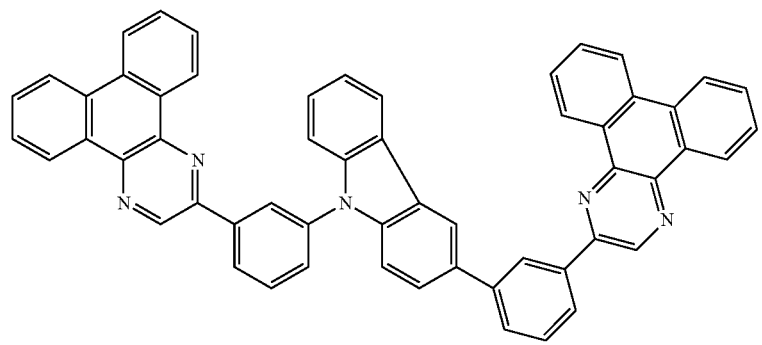
(127)

(128)
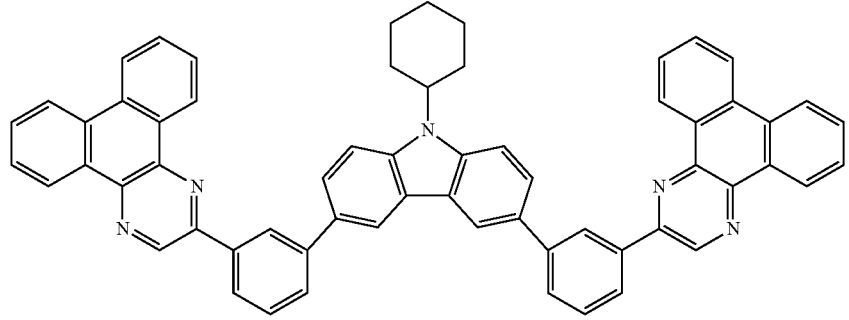
(129)
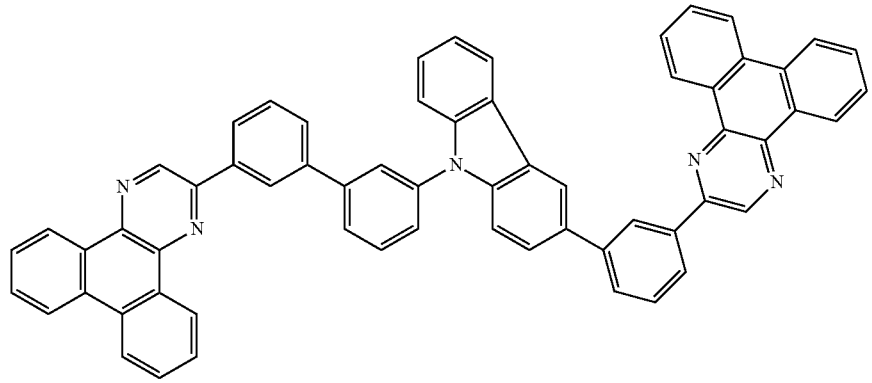
(130)
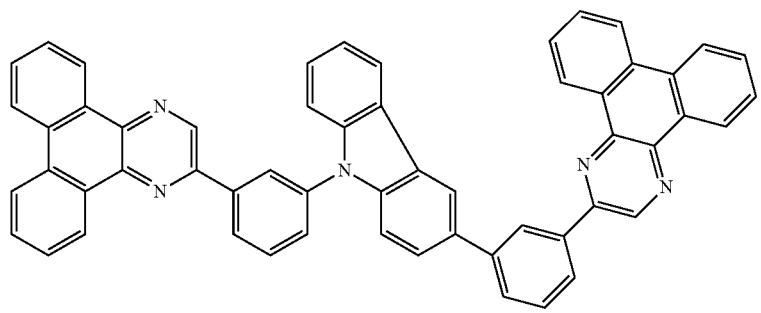
(131)
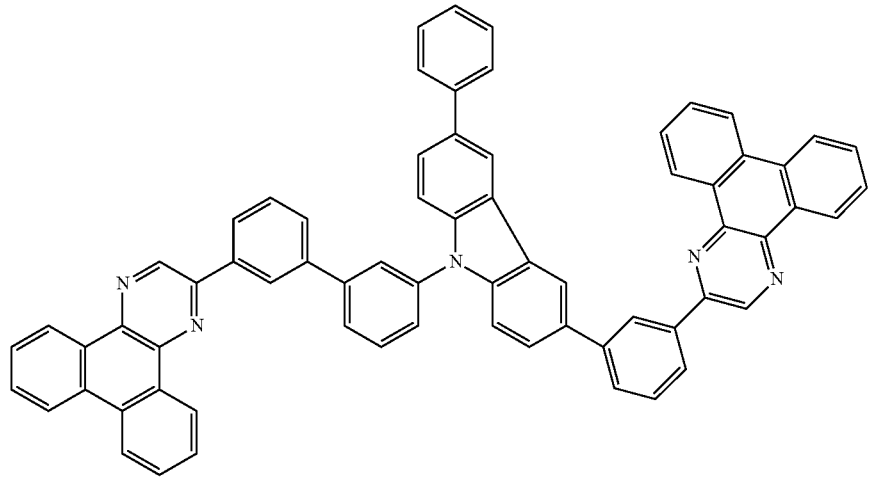

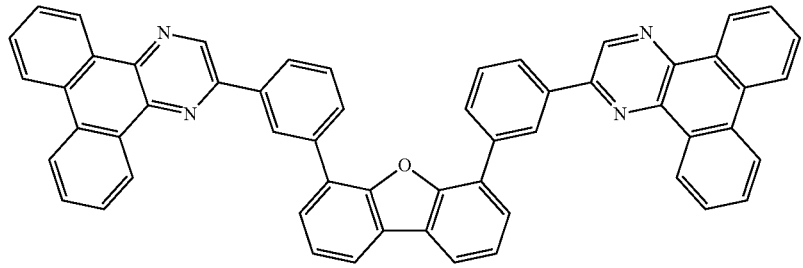
(132)
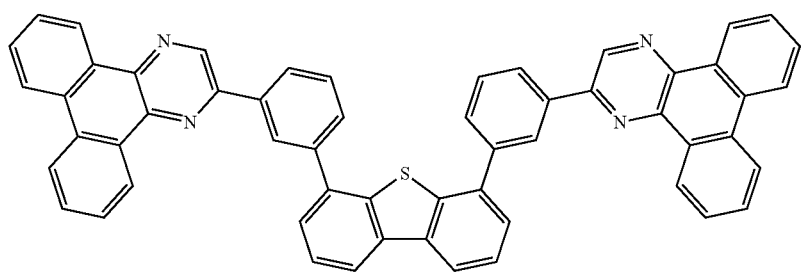
(133)
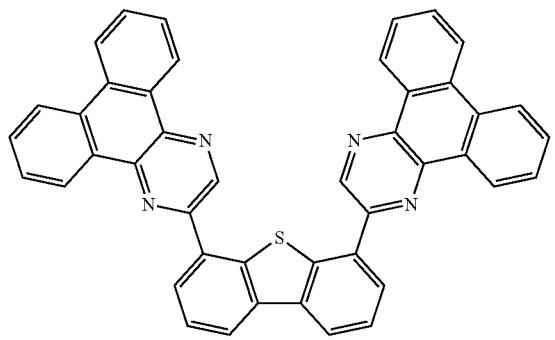
(134)
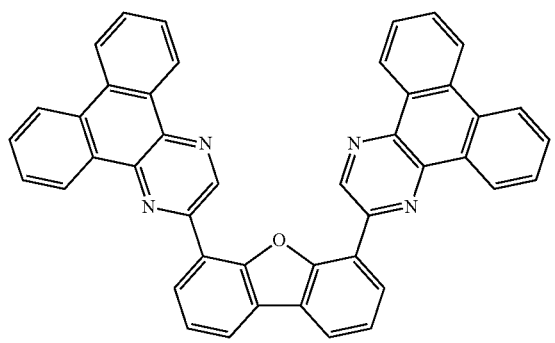
(135)

-continued
(136)
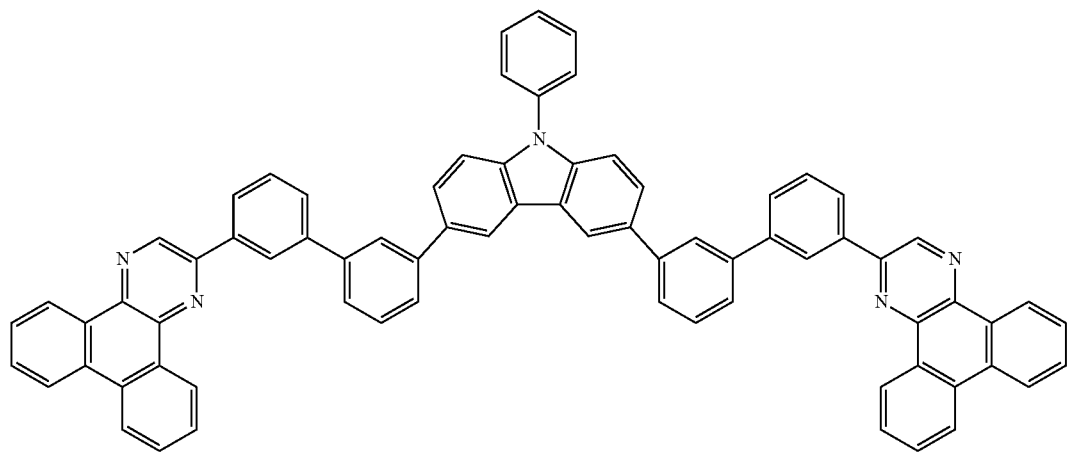
(137)
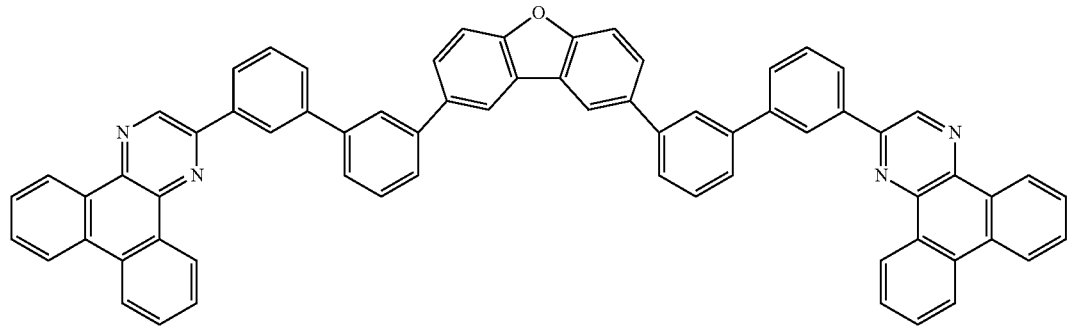
(138)
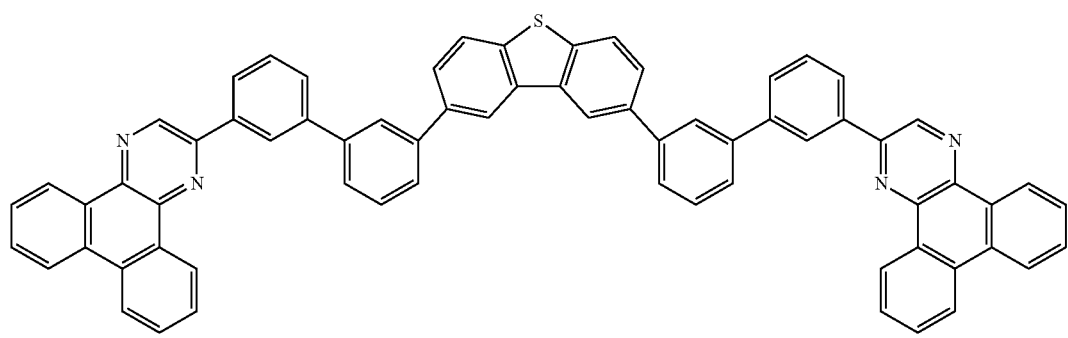
(139)
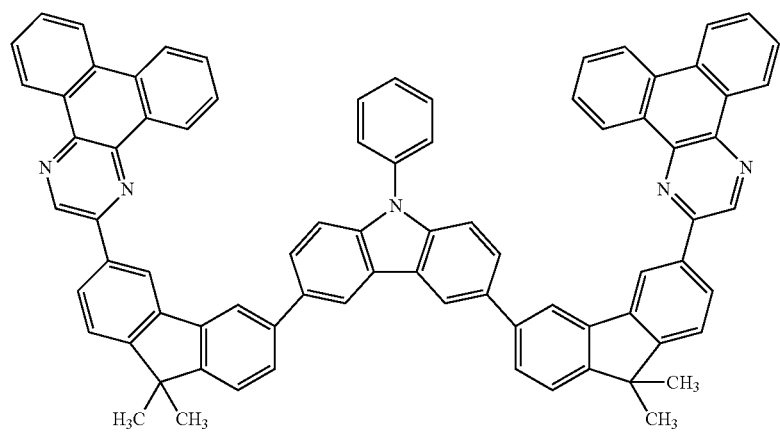

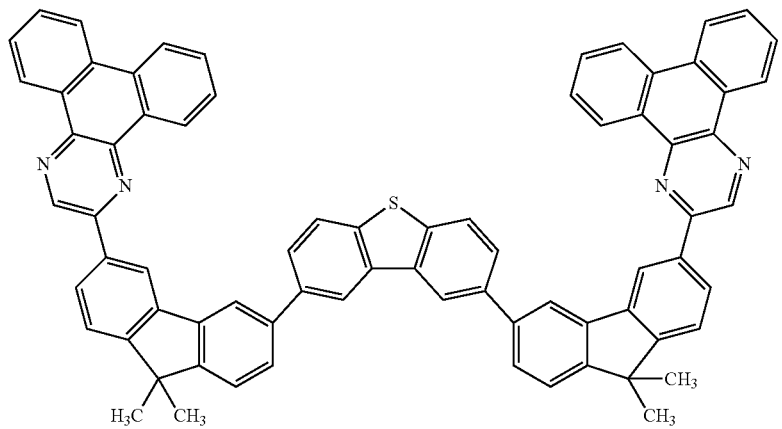
(140)
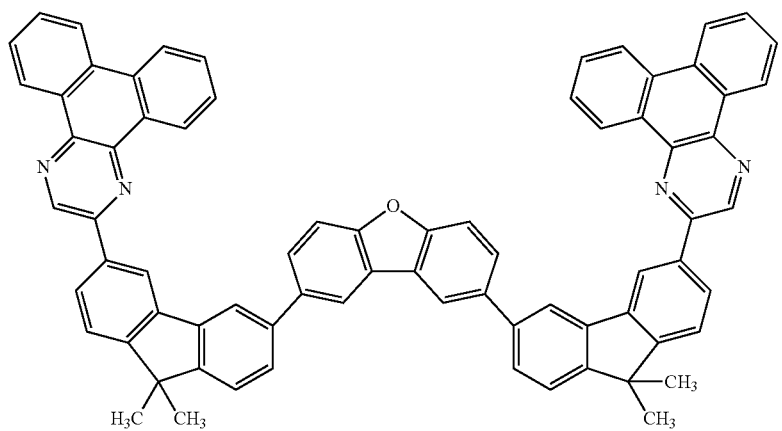
(141)
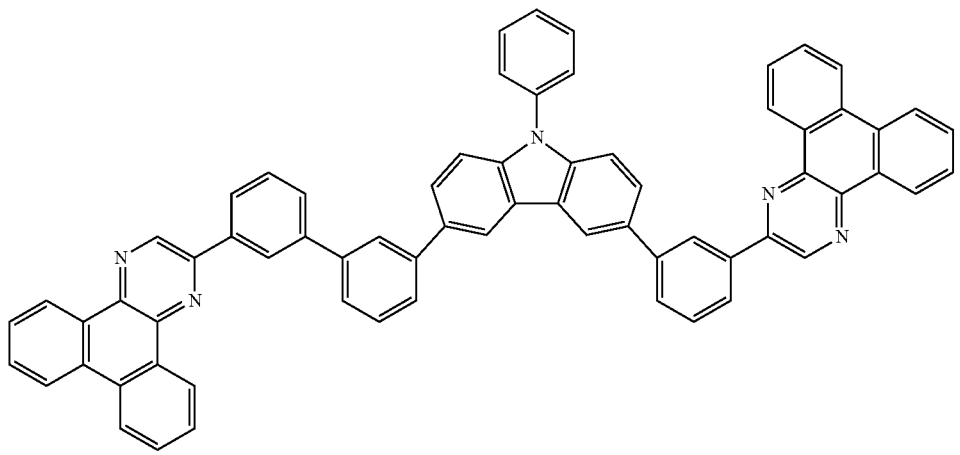
(142)

(143)
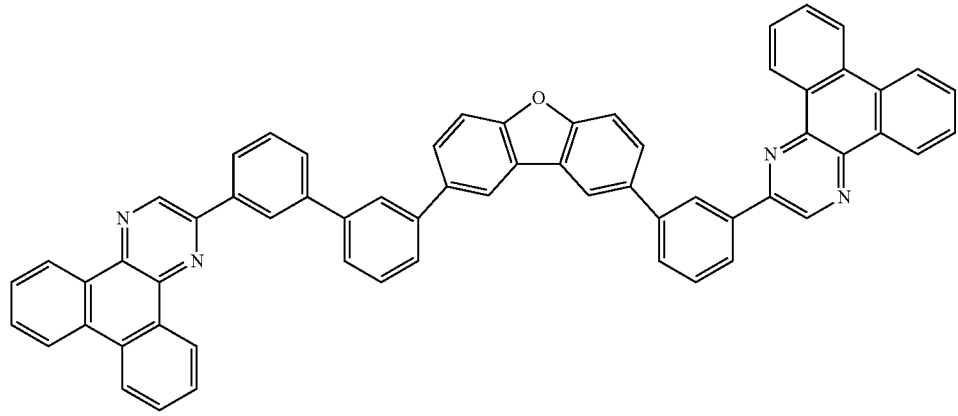
(144)
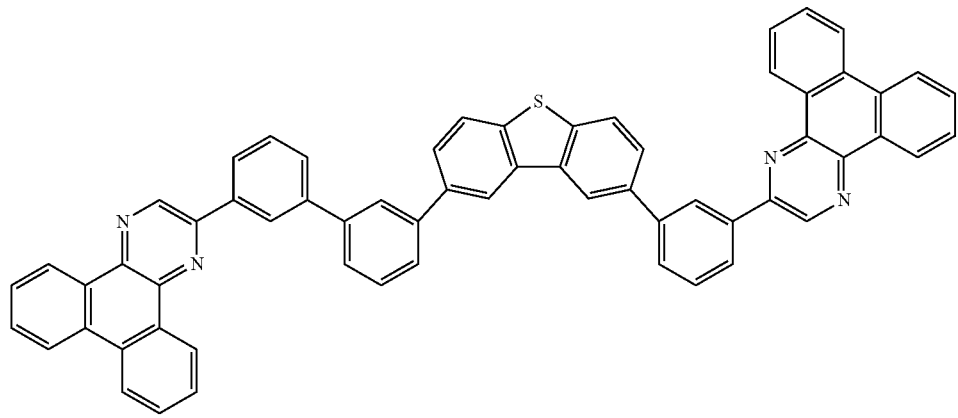
(145)
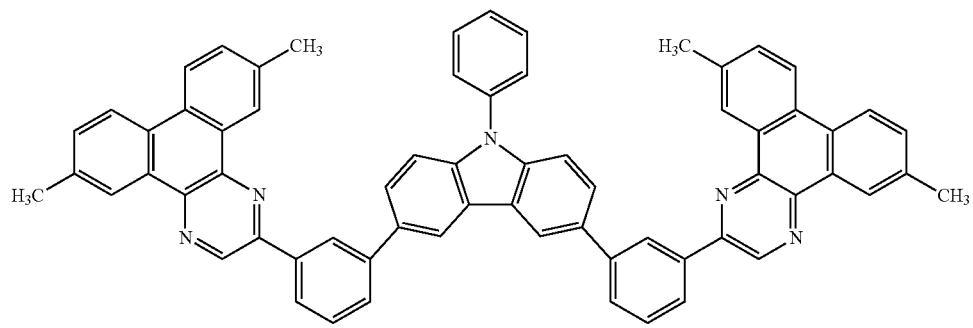
(146)
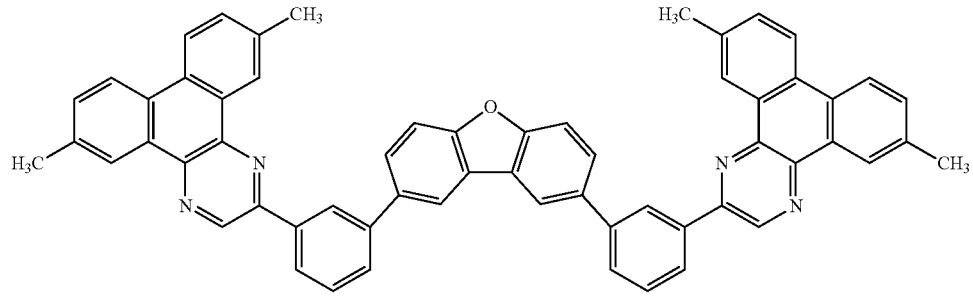

-continued
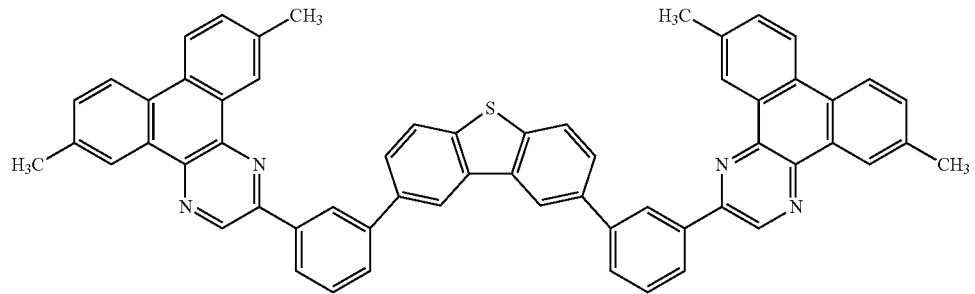
(147)
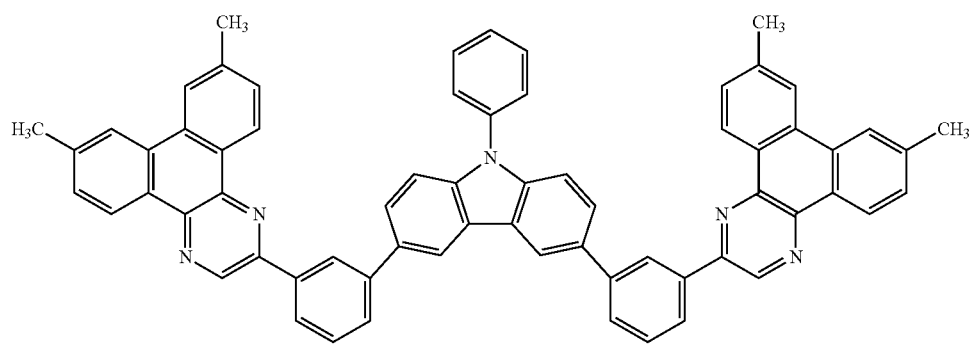
(148)
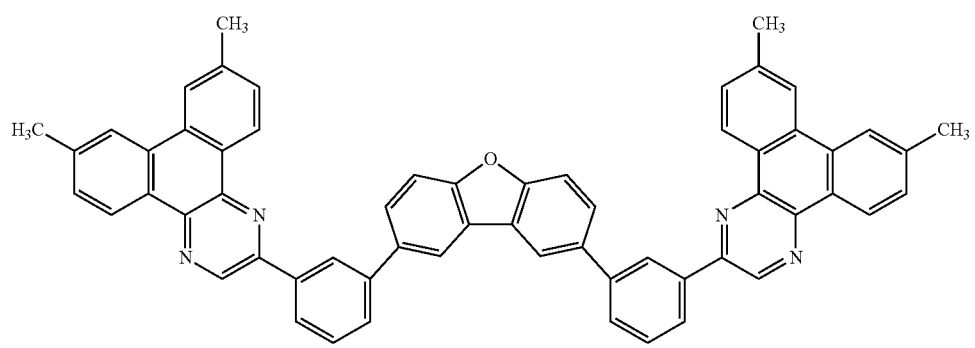
(149)
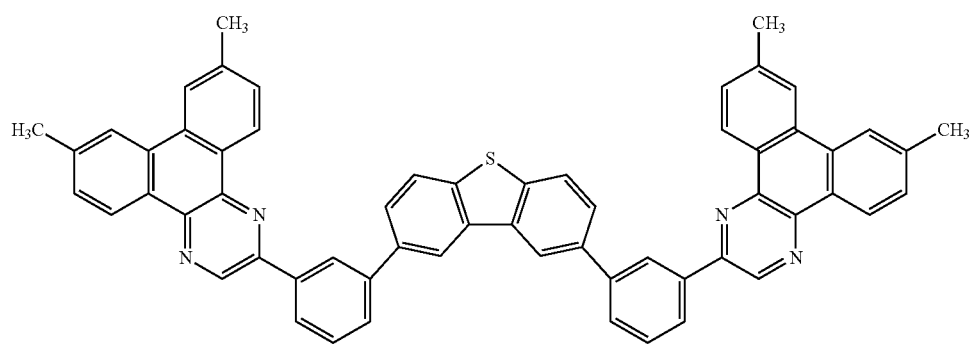
(150)

-continued
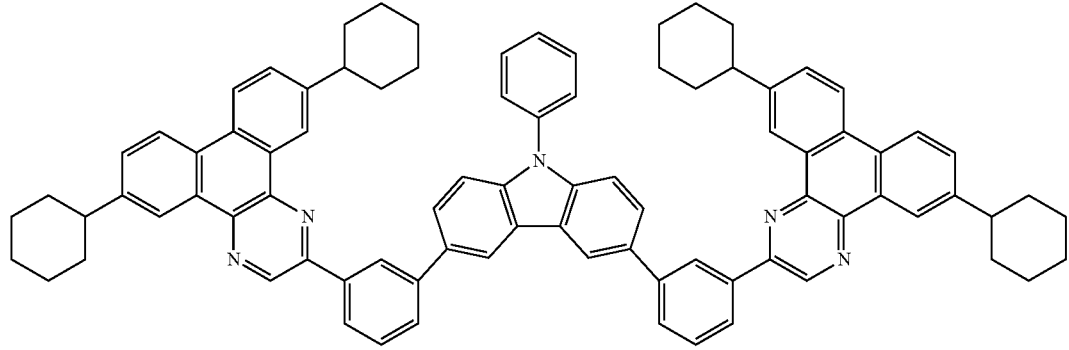
(151)
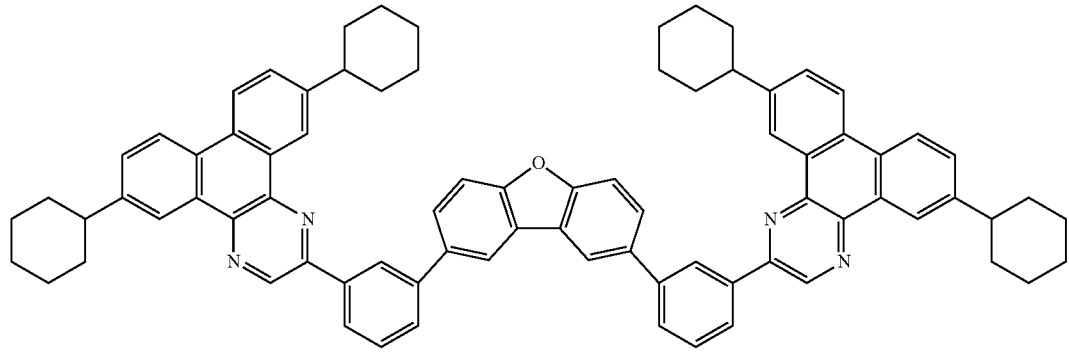
(152)
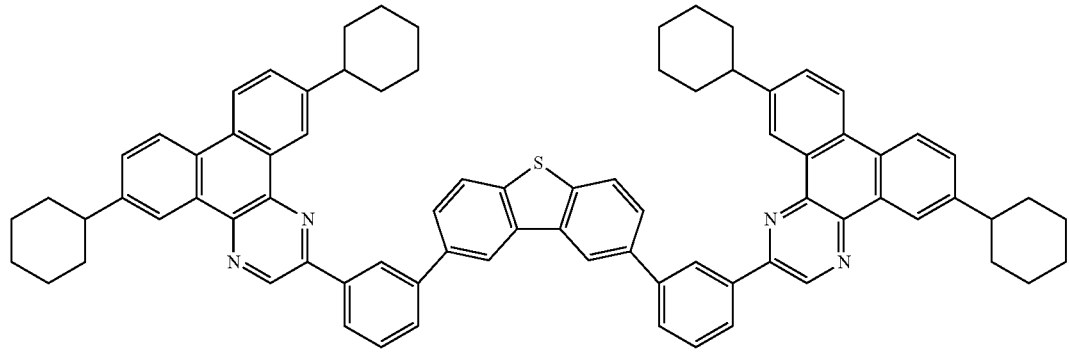
(153)
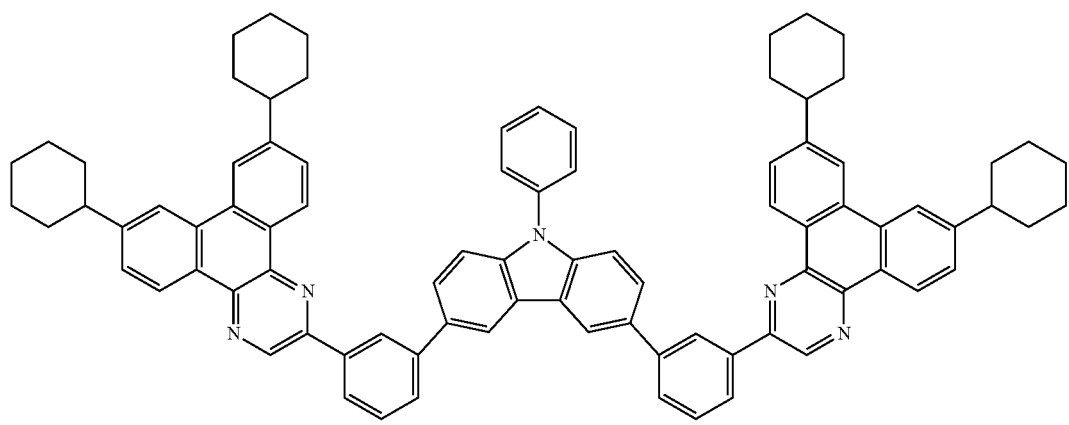
(154)

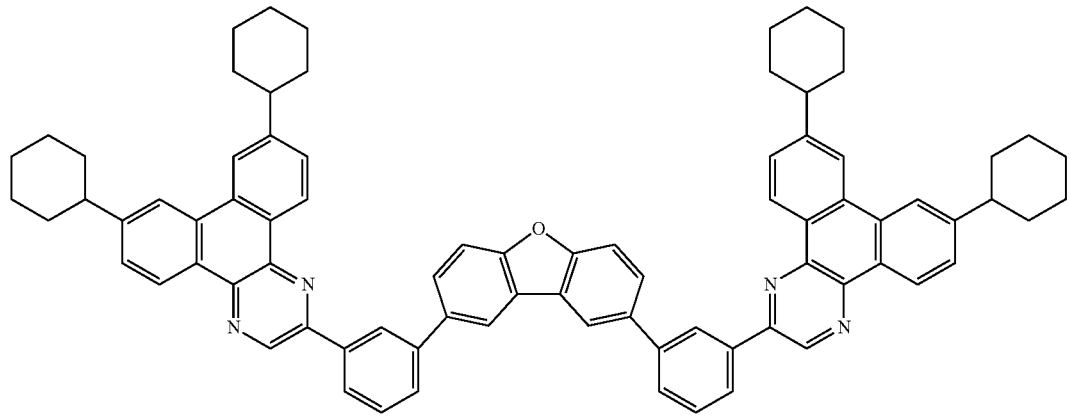
(155)
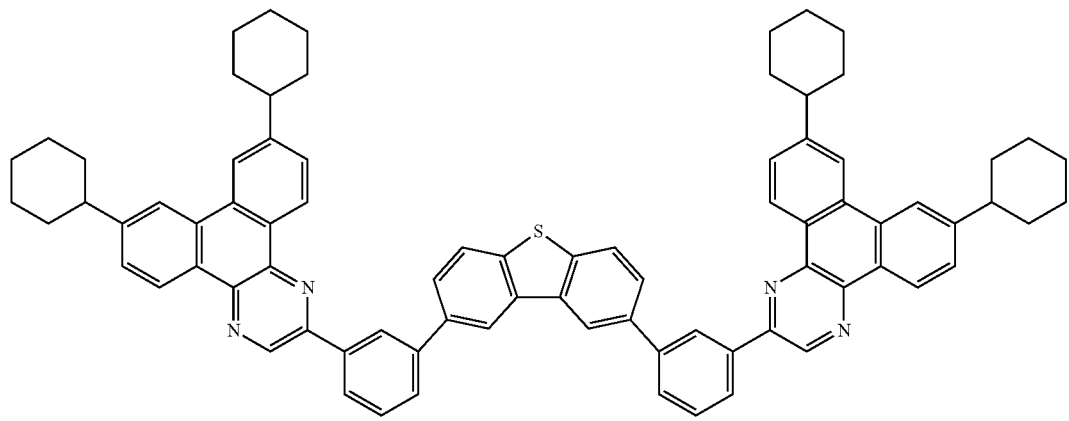
(156)
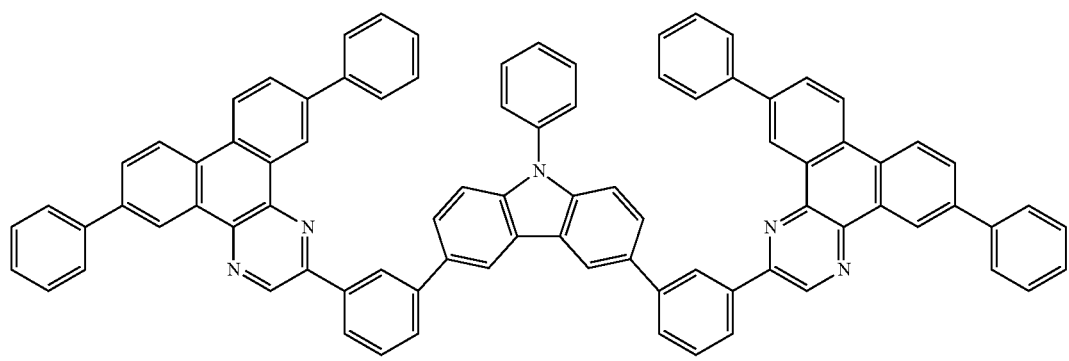
(157)
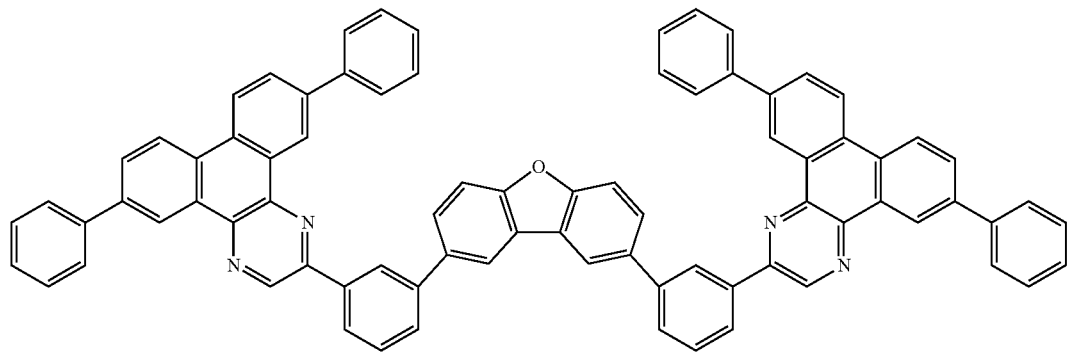
(158)

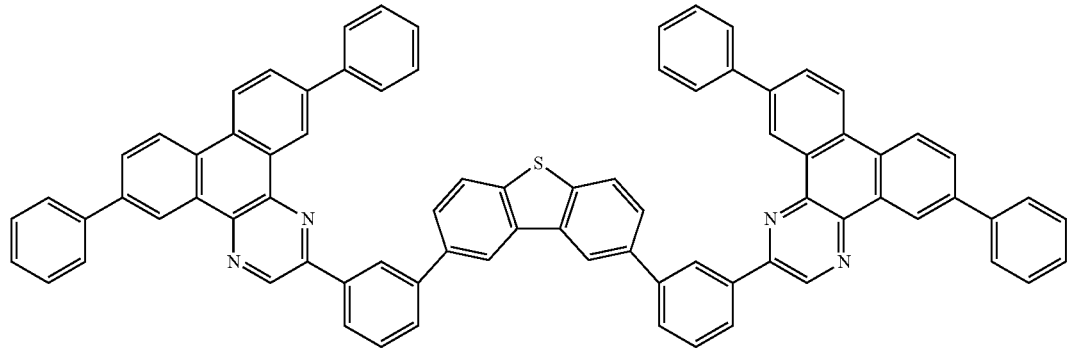
(159)
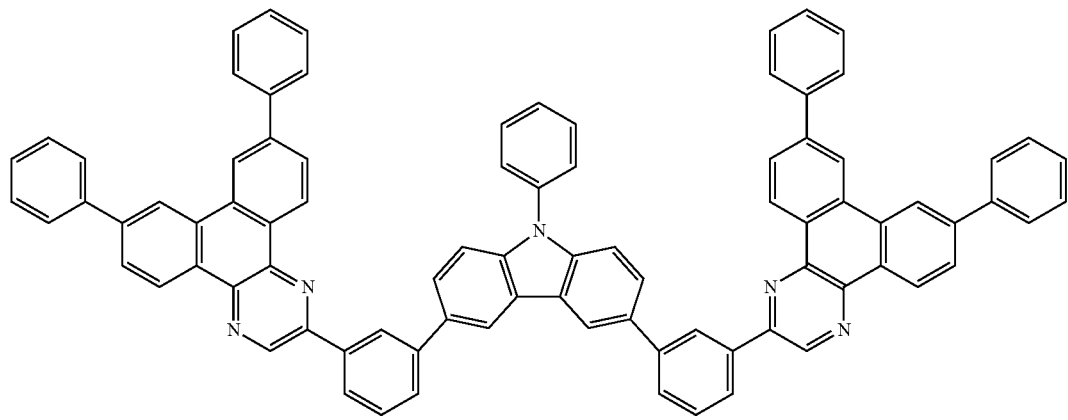
(160)
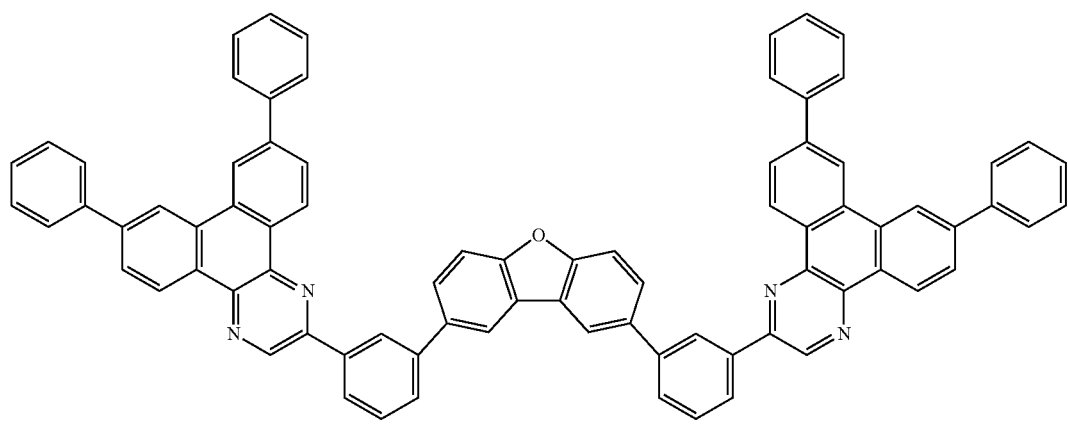
(161)
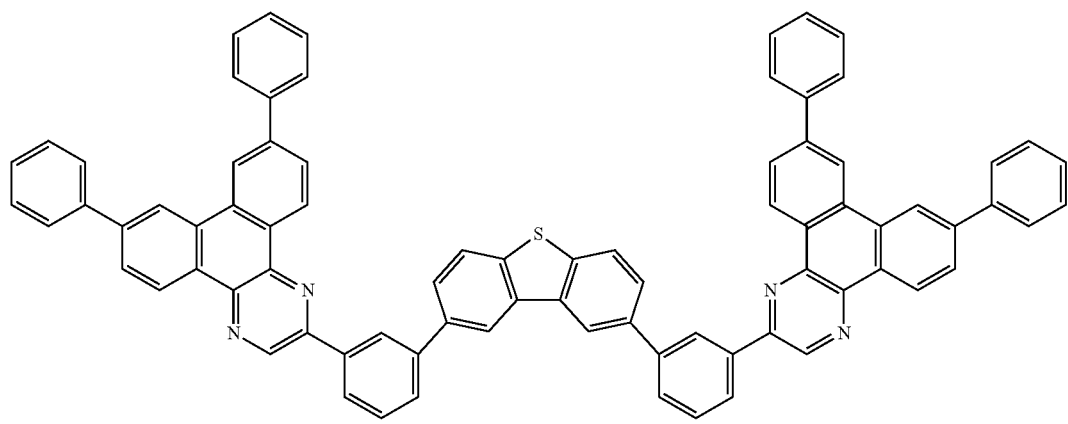
(162)

(163)
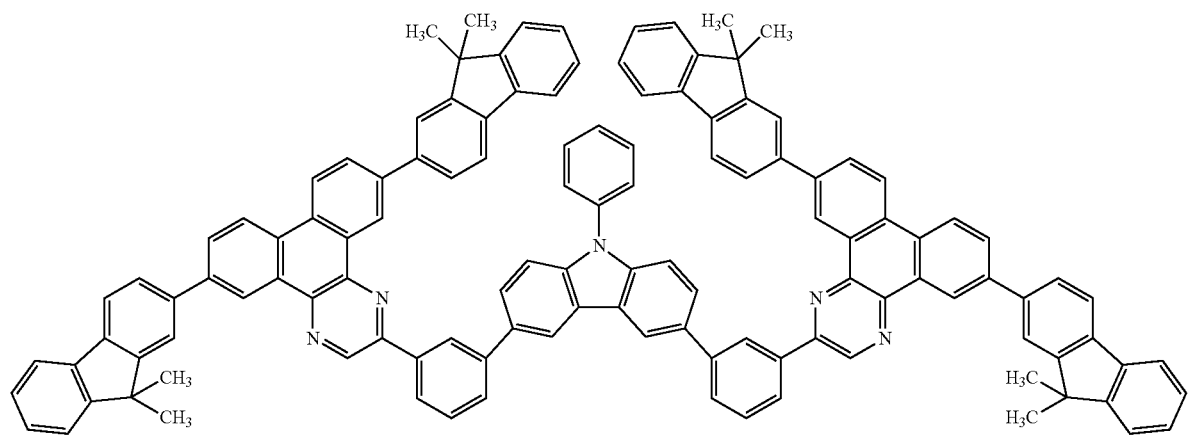
(164)
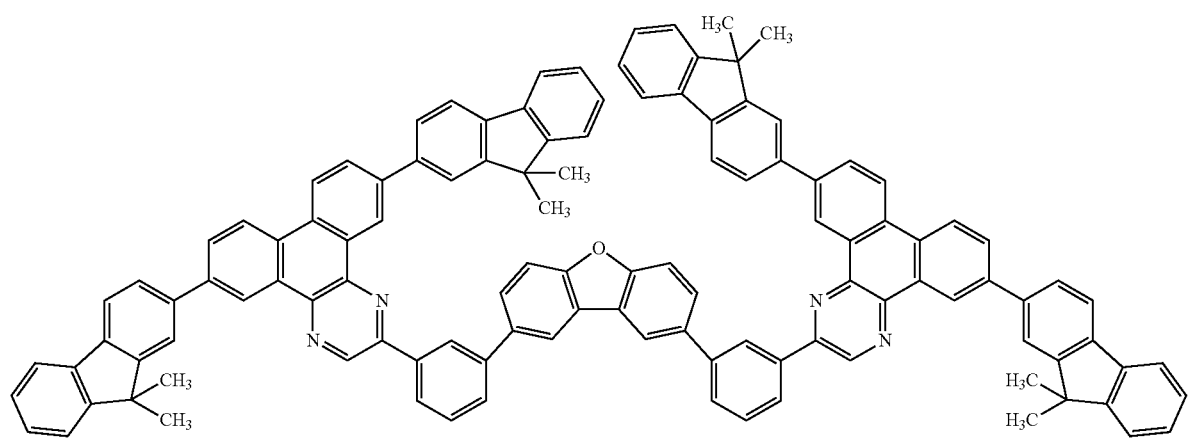
(165)
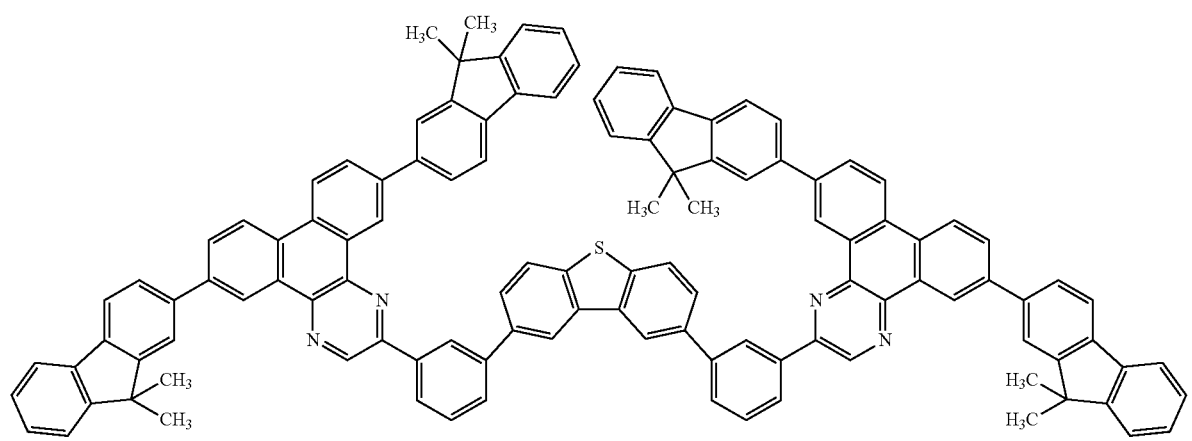

(166)
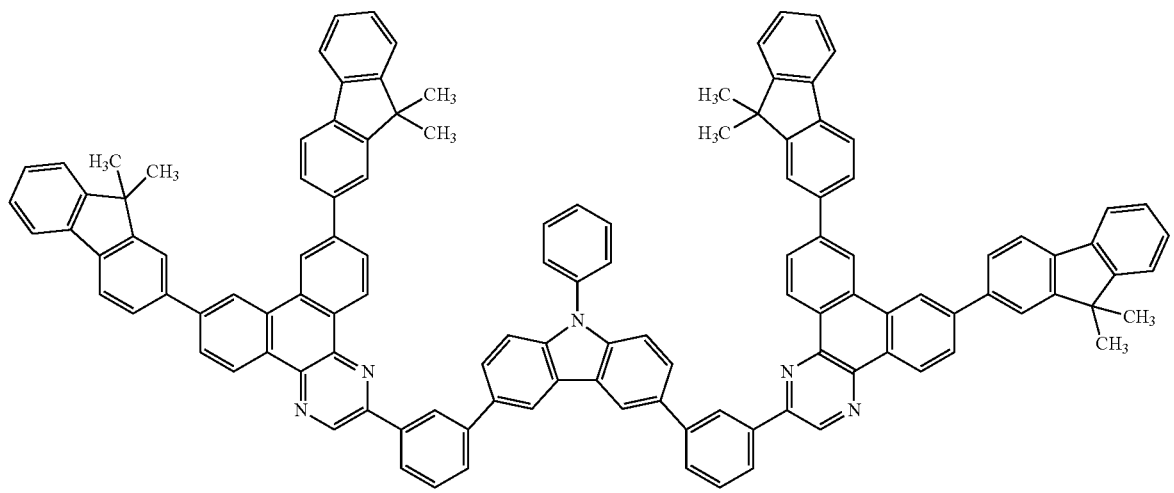
(167)
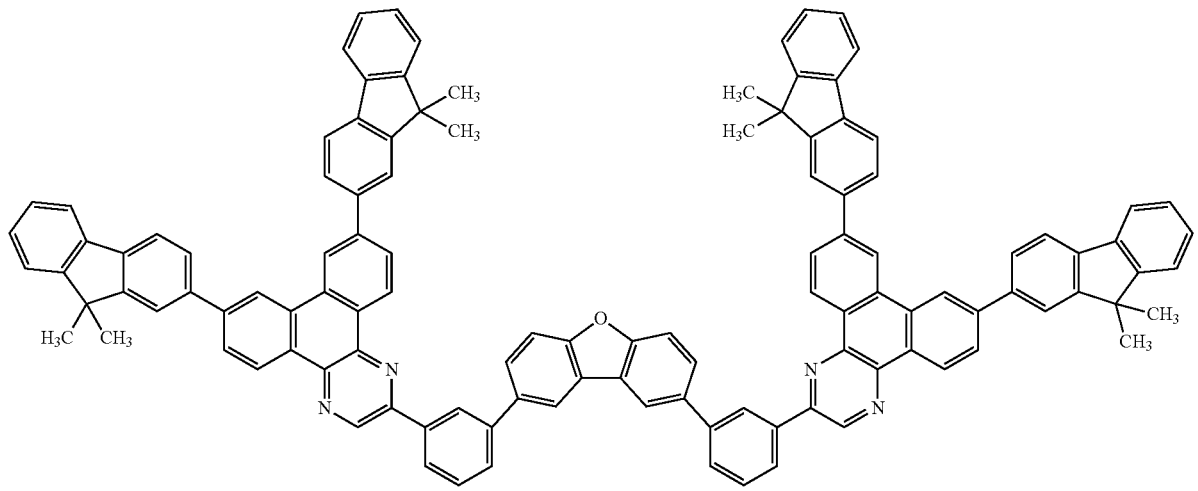
(168)
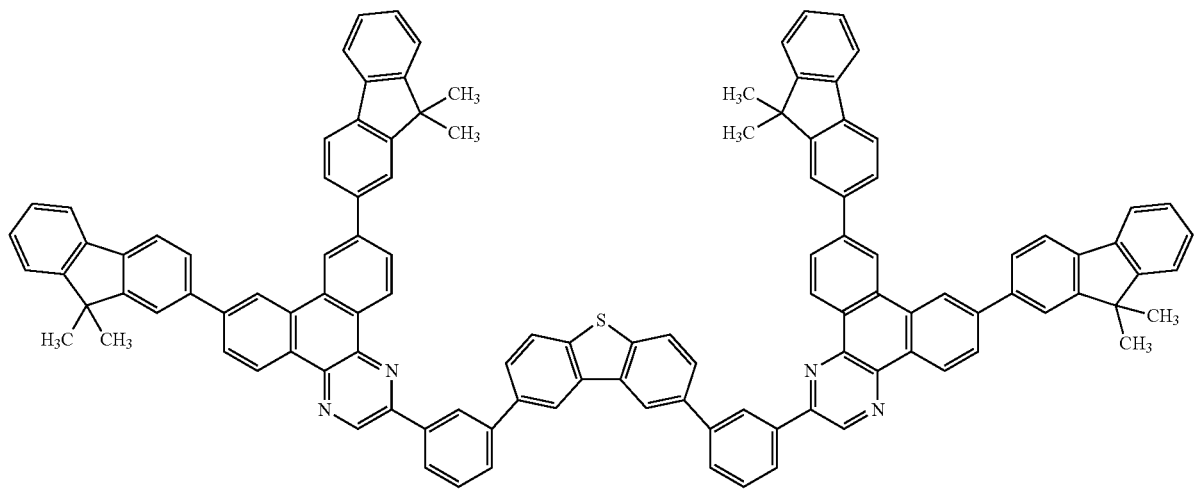

-continued
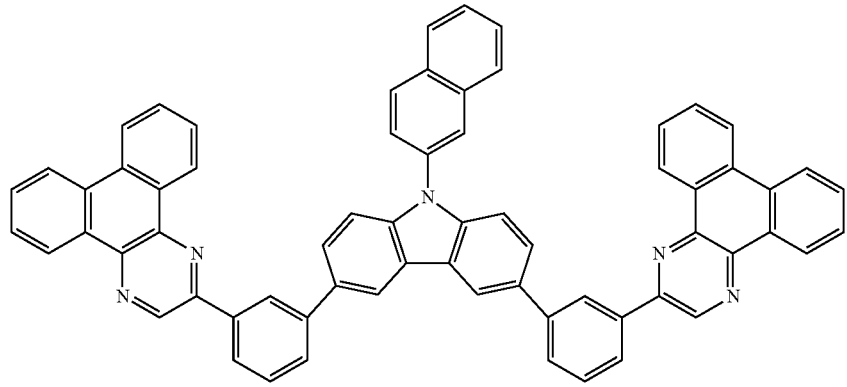
(169)
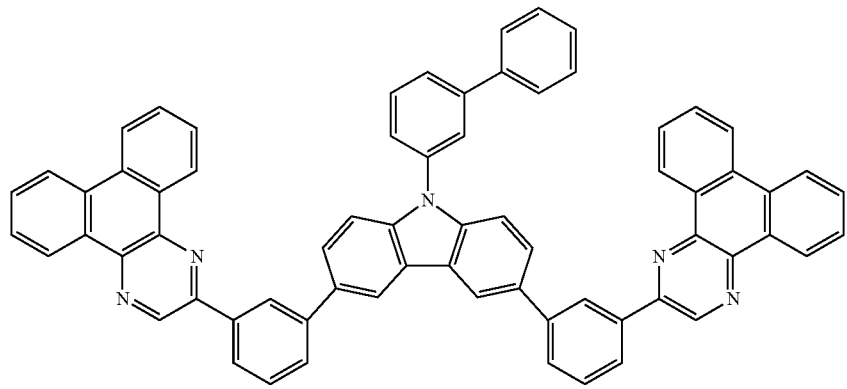
(170)
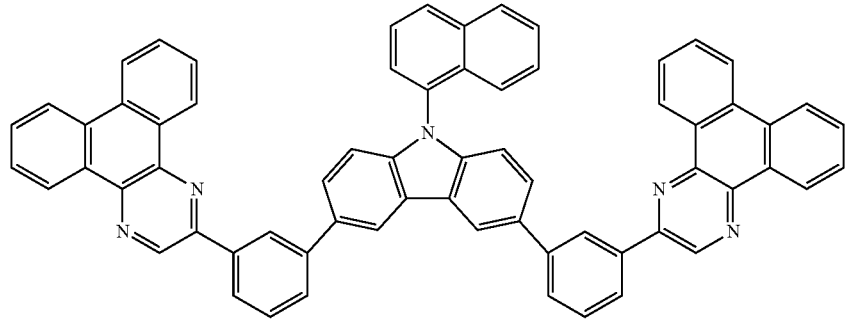
(171)
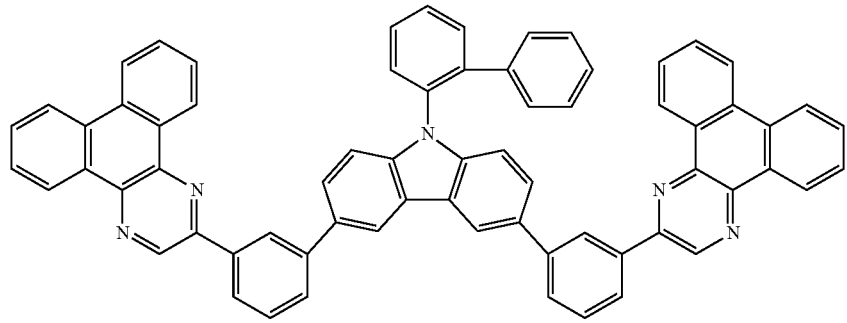
(172)

-continued
(173)
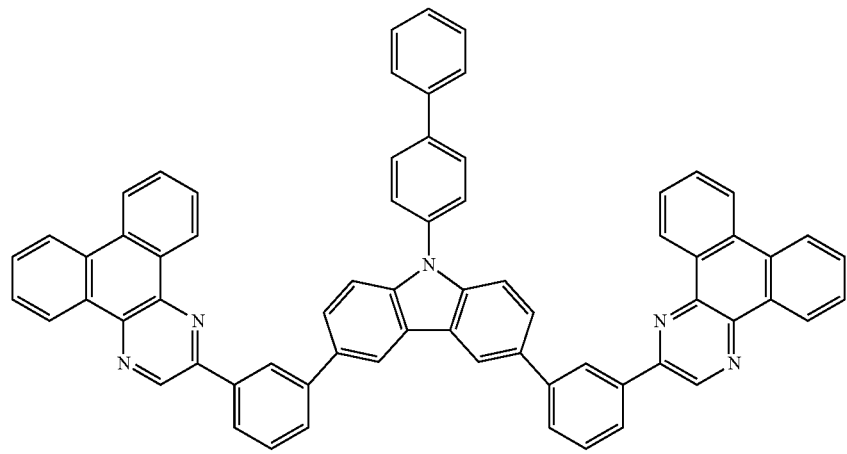
(174)
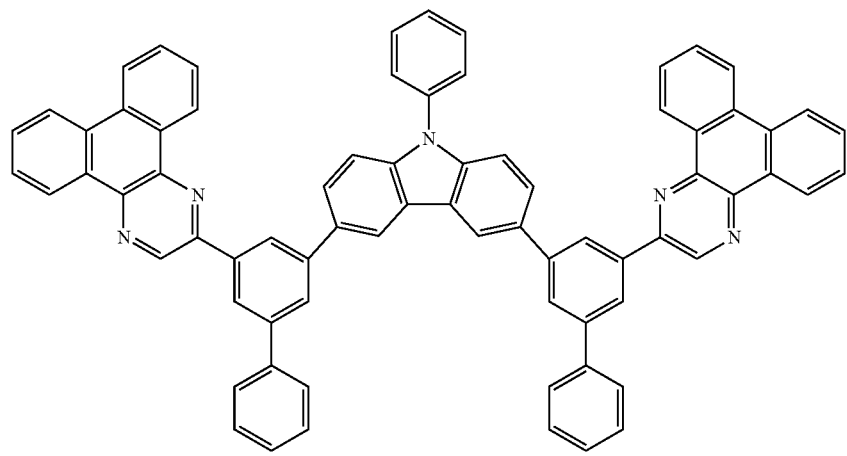
(175)
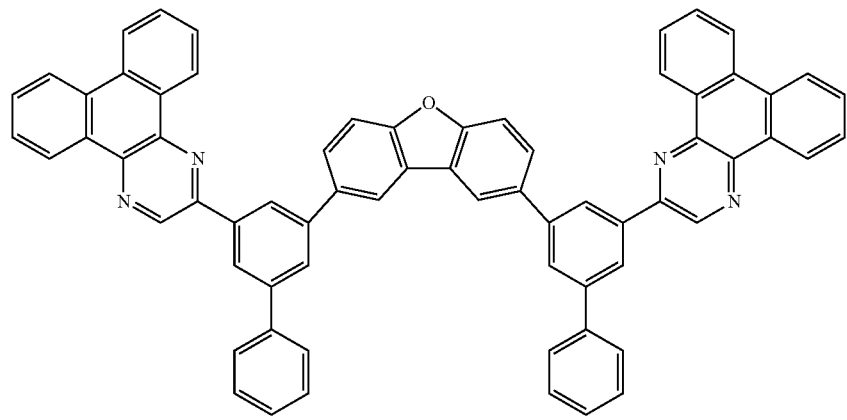
(176)
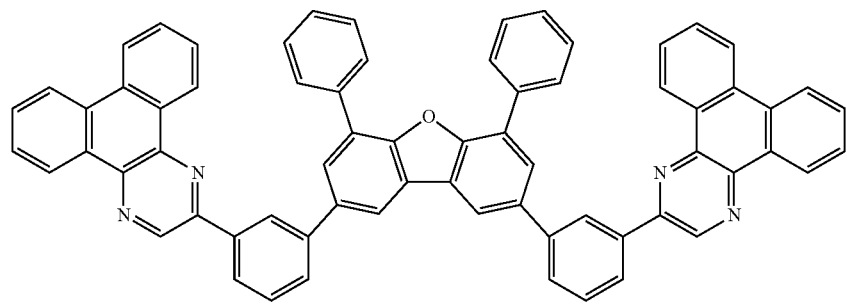

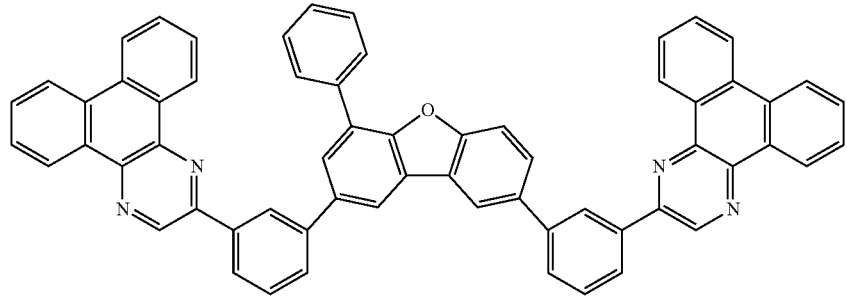
(177)
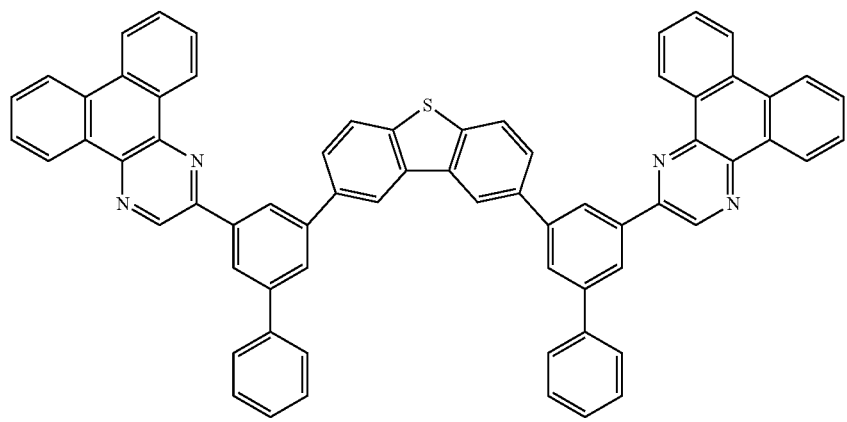
(178)
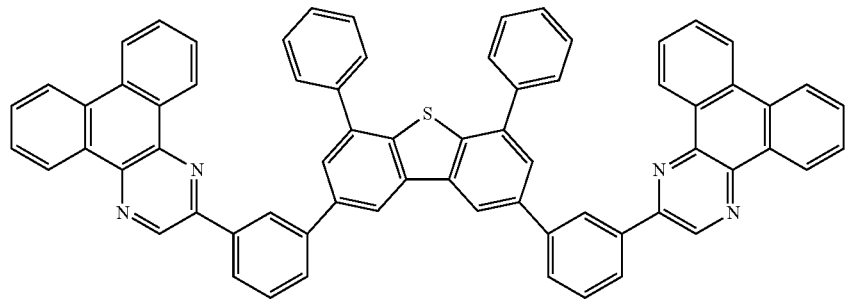
(179)
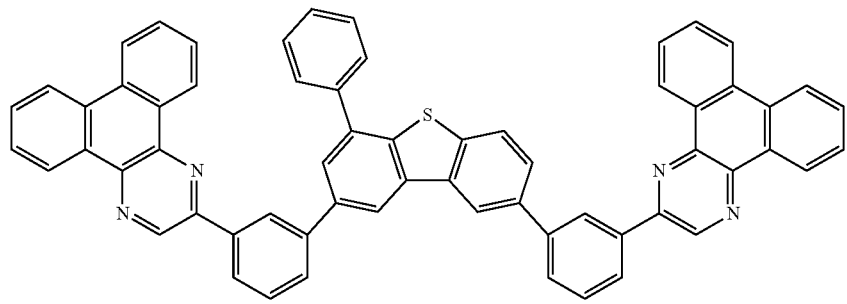
(180)

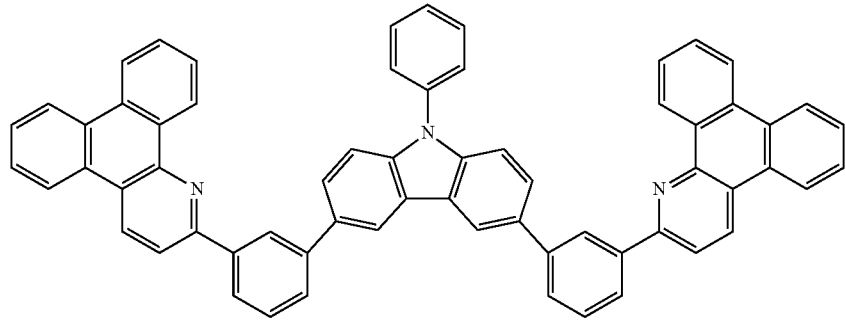
(181)
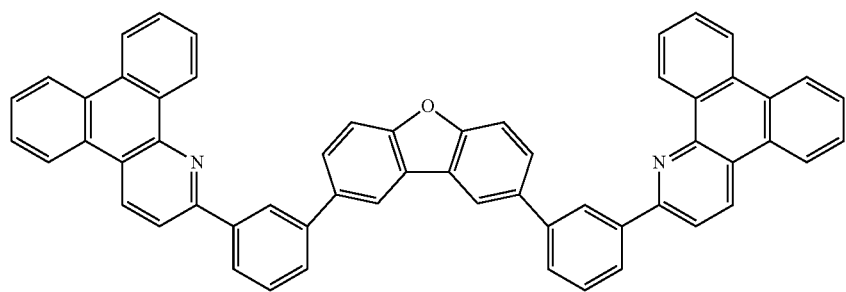
(182)
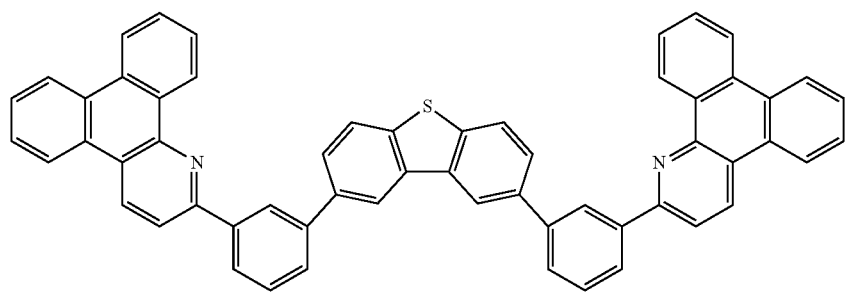
(183)
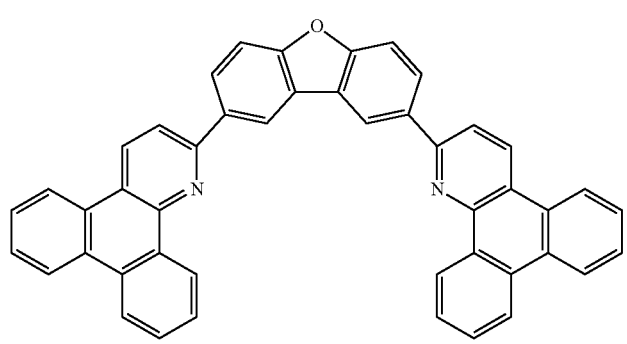
(184)

-continued
(185)
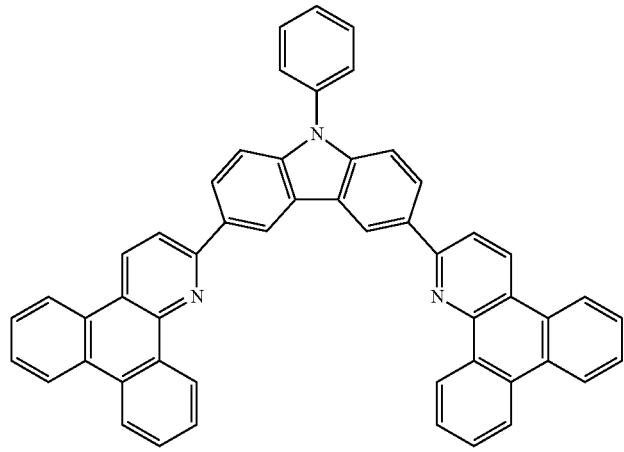
(186)
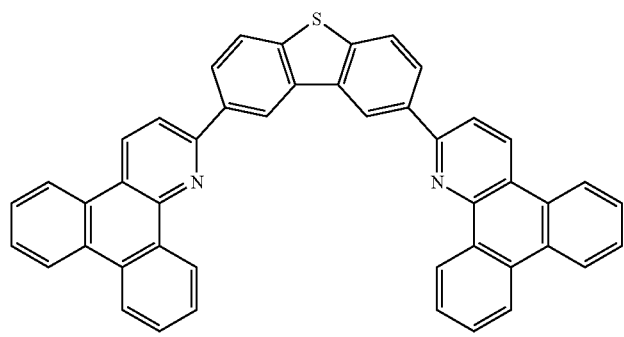
(187)
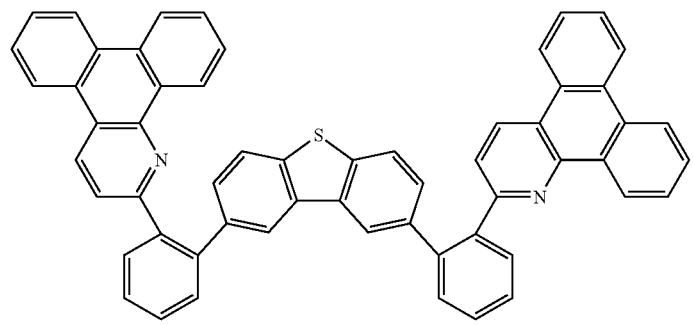
(188)
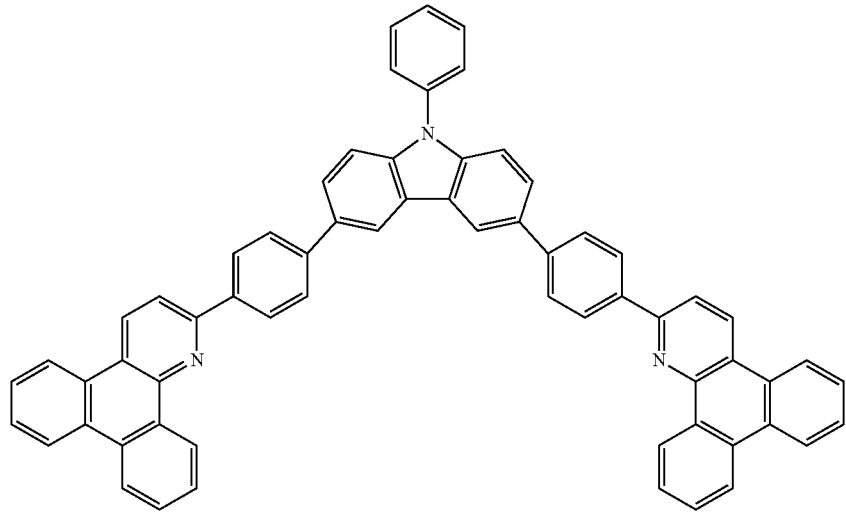

-continued

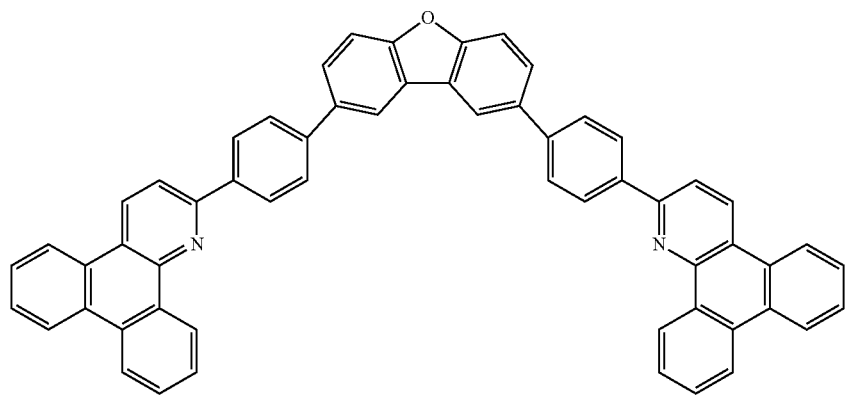
(189)

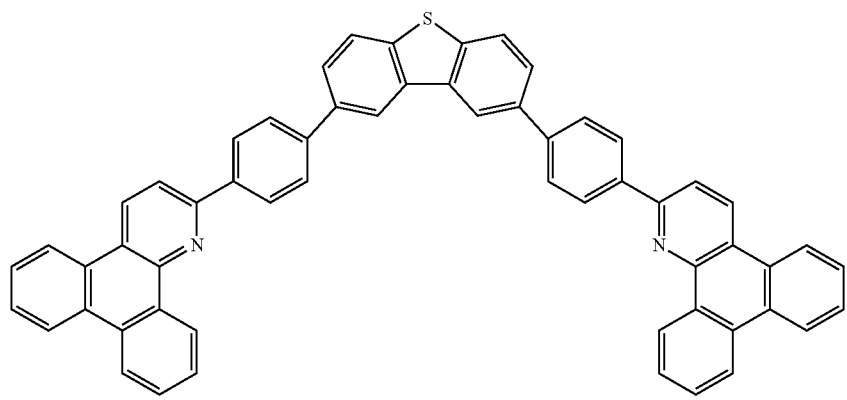
(190)

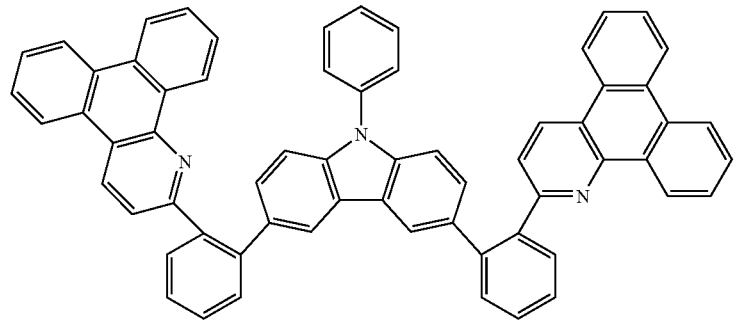
(191)

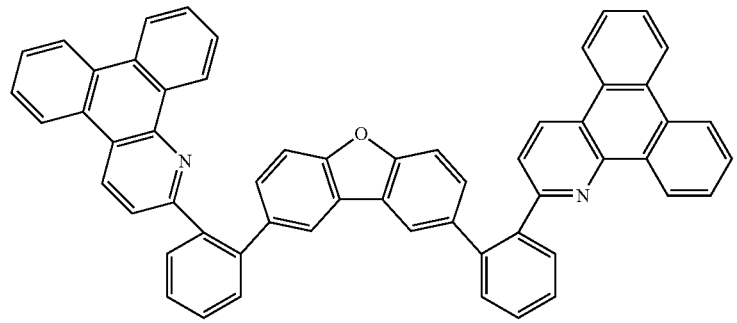
(192)

Next, an example of a method of synthesizing the organic compound represented by the General Formula (G1) will be described. A variety of reactions can be applied, and they can be synthesized through synthesis reactions described below, for example. Note that the synthetic method is not limited to the following reaction.

<<Method of Synthesizing Organic Compound Represented by General Formula (G1)>>

The organic compound represented by General Formula (G1) can be synthesized as shown in Synthesis Scheme (a-1) shown below. By the coupling of Compound 1 (a dibenzo[f,h]quinoxaline compound or a dibenzo[f,h]quinoline compound), Compound 2 (a dibenzo[f,h]quinoxaline compound or a dibenzo[f,h]quinoline compound), and Compound 3 (a dibenzofuran compound, a dibenzothiophene compound, or a 9H-carbazole compound), an organic compound represented by General Formula (G1) can be obtained.

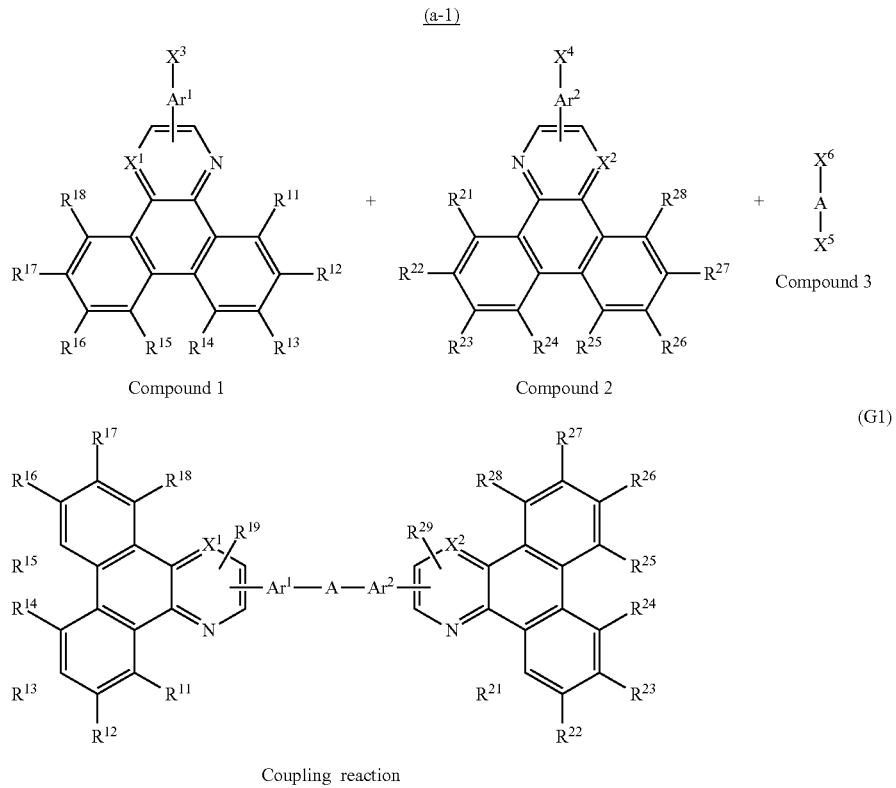

In Synthesis Scheme (a-1), A represents a substituted or unsubstituted dibenzofuran-diyl group, a substituted or unsubstituted dibenzothiophene-diyl group, a substituted or unsubstituted N-aryl-9H-carbazole-diyl group, or a substituted or unsubstituted N-alkyl-9H-carbazole-diyl group; $Ar^1$ and $Ar^2$ each independently represent a single-bond or a substituted or unsubstituted arylene group; $R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; $X^1$ and $X^2$ each independently represent a carbon atom or a nitrogen atom; the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms; and $X^3$ to $X^6$ each independently represent halogen, a boronic acid, a boronic ester, or a triflate group, and the halogen is preferably iodine, bromine, or chlorine.

In Synthesis Scheme (a-1), when the Suzuki-Miyaura coupling using a palladium catalyst is performed, it is preferable that $X^3$ and $X^4$ each independently represent halogen, a boronic acid, a boronic ester, or a triflate group. The halogen is preferred to be iodine, bromine, or chlorine. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butyl-phosphine, 2-dicyclohexylphosphino-2',6'-dimethoxybiphenyl, or tri(ortho-tolyl)phosphine can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, ethanol, methanol, water, or the like can be used as a solvent. Note that reagents that can be used in the reaction are not limited thereto.

The reaction performed in Synthesis Scheme (a-1) is not limited to the Suzuki-Miyaura coupling reaction. For example, the Migita-Kosugi-Stille coupling using an organotin compound, the Kumada-Tamao-Corriu coupling using the Grignard reagent, the Negishi coupling using an organozinc compound, or a reaction using copper or a copper compound can be employed.

The method of synthesizing the organic compound represented by General Formula (G1) is not limited to Synthesis Scheme (a-1).

Through the above-described steps, the organic compound of this embodiment can be synthesized.

Since the organic compound of one embodiment of the present invention has a high $S_1$ level, a high $T_1$ level, and a wide energy gap (Eg) between the HOMO level and the LUMO level, high current efficiency can be obtained by using the organic compound in a light-emitting element as a host material of a light-emitting layer, in which a light-emitting substance is dispersed. In particular, the organic compound of one embodiment of the present invention is suitably used as a host material in which a phosphorescent compound is dispersed. Further, since the organic compound of one embodiment of the present invention is a substance having a high electron-transport property, it can be suitably used as a material for an electron-transport layer in a light-emitting element. By using the organic compound of one embodiment of the present invention, a light-emitting element with low driving voltage and high current efficiency can be obtained. Furthermore, by using this light-emitting element, a light-emitting device, an electronic device, and a lighting device each having reduced power consumption can be obtained.

Embodiment 2

In this embodiment, a light-emitting element in which an organic compound of one embodiment of the present invention is used for a light-emitting layer will be described with reference to FIGS. 1A to 1C.

In the light-emitting element of this embodiment, the EL layer having at least a light-emitting layer is interposed between a pair of electrodes. The EL layer may also have a plurality of layers in addition to the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. In this specification, the layer containing a substance having a high carrier-injection or a high carrier-transport property is also called functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 is provided between a pair of electrodes, a first electrode 101 and a second electrode 103, which is located over a substrate 100. The EL layer 102 includes a hole-injection layer 111, a hole-transport layer 112, the light-emitting layer 113, an electron-transport layer 114, and an electron-injection layer 115. Note that, in the light-emitting element described in this embodiment, the first electrode 101 functions as an anode and the second electrode 103 functions as a cathode.

A substrate 100 is used as a support of the light-emitting element. For example, glass, quartz, plastic, or the like can be used for the substrate 100. A flexible substrate may be used. The flexible substrate is a substrate that can be bent, such as a plastic substrate made of, for example, a polycarbonate, a polyarylate, or a poly(ether sulfone). Alternatively, a film (made of polypropylene, a polyester, poly(vinyl fluoride), poly(vinyl chloride), or the like), a film on which an inorganic substance is deposited by evaporation, or the like can be used. Note that a different substrate can be used as long as it can function as a support in a process of manufacturing the light-emitting element.

For the first electrode 101 and the second electrode 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide, indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, examples of which are an alkali metal such as lithium (Li) or cesium (Cs) and an alkaline earth metal such as calcium (Ca), or strontium (Sr), an alloy containing such an element, a rare earth metal such as europium (Eu) or ytterbium (Yb), an alloy containing such an element, magnesium (Mg), graphene, and the like can be used. The first electrode 101 and the second electrode 103 can be formed by, for example, a sputtering method, an evaporation method (including a vacuum evaporation method), or the like.

The EL layer 102 formed over the first electrode 101 includes at least the light-emitting layer 113, and part of the EL layer 102 is formed using the organic compound of one embodiment of the present invention. For the EL layer 102, a variety of substances can be used, and either a low molecular compound or a high molecular compound can be used. Note that the substance used for forming the EL layer 102 may have not only a structure formed of only an organic compound but also a structure in which an inorganic compound is partially contained.

As a substance with a high hole-transport property that is used for the hole-injection layer 111 and the hole-transport layer 112, a π-electron rich heteroaromatic compound (e.g., a carbazole derivative or an indole derivative) or an aromatic amine compound can be used. For example, the following substances can be used: a compound having an aromatic amine skeleton such as 4,4'-bis[N-(1-naphthyl)-N-phenylamino]biphenyl (abbreviation: NPB), N,N-bis(3-methylphenyl)-N,N'-diphenyl-[1',1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II).

In the above-mentioned substances, a compound having a carbazole skeleton is preferable because the compound is highly reliable and has a high hole-transport property to contribute to a reduction in drive voltage.

Furthermore, as a material that can be used for the hole-injection layer 111 and the hole-transport layer 112, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N-bis(4-butylphenyl)-N,N-bis(phenyl)benzidine] (abbreviation: Poly-TPD) can be used.

A layer in which any of the substances with a high hole-transport property given above and a substance with an acceptor property are mixed is preferably used as the hole-injection layer 111 and the hole-transport layer 112, in which case a favorable carrier-injection property is obtained. Examples of the acceptor substance to be used include a transition metal oxide and an oxide of a metal belonging to any of Groups 4 to 8 of the periodic table. Specifically, molybdenum oxide is particularly preferable.

The light-emitting layer 113 preferably contains, for example, an electron-transport material as a host material (a first organic compound), a fluorescent compound as a guest material (a second organic compound), and a hole-transport material as an assist material (a third organic compound). Note that a relation regarding the carrier-transport property between the host material and the assist material is not limited to the above; an electron-transport material may be used as the assist material and a hole-transport material may be used as the host material.

The organic compound of one embodiment of the present invention described in Embodiment 1 can be used as a host material in the light-emitting layer 113.

Note that the organic compounds of one embodiment of the present invention have a high $T_1$ level and thus also have a high $S_1$ level. Thus, they can also be used as a host material for a fluorescence compound.

As examples of the guest material, a phosphorescent compound and a thermally activated delayed fluorescent (TADF) material can be given.

As the phosphorescent compound, for example, a phosphorescent compound having an emission peak between 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris{2-[5-(2-methylphenyl)-4-(2,6-diisopropylphenyl)-4H-1,2,4-triazol-3-yl-κN2]phenyl-κC}iridium(III) (abbreviation: Ir(mpptz-diPrp)$_3$), tris(5-methyl-3,4-diphenyl-4H-1,2,4-triazolato)iridium(III) (abbreviation: [Ir(Mptz)$_3$], and tris[4-(3-biphenyl)-5-isopropyl-3-phenyl-4H-1,2,4-triazolato]iridium(III) (abbreviation: Ir(iPrptz-3b)$_3$); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: Ir(Prptz1-Me)$_3$); organometallic iridium complexes having imidazole skeletons, such as fac-tris[1-(2,6-diisopropylphenyl)-2-phenyl-1H-imidazole]iridium(III) (abbreviation: Ir(iPrPim)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: FIr(acac)). Among the materials given above, the organometallic iridium complex having a 4H-triazole skeleton has high reliability and high emission efficiency and is thus especially preferable.

Examples of the phosphorescent compound having an emission peak between 520 nm to 600 nm include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium(III) (endo- and exo-mixture) (abbreviation: Ir(nbppm)$_2$(acac)), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$], and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). Among the materials given above, the organometallic iridium complex having a pyrimidine skeleton has distinctively high reliability and emission efficiency and is thus especially preferable.

Examples of the phosphorescent compound having an emission peak between 600 nm to 700 nm include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato] (dipivaloylmethanato)iridium(III) (abbreviation: [Ir(5mdppm)$_2$(dpm)]), and bis[4,6-di(naphthalen-1-yl)pyrimidinato] (dipivaloylmethanato)iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato) (dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(2,6-dimethylphenyl)-3-(3,5-dimethylphenyl)-2-pyrazinyl-kN]phenyl-kC}(2,4-pentanedionato-k$^2$O,O')iridium(III) (abbreviation: [Ir(dmdppr-dmp)$_2$(acac)]), bis{4,6-dimethyl-2-[5-(2,6-dimethylphenyl)-3-(3,5-dimethylphenyl)-2-pyrazinyl-κN]phenyl-κC}(2,8-dimethyl-4,6-nonanedionato-κ$^2$O,O')iridium(III) (abbreviation: [Ir(dmdppr-dmp)$_2$(divm)]), and (acetylacetonato)bis[2,3-bis(4-fluorophenyl)quinoxalinato] iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$) iridium(III) acetylacetonate (abbreviation: [Ir(piq)$_2$(acac)]); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the materials given above, the organometallic iridium complex having a pyrimidine skeleton has distinctively high reliability and emission efficiency and is thus especially preferable. Further, the organometallic iridium complex having a pyrazine skeleton can provide red light emission with excellent chromaticity.

As the assist material, a substance with a high hole-transport property which can be used for the hole-injection layer 111 and the hole-transport layer 112 may be used.

Specifically, a compound having a carbazole skeleton is preferably used as the assist material because the compound is highly reliable and has a high hole-transport property to contribute to a reduction in drive voltage.

It is preferable that each of the host material and the assist material do not have an absorption in a wavelength range of blue light. Specifically, an absorption cutoff is preferably at 440 nm or less.

The electron-transport layer 114 is a layer containing a substance with a high electron-transport property. The organic compound of one embodiment of the present invention can be used for the electron-transport layer 114 due to its high electron-transport property. In addition to the organic compound of one embodiment of the present invention, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-benzoxazolyl)phenolato]zinc (abbreviation: Zn(BOX)$_2$), or bis[2-(2-hydroxyphenyl)benzothiazolato]zinc (abbreviation: Zn(BTZ)$_2$) can be used for the electron-transport layer 114. Furthermore, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4''-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6-diyl)] (abbreviation: PF-BPy) can be used. The substances given here are mainly ones having an electron mobility of 10$^{-6}$ cm$^2$/Vs or higher. Note that any other substance may be used for the electron-transport layer 114 as long as the substance has an electron-transport property higher than a hole-transport property.

The electron-transport layer 114 is not limited to a single layer, and may be a stack of two or more layers containing any of the above substances.

The electron-injection layer 115 is a layer containing a substance with a high electron-injection property. For the electron-injection layer 115, an alkali metal compound or an alkaline earth metal compound, such as lithium fluoride (LiF), cesium fluoride (CsF), calcium fluoride (CaF$_2$), or lithium oxide (LiO$_x$) can be used. A rare earth metal compound such as erbium fluoride (ErF$_3$) can also be used. In addition, an electride may be used for the electron-injection layer 115. As an example of electride, a substance in which electrons are added to a mixed oxide containing calcium and aluminum is given. Any of the substances for forming the electron-transport layer 114, which are given above, can also be used.

Alternatively, a composite material in which an organic compound and an electron donor are mixed may be used for the electron-injection layer 115. Such a composite material is excellent in an electron-injection property and an electron-transport property because electrons are generated in the organic compound by the electron donor. In this case, the organic compound is preferably a material excellent in a property of transporting the generated electrons. Specifically, for example, the substances for forming the electron-transport layer 114 (e.g., a metal complex and a heteroaromatic compound), which are given above, can be used. As the electron donor, a substance exhibiting an electron-donating property to the organic compound may be used. Specifically, an alkali metal, an alkaline earth metal, and a rare earth metal are preferable, and lithium, cesium, magnesium, calcium, erbium, and ytterbium are given. Further, an alkali metal oxide or an alkaline earth metal oxide is preferable and for example, lithium oxide, calcium oxide, barium oxide, and the like can be given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115, can be formed by a method such as an evaporation method (e.g., a vacuum evaporation method), an inkjet method, or a coating method.

In the above-described light-emitting element, current flows due to a potential difference applied between the first electrode 101 and the second electrode 103 and holes and electrons recombine in the EL layer 102, whereby light is emitted. Then, the emitted light is extracted outside through the first electrode 101, the second electrode 103, or both. Thus, the first electrode 101, the second electrode 103, or both are electrodes having light-transmitting properties.

A structure of a layer provided between the first electrode 101 and the second electrode 103 is not limited to the above. A structure other than the above may be employed as long as a light-emitting region in which holes and electrons recombine is provided in a portion away from the first electrode 101 and the second electrode 103 in order to prevent quenching due to proximity of the light-emitting region to a metal.

In other words, there is no particular limitation on a stack structure of the layers. A layer containing a substance with a high electron-transport property, a substance with a high hole-transport property, a substance with a high electron-injection property, a substance with a high hole-injection property, a bipolar substance (substance having a high electron-transport property and a high hole-transport property), a hole-blocking material, or the like may freely be combined with a light-emitting layer containing the organic compound of one embodiment of the present invention.

When the organic compound of one embodiment of the present invention is used in both the light-emitting layer (particularly, as a host material for the light-emitting layer) and the electron-transport layer, extremely low driving voltage can be achieved.

Next, the light-emitting elements illustrated in FIGS. 1B and 1C will be described.

Figure 1B:
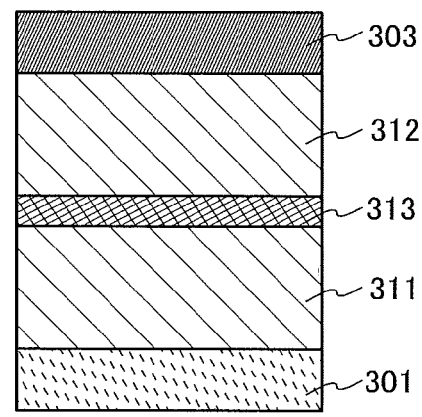

The light-emitting element illustrated in FIG. 1B is a tandem light-emitting element including a plurality of light-emitting layers (a first light-emitting layer 311 and a second light-emitting layer 312) between a first electrode 301 and a second electrode 303.

The first electrode 301 functions as an anode, and the second electrode 303 functions as a cathode. Note that the first electrode 301 and the second electrode 303 can have structures similar to those of the first electrode 101 and the second electrode 103.

The first light-emitting layer 311 and the second light-emitting layer 312 can have a structure similar to that of the light-emitting layer 113. Note that the structures of the first light-emitting layer 311 and the second light-emitting layer 312 may be the same or different from each other as long as at least one of the first light-emitting layer 311 and the second light-emitting layer 312 has a structure similar to that of the light-emitting layer 113. Further, in addition to the first light-emitting layer 311 and the second light-emitting layer 312, the hole-injection layer 111, the hole-transport layer 112, the electron-transport layer 114, and the electron-injection layer 115 which are described above may be provided as appropriate.

A charge-generation layer 313 is provided between the first light-emitting layer 311 and the second light-emitting layer 312. The charge-generation layer 313 has a function of injecting electrons into one of the light-emitting layers and injecting holes into the other of the light-emitting layers when voltage is applied between the first electrode 301 and the second electrode 303. In this embodiment, when voltage is applied such that the potential of the first electrode 301 is higher than that of the second electrode 303, the charge-generation layer 313 injects electrons into the first light-emitting layer 311 and injects holes into the second light-emitting layer 312.

Note that in terms of light extraction efficiency, the charge-generation layer 313 preferably has a light-transmitting property with respect to visible light (specifically, the charge-generation layer 313 has a visible light transmittance of 40% or more). The charge-generation layer 313 functions even if it has lower conductivity than the first electrode 301 or the second electrode 303.

The charge-generation layer 313 may have either a structure in which an electron acceptor is added to an organic compound having a high hole-transport property or a structure in which an electron donor is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(Spiro-9,9'-bifluoren-2-yl)-N-phenylamino]biphenyl (abbreviation: BSPB), or the like can be used. The substances given here are mainly ones having a hole mobility of $10^{-6}$ cm$^2$/Vs or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these metal oxides, molybdenum oxide is especially preferable since it is stable in the air, has a low hygroscopic property, and is easily handled.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$, or the like can be used. Other than metal complexes, PBD, OXD-7, TAZ, BPhen, BCP, or the like can be used. The substances given here are mainly ones having an electron mobility of $10^{-6}$ cm$^2$/Vs or higher. Note that substances other than the above substances may be used as long as they are organic compounds having an electron-transport property higher than a hole-transport property.

As the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may also be used as the electron donor.

Figure 1C:
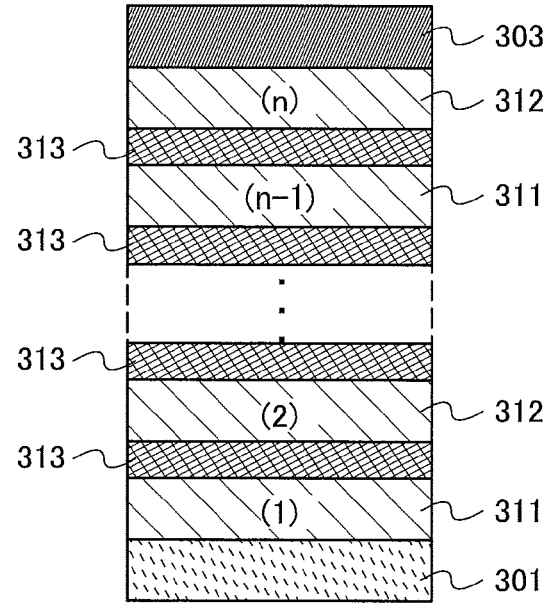

Although the light-emitting element having two light-emitting layers is illustrated in FIG. 1B, the present invention can be similarly applied to a light-emitting element in which n light-emitting layers (n is three or more) are stacked as illustrated in FIG. 1C. In the case where a plurality of light-emitting layers are provided between a pair of electrodes as in the light-emitting element of this embodiment, by providing the charge-generation layer 313 between the light-emitting layers, the light-emitting element can emit light in a high luminance region while the current density is kept low. Since the current density can be kept low, the element can have a long lifetime.

By making emission colors of the light-emitting layers different, light of a desired color can be obtained from the light-emitting element as a whole. For example, by forming a light-emitting element having two light-emitting layers such that the emission color of the first light-emitting layer and the emission color of the second light-emitting layer are complementary colors, the light-emitting element can provide white light emission as a whole. Note that "complementary colors" refer to colors which produce an achromatic color when mixed. In other words, emission of white light can be obtained by mixture of light emitted from substances whose emission colors are complementary colors.

Further, the same can be applied to a light-emitting element having three light-emitting layers. For example, the light-emitting element as a whole can provide white light emission when the emission color of the first light-emitting layer is red, the emission color of the second light-emitting layer is green, and the emission color of the third light-emitting layer is blue.

As described above, the organic compound of one embodiment of the present invention is used in the light-emitting layer of the light-emitting element of this embodiment. Since the organic compound of one embodiment of the present invention has a wide energy gap, high current efficiency can be obtained by using the organic compound in a light-emitting element as a host material of a light-emitting layer in which a light-emitting substance is dispersed. In particular, the organic compound of one embodiment of the present invention is suitably used as a host material in which a phosphorescent compound is dispersed.

Furthermore, a light-emitting element which includes the above organic compound in a light-emitting layer can be driven at low voltage. The light-emitting element can also have a long lifetime.

Note that the structure described in this embodiment can be combined as appropriate with any of the structures described in the other embodiments.

Embodiment 3

In this embodiment, a light-emitting element in which the organic compound of one embodiment of the present invention is used for a light-emitting layer will be described with reference to FIG. 2. The light-emitting element of this embodiment includes an EL layer between a pair of electrodes, and a light-emitting layer in the EL layer contains an organic compound of one embodiment of the present invention and two or more kinds of organic compounds.

Figure 2:
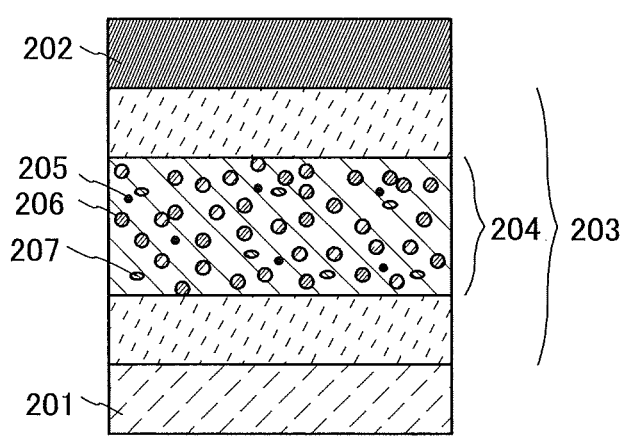
FIG. 2 illustrates a light-emitting element of one embodiment of the present invention.

A light-emitting element described in this embodiment includes an EL layer 203 between a pair of electrodes (a first electrode 201 and a second electrode 202) as illustrated in FIG. 2. The EL layer 203 includes at least a light-emitting layer 204 and may include a hole-injection layer, a hole-transport layer, an electron-transport layer, an electron-injection layer, a charge generating layer, and the like as appropriate between the first electrode 201 and the light-emitting layer 204 and between the second electrode 202 and the light-emitting layer 204. As substances for the hole-injection layer, the hole-transport layer, the electron-transport layer, the electron-injection layer, and the charge-generation layer, the substances described in Embodiment 2 can be used. Note that the first electrode 201 is used as an anode and the second electrode 202 is used as a cathode in this embodiment.

The light-emitting layer 204 described in this embodiment contains, as a first organic compound 206, the organic compound of one embodiment of the present invention described in Embodiment 1 in addition to a second organic compound 207 and a phosphorescent compound 205. The phosphorescent compound 205 is a guest material, and one of the first organic compound 206 and the second organic compound 207, the content of which is higher than that of the other in the light-emitting layer 204, is a host material. Here, a structure in which the first organic compound 206 is used as a host material is described.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

It is preferable that a $T_1$ level of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205 which contributes to light emission is quenched by the first organic compound 206 (or the second organic compound 207) and accordingly the emission efficiency is decreased.

Here, for improvement in efficiency of energy transfer from a host material to a guest material, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, an absorption band on the longest wavelength side). However, in general, it is difficult to obtain an overlap between a fluorescence spectrum of a host material and an absorption band on the longest wavelength side of a guest material so as to maximize energy transfer from a singlet excited state of a host material. The reason for this is as follows: if the fluorescence spectrum of the host material overlaps with the absorption band on the longest wavelength side of the guest material, since a phosphorescence spectrum of the host material is located on a longer wavelength side than the fluorescence spectrum, the $T_1$ level of the host material cannot be higher than the $T_1$ level of the phosphorescent compound and the above-described quenching occurs; yet, when the host material is designed in such a manner that the $T_1$ level of the host material is higher than the $T_1$ level of the phosphorescent compound to avoid the quenching, the fluorescence spectrum of the host material is shifted to the shorter wavelength side, and thus the fluorescence spectrum negligibly overlaps with the absorption band on the longest wavelength side of the guest material.

Thus, in this embodiment, a combination of the first organic compound 206 and the second organic compound 207 preferably forms an exciplex. In that case, the first organic compound 206 and the second organic compound 207 form an exciplex at the time of recombination of carriers in the light-emitting layer 204. Thus, the light-emitting layer 204 gives an emission spectrum of the exciplex on a longer wavelength side compared with those of the first organic compound 206 and that of the second organic compound 207. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex is assumed to occur instead of the energy transfer from the first organic compound 206 or the second organic compound 207.

As the phosphorescent compound 205, for example, the phosphorescent compound described in Embodiment 2 can be used. It is also possible to use the thermally activated delayed fluorescent material instead of the phosphorescent compound. As the first organic compound 206, for example, the organic compound of one embodiment of the present invention can be used. The organic compound of one embodiment of the present invention is a compound that easily accepts electrons (an electron-trapping compound). As the second organic compound 207, for example, a compound that easily accepts holes (a hole-trapping compound) can be used.

As a compound which is likely to accept holes, it is possible to use, for example, PCBA1BP, 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), 4-phenyldiphenyl-(9-phenyl-9H-carbazol-3-yl) amine (abbreviation: PCA1BP), N,N',N"-triphenyl-N,N', N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N-di(biphenyl-4-yl)-N-(9-phenyl-9H-carbazol-3-yl)amine (abbreviation: PCzBBA1), N,N'-bis[4-(carbazol-9-yl)phenyl]-N,N'-diphenyl-9,9-dimethylfluorene-2,7-diamine (abbreviation: YGA2F), TPD, 4,4'-bis[N-(4-diphenylaminophenyl)-N-phenylamino] biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), 3,6-bis[N-(9-phenylcarbazol-3-yl)-N-phenylamino]-9-phenylcarbazole (abbreviation: PCzPCA2), or the like.

The above-described first and second organic compounds 206 and 207 are not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio (weight ratio) of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that the structure described in this embodiment can be combined as appropriate with any of the structures described in the other embodiments.

Embodiment 4

Figure 3A:
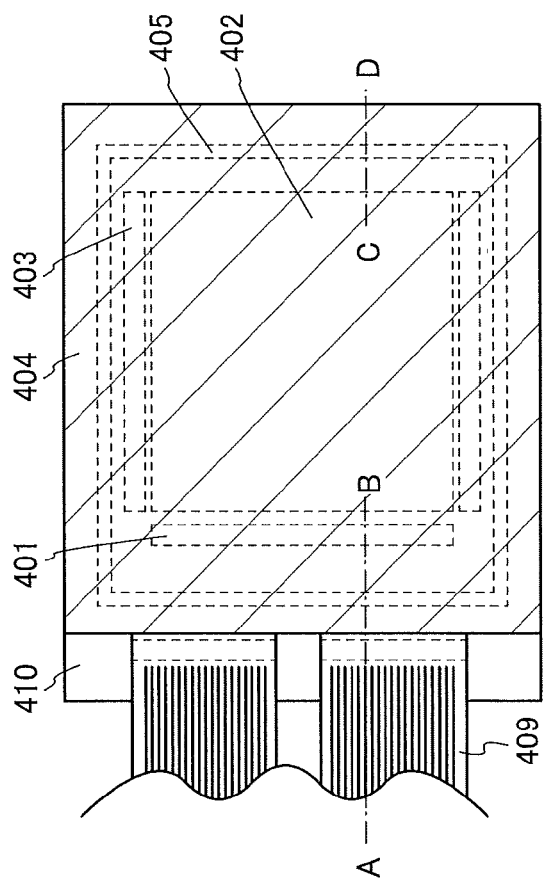
FIGS. 3A and 3B illustrate a light-emitting device of one embodiment of the present invention.
Figure 3B:
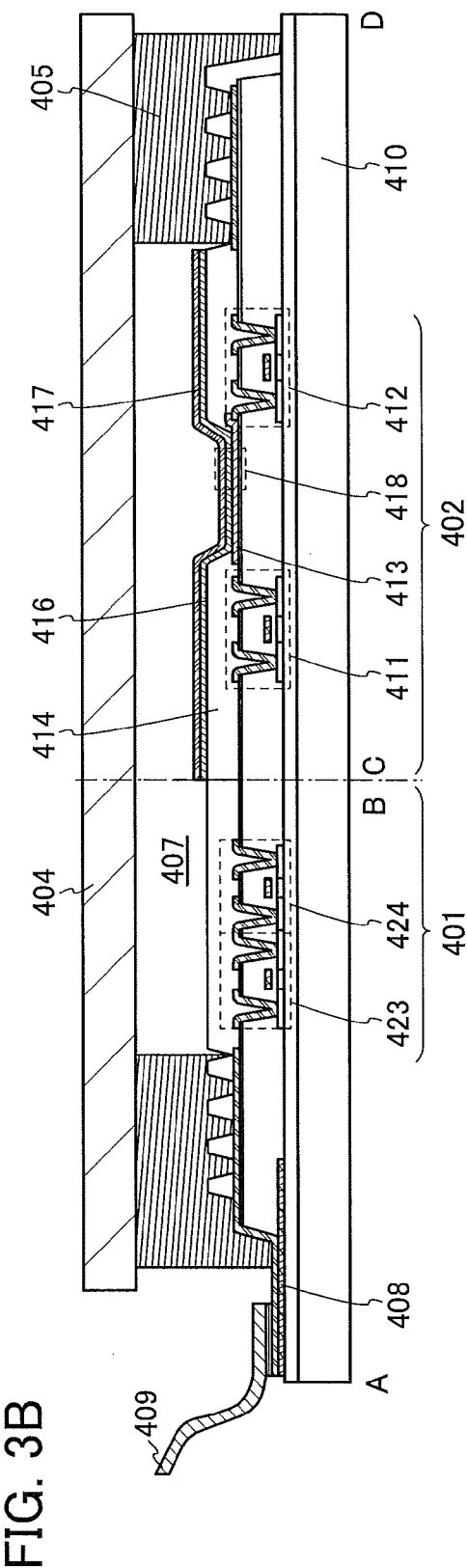

In this embodiment, a light-emitting device which includes the light-emitting element of one embodiment of the present invention will be described with reference to FIGS. 3A and 3B. FIG. 3A is a top view illustrating the light-emitting device, and FIG. 3B is a cross-sectional view taken along lines A-B and C-D of FIG. 3A.

The light-emitting device of this embodiment includes a source side driver circuit 401 and a gate side driver circuit 403 which are driver circuit portions, a pixel portion 402, a sealing substrate 404, a sealing material 405, a flexible printed circuit (FPC) 409, and an element substrate 410. A portion enclosed by the sealing material 405 is a space 407.

A lead wiring 408 is a wiring for transmitting signals that are to be input to the source side driver circuit 401 and the gate side driver circuit 403, and receives a video signal, a clock signal, a start signal, a reset signal, and the like from the FPC 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

The driver circuit portion and the pixel portion are formed over an element substrate 410 illustrated in FIG. 3A. In FIG. 3B, the source side driver circuit 401 which is the driver circuit portion and one pixel in the pixel portion 402 are illustrated.

Note that the source side driver circuit 401 includes an FET 423 and an FET 424. The source side driver circuit 401 that includes the FET 423 and the FET 424 may be formed with a circuit including transistors having the same conductivity type (either an n-channel transistor or a p-channel transistor) or a CMOS circuit including an n-channel transistor and a p-channel transistor. Although a driver-integration type in which the driver circuit is formed over a substrate is described in this embodiment, one embodiment of the present invention is not limited to this type, and the driver circuit can be formed outside the substrate.

The pixel portion 402 is formed of a plurality of pixels each of which includes a switching FET 411, a current control FET 412, and a first electrode 413 electrically connected to a wiring (a source electrode or a drain electrode) of the current control FET 412. In this embodiment, the pixel portion 402 includes two FETs, the switching FET 411 and the current control FET 412, but one embodiment of the present invention is not limited thereto. The pixel portion 402 may include, for example, three or more FETs and a capacitor in combination.

As the FETs 411, 412, 423, and 424, for example, a staggered transistor or an inverted staggered transistor can be used. Examples of a semiconductor material that can be used for the FETs 411, 412, 423, and 424 include Group IV semiconductors (e.g., silicon and gallium), compound semiconductors, oxide semiconductors, and organic semiconductors. In addition, there is no particular limitation on the crystallinity of the semiconductor material, and an amorphous semiconductor or a crystalline semiconductor can be used. In particular, an oxide semiconductor is preferably used for the FETs 411, 412, 423, and 424. Examples of the oxide semiconductor include an In—Ga oxide and an In-M-Zn oxide (M represents Al, Ga, Y, Zr, La, Ce, or Nd). For example, an oxide semiconductor that has an energy gap of 2 eV or higher, preferably 2.5 eV or higher, further preferably 3 eV or higher is used for the FETs 411, 412, 423, and 424, so that the off-state current of the transistors can be reduced.

An insulator 414 is formed to cover an end portion of the first electrode 413. Here, the insulator 414 is formed using a positive photosensitive acrylic resin. The first electrode 413 is used as an anode in this embodiment.

The insulator 414 preferably has a curved surface with curvature at an upper end portion or a lower end portion thereof. This enables the coverage with a film to be formed over the insulator 414 to be favorable. The insulator 414 can be formed using, for example, either a negative photosensitive resin or a positive photosensitive resin. The material of the insulator 414 is not limited to an organic compound, and an inorganic compound such as silicon oxide, silicon oxynitride, or silicon nitride can also be used.

An EL layer 416 and a second electrode 417 are stacked over the first electrode 413. The EL layer 416 is provided with at least a light-emitting layer. In addition to the light-emitting layer, a hole-injection layer, a hole-transport layer, an electron-transport layer, an electron-injection layer, a charge-generation layer, and the like can be provided as appropriate in the EL layer 416. Note that in this embodiment, the second electrode 417 is used as a cathode.

A light-emitting element 418 has a stacked structure of the first electrode 413, the EL layer 416, and the second electrode 417. For the first electrode 413, the EL layer 416, and the second electrode 417, the materials described in the above embodiments can be used. Although not illustrated, the second electrode 417 is electrically connected to the FPC 409 that is an external input terminal.

Although the cross-sectional view of FIG. 3B illustrates only one light-emitting element 418, a plurality of light-emitting elements are arranged in a matrix in the pixel portion 402. Light-emitting elements that emit light of three kinds of colors (R, G, and B) are selectively formed in the pixel portion 402, whereby a light-emitting device capable of full color display can be fabricated. In addition to the light-emitting elements that emit light of three kinds of colors (R, G, and B), for example, light-emitting elements that emit light of white (W), yellow (Y), magenta (M), and cyan (C) may be formed. In that case, advantages of high color purity and low power consumption can be obtained. Alternatively, a light-emitting device capable of full color display may be fabricated by a combination with color filters.

The sealing substrate 404 is attached to the element substrate 410 with the sealing material 405, so that a light-emitting element 418 is provided in the space 407 enclosed by the element substrate 410, the sealing substrate 404, and the sealing material 405. The space 407 may be filled with an inert gas (such as nitrogen or argon) or the sealing material 405.

An epoxy-based resin is preferably used as the sealing material 405. Such a material preferably allows as little moisture and oxygen as possible to pass therethrough. As a material used for the sealing substrate 404, a plastic substrate formed of fiber-reinforced plastics (FRP), poly(vinyl fluoride) (PVF), a polyester resin, an acrylic resin, or the like can be used other than a glass substrate or a quartz substrate.

As described above, the active matrix light-emitting device including the light-emitting element of one embodiment of the present invention can be obtained.

Figure 4A:
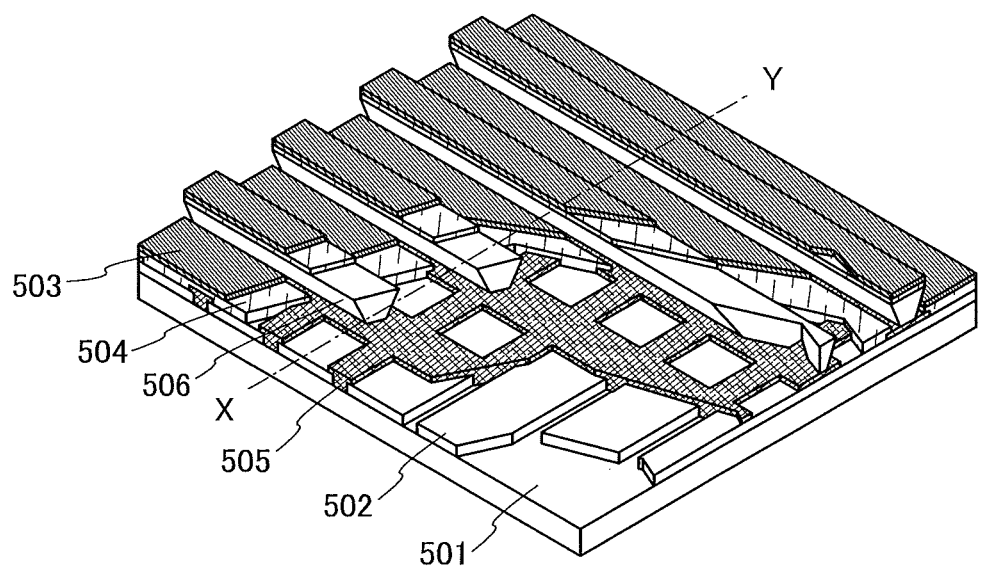
FIGS. 4A and 4B illustrate a light-emitting device of one embodiment of the present invention.
Figure 4B:
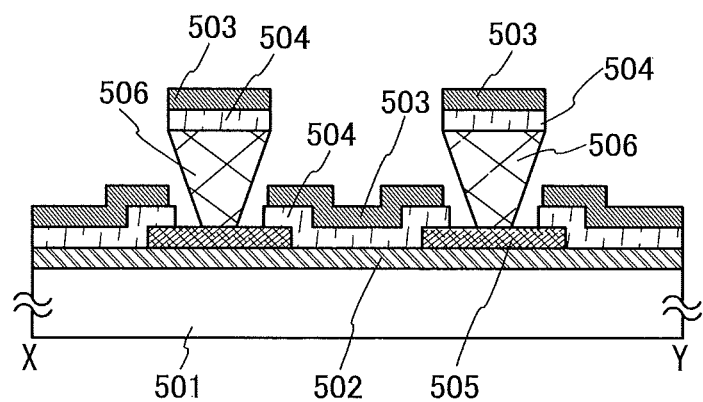

Further, a light-emitting element of one embodiment of the present invention can be used for a passive matrix light-emitting device as well as the above active matrix light-emitting device. FIGS. 4A and 4B illustrate a perspective view and a cross-sectional view of a passive matrix light-emitting device including a light-emitting element of one embodiment of the present invention. Note that the cross-sectional view of FIG. 4B is taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). With the partition layer 506 provided in such a way, a defect of a light-emitting element due to crosstalk or the like can be prevented.

Thus, the light-emitting device which includes the light-emitting element of one embodiment of the present invention can be obtained.

The light-emitting devices described in this embodiment are formed using the light-emitting element of one embodiment of the present invention, and accordingly, the light-emitting devices can have low power consumption.

Note that this embodiment can be implemented in appropriate combination with any of the other embodiments.

Embodiment 5

In this embodiment, with reference to FIGS. 5A to 5E and FIGS. 6A and 6B, examples of a variety of electronic devices and lighting devices that are each completed by the use of a light-emitting device of one embodiment of the present invention will be described.

Examples of the electronic devices are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like.

An electronic device or a lighting device that has a light-emitting portion with a curved surface can be obtained with a light-emitting element including any of the organic compounds of embodiments of the present invention, which is fabricated over a substrate having flexibility.

In addition, an electronic device or a lighting device that has a see-through light-emitting portion can be obtained with a light-emitting element including any of the organic compounds of embodiments of the present invention in which a pair of electrodes are formed using a material having a property of transmitting visible light.

Further, a light-emitting device to which one embodiment of the present invention is applied can also be applied to lighting for motor vehicles, examples of which are lighting for a dashboard, a windshield, a ceiling, and the like.

Figure 5A:
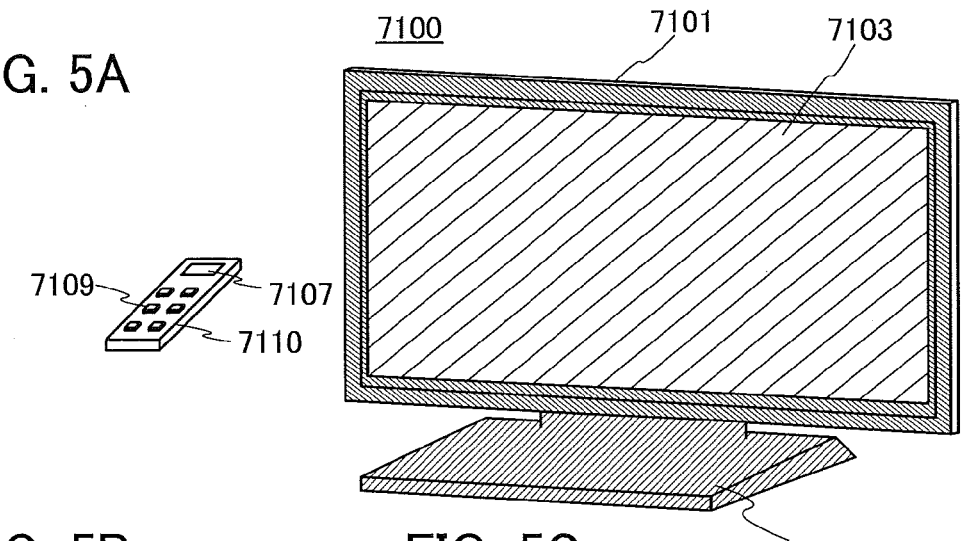
FIGS. 5A to 5E each illustrate an electronic device of one embodiment of the present invention.

In FIG. 5A, an example of a television device is illustrated. In a television device 7100, a display portion 7103 is incorporated in a housing 7101. The display portion 7103 is capable of displaying images, and the light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
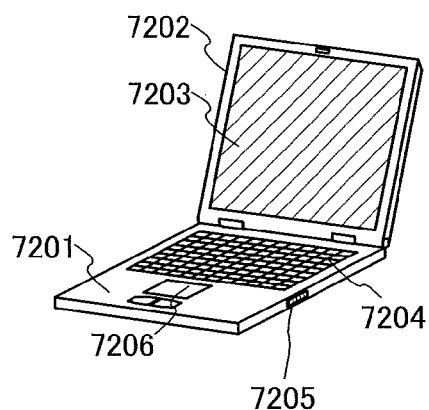

In FIG. 5B, a computer is illustrated, which includes a main body 7201, a housing 7202, a display portion 7203, a keyboard 7204, an external connection port 7205, a pointing device 7206, and the like. This computer is manufactured with the use of the light-emitting device for the display portion 7203.

Figure 5C:
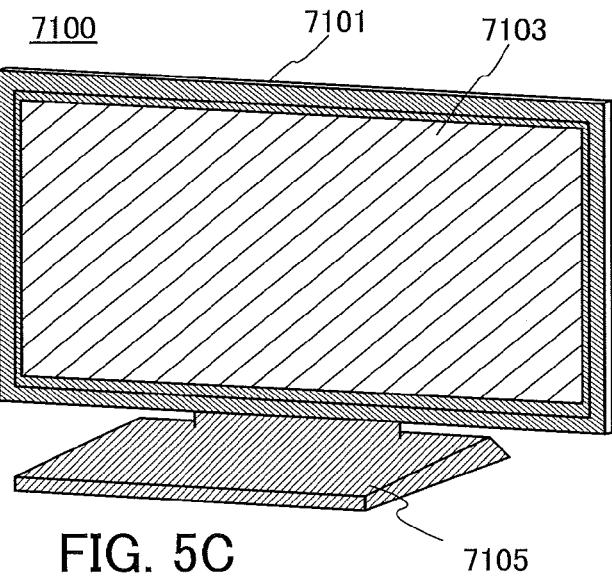

In FIG. 5C, a portable amusement machine is illustrated, which includes two housings, a housing 7301 and a housing 7302, connected with a joint portion 7303 so that the portable amusement machine can be opened or closed. A display portion 7304 is incorporated in the housing 7301 and a display portion 7305 is incorporated in the housing 7302. In addition, the portable amusement machine illustrated in FIG. 5C includes a speaker portion 7306, a recording medium insertion portion 7307, an LED lamp 7308, input means (an operation key 7309, a connection terminal 7310, a sensor 7311 (a sensor having a function of measuring or sensing force, displacement, position, speed, acceleration, angular velocity, rotational frequency, distance, light, liquid, magnetism, temperature, chemical substances, sound, time, hardness, electric field, current, voltage, electric power, radiation, flow rate, humidity, gradient, oscillation, odor, or infrared rays), and a microphone 7312), and the like. It is needless to say that the structure of the portable amusement machine is not limited to the above as long as the light-emitting device is used for at least either the display portion 7304 or the display portion 7305, or both, and may include other accessories as appropriate. The portable amusement machine illustrated in FIG. 5C has a function of reading out a program or data stored in a storage medium to display it on the display portion, and a function of sharing information with another portable amusement machine by wireless communication. Note that functions of the portable amusement machine illustrated in FIG. 5C are not limited to the above, and the portable amusement machine can have a variety of functions.

Figure 5D:
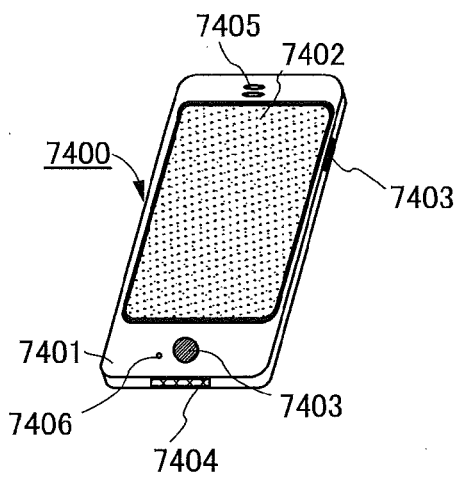

In FIG. 5D, an example of a cellular phone is illustrated. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured with the use of the light-emitting device for the display portion 7402.

When the display portion 7402 of the cellular phone 7400 illustrated in FIG. 5D is touched with a finger or the like, data can be input to the cellular phone 7400. Further, operations such as making a phone call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as a character. The third mode is a display-and-input mode in which two modes of the display mode and the input mode are mixed.

For example, in the case of making a phone call or creating e-mail, the character input mode mainly for inputting a character is selected for the display portion 7402 to input a character on a screen. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. The screen modes can also be switched depending on kinds of images displayed on the display portion 7402. For example, when a signal for an image to be displayed on the display portion is for moving images, the screen mode is switched to the display mode; when the signal is for text data, the screen mode is switched to the input mode.

Moreover, in the input mode, if an optical sensor in the display portion 7402 determines that touch on the display portion 7402 is not performed for a certain period, the screen mode may be changed from the input mode to the display mode.

The display portion 7402 may function as an image sensor. For example, an image of a palm print, a fingerprint, or the like is taken by touch on the display portion 7402 with the palm or the finger, so that personal identification can be performed. Furthermore, by provision of a backlight or a sensing light source emitting near-infrared light to the display portion, an image of a finger vein, a palm vein, or the like can also be taken.

Figure 5E:
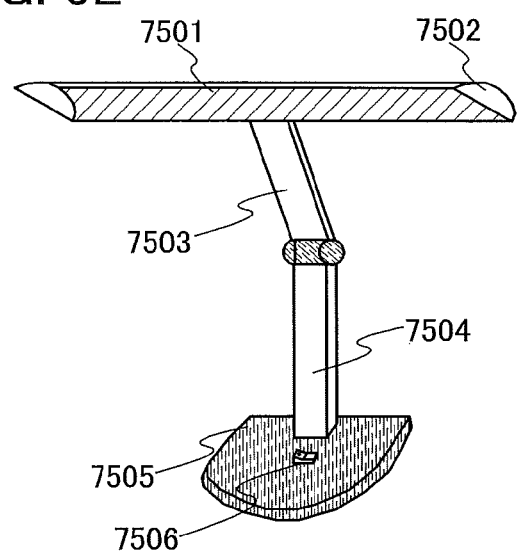

In FIG. 5E, a desk lamp is illustrated, which includes a lighting portion 7501, a shade 7502, an adjustable arm 7503, a support 7504, a base 7505, and a power switch 7506. The desk lamp is manufactured with the use of the light-emitting device for the lighting portion 7501. Note that the "lighting device" also includes ceiling lights, wall lights, and the like.

Figure 6A:
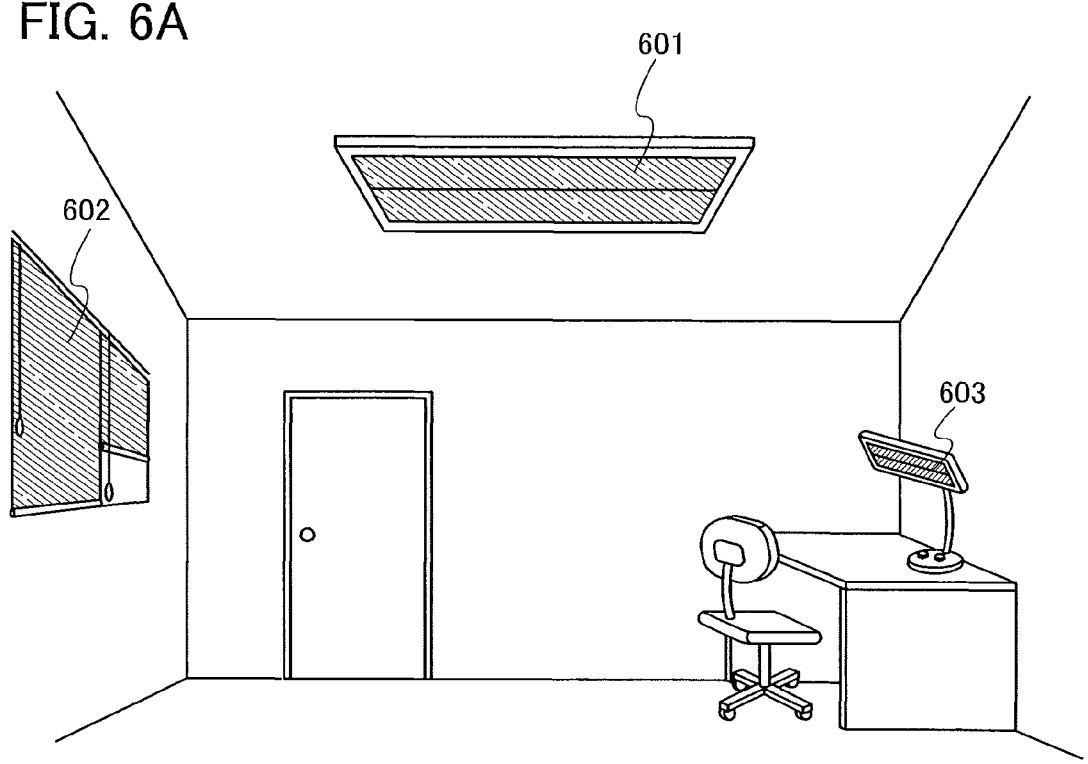
FIGS. 6A and 6B illustrate lighting devices of embodiments of the present invention.

In FIG. 6A, an example in which the light-emitting device is used for an interior lighting device 601 is illustrated. Since the light-emitting device can have a larger area, it can be used as a lighting device having a large area. Furthermore, the light-emitting device can be used as a roll-type lighting device 602. As illustrated in FIG. 6A, the desk lamp 603 described with reference to FIG. 5E may also be used in a room provided with the interior lighting device 601.

Figure 6B:
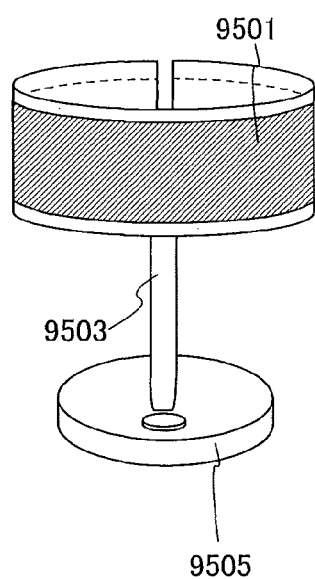

In FIG. 6B, an example of another lighting device is illustrated. A table lamp illustrated in FIG. 6B includes a lighting portion 9501, a support 9503, a support base 9505, and the like. The lighting portion 9501 includes any of the organic compounds of embodiments of the present invention. Thus, a lighting device that has a curved surface or a lighting portion that can be flexibly bent can be provided by fabrication of a light-emitting element over a substrate having flexibility. Such use of a flexible light-emitting device for a lighting device enables a place having a curved surface, such as the ceiling or dashboard of a motor vehicle, to be provided with the lighting device, as well as increases the degree of freedom in design of the lighting device.

In the above-described manner, electronic devices or lighting devices can be obtained by application of the light-emitting device. Application range of the light-emitting device is so wide that the light-emitting device can be applied to electronic devices in a variety of fields.

Note that the structure described in this embodiment can be combined with any of the structures described in the other embodiments as appropriate.

Example 1

Synthesis Example 1

In this example, a method of synthesizing 2,2'-(dibenzothiophene-2,8-diyl)di(dibenzo[f,h]quinoxaline) (abbreviation: 2,8DBq2DBt) represented by Structural Formula (105)

in Embodiment 1 will be described in detail. A structure of 2,8DBq2DBt is shown below.

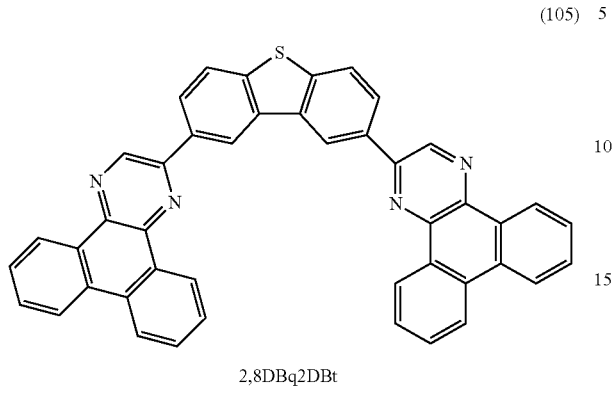

(105)

2,8DBq2DBt

A synthesis scheme of 2,8DBq2DBt is shown below.

Step 1: Synthesis of 2,2'-(dibenzothiophene-2,8-diyl)di(dibenzo[f,h]quinoxaline)

First, into a 200-mL three-neck flask were put 0.88 g (3.3 mmol) of 2-chlorodibenzo[f,h]quinoxaline, 0.80 g (1.8 mmol) of 2,2'-(2,8-dibenzothiophene-diyl)bis(4,4,5,5-tetramethyl-1,3,2-dioxaborolane), 0.10 g (0.33 mmol) of tris(2-methylphenyl)phosphine, 20 mL of toluene, 2 mL of ethanol, and 2 mL of a potassium carbonate solution (2.0 mol/L). This mixture was degassed by being stirred while the pressure in the flask was reduced. After the degassing, the atmosphere in the flask was replaced with nitrogen, and the mixture was heated to 80° C. At the same temperature, 10 mg (40 μmol) of palladium(II) acetate was added to this mixture and stirring was performed for 5 hours. This mixture was naturally cooled down to room temperature and then degassed while the pressure in the flask was reduced, and the atmosphere in the flask was replaced with nitrogen. Then, 10 mg (40 μmol) of palladium(II) acetate was added and the mixture was stirred at 80° C. for 4.5 hours. After the stirring, the resulting mixture was suction-filtered to give a residue. The residue was washed with water and ethanol, and suction-filtered to give a solid. The solid was washed with dimethylformamide, so that 0.80 g of the target brown solid was obtained in a yield of 75%. Synthesis scheme (A-1) of Step 1 is shown below.

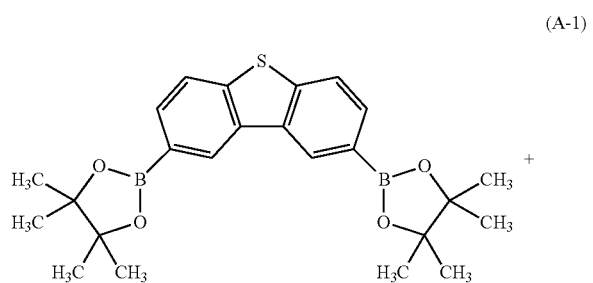

(A-1)

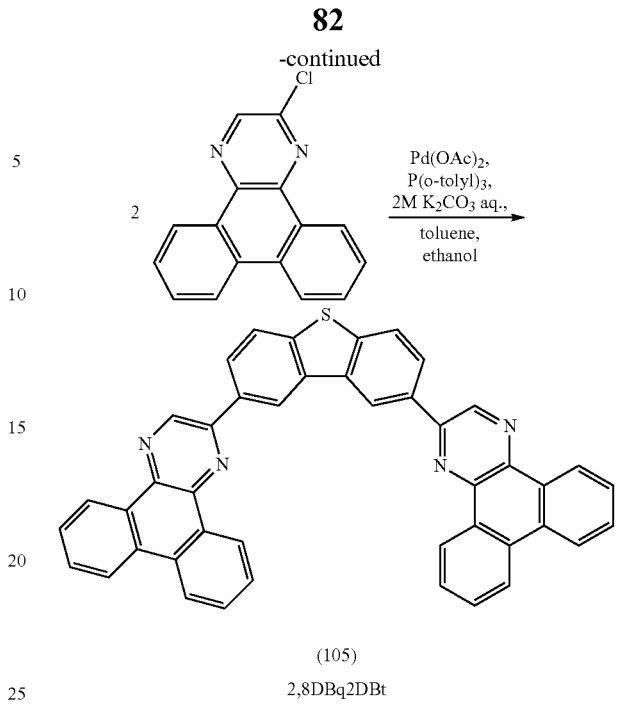

(105)

2,8DBq2DBt

Next, 0.80 g of the solid was purified by train sublimation. In the purification by sublimation, the solid was heated at 380° C. under a pressure of 2.9 Pa with a flow rate of argon of 5.0 mL/min for 1 hour. After the heating, 0.68 g of the target white powder was collected in 86%.

This compound was identified as 2,8DBq2DBt, which was the target substance, by nuclear magnetic resonance ($^1$H NMR).

$^1$H NMR data of the obtained compound is shown below.
$^1$H NMR (1,1,2,2-tetrachloroethane-$d_2$, 500 MHz): δ=7.83-7.92 (m, 8H), 8.21 (d, J=8.5 Hz, 2H), 8.59 (d, J=8.5 Hz, 2H), 8.72-8.75 (m, 4H), 9.36-9.38 (m, 4H), 9.59-9.61 (m, 2H), 9.67 (s, 2H).

Figure 7A:
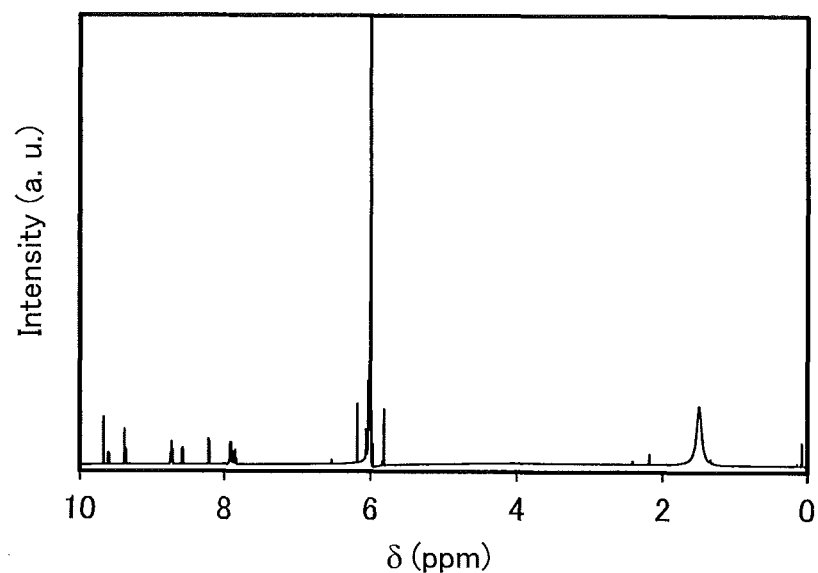
FIGS. 7A and 7B are $^1$H NMR charts of 2,8DBq2DBt.
Figure 7B:
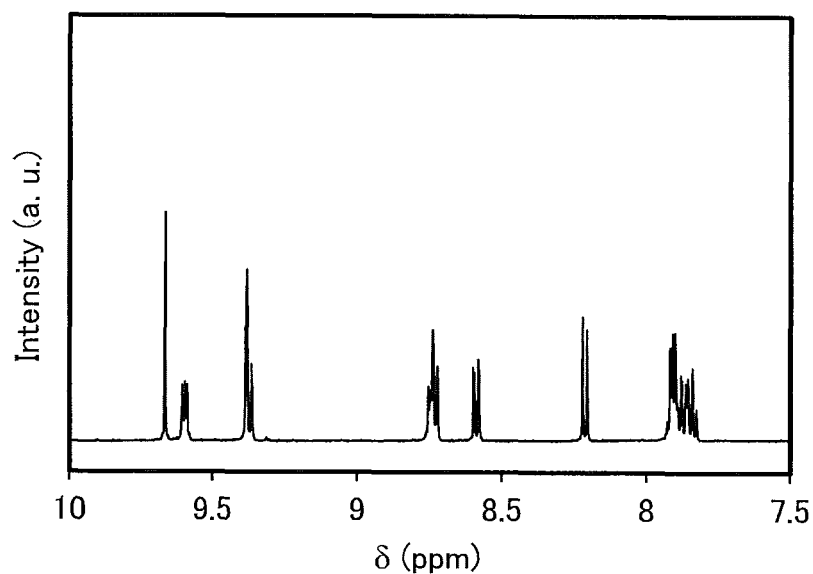

The $^1$H NMR charts are shown in FIGS. 7A and 7B. FIG. 7B is an enlarged chart showing a range of from 7.5 ppm to 10.0 ppm in FIG. 7A.

Figure 8A:
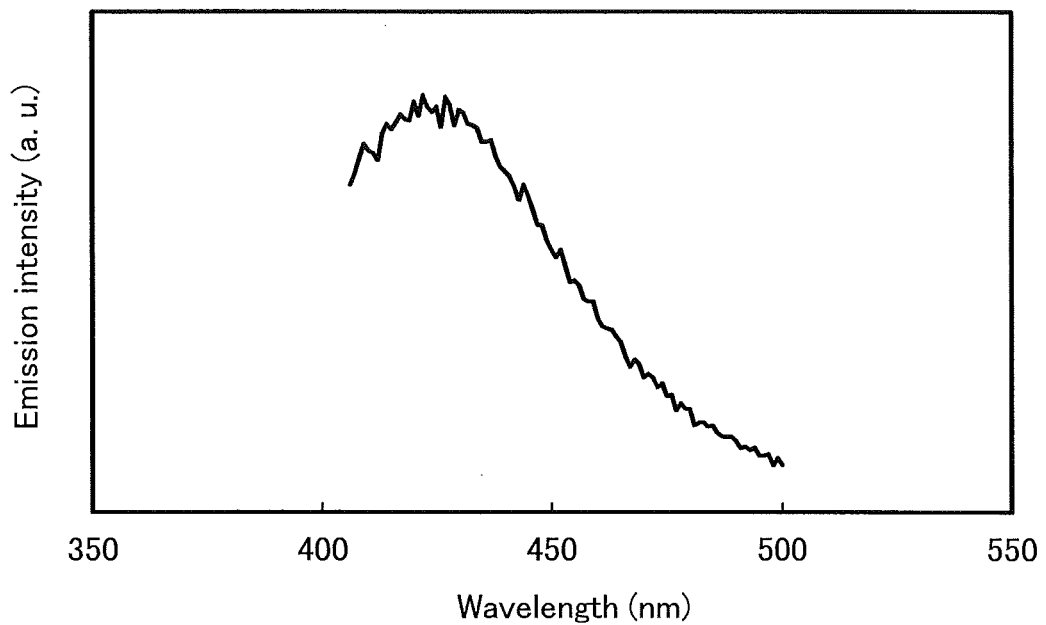
FIGS. 8A and 8B show an emission spectrum and an absorption spectrum of a dimethylformamide solution of 2,8DBq2DBt.
Figure 8B:
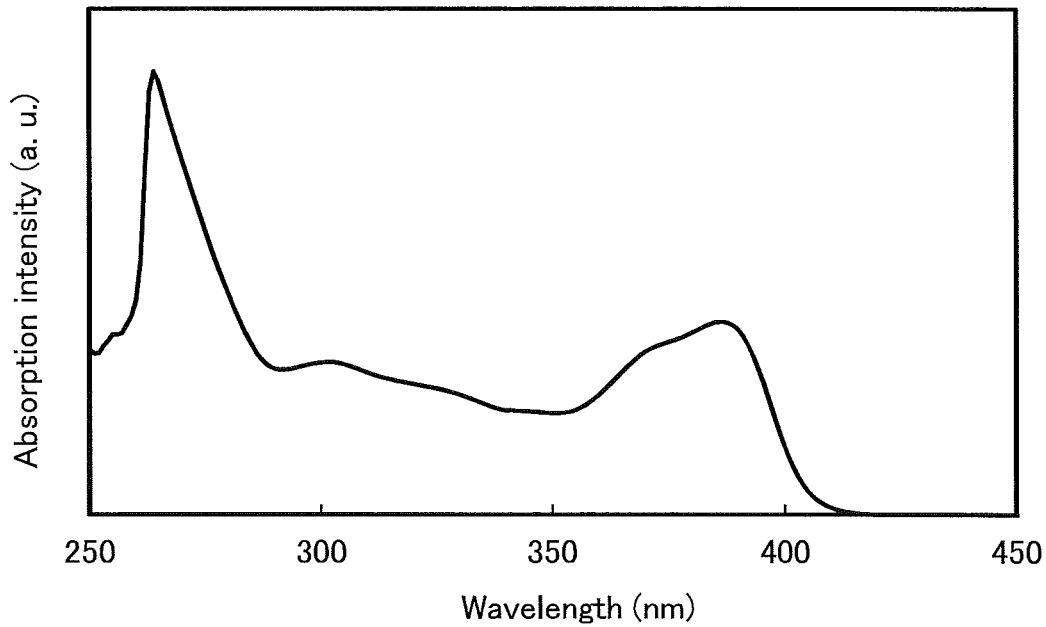
Figure 9A:
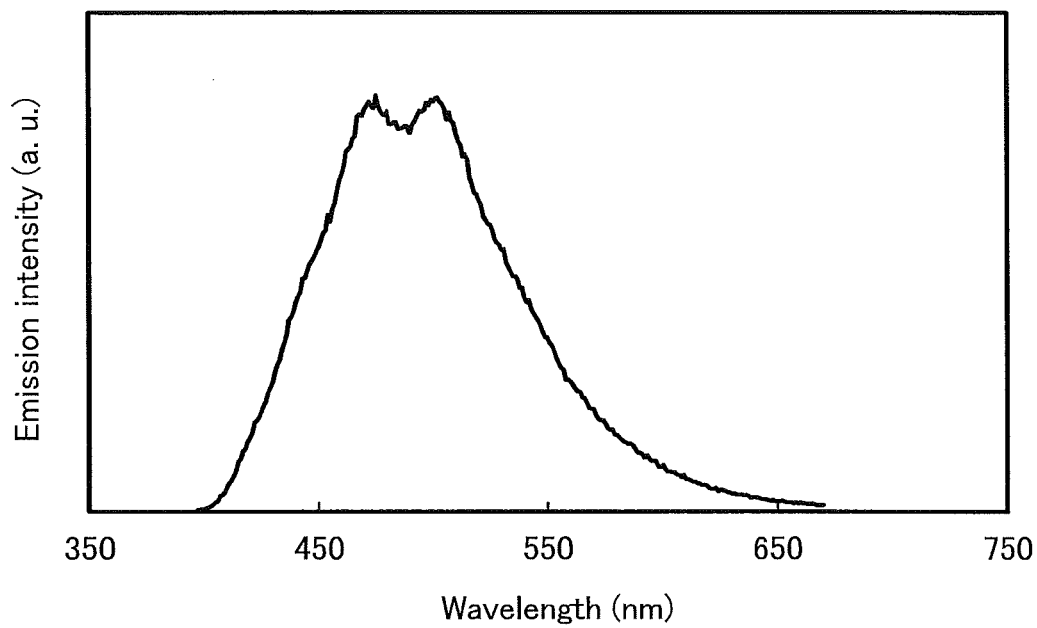
FIGS. 9A and 9B show an emission spectrum and an absorption spectrum of a thin film of 2,8DBq2DBt.
Figure 9B:
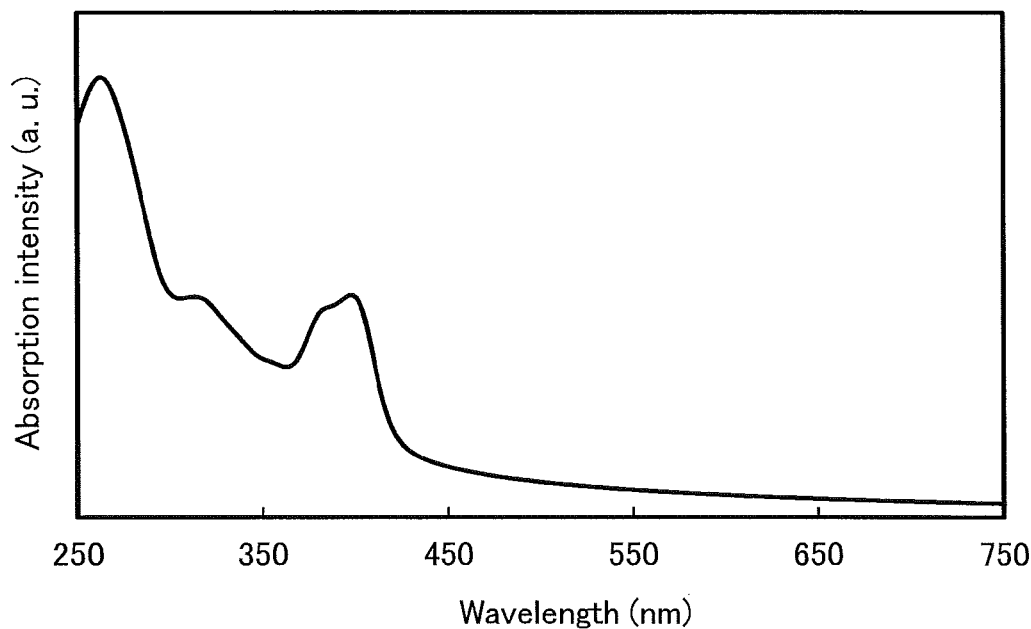

FIG. 8A shows the emission spectrum of a dimethylformamide solution of 2,8DBq2DBt, and FIG. 8B shows the absorption spectrum thereof. FIG. 9A shows the emission spectrum of a thin film of 2,8DBq2DBt, and FIG. 9B shows the absorption spectrum thereof. In each of FIG. 8A and FIG. 9A, the horizontal axis represents wavelength (nm) and the vertical axis represents emission intensity (arbitrary unit). In each of FIG. 8B and FIG. 9B, the horizontal axis represents wavelength (nm) and the vertical axis represents absorption intensity (arbitrary unit). In the case of the dimethylformamide solution, an emission peak is observed at 422 nm (excitation wavelength: 389 nm) and absorption peaks are observed at 264 nm, 370 nm, and 387 nm. In the case of the thin film, emission peaks are observed at 447 nm, 475 nm, 501 nm, and 525 nm (excitation wavelength: 381 nm) and absorption peaks are observed at 262 nm, 332 nm, 353 nm, 384 nm, and 398 nm.

The absorption spectra were measured with an ultraviolet-visible spectrophotometer (V-550, produced by JASCO Corporation). The measurement of emission spectra and absorption spectra was performed with samples prepared in such a manner that the solution was put in a quartz cell and the thin film was obtained by evaporation onto a quartz substrate. Note that the absorption spectrum of the solution was obtained by subtraction of the absorption spectra of the quartz cell and dimethylformamide from the measured spectrum, and the absorption spectrum of the thin film was obtained by subtraction of the absorption spectrum of the quartz substrate from the measured spectrum.

The thermogravimetry-differential thermal analysis of 2,8DBq2DBt prepared in Synthesis example 1 was performed. For the measurement, a high vacuum differential type differential thermal balance (TG-DTA 2410SA, produced by Bruker AXS K.K.) was used. The measurement was performed under normal pressure under a nitrogen stream (at a flow rate of 200 mL/min) at a rate of temperature increase of 10° C./min. From the relationship between the weight and the temperature (thermogravimetry), it was found that a 5% weight loss of 2,8DBq2DBt was seen at a temperature of 500° C. or higher.

Furthermore, differential scanning calorimetry of 2,8DBq2DBt made in Synthesis example 1 was performed. For the measurement, a differential scanning calorimeter (Pyris 1, produced by PerkinElmer Japan Co., Ltd.) was used. One cycle in the measurement was as follows: the temperature was increased from −10° C. to 440° C. at a rate of 50° C./min, kept at 440° C. for 1 minute, and decreased from 440° C. to −10° C. at a rate of 50° C./min. In this measurement, two cycles were performed. From the result at the rising temperature in the second cycle, the glass transition temperature (Tg) was not observed and it was found that the melting point (Tm) was 429° C. Therefore, 2,8DBq2DBt has high heat resistance.

Example 2

Synthesis Example 2

In this example, a method of synthesizing 2,2'-[(dibenzofuran-2,8-diyl)di(3,1-phenylene)]di(dibenzo[f,h]quinoxaline) (abbreviation: 2,8DBqP2DBf) represented by Structural Formula (102) in Embodiment 1 will be described in detail. A structure of 2,8DBqP2DBf is shown below.

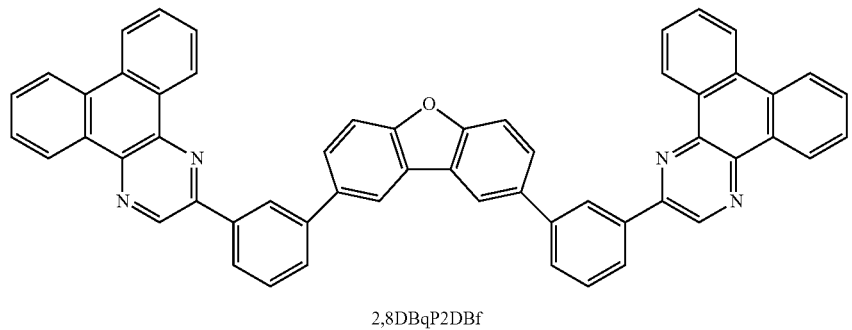

2,8DBqP2DBf

A synthesis scheme of 2,8DBqP2DBf is shown below.

Step 1: Synthesis of 2,2'-(dibenzofuran-2,8-diyl)bis(4,4,5,5-tetramethyl-1,3,2-dioxaborolane)

First, into a 200-mL three-neck flask were put 4.2 g (10 mmol) of 2,8-diiododibenzofuran, 5.6 g (22 mmol) of bis(pinacolato)diboron, and 5.9 g (60 mmol) of potassium acetate, and the atmosphere in the flask was replaced with nitrogen. To this mixture was added 80 mL of dimethyl sulfoxide (DMSO), the atmosphere in the flask was replaced with nitrogen, and the mixture was heated to 90° C. At the same temperature, 0.70 g (1.0 mmol) of bis(triphenylphosphine)palladium(II) dichloride (abbreviation: PdCl$_2$(PPh)$_2$) was added thereto, and this mixture was stirred at the same temperature for 5 hours. The mixture was naturally cooled down to room temperature and degassed again while the pressure in the flask was reduced. The atmosphere in the flask was replaced with nitrogen again, 0.70 g (1.0 mmol) of bis(triphenylphosphine)palladium(II) dichloride was added to the mixture, and the mixture was stirred at 90° C. for 4 hours. After the stirring, the resulting mixture was suction-filtered, and the collected solid was washed with dichloromethane while being suction-filtered. The obtained filtrate was washed with water, and an aqueous layer was subjected to extraction with dichloromethane. The extracted solution was washed with water, and magnesium sulfate was added to the extracted solution. This mixture was gravity-filtered, and the obtained filtrate was concentrated to give an oily substance. This oily substance was purified by silica gel column chromatography (developing solvent: a mixed solvent of hexane and ethyl acetate in a ratio of 10:1), so that 2.5 g of the target white powder was obtained in a yield of 58%. Synthesis scheme (B-1) of Step 1 is shown below.

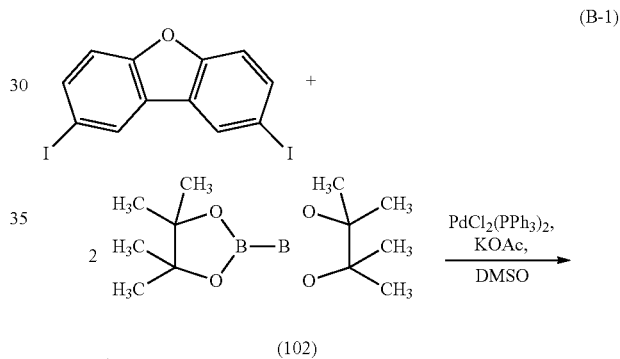

(102)

-continued

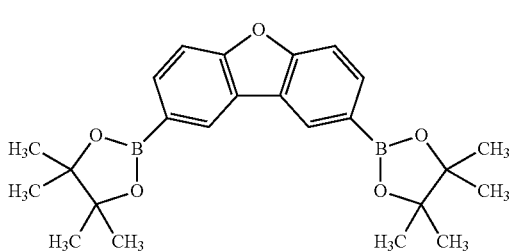

Step 2: Synthesis of 2,2'-[(dibenzofuran-2,8-diyl)di(3,1-phenylene)]di(dibenzo[f,h]quinoxaline)

Next, into a 200-mL three-neck flask were put 2.1 g (5.5 mmol) of 2-(3-bromophenyl)dibenzo[f,h]quinoxaline, 1.3 g (3.0 mmol) of 2,2'-(dibenzofuran-2,8-diyl)bis(4,4,5,5-tetramethyl-1,3,2-dioxaborolane, 0.17 g (0.56 mmol) of tris(2-methylphenyl)phosphine, 25 mL of toluene, 3 mL of ethanol, and 10 mL of a potassium carbonate solution (2 mol/L). This mixture was degassed by being stirred while the pressure in the flask was reduced. After the degassing, the atmosphere in the flask was replaced with nitrogen, and the mixture was heated to 80° C. The mixture was naturally cooled down to room temperature and degassed while the pressure in the flask was reduced. The atmosphere in the flask was replaced with nitrogen again, 20 mg (90 μmol) of palladium(II) acetate was added to the mixture at the same temperature, and stirring was performed at the same temperature for 9 hours. Then, 20 mg (90 μmol) of palladium(II) acetate was added to the mixture, and stirring was further performed at 80° C. for 9 hours. After the stirring, the resulting mixture was suction-filtered to give a residue. The residue was washed with water and ethanol to give a solid. The solid was dissolved in toluene, and the mixture was subjected to hot filtration to give a powder A. The obtained filtrate was concentrated, chloroform was added thereto, and the mixture was subjected to hot filtration to give a powder B. Thus, 1.3 g of the target black powder (the total amount of the powder A and the powder B) was obtained in a yield of 60%. Synthesis scheme (B-2) of Step 2 is shown below.

$^1$H NMR data of the obtained compound is shown below. $^1$H NMR (1,1,2,2-tetrachloroethane-d$_2$, 500 MHz): δ=7.69-7.87 (m, 12H), 7.95 (t, J=8.5 Hz, 4H), 8.40 (d, J=8.0 Hz, 2H), 8.47 (s, 2H), 8.68-8.70 (m, 4H), 8.73 (s, 2H), 9.33 (d, J=8.5 Hz, 2H), 9.49 (d, J=7.0 Hz, 2H), 9.56 (s, 2H).

Figure 10A:
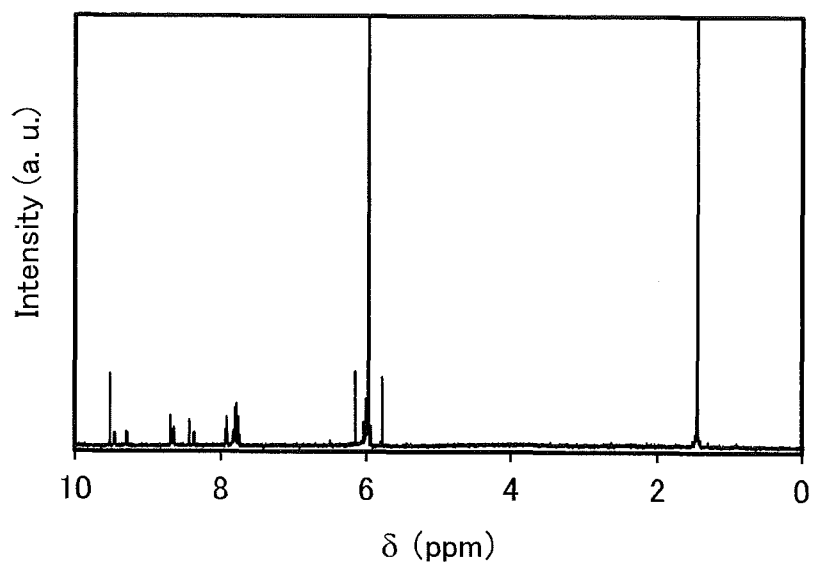
FIGS. 10A and 10B are $^1$H NMR charts of 2,8DBqP2DBf.
Figure 10B:
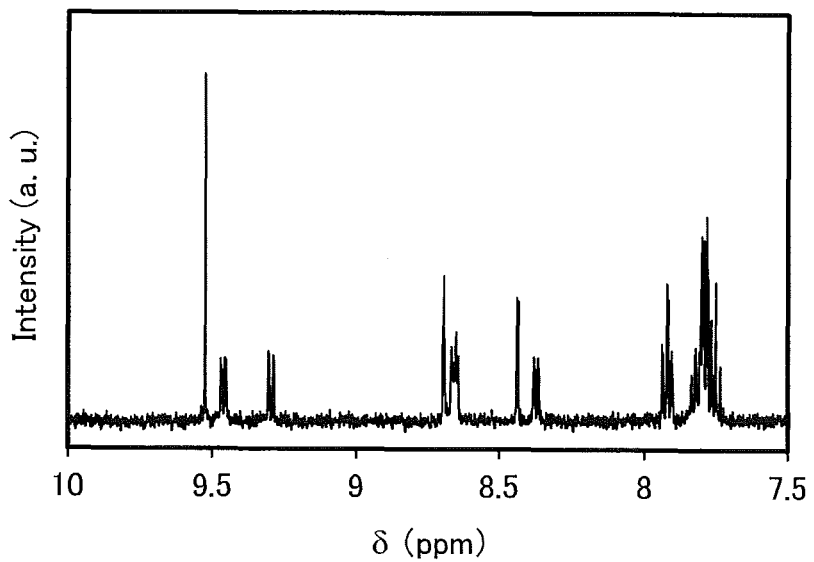

The $^1$H NMR charts are shown in FIGS. 10A and 10B. FIG. 10B is an enlarged chart showing a range of from 7.5 ppm to 10.0 ppm in FIG. 10A.

Figure 11A:
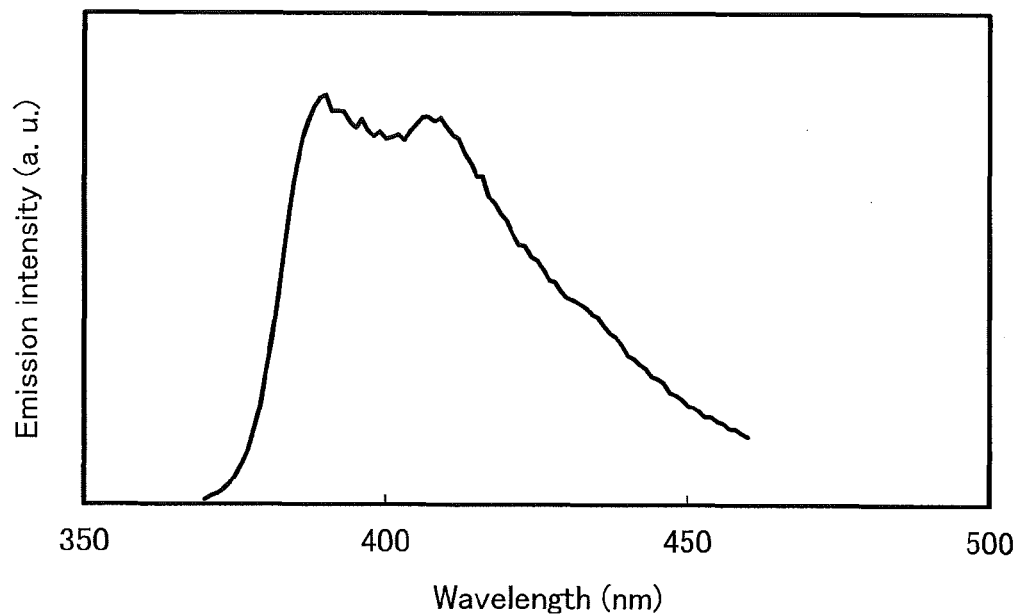
FIGS. 11A and 11B show an emission spectrum and an absorption spectrum of a dimethylformamide solution of 2,8DBqP2DBf.
Figure 11B:
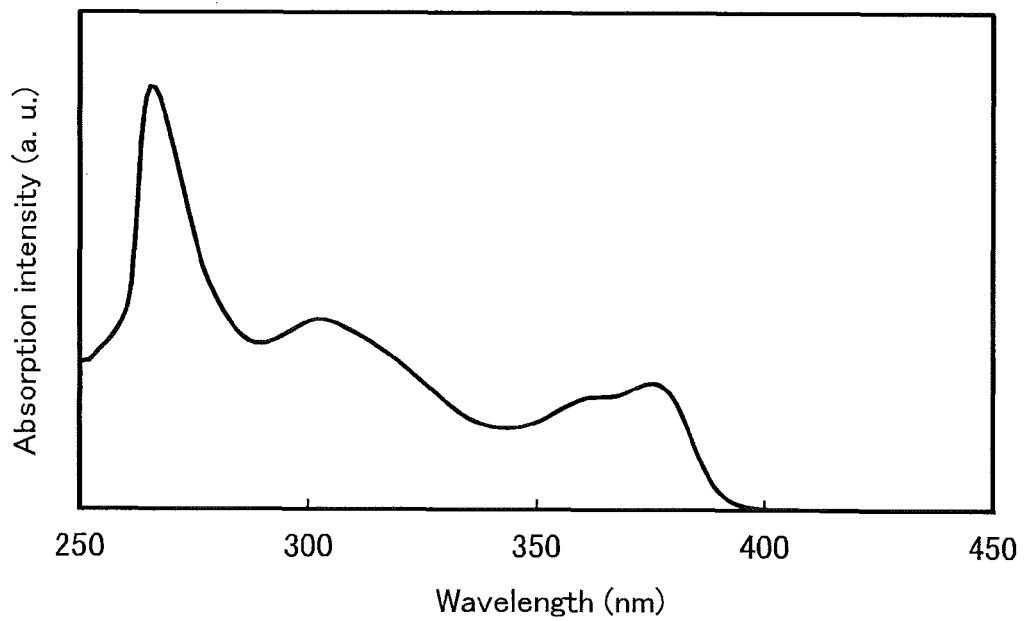
Figure 12A:
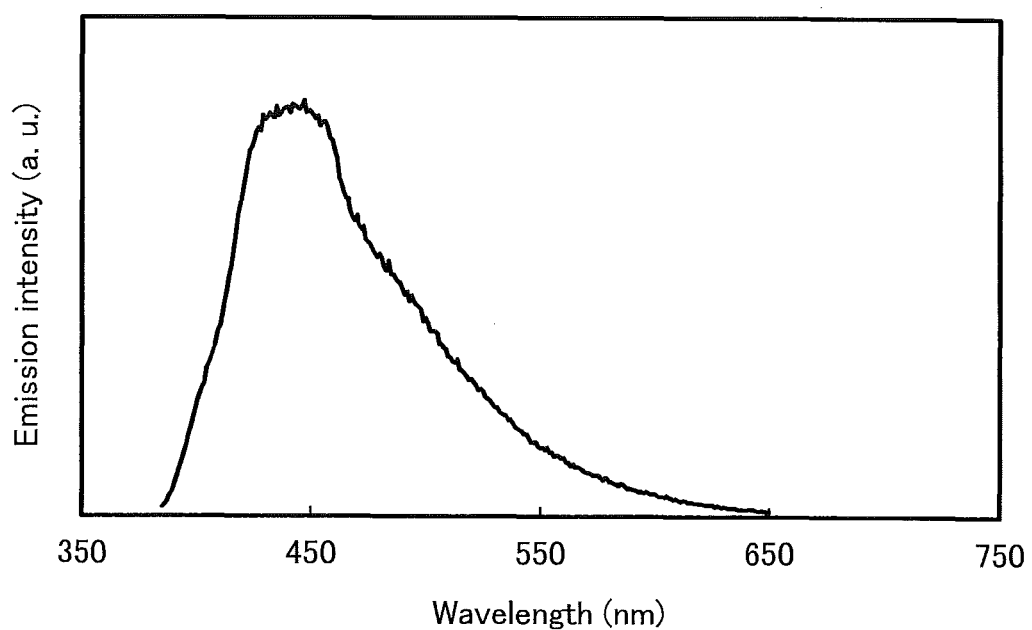
FIGS. 12A and 12B show an emission spectrum and an absorption spectrum of a thin film of 2,8DBqP2DBf.
Figure 12B:
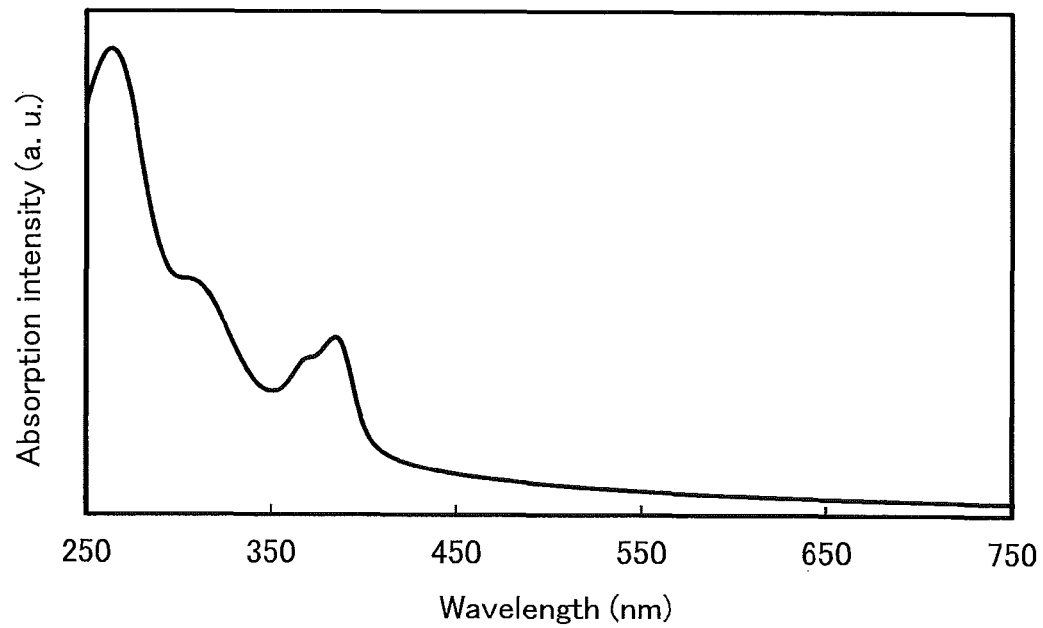

FIG. 11A shows the emission spectrum of a dimethylformamide solution of 2,8DBqP2DBf, and FIG. 11B shows the absorption spectrum thereof. FIG. 12A shows the emission spectrum of a thin film of 2,8DBqP2DBf, and FIG. 12B shows the absorption spectrum thereof. In each of FIG. 11A and FIG. 12A, the horizontal axis represents wavelength (nm) and the vertical axis represents emission intensity (arbitrary unit). In each of FIG. 11B and FIG. 12B, the horizontal axis represents wavelength (nm) and the vertical axis represents absorption intensity (arbitrary unit). In the case of the dimethylformamide solution, emission peaks are observed at 390 nm and 407 nm (excitation wavelength: 271 nm), and absorption peaks are observed at 265 nm, 302 nm, 362 nm, and 375 nm. In the case of the thin film, emission peaks are observed at 406 nm, 443 nm and 485 nm (excitation wavelength: 369 nm) and absorption peaks are observed at 264 nm, 307 nm, 369 nm, and 385 nm.

Note that the absorption spectra were measured with the apparatus described in Example 1, and the emission spectra and absorption spectra were measured by the method described in Example 1.

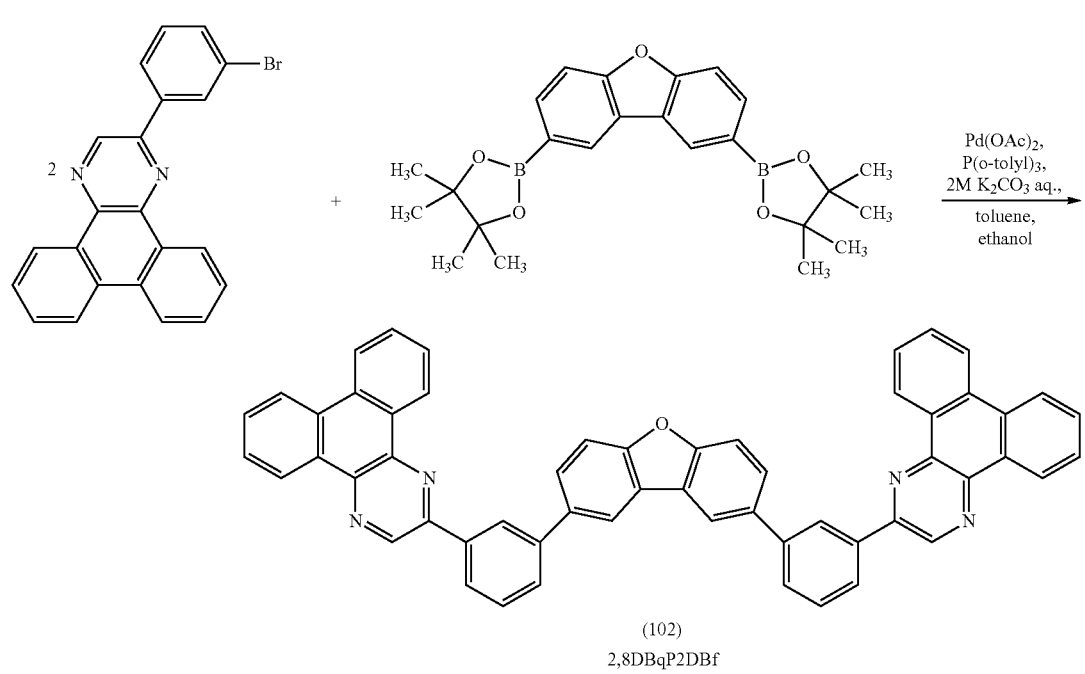

(B-2)

(102) 2,8DBqP2DBf

Next, 1.2 g of the obtained black powder was purified by train sublimation. In the purification by sublimation, the black powder was heated at 395° C. under a pressure of 2.2×10$^{-2}$ Pa for 1 hour. After the purification by sublimation, 0.75 g of the target white powder was collected in 59%.

This compound was identified as 2,8DBqP2DBf, which was the target substance, by nuclear magnetic resonance ($^1$H NMR).

The thermogravimetry-differential thermal analysis of 2,8DBqP2DBf prepared in Synthesis example 2 was performed. The relationship between weight and temperature (thermogravimetry) shows that the 5% weight loss temperature of 2,8DBqP2DBf is 500° C. or higher. Note that the thermogravimetry-differential thermal analysis was performed using the apparatus and the method which are described in Example 1.

Differential scanning calorimetry of 2,8DBqP2DBf prepared in Synthesis example 2 was performed. One cycle in the measurement was as follows: the temperature was increased from −10° C. to 385° C. at a rate of 50° C./min, kept at 385° C. for 1 minute, and decreased from 385° C. to −10° C. at a rate of 50° C./min. In this measurement, two cycles were performed. From the result at the rising temperature in the second cycle, it was found that the glass transition temperature (Tg) was 172° C. and the melting points (Tm) were 342° C. and 361° C. Therefore, 2,8DBqP2DBf has high heat resistance. Note that the differential scanning calorimeter was the same as that described in Example 1.

Example 3

Synthesis Example 3

In this example, a method of synthesizing 2,2'-[(dibenzothiophene-2,8-diyl)di(3,1-phenylene)]di(dibenzo[f,h]quinoline) (abbreviation: 2,8DBQuP2DBt) represented by Structural Formula (183) in Embodiment 1 will be described in detail. A structure of 2,8DBQuP2DBt is shown below.

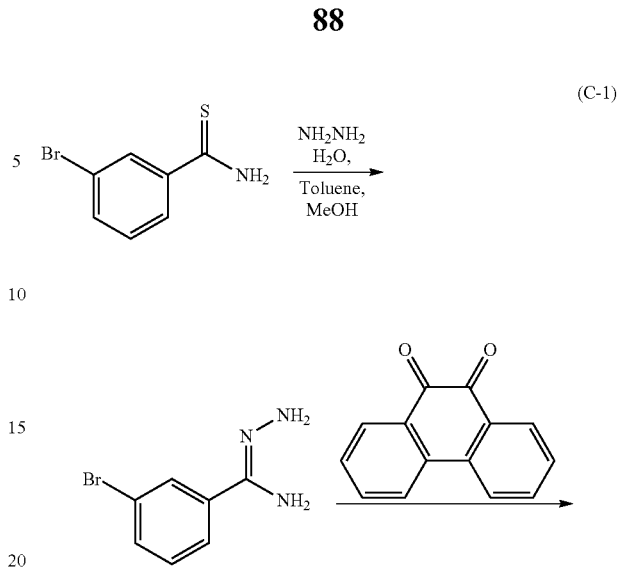

(183)

2,8DBQuP2DBt

A synthesis scheme of 2,8DBQuP2DBt is shown below.

Step 1: Synthesis of 3-(3-bromophenyl)-1,2,4-triazatriphenylene

First, into a 500-mL three-neck flask were put 2.2 g (10 mmol) of 3-bromothiobenzamide and 80 mL of toluene. Then, to this solution was added 20 mL of a solution in which methanol and 0.5 mL (10 mmol) of hydrazine monohydrate were mixed, and the mixture was stirred at 60° C. for 6.5 hours. Then, 2.1 g (10 mmol) of 9,10-phenanthrenequinone was added thereto, and stirring was further performed at 60° C. for 9 hours. After the stirring, the resulting mixture was suction-filtered to give a residue. The residue was washed with water and ethanol to give 2.5 g of a yellow-brown solid in a crude yield of 63%. Synthesis scheme (C-1) of Step 1 is shown below.

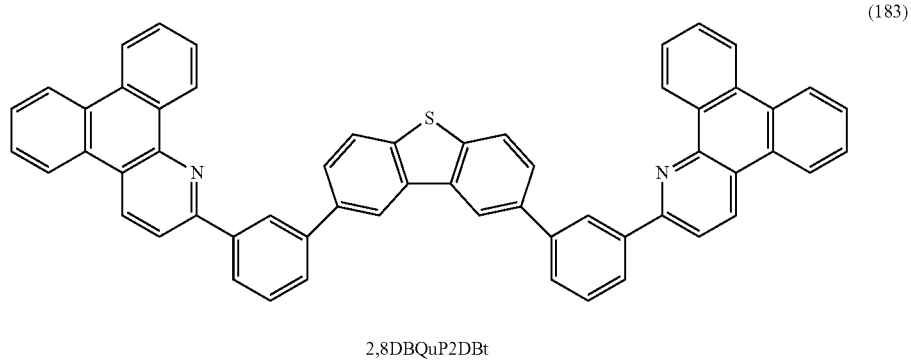 [SMILES: c1cc(-c2ccc3sc4ccc(-c5cccc(-c6ccc7c8ccccc8c8ccccc8c7n6)c5)cc4c3c2)cc(-c2ccc3c4ccccc4c4ccccc4c3n2)c1]

-continued

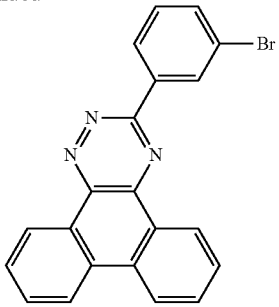

Step 2: Synthesis of 2-(3-bromophenyl)dibenzo[f,h]quinoline

Next, into a 200-mL three-neck flask were put 2.6 g (6.7 mmol) of 3-(3-bromophenyl)-1,2,4-triazatriphenylene, 2.7 mL (27 mmol) of 2,5-norbornadiene, and 33 mL of 1,2-dichlorobenzene, and this mixture was stirred at 180° C. for 1 hour. Then, 2,5-norbornadiene was added to the mixture every few hours (the total amount: 13 mL (0.13 mol)), and the mixture was stirred at 180° C. for 30 hours. After the stirring, the resulting mixture was suction-filtered to give a residue. The residue was washed with hexane and 1,2-dichlorobenzene, so that a yellow powder was obtained. The powder was dissolved in a mixed solvent of chloroform and hexane in a ratio of 4:1, and the mixture was filtered. The obtained filtrate was purified by silica gel column chromatography (developing solvent: a mixed solvent of chloroform and hexane in a ratio of 1:1), so that 1.0 g of the white powder was obtained in a yield of 39%. Synthesis scheme (C-2) of Step 2 is shown below.

Step 3: Synthesis of 2,2'-[(dibenzothiophene-2,8-diyl)di(3,1-phenylene)]di(dibenzo[f,h]quinoline) (Abbreviation: 2,8DBQuP2 DBt)

Next, into a 200-mL three-neck flask were put 0.58 g (1.5 mmol) of 2-(3-bromophenyl)dibenzo[f,h]quinoline, 0.36 g (0.83 mmol) of 2,2'-(dibenzothiophene-2,8-diyl)bis(4,4,5,5-tetramethyl-1,3,2-dioxaborolane), 23.0 mg (70 μmol) of tris(2-methylphenyl)phosphine, 7 mL of toluene, 1 mL of ethanol, and 2 mL of a potassium carbonate solution (2 mol/L), and this mixture was degassed by being stirred while the pressure in the flask was reduced. After the degassing, the atmosphere in the flask was replaced with nitrogen, and the mixture was heated to 80° C. At the same temperature, 3 mg (13 μmol) of palladium(II) acetate was added thereto and the mixture was stirred for 5.5 hours. Then, 3 mg (13 μmol) of palladium(II) acetate was added to this mixture, and the mixture was stirred at 80° C. for 5 hours. After the stirring, the mixture was naturally cooled down to room temperature and then degassed while the pressure in the flask was reduced, and the atmosphere in the flask was replaced with nitrogen again. Then, 10 mg (45 μmol) of palladium(II) acetate was added and the mixture was further stirred at 80° C. for 6.5 hours. The mixture was naturally cooled down to room temperature and then degassed while the pressure in the flask was reduced, and the atmosphere in the flask was replaced with nitrogen again. The mixture was suction-filtered to give a solid. The solid was washed with water and ethanol. After the washing, the obtained solid was washed with hot toluene to give 0.46 g of the target solid in a yield of 78%. Synthesis scheme (C-3) of Step 3 is shown below.

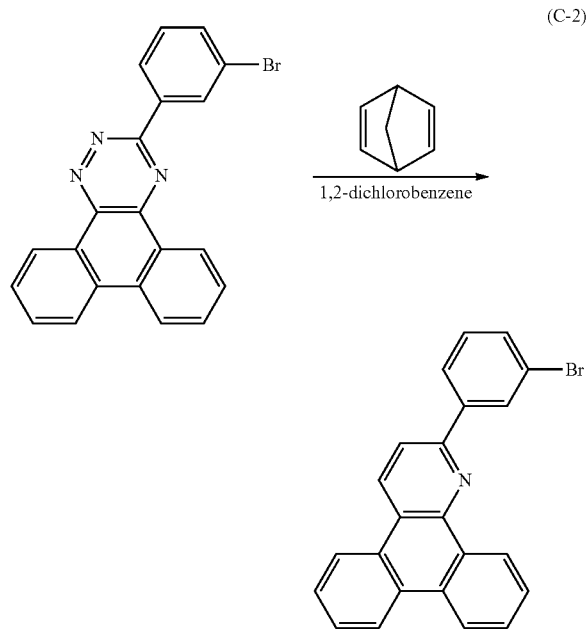

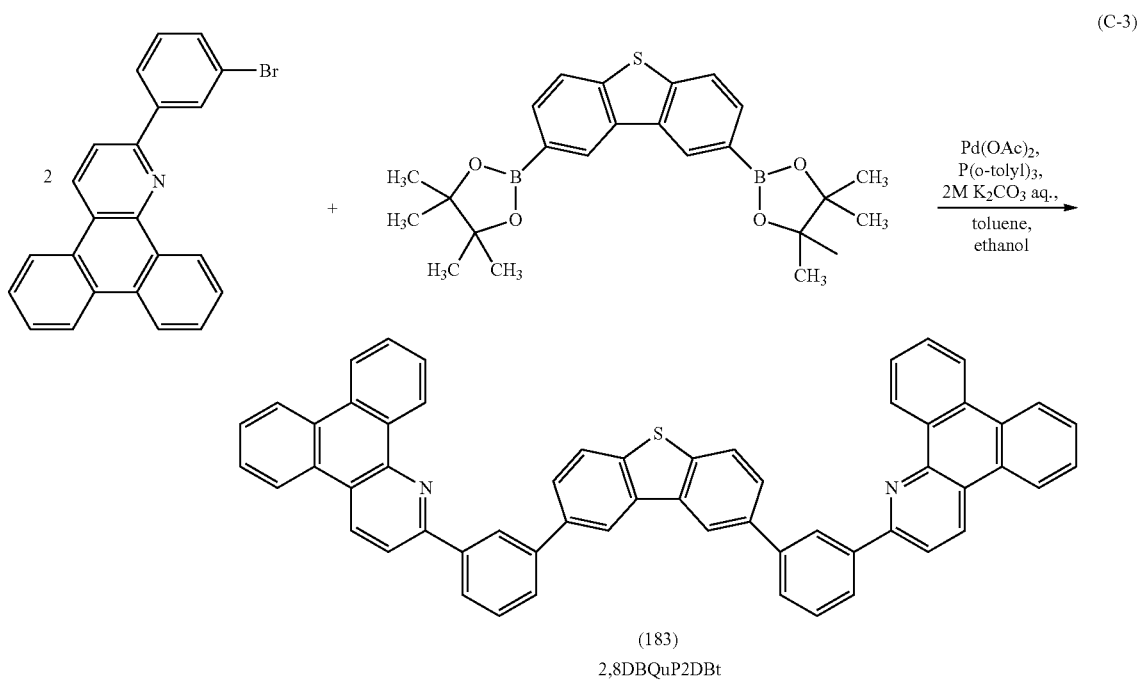

Next, 0.42 g of the obtained solid was purified by train sublimation. In the purification by sublimation, the solid was heated at 420° C. under a pressure of 2.3 Pa with a flow rate of argon of 5 mL/min for 2 hours. After the purification by sublimation, 0.32 g of the target white powder was collected in 76%.

This compound was identified as 2,8DBQuP2DBt, which was the target substance, by nuclear magnetic resonance ($^1$H NMR).

$^1$H NMR data of the obtained compound is shown below.
$^1$H NMR (1,1,2,2-tetrachloroethane-d$_2$, 500 MHz): δ=7.71-7.78 (m, 10H), 7.93 (d, J=7.5 Hz, 2H), 7.97 (d, J=8.0 Hz, 2H), 8.10 (d, J=8.5 Hz, 2H), 8.20 (d, J=8.5 Hz, 2H), 8.42 (d, J=8.5 Hz, 2H), 8.61 (t, J=4.5 Hz, 4H), 8.68 (d, J=7.5 Hz, 2H), 8.72 (s, 2H), 8.80 (s, 2H), 8.96 (d, J=8.5 Hz, 2H), 9.60-9.61 (m, 2H).

Figure 13A:
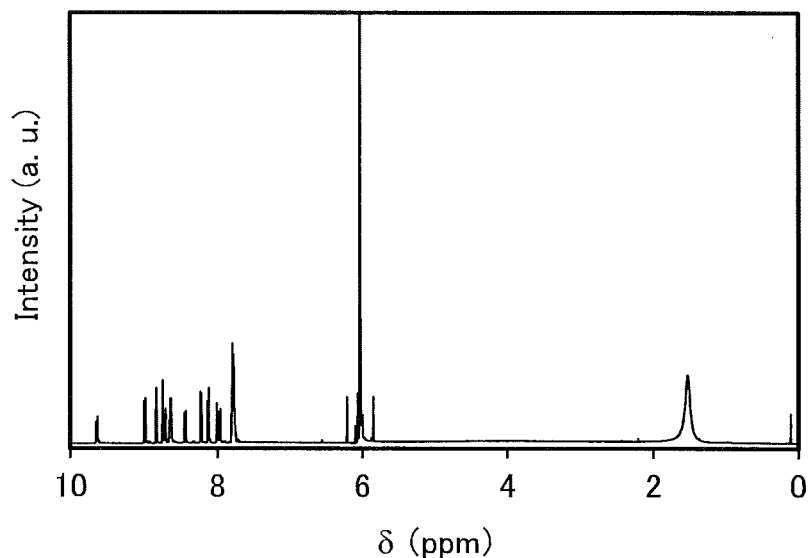
FIGS. 13A and 13B are $^1$H NMR charts of 2,8DBQuP2DBt.
Figure 13B:
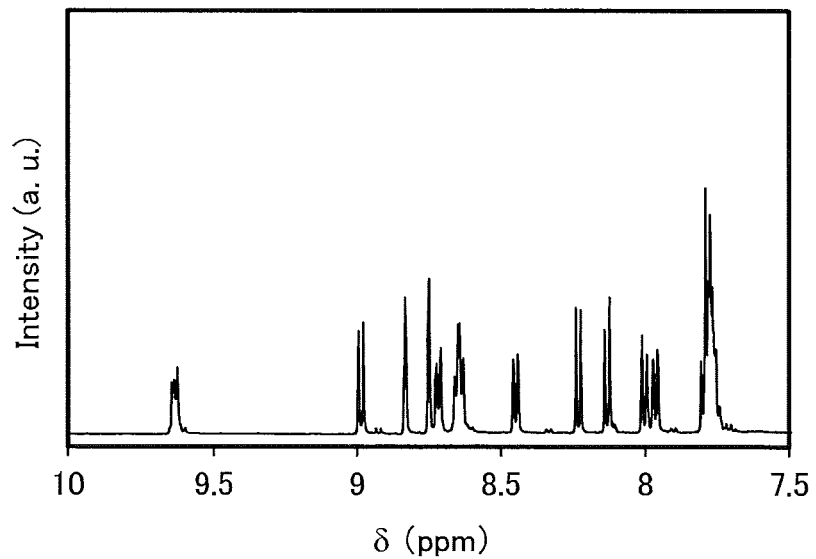

The $^1$H NMR charts are shown in FIGS. 13A and 13B. FIG. 13B is an enlarged chart showing a range of from 7.5 ppm to 10.0 ppm in FIG. 13A.

Figure 14A:
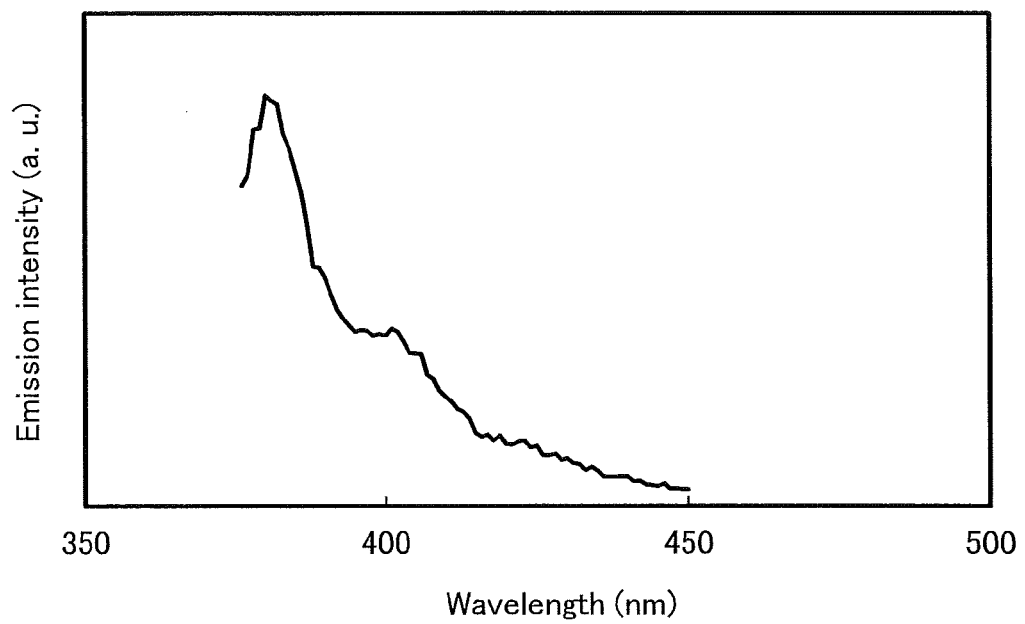
FIGS. 14A and 14B show an emission spectrum and an absorption spectrum of a dimethylformamide solution of 2,8DBQuP2DBt.
Figure 14B:
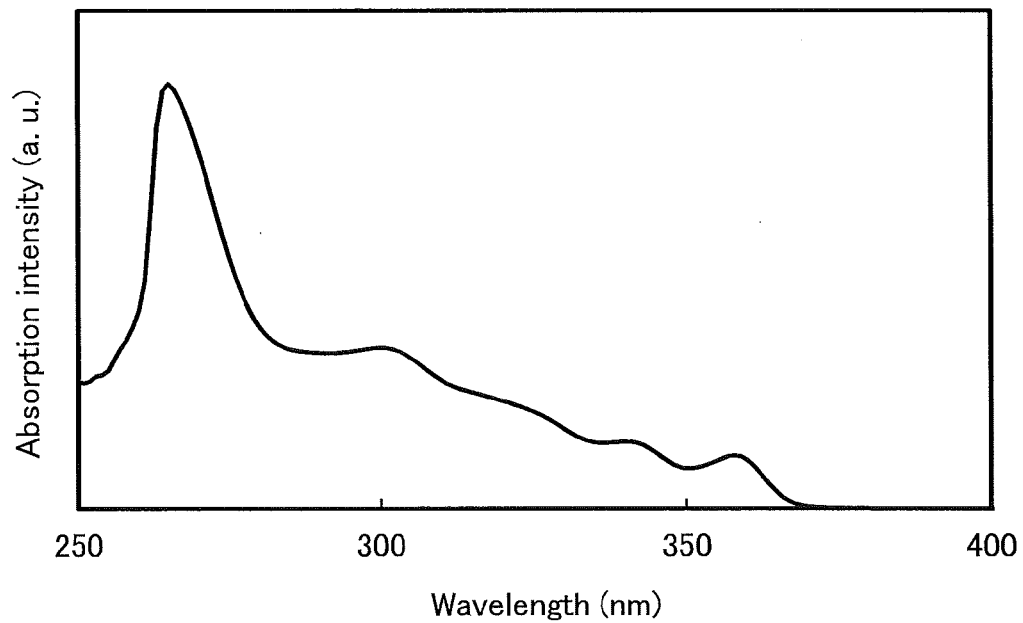
Figure 15A:
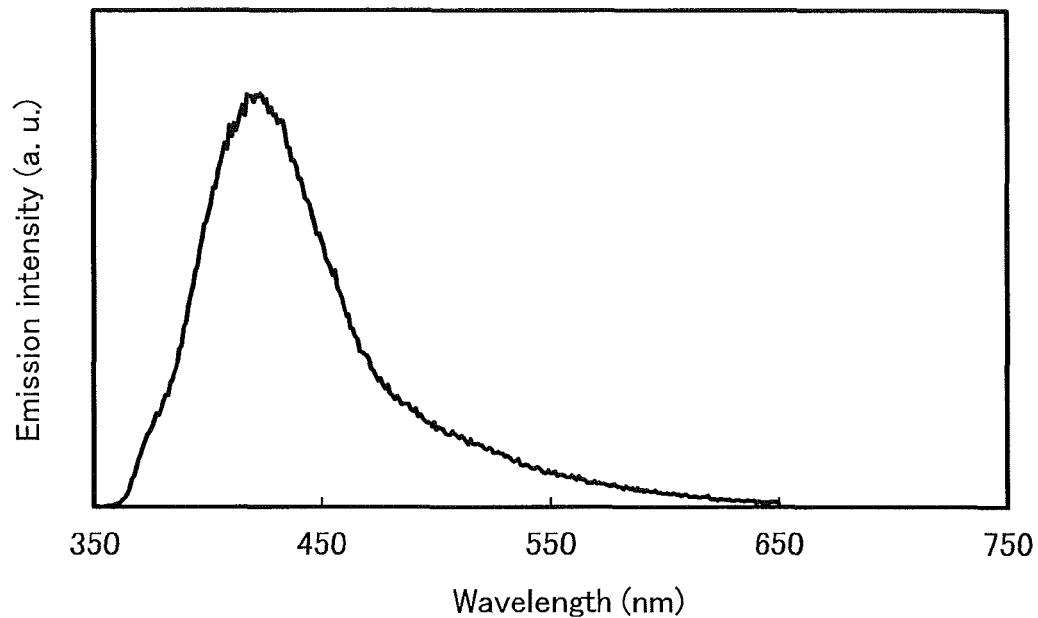
FIGS. 15A and 15B show an emission spectrum and an absorption spectrum of a thin film of 2,8DBQuP2DBt.
Figure 15B:
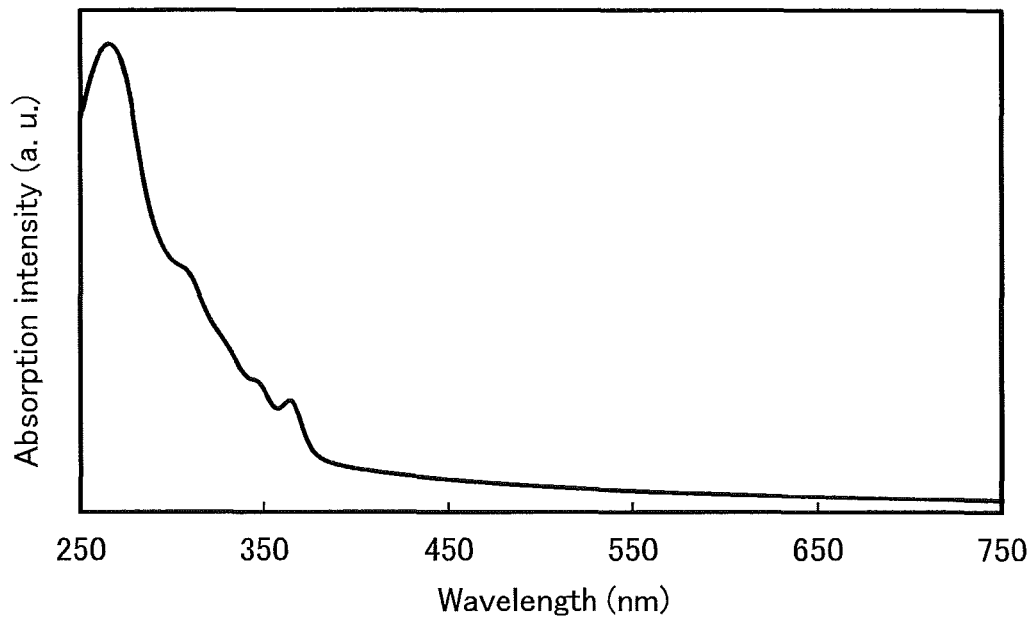

FIG. 14A shows the emission spectrum of a dimethylformamide solution of 2,8DBQuP2DBt, and FIG. 14B shows the absorption spectrum thereof. FIG. 15A shows the emission spectrum of a thin film of 2,8DBQuP2DBt, and FIG. 15B shows the absorption spectrum thereof. In each of FIG. 14A and FIG. 15A, the horizontal axis represents wavelength (nm) and the vertical axis represents emission intensity (arbitrary unit). In each of FIG. 14B and FIG. 15B, the horizontal axis represents wavelength (nm) and the vertical axis represents absorption intensity (arbitrary unit). In the case of the dimethylformamide solution, emission peaks are observed at 380 nm and 401 nm (excitation wavelength: 359 nm) and absorption peaks are observed at 265 nm, 300 nm, 342 nm, and 358 nm. In the case of the thin film, emission peaks are observed at 374 nm, 423 nm, and 507 nm (excitation wavelength: 332 nm) and absorption peaks are observed at 265 nm, 307 nm, 328 nm, 346 nm, and 364 nm.

Note that the absorption spectra were measured with the apparatus described in Example 1, and the emission spectra and absorption spectra were measured by the method described in Example 1.

The thermogravimetry-differential thermal analysis of 2,8DBQuP2DBt prepared in Synthesis example 3 was performed. The relationship between weight and temperature (thermogravimetry) shows that the 5% weight loss temperature of 2,8DBQuP2DBt is 500° C. or higher. Note that the thermogravimetry-differential thermal analysis was performed using the apparatus and the method which are described in Example 1.

Differential scanning calorimetry of 2,8DBQuP2DBt prepared in Synthesis example 3 was performed. One cycle in the measurement was as follows: the temperature was increased from 30° C. to 500° C. at a rate of 50° C./min, kept at 500° C. for 1 minute, and decreased from 500° C. to 30° C. at a rate of 50° C./min. In this measurement, two cycles were performed. From the result at the rising temperature in the second cycle, it was found that the glass transition temperature (Tg) was 175° C. and the melting point (Tm) was 349° C. Therefore, 2,8DBQuP2DBt has high heat resistance. Note that the differential scanning calorimeter was the same as that described in Example 1.

Example 4

Synthesis Example 4

In this example, a method of synthesizing 2,2'-[(dibenzothiophene-2,8-diyl)di(3,1-phenylene)]di(dibenzo[f,h]quinoxaline) (abbreviation: 2,8mDBqP2DBT) represented by Structural Formula (101) in Embodiment 1 will be described in detail. A structure of 2,8mDBqP2DBT is shown below.

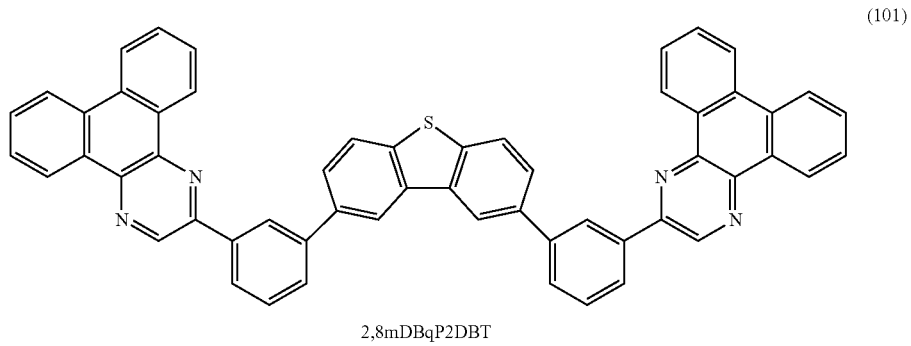 [SMILES: c1cc(-c2ccc3sc4ccc(-c5cccc(-c6cnc7c8ccccc8c8ccccc8c7n6)c5)cc4c3c2)cc(-c2cnc3c4ccccc4c4ccccc4c3n2)c1]

2,8mDBqP2DBT (101)

A synthesis scheme of 2,8mDBqP2DBT is shown below.

Step 1: Synthesis of 2,2'-(2,8-dibenzothiophene-diyl)bis(4,4,5,5-tetramethyl-1,3,2-dioxaborolane)

First, into a 200-mL three-neck flask were put 2.7 g (7.9 mmol) of 2,8-dibromodibenzothiophene, 4.5 g (18 mmol) of bis(pinacolato)diboron, and 10 g (0.11 mol) of potassium acetate, and the atmosphere in the flask was replaced with nitrogen. To this mixture was added 70 mL of dimethyl sulfoxide(DMSO), the atmosphere in the flask was replaced with nitrogen, and the mixture was heated to 90° C. At the same temperature, 0.56 g (0.79 mmol) of bis(triphenylphosphine)palladium(II) dichloride was added thereto, and this mixture was stirred at the same temperature for 7 hours. After the stirring, the resulting mixture was suction-filtered, and the collected solid was washed with dichloromethane while being suction-filtered. The obtained filtrate was washed with water, and an aqueous layer was subjected to extraction with dichloromethane. The extracted solution was washed with water, and magnesium sulfate was added to the extracted solution. This mixture was gravity-filtered, and the obtained filtrate was concentrated to give an oily substance. This oily substance was purified by silica gel column chromatography (developing solvent:hexane:a mixed solvent of hexane and ethyl acetate in a ratio of 10:1), so that 2.5 g of the target white powder was obtained in a yield of 72%. Synthesis scheme (D-1) of Step 1 is shown below.

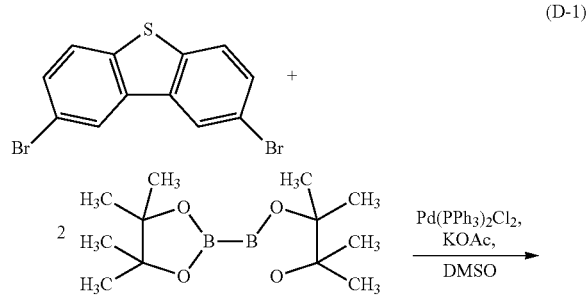

(D-1)

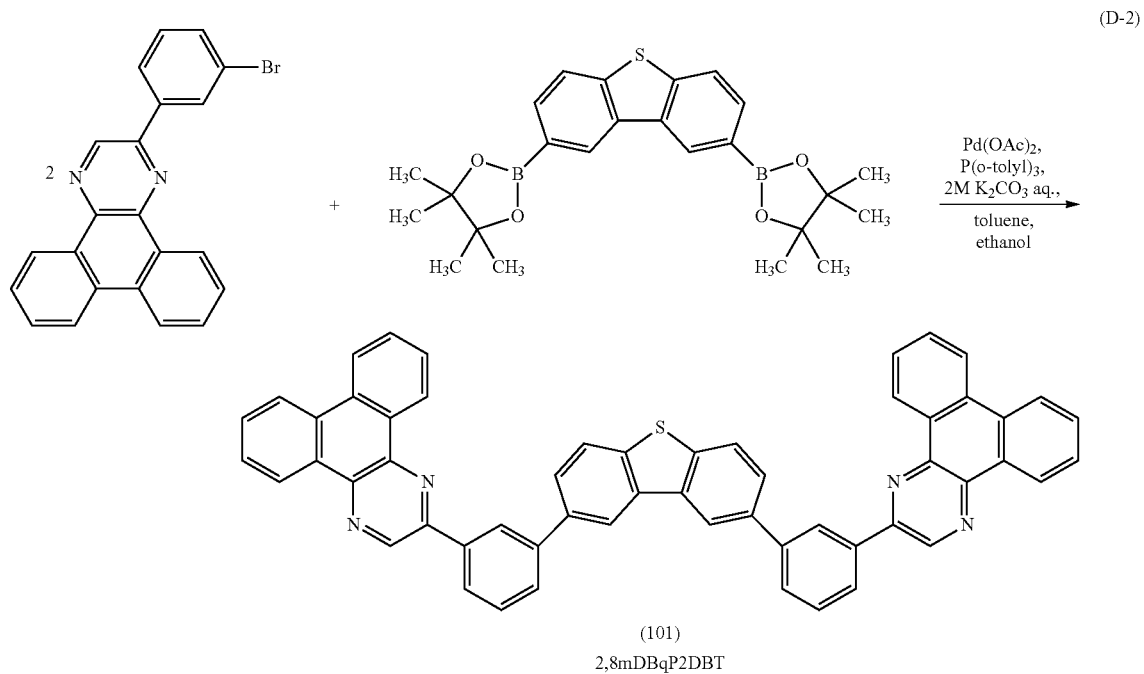

(D-2)

(101)
2,8mDBqP2DBT

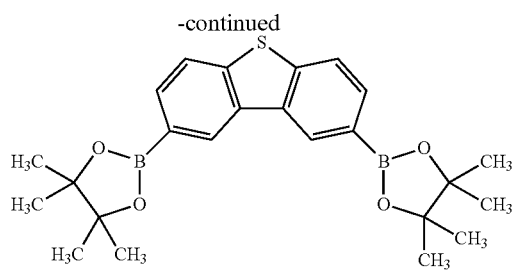

Step 2: Synthesis of 2,2'-[(dibenzothiophene-2,8-diyl)di(3,1-phenylene)]di(dibenzo[f,h]quinoxaline)

Next, into a 200-mL three-neck flask were put 1.6 g (4.2 mmol) of 2-(3-bromophenyl)dibenzo[f,h]quinoxaline, 1.0 g (2.3 mmol) of 2,2'-(2,8-dibenzothiophene-diyl)bis(4,4,5,5-tetramethyl-1,3,2-dioxaborolane), 60 mg (0.20 mmol) of tris(2-methylphenyl)phosphine, 20 mL of toluene, 2 mL of ethanol, and 10 in L of a potassium carbonate solution (2 mol/L). This mixture was degassed by being stirred while the pressure in the flask was reduced. After the degassing, the atmosphere in the flask was replaced with nitrogen, and the mixture was heated to 80° C. At the same temperature, 10 mg (44 μmol) of palladium(II) acetate was added to this mixture and stirring was performed at the same temperature for 3 hours. Then, 10 mg (44 μmol) of palladium(II) acetate was added thereto and stirring was further performed at 80° C. for 7 hours. After the stirring, the resulting mixture was suction-filtered to give a residue. The residue was washed with water and ethanol, and the obtained solid was suspended in toluene. The mixture was subjected to hot filtration, so that 1.4 g of the target black powder was obtained in a yield of 85%. Synthesis scheme (D-2) of Step 2 is shown below.

Next, 1.2 g of the obtained black powder was purified by train sublimation. In the purification by sublimation, the black powder was heated at 420° C. under a pressure of $1.5 \times 10^{-2}$ Pa for 2 hours. After the purification by sublimation, 0.39 g of the target white powder was collected in 33%.

This compound was identified as 2,8mDBqP2DBT, which was the target substance, by nuclear magnetic resonance ($^1$H NMR).

$^1$H NMR data of the obtained compound is shown below.
$^1$H NMR (1,1,2,2-tetrachloroethane-d$_2$, 500 MHz): δ=7.70-7.79 (m, 10H), 7.95 (t, J=7.5 Hz, 4H), 8.08 (d, J=8.5 Hz, 2H), 8.38 (d, J=8.0 Hz, 2H), 8.57 (t, J=8.0 Hz, 4H), 8.68 (s, 2H), 8.78 (s, 2H), 9.26 (d, J=7.5 Hz, 2H), 9.42 (d, J=7.5 Hz, 2H), 9.51 (s, 2H).

Figure 16A:
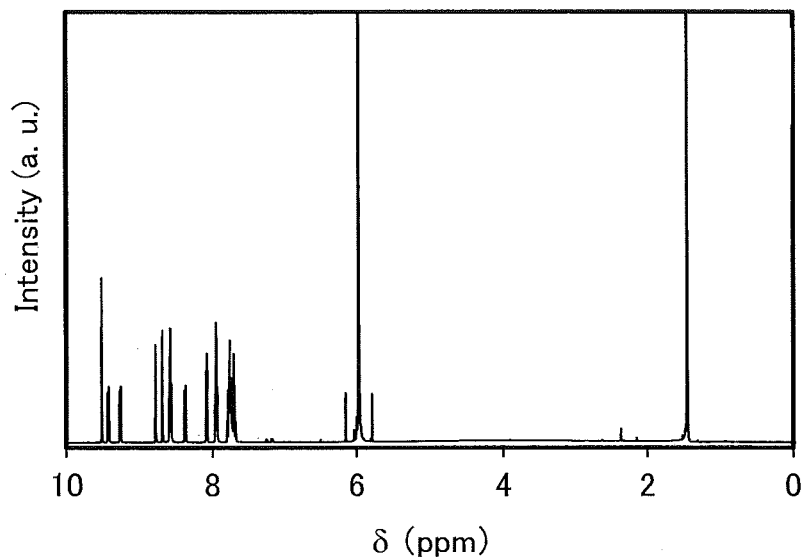
FIGS. 16A and 16B are $^1$H NMR charts of 2,8mDBqP2DBT.
Figure 16B:
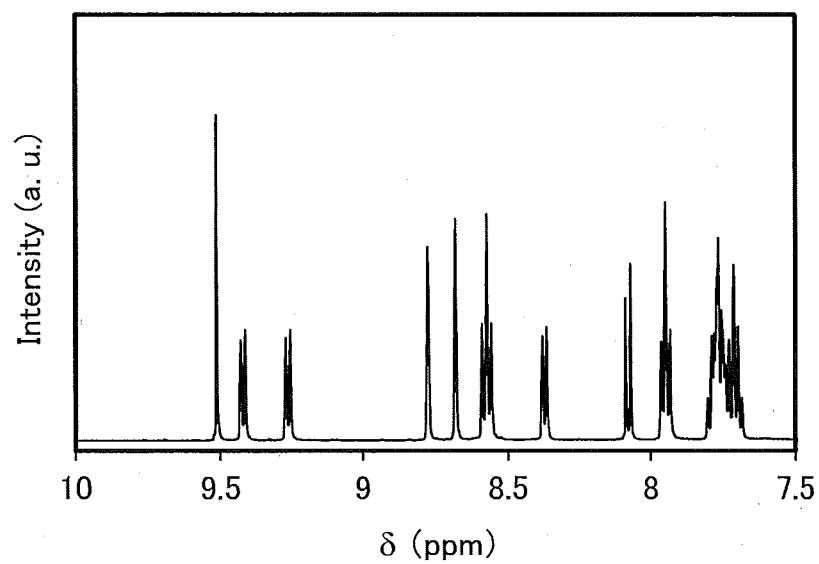

The $^1$H NMR charts are shown in FIGS. 16A and 16B. FIG. 16B is an enlarged chart showing a range of from 7.5 ppm to 10.0 ppm in FIG. 16A.

Figure 17A:
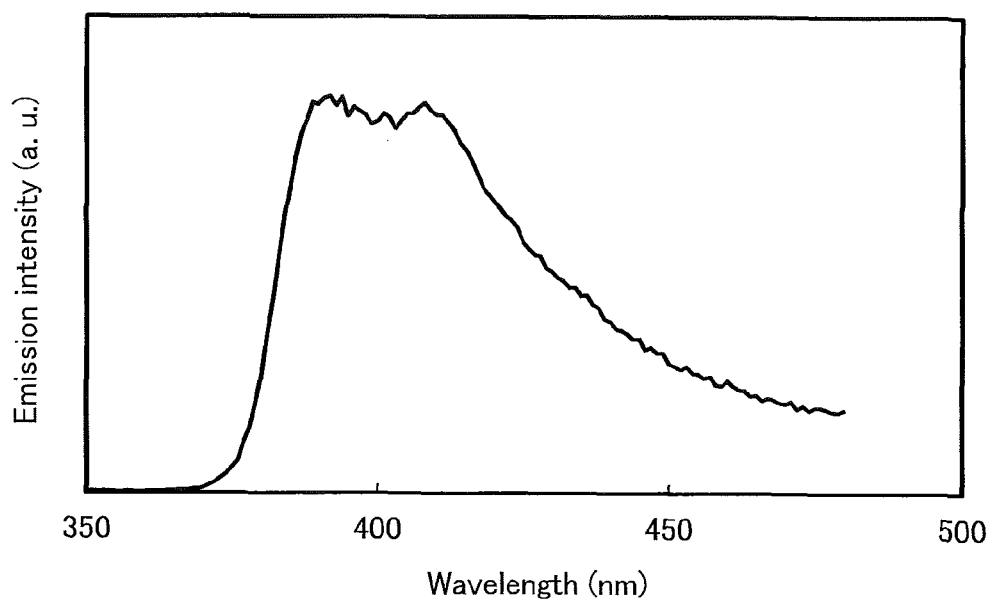
FIGS. 17A and 17B show an emission spectrum and an absorption spectrum of a dimethylformamide solution of 2,8mDBqP2DBT.
Figure 17B:
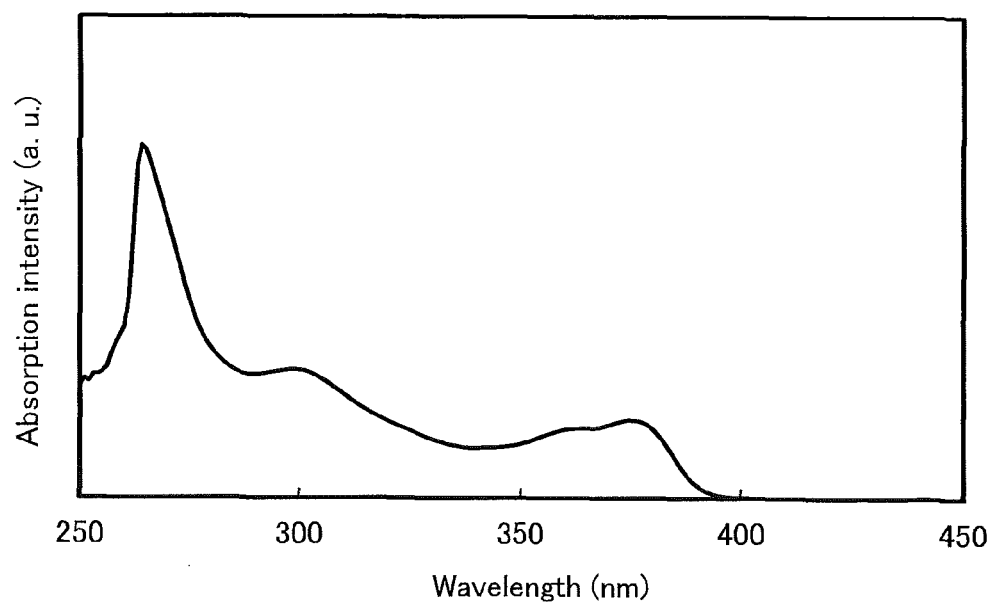
Figure 18A:
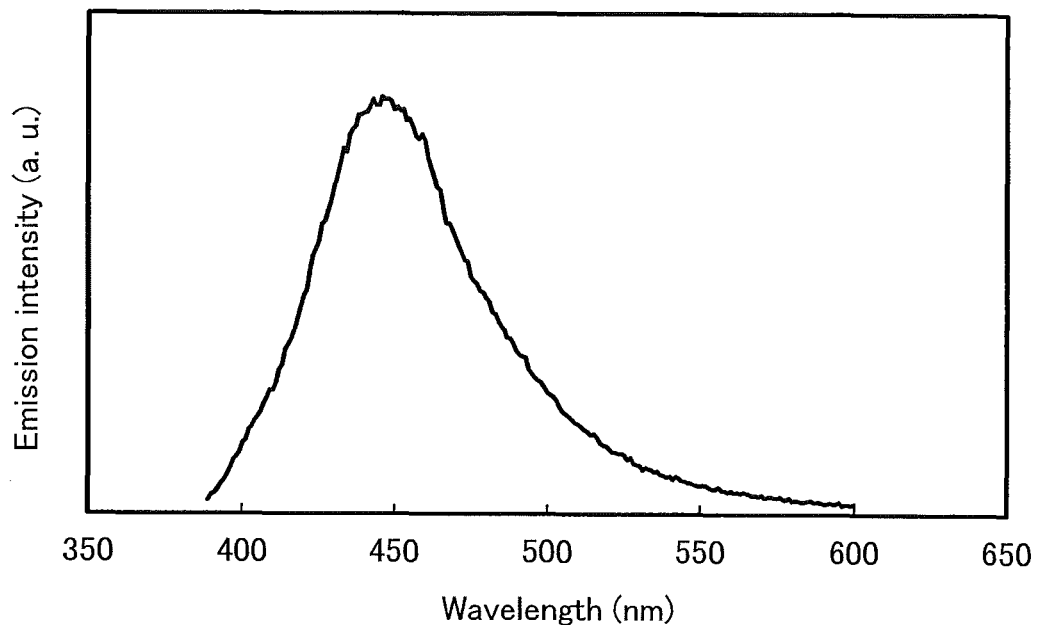
FIGS. 18A and 18B show an emission spectrum and an absorption spectrum of a thin film of 2,8mDBqP2DBT.

FIG. 17A shows the emission spectrum of a dimethylformamide solution of 2,8mDBqP2DBT, and FIG. 17B shows the absorption spectrum thereof. FIG. 18A shows the emission spectrum of a thin film of 2,8mDBqP2DBT, and FIG.

Figure 18B:
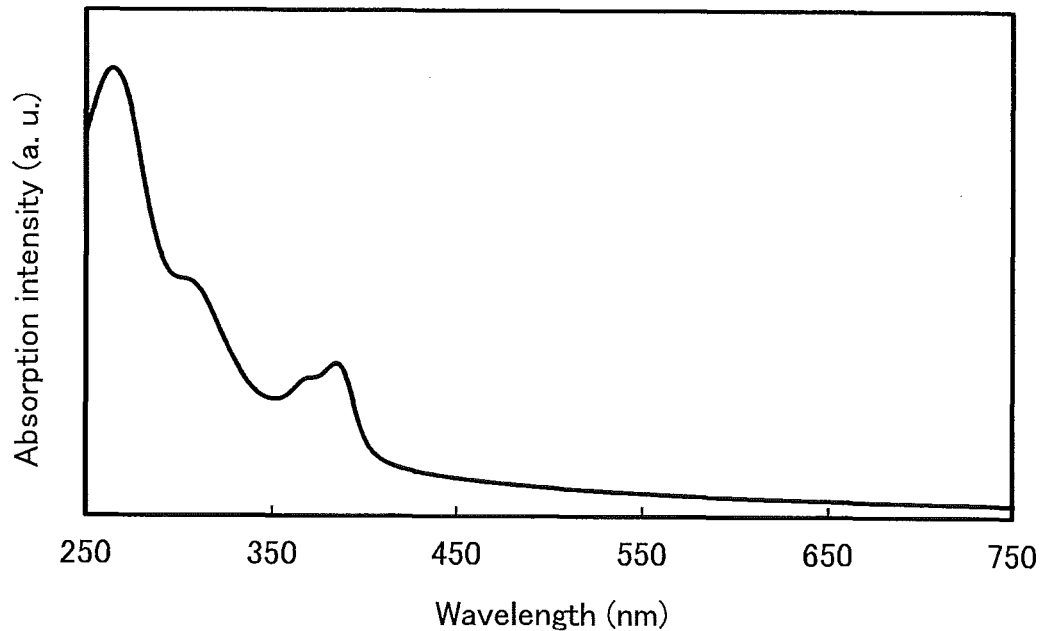

18B shows the absorption spectrum thereof. In each of FIG. 17A and FIG. 18A, the horizontal axis represents wavelength (nm) and the vertical axis represents emission intensity (arbitrary unit). In each of FIG. 17B and FIG. 18B, the horizontal axis represents wavelength (nm) and the vertical axis represents absorption intensity (arbitrary unit). In the case of the dimethylformamide solution, emission peaks are observed at 392 nm and 407 nm (excitation wavelength: 272 nm) and absorption peaks are observed at 264 nm, 299 nm, 363 nm, and 375 nm. In the case of the thin film, an emission peak is observed at 446 nm (excitation wavelength: 373 nm) and absorption peaks are observed at 264 nm, 304 nm, 370 nm, and 385 nm.

Note that the absorption spectra were measured with the apparatus described in Example 1, and the emission spectra and absorption spectra were measured by the method described in Example 1.

The thermogravimetry-differential thermal analysis of 2,8mDBqP2DBT prepared in Synthesis example 4 was performed. The relationship between weight and temperature (thermogravimetry) shows that the 5% weight loss temperature of 2,8mDBqP2DBT is 500° C. or higher. Note that the thermogravimetry-differential thermal analysis was performed using the apparatus and the method which are described in Example 1.

Differential scanning calorimetry of 2,8mDBqP2DBT prepared in Synthesis example 4 was performed. One cycle in the measurement was as follows: the temperature was increased from −10° C. to 385° C. at a rate of 50° C./min, kept at 385° C. for 1 minute, and decreased from 385° C. to −10° C. at a rate of 50° C./min. In this measurement, two cycles were performed. From the result at the rising temperature in the second cycle, it was found that the glass transition temperature (Tg) was 177° C. and the melting point (Tm) was 350° C. Therefore, 2,8mDBqP2DBT has high heat resistance. Note that the differential scanning calorimeter was the same as that described in Example 1.

Example 5

Synthesis Example 5

In this example, a method of synthesizing 2,2′-[(dibenzothiophene-2,8-diyl)di(4,1-phenylene)]di(dibenzo[f,h]quinoxaline) (abbreviation: 2,8pDBqP2DBt) represented by Structural Formula (107) in Embodiment 1 will be described in detail. A structure of 2,8pDBqP2DBt is shown below.

A synthesis scheme of 2,8pDBqP2DBt is shown below.

Step 1: Synthesis of 2-(4-chlorophenyl)dibenzo[f,h]quinoxaline

First, into a 200-mL three-neck flask were put 2.6 g (9.7 mmol) of 2-chlorodibenzo[f,h]quinoxaline, 1.7 g (11 mmol) of 4-chlorophenylboronic acid, 0.24 g (0.79 mmol) of tris(2-methylphenyl)phosphine, 50 mL of toluene, 5 mL of ethanol, and 20 mL of a potassium carbonate solution (2 mol/L). This mixture was degassed by being stirred while the pressure in the flask was reduced. After the degassing, the atmosphere in the flask was replaced with nitrogen, and the mixture was heated at 80° C. At the same temperature, 40 mg (0.18 mmol) of palladium(II) acetate was added to this mixture and stirring was performed at the same temperature for 7.5 hours. After the stirring, this mixture was naturally cooled down to room temperature and then degassed while the pressure in the flask was reduced, and the atmosphere in the flask was replaced with nitrogen again. Then, 40 mg (0.18 mmol) of palladium(II) acetate was added and the mixture was stirred for 7.5 hours. The resulting mixture was further naturally cooled down to room temperature and then degassed while the pressure in the flask was reduced, and the atmosphere in the flask was replaced with nitrogen again. Then, 40 mg (0.18 mmol) of palladium(II) acetate was added and the mixture was stirred for 7 hours. After the stirring, the resulting mixture was suction-filtered to give a residue. The residue was washed with water and ethanol, and the obtained solid was dissolved in toluene. This solution was filtered through Celite (produced by Wako Pure Chemical Industries, Ltd., Catalog No. 531-16855) and alumina. The obtained filtrate was concentrated to give a white powder. The white powder was recrystallized with toluene, so that 1.9 g of the target white powder was obtained in a yield of 57%. Synthesis scheme (E-1) of Step 1 is shown below.

(107)

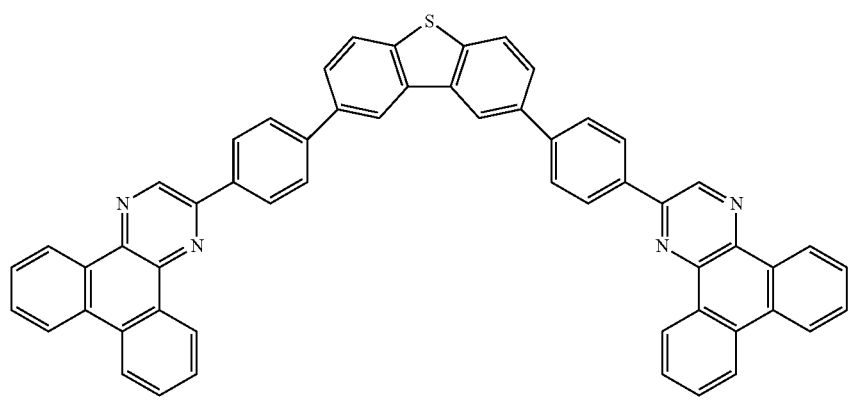

2,8pDBqP2DBt

Step 2: Synthesis of 2,2'-[(dibenzothiophene-2,8-diyl)di(4,1-phenylene)]di(dibenzo[f,h]quinoxaline)

Next, into a 200-mL three-neck flask were put 1.9 g (5.5 mmol) of 2-(4-chlorophenyl)dibenzo[f,h]quinoxaline, 1.4 g (3.1 mmol) of 2,2'-(dibenzothiophene-2,8-diyl)bis(4,4,5,5-tetramethyl-1,3,2-dioxaborolane), 0.10 g (0.28 mmol) of di(1-adamantyl)-n-butylphosphine, and 3.9 g (18 mmol) of tripotassium phosphatem (abbreviation: K₃PO₄). The atmosphere in the flask was replaced with nitrogen. To the mixture was added 25 mL of 1,4-dioxane, and the temperature of this mixture was raised to 90° C. Then, 10 mg (45 μmol) of palladium(II) acetate was added to this mixture, and stirring was performed at the same temperature for 1 hour. After the stirring, the resulting mixture was suction-filtered to give a residue. The residue was washed with water and ethanol, and the obtained solid was washed with dimethylfonuamide, so that 0.70 g of the target solid was obtained in a yield of 32%. Synthesis scheme (E-2) of Step 2 is shown below.

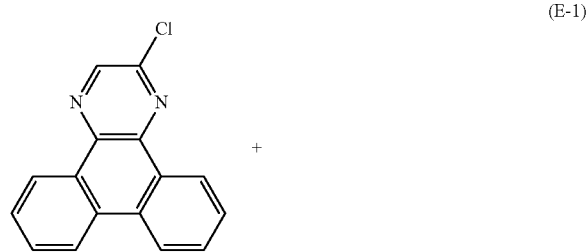

(E-1)

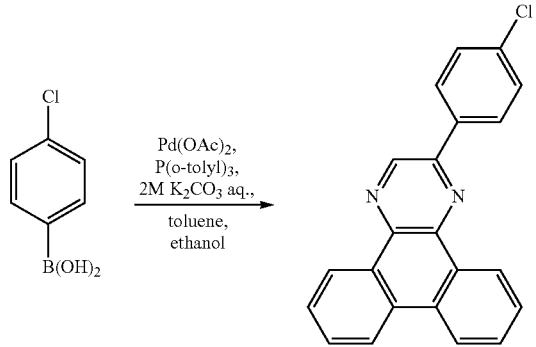

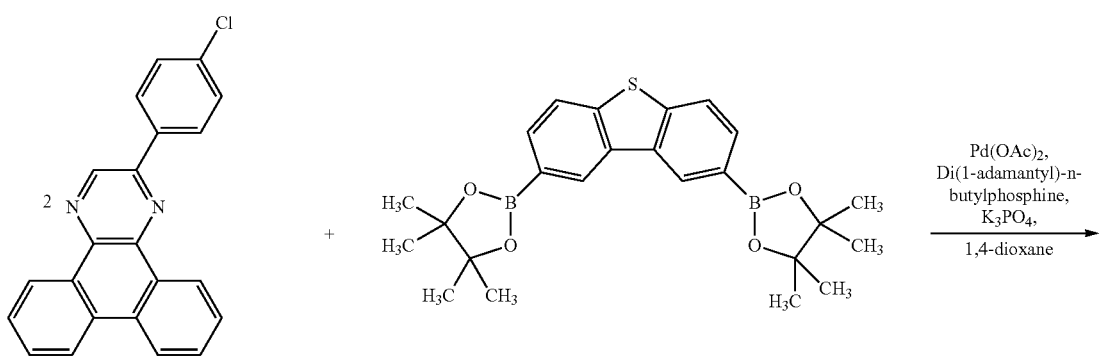

(E-2)

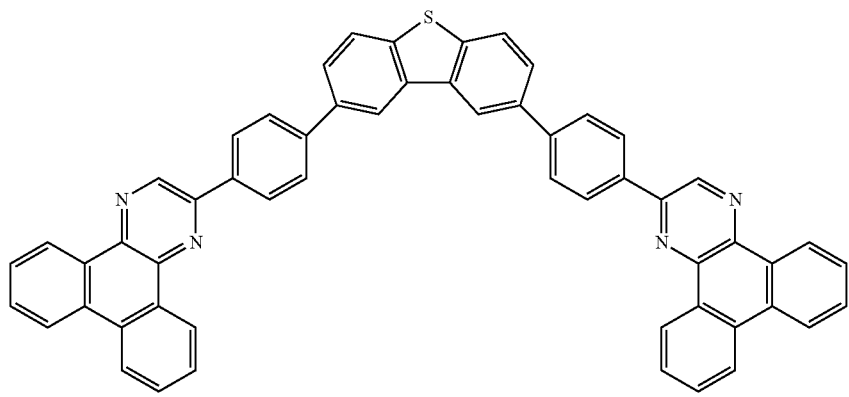

(107)
2,8pDBqP2DBt

Next, 0.53 g of the obtained solid was purified by train sublimation. In the purification by sublimation, the solid was heated at 420° C. under a pressure of $6.0 \times 10^{-2}$ Pa for 1.5 hours. After the purification by sublimation, 0.20 g of the target white powder was collected in 38%.

This compound was identified as 2,8pDBqP2DBt, which was the target substance, by electron impact-mass spectrometry (EI-MS).

The measurement result of EI-MS of the obtained compound is shown below. EI-MS[M+H]$^+$=793.3 (Exact Mass=792.2).

Figure 19A:
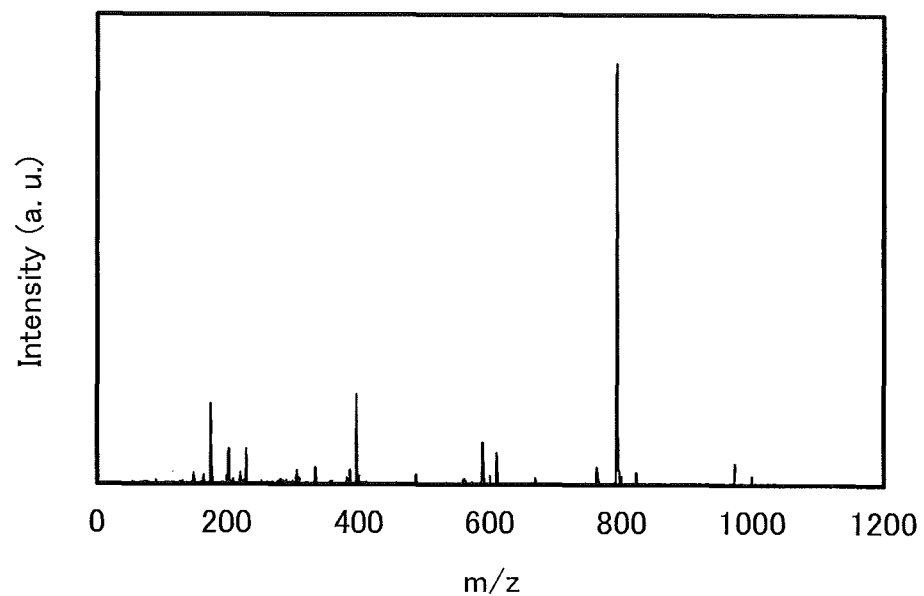
FIGS. 19A and 19B show measurement results of EI-MS of 2,8pDBqP2DBt.
Figure 19B:
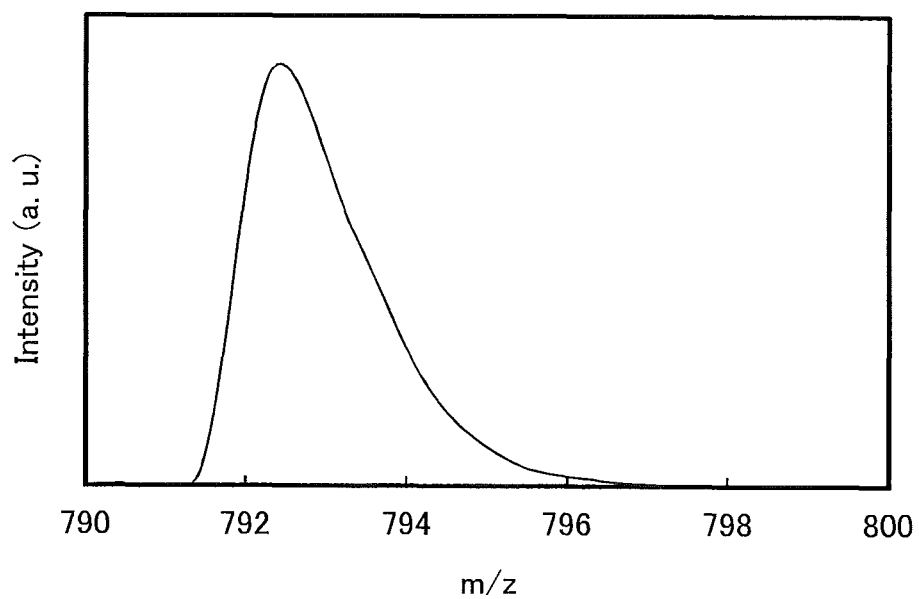

FIGS. 19A and 19B show measurement results of EI-MS. In each of FIGS. 19A and 19B, the horizontal axis represents m/z (mass-to-charge ratio) and the vertical axis represents intensity (arbitrary unit).

Figure 20A:
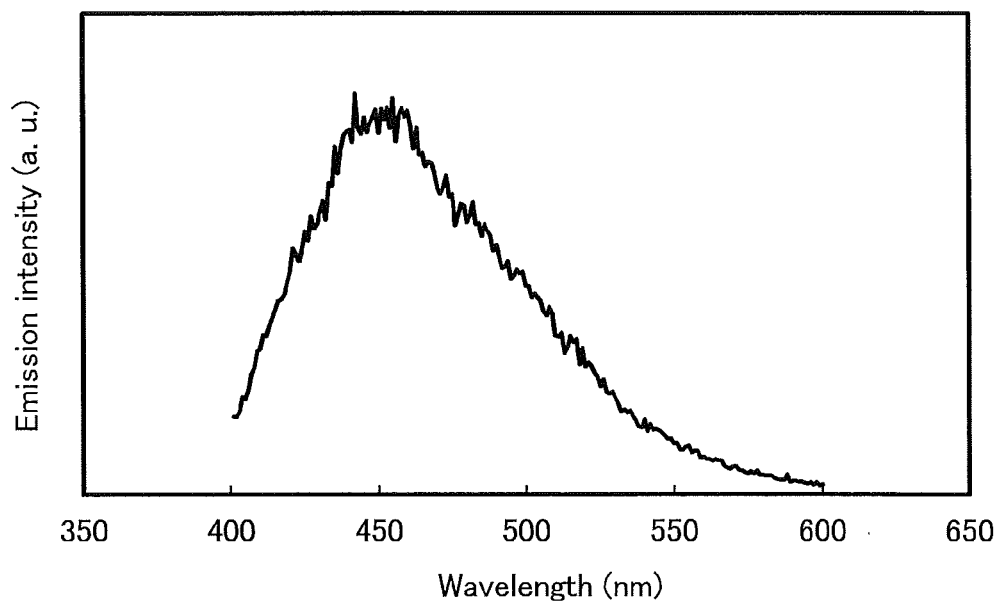
FIGS. 20A and 20B show an emission spectrum and an absorption spectrum of a dimethylformamide solution of 2,8pDBqP2DBt.
Figure 20B:
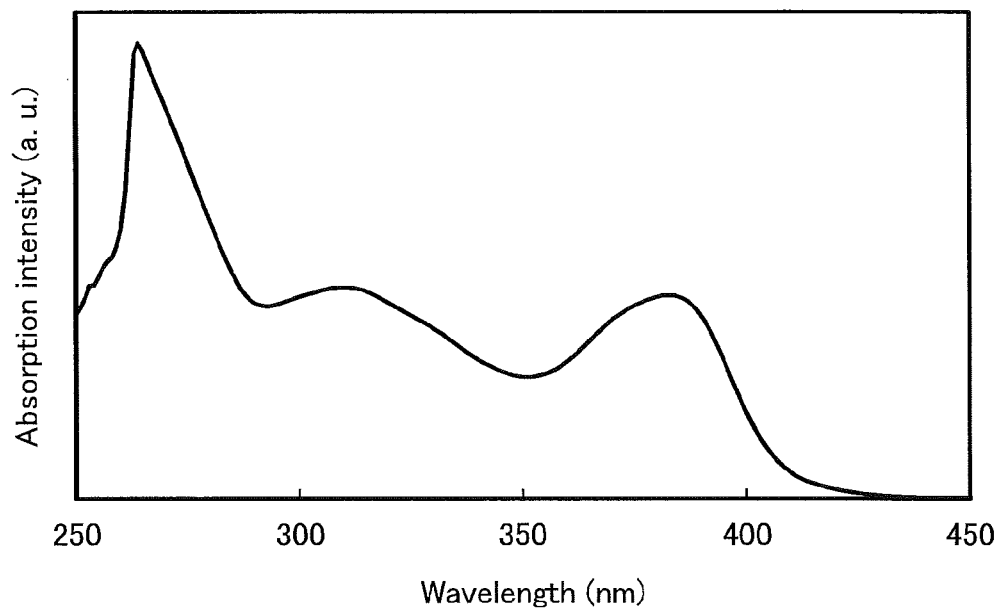
Figure 21A:
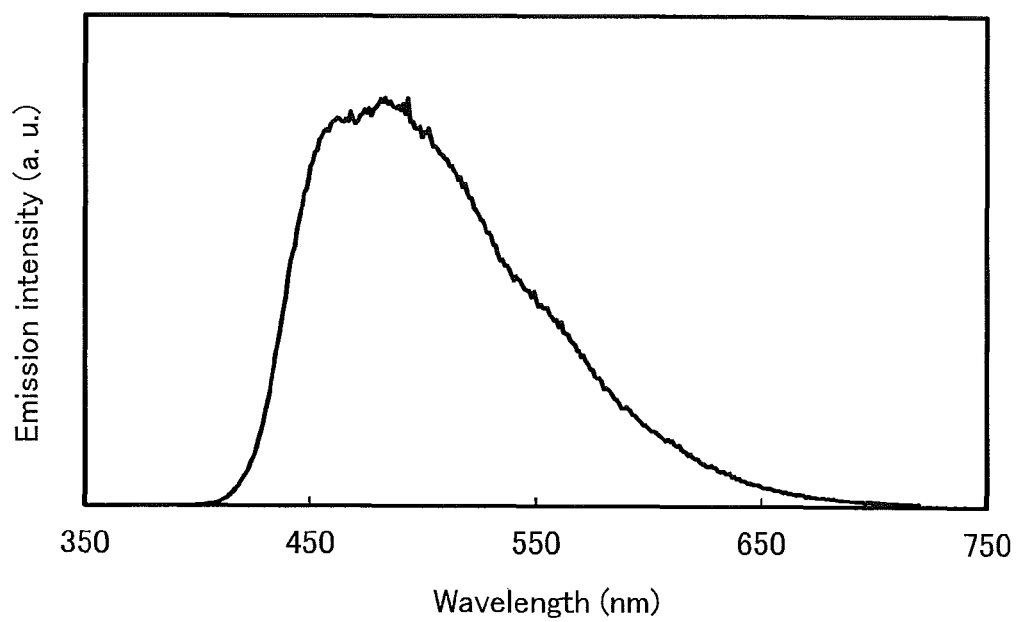
FIGS. 21A and 21B show an emission spectrum and an absorption spectrum of a thin film of 2,8pDBqP2DBt.
Figure 21B:
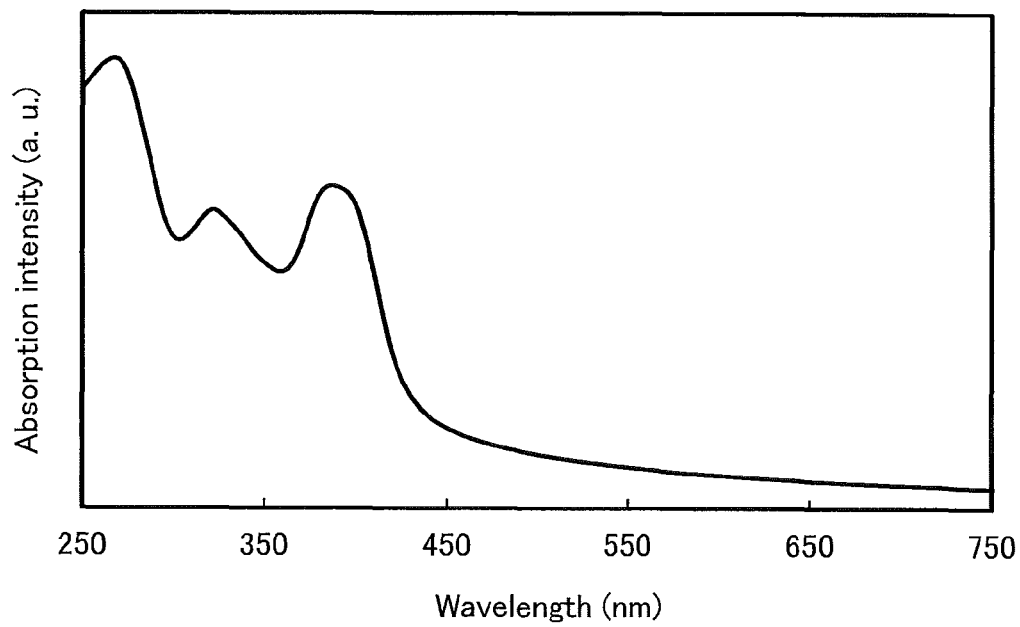

FIG. 20A shows an emission spectrum of 2,8pDBqP2DBt in a dimethylformamide solution and FIG. 20B shows an absorption spectrum thereof. FIG. 21A shows an emission spectrum of a thin film of 2,8pDBqP2DBt and FIG. 21B shows an absorption spectrum thereof. In each of FIG. 20A and FIG. 21A, the horizontal axis represents wavelength (nm) and the vertical axis represents emission intensity (arbitrary unit). In each of FIG. 20B and FIG. 21B, the horizontal axis represents wavelength (nm) and the vertical axis represents absorption intensity (arbitrary unit). In the case of the dimethylformamide solution, an emission peak is observed at 451 nm (excitation wavelength: 385 nm) and absorption peaks are observed at 264 nm, 309 nm, and 383 nm. In the case of the thin film, emission peaks are observed at 462 nm, 482 nm, 506 nm, and 553 nm (excitation wavelength: 382 nm) and absorption peaks are observed at 267 nm, 322 nm, 334 nm, 387 nm, and 396 nm.

Note that the absorption spectra were measured with the apparatus described in Example 1, and the emission spectra and absorption spectra were measured by the method described in Example 1.

The thermogravimetry-differential thermal analysis of 2,8pDBqP2DBt prepared in Synthesis example 5 was performed. The relationship between weight and temperature (thermogravimetry) shows that the 5% weight loss temperature of 2,8pDBqP2DBt is 500° C. or higher. Note that thermogravimetry-differential thermal analysis was performed using the apparatus and the method which are described in Example 1.

Example 6

Synthesis Example 6

In this example, a method of synthesizing 2,7-di[3-(2-dibenzo[f,h]quinoxalinyl)phenyl]-9-phenyl-9H-carbazole (abbreviation: mDBqP2PC) represented by Structural Formula (100) in Embodiment 1 will be described in detail. A structure of mDBqP2PC is shown below.

A synthesis scheme of mDBqP2PC is shown below.

Step 1: Synthesis of 3,6-dibromo-9-phenyl-9H-carbazole

First, into a 200-mL Mayer flask were put 3.7 g (15 mmol) of 9-phenyl-9H-carbazole, 5.4 g (30 mmol) of N-bromosuccinimide (abbreviation: NBS), and 75 mL of ethyl acetate. At room temperature, this solution was stirred in the air for 52 hours. Then, water was added thereto and this mixture was further stirred. An aqueous layer of the mixture was subjected to extraction with ethyl acetate three times. The extracted solution and an organic layer were combined, the mixture was washed with water and saturated saline, and then magnesium sulfate was added thereto. The obtained mixture was gravity-filtered and the filtrate was concentrated, so that 5.5 g of the target white powder was obtained in a yield of 92%. Synthesis scheme (F-1) of Step 1 is shown below.

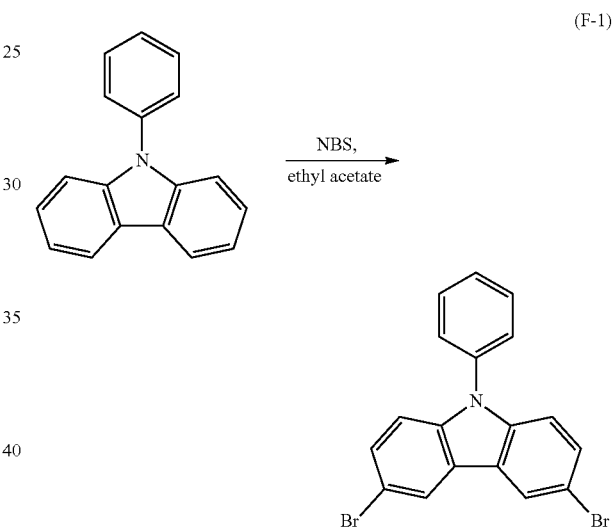

(F-1)

Step 2: Synthesis of 2-[3-(2-dibenzo[f,h]quinoxalinyl)phenyl]-4,4,5,5-tetramethyl-1,3,2-dioxaborolane Next, into a 100-mL three-neck flask were put 3.9 g (10 mmol) of 2-(3-bromophenyl)dibenzo[f,h]quinoxaline and

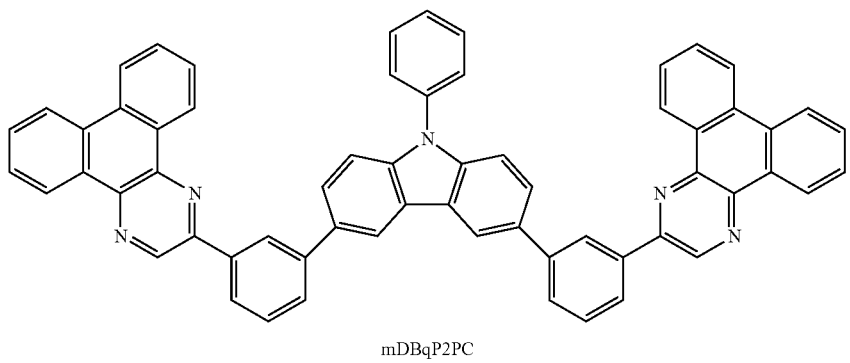

(100)

mDBqP2PC 3.8 g (15 mmol) of bis(pinacolato)diboron, and the atmosphere in the flask was replaced with nitrogen. After that, 33 mL of 1,4-dioxane, 2.9 g (30 mmol) of potassium acetate, and 0.41 g (0.58 mmol) of [1,1'-bis(diphenylphosphino)ferrocene]palladium(II)dichloride were added thereto, and the mixture was stirred at 90° C. for 5 hours. After the stirring, water was added to the obtained mixture to separate the mixture into an organic layer and an aqueous layer. The aqueous layer was subjected to extraction with toluene three times. The extracted solution and the organic layer were combined, the mixture was washed with saturated saline, and magnesium sulfate was added thereto. The mixture was gravity-filtered, and the filtrate was concentrated to give a brown solid. This solid was dissolved in toluene, and this solution was filtered through Celite (produced by Wako Pure Chemical Industries, Ltd., Catalog No. 531-16855). The obtained filtrate was concentrated to give 2.71 g of the target brown powder in a yield of 42%. Synthesis scheme (F-2) of Step 2 is shown below.

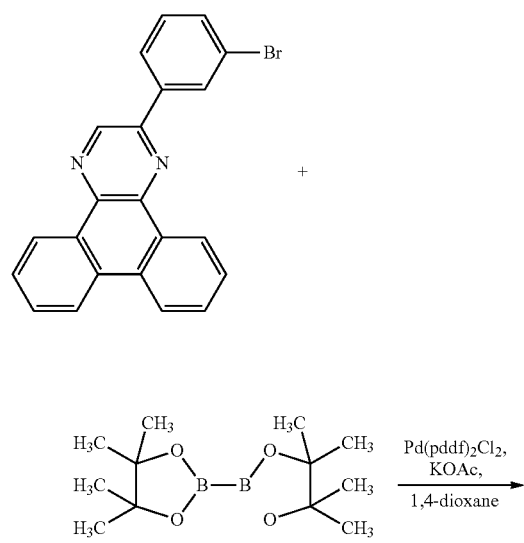

(F-2)

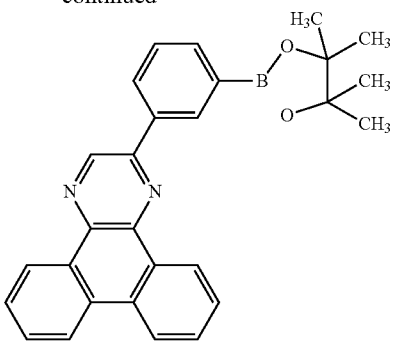

Step 3: Synthesis of 2,7-di[3-(2-dibenzo[f,h]quinoxalinyl)phenyl]-9-phenyl-9H-carbazole Next, into a 300-mL three-neck flask were put 6.1 g (14 mmol) of 2-[3-(2-dibenzo[f,h]quinoxalinyl)phenyl]-4,4,5,5-tetramethyl-1,3,2-dioxaborolane, 2.4 g (6.0 mmol) of 3,6-dibromo-9-phenyl-9H-carbazole, 0.18 g (0.59 mmol) of tris(2-methylphenyl)phosphine, 20 mL of a potassium carbonate solution (2 mol/L), 30 mL of toluene, and 3 mL of ethanol. This mixture was degassed by being stirred while the pressure in the flask was reduced. After the degassing, the atmosphere in the flask was replaced with nitrogen and then the mixture was heated to 80° C. At the same temperature, 30 mg (0.13 mmol) of palladium(II) acetate was added to the mixture, and stirring was performed at the same temperature for 3 hours. A precipitate was collected by suction filtration, and washed with water and ethanol. After the washing, the obtained solid was washed with dimethylformamide, so that 2.7 g of the target solid was obtained in a yield of 53%. Synthesis scheme (F-3) of Step 3 is shown below.

(F-3)

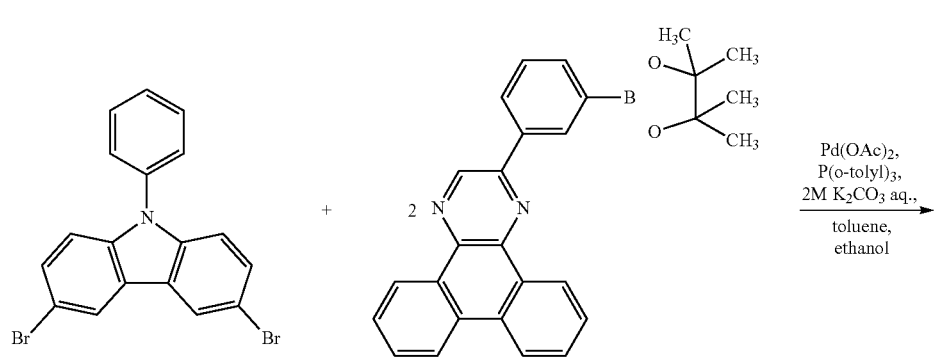

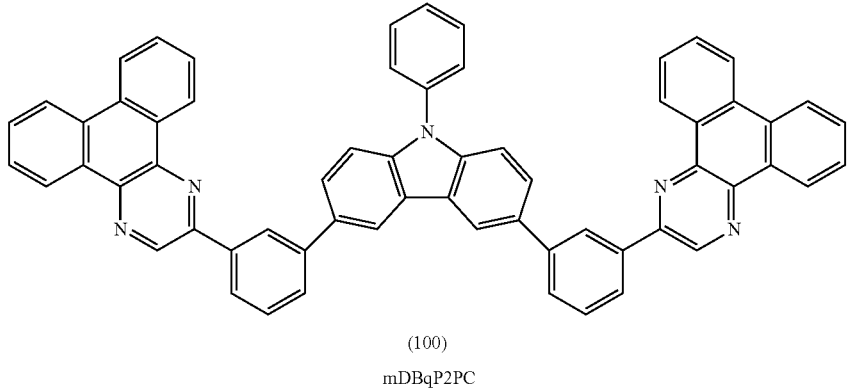

(100)
mDBqP2PC

Next, 1.2 g of the obtained solid was purified by train sublimation. In the purification by sublimation, the solid was heated at 420° C. under a pressure of 2.7 Pa with a flow rate of argon of 5 mL/min for 1 hour. After the purification by sublimation, 0.67 g of the target powder was collected in 56%.

This compound was identified as mDBqP2PC, which was the target substance, by nuclear magnetic resonance ($^1$H NMR).

$^1$H NMR data of the obtained compound is shown below.
$^1$H NMR (1,1,2,2-tetrachloroethane-d$_2$, 500 MHz): δ=7.57-7.59 (m, 1H), 7.66 (d, J=10 Hz, 2H), 7.72-7.86 (m, 14H), 7.91 (d, J=5.0 Hz, 2H), 7.98 (d, J=10 Hz, 2H), 8.35 (d, J=5.0 Hz, 2H), 8.64-8.68 (m, 6H), 8.75-7.66 (s, 2H), 9.26 (d, J=5.0 Hz, 2H), 9.44 (d, J=2.5 Hz, 1H), 9.46 (s, 1H), 9.54 (s, 2H).

Figure 22A:
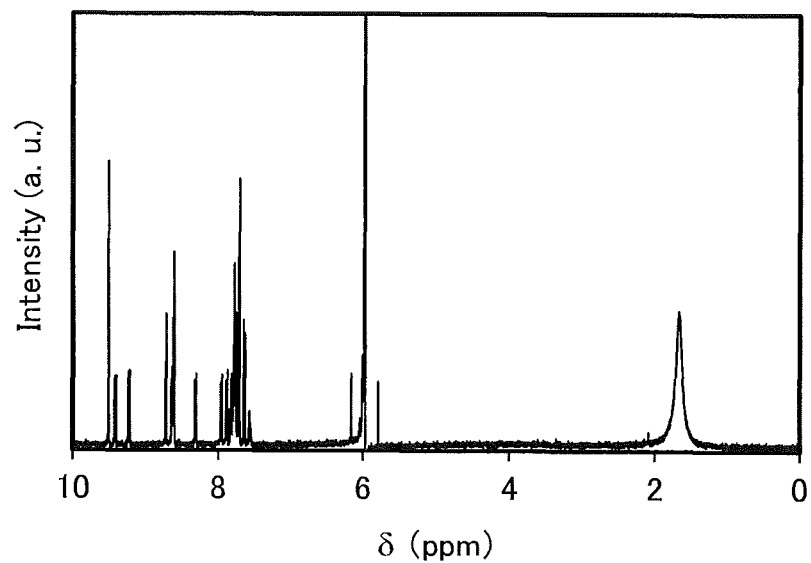
FIGS. 22A and 22B are $^1$H NMR charts of mDBqP2PC.
Figure 22B:
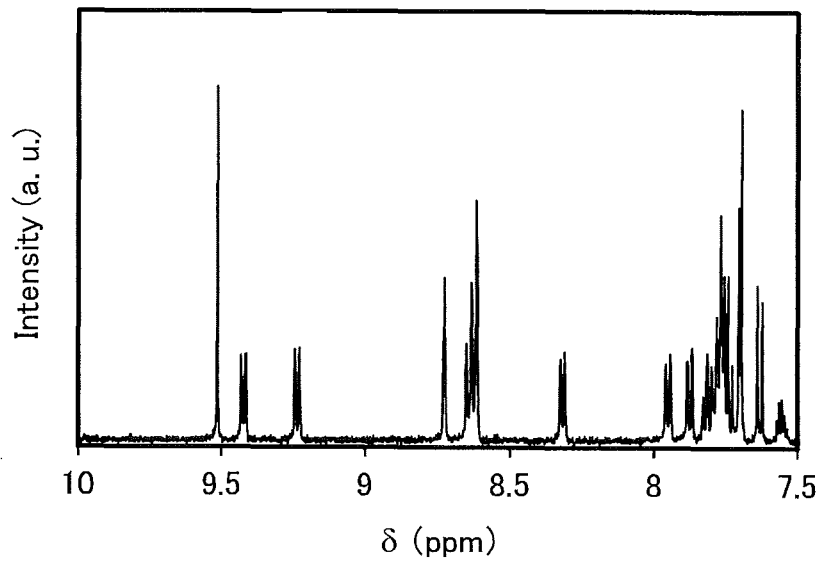

The $^1$H NMR charts are shown in FIGS. 22A and 22B. FIG. 22B is an enlarged chart showing a range of from 7.5 ppm to 10.0 ppm in FIG. 22A.

Figure 23A:
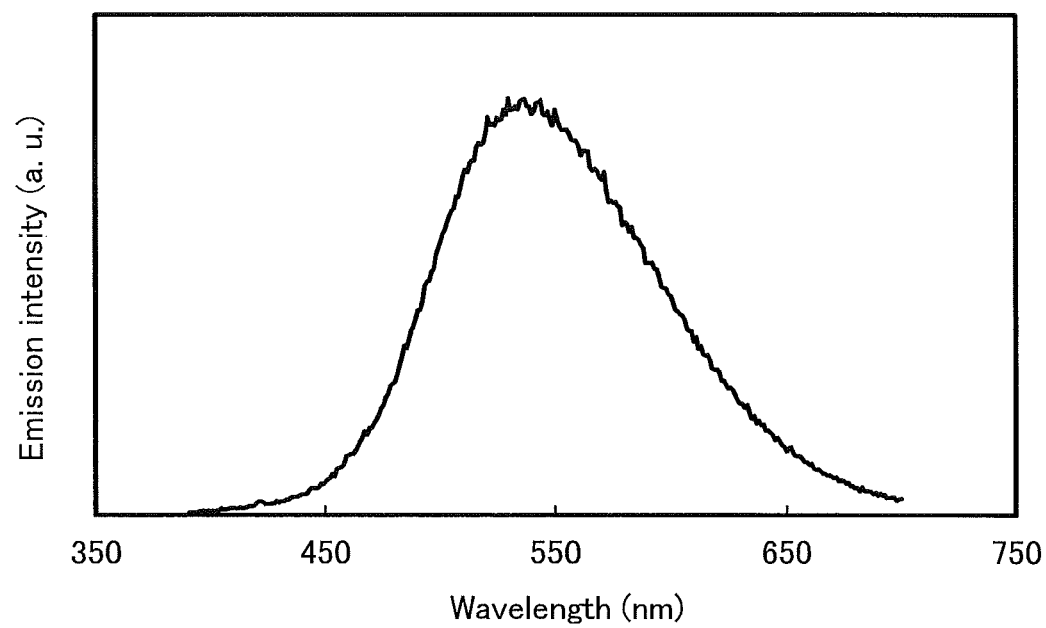
FIGS. 23A and 23B show an emission spectrum and an absorption spectrum of a dimethylformamide solution of mDBqP2PC.
Figure 23B:
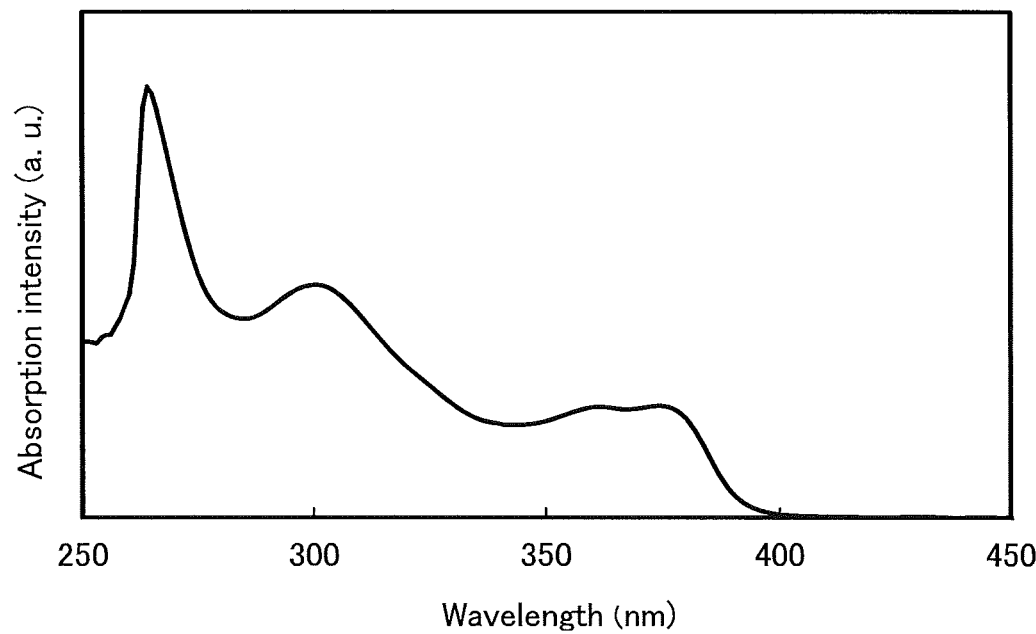
Figure 24A:
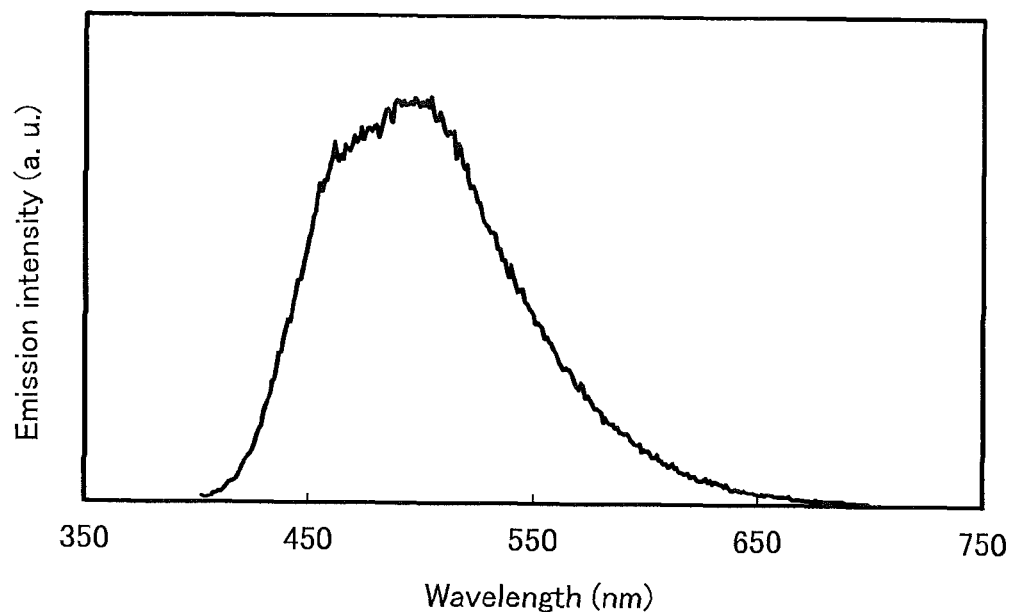
FIGS. 24A and 24B show an emission spectrum and an absorption spectrum of a thin film of mDBqP2PC.
Figure 24B:
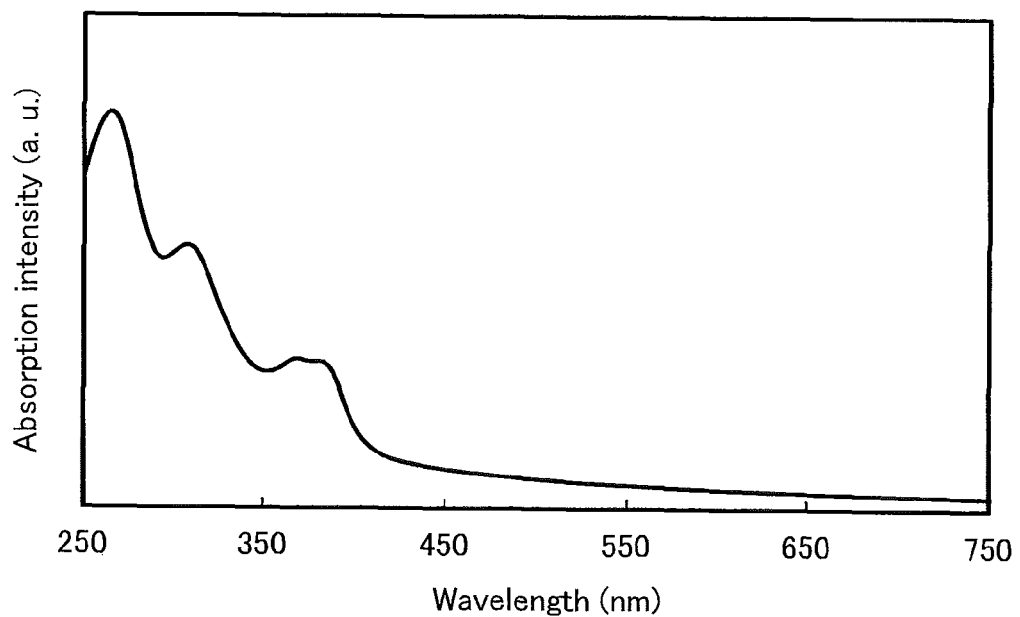

FIG. 23A shows the emission spectrum of mDBqP2PC in dimethylformamide, and FIG. 23B shows the absorption spectrum thereof. FIG. 24A shows the emission spectrum of a thin film of mDBqP2PC, and FIG. 24B shows the absorption spectrum thereof. In FIG. 23A and FIG. 24A, the horizontal axis represents wavelength (nm) and the vertical axis represents emission intensity (arbitrary unit). In FIG. 23B and FIG. 24B, the horizontal axis represents wavelength (nm) and the vertical axis represents absorption intensity (arbitrary unit). In the case of the dimethylformamide solution, an emission peak is observed at 536 nm (excitation wavelength: 376 nm), and absorption peaks are observed at 299 nm, 361 nm, and 374 nm. In the case of the thin film, emission peaks are observed at 479 nm and 497 nm (excitation wavelength: 387 nm) and absorption peaks are observed at 265 nm, 307 nm, 369 nm, and 381 nm.

Note that the absorption spectra were measured with the apparatus described in Example 1, and the emission spectra and absorption spectra were measured by the method described in Example 1.

The thermogravimetry-differential thermal analysis of mDBqP2PC prepared in Synthesis example 6 was performed. The relationship between weight and temperature (thermogravimetry) shows that the 5% weight loss temperature of mDBqP2PC is 500° C. or higher. Note that the thermogravimetry-differential thermal analysis was performed using the apparatus and the method which are described in Example 1.

Differential scanning calorimetry of mDBqP2PC prepared in Synthesis example 6 was performed. One cycle in the measurement was as follows: the temperature was increased from 30° C. to 500° C. at a rate of 50° C./min, kept at 500° C. for 1 minute, and decreased from 500° C. to 30° C. at a rate of 50° C./min. In this measurement, two cycles were performed. From the result at the rising temperature in the second cycle, it was found that the glass transition temperature (Tg) was 180° C. Therefore, mDBqP2PC has high heat resistance. Note that the differential scanning calorimeter was the same as that described in Example 1.

Example 7

Figure 25:
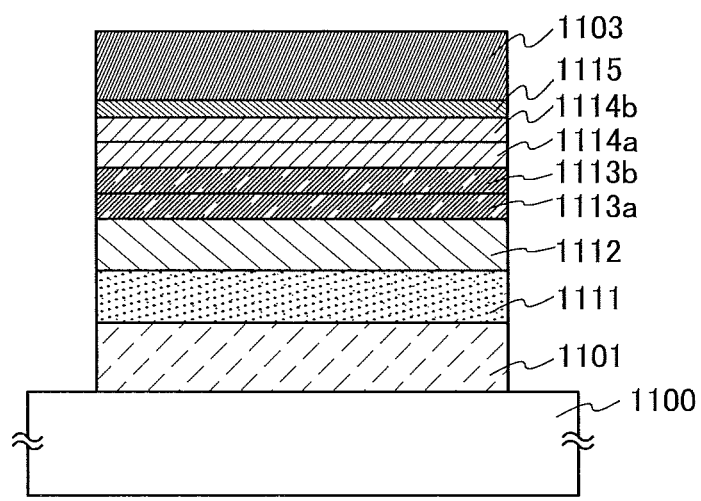
FIG. 25 illustrates a light-emitting element of Example.
Figure 26:
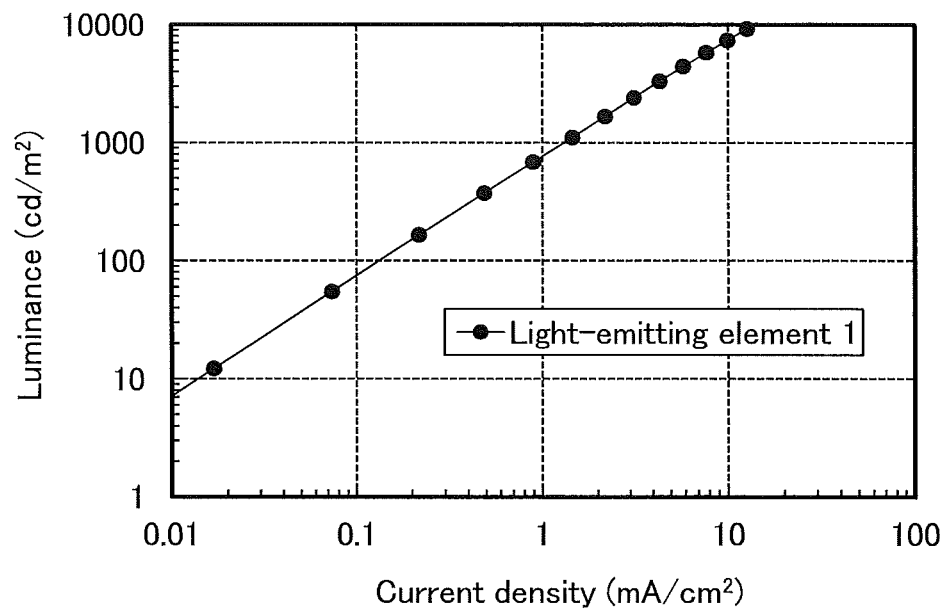
FIG. 26 shows current density-luminance characteristics of Light-emitting element 1 of Example.
Figure 27:
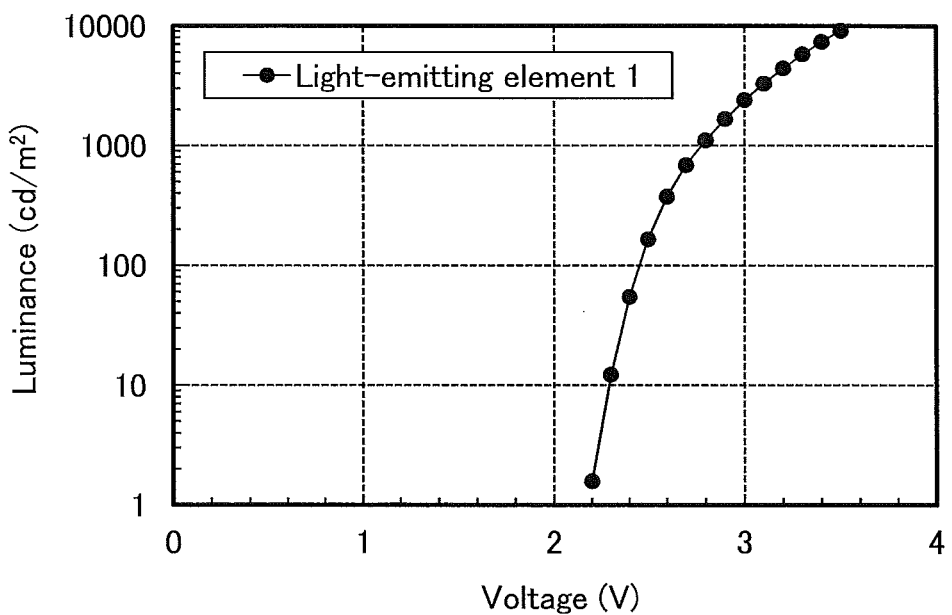
FIG. 27 shows voltage-luminance characteristics of Light-emitting element 1 of Example.
Figure 28:
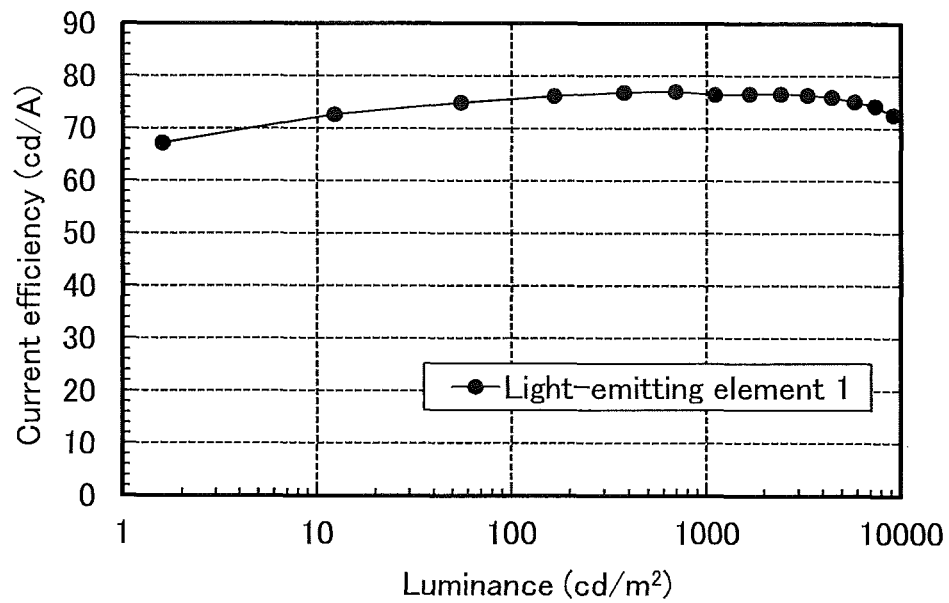
FIG. 28 shows luminance-current efficiency characteristics of Light-emitting element 1 of Example.
Figure 29:
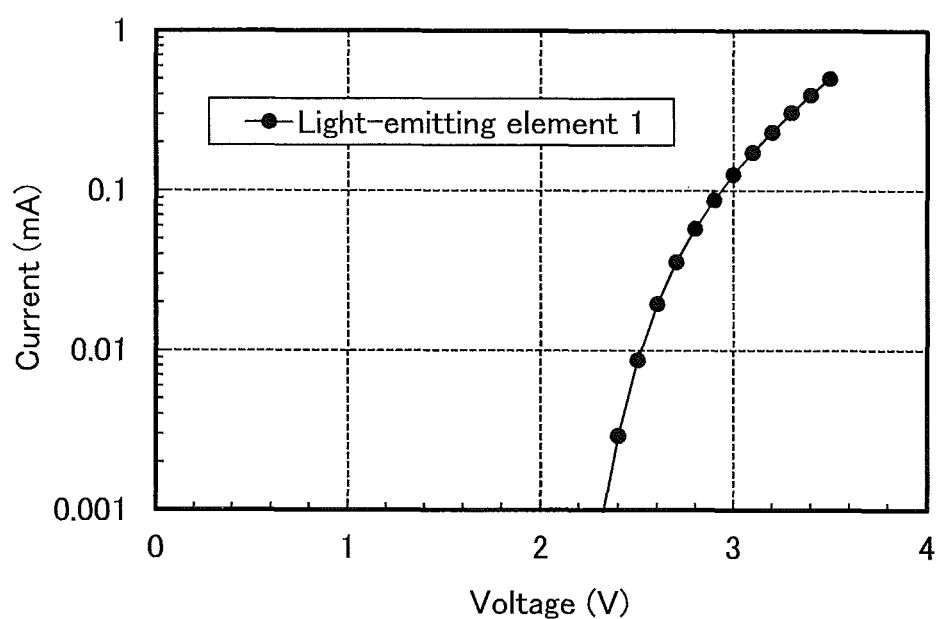
FIG. 29 shows voltage-current characteristics of Light-emitting element 1 of Example.

In this example, light-emitting elements (Light-emitting elements 1 to 6) of one embodiment of the present invention will be described with reference to FIG. 25. Chemical formulae of materials used in this example are shown below.

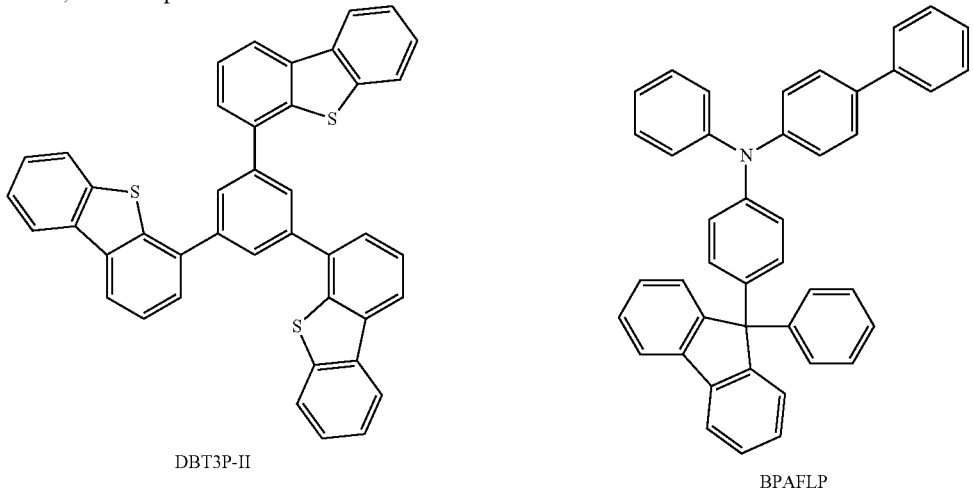

DBT3P-II

BPAFLP

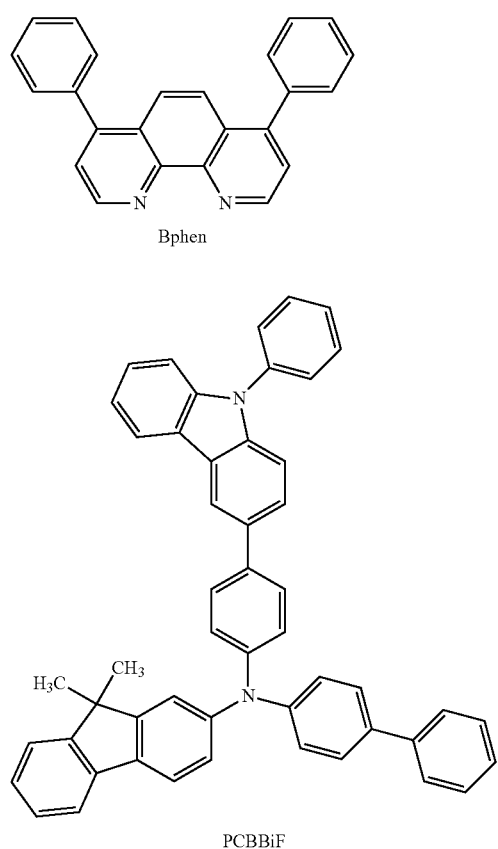
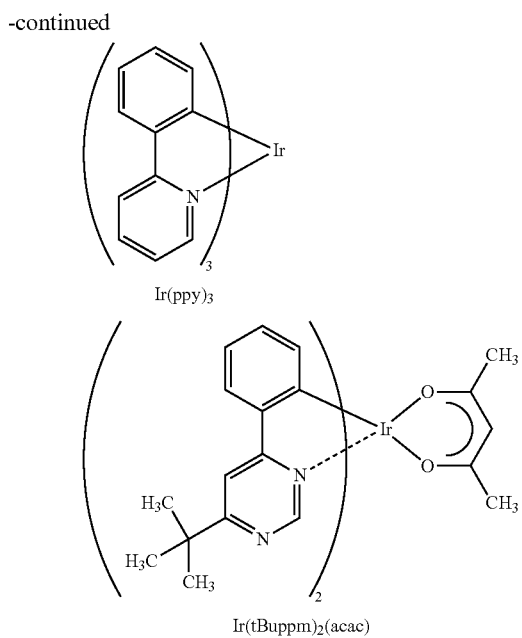
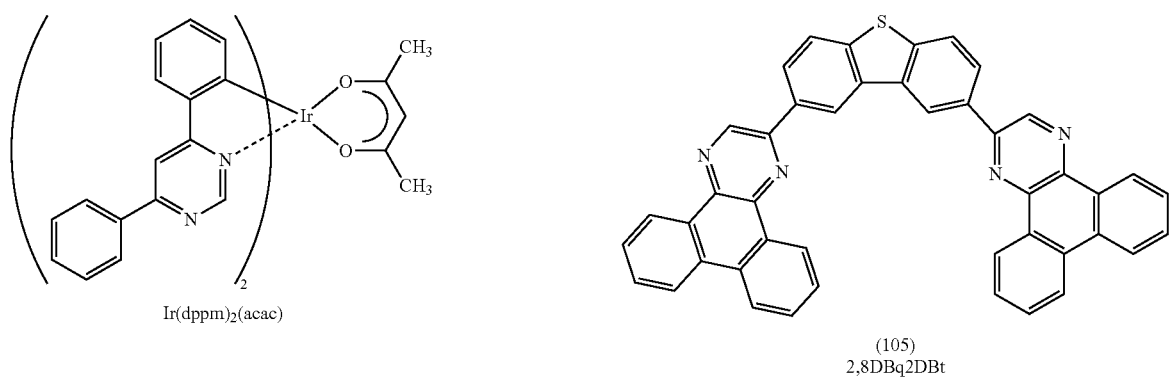
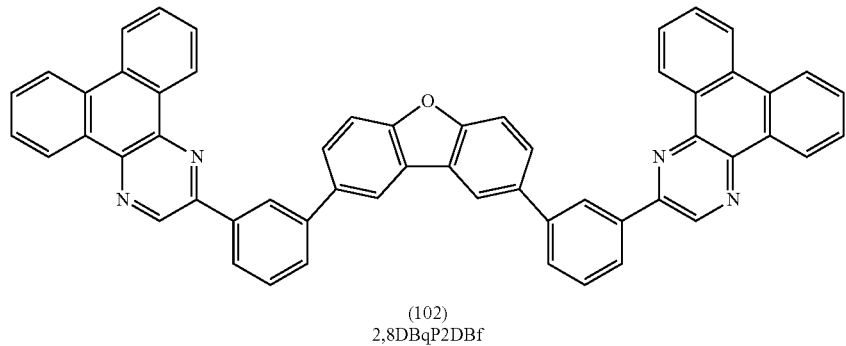

-continued

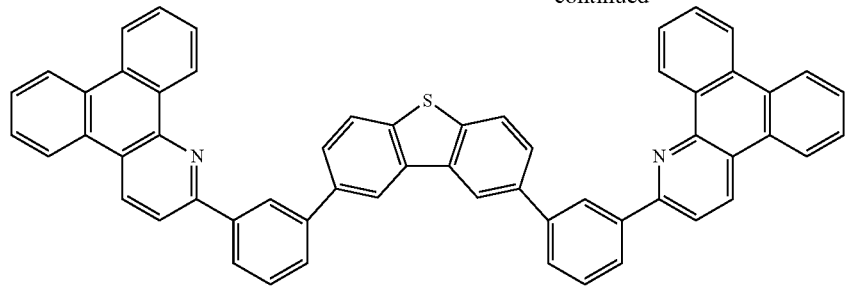

(183)
2,8DBQuP2DBt

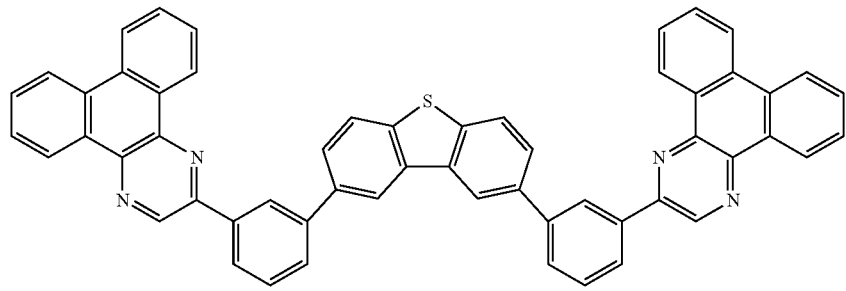

(101)
2,8mDBqP2DBT

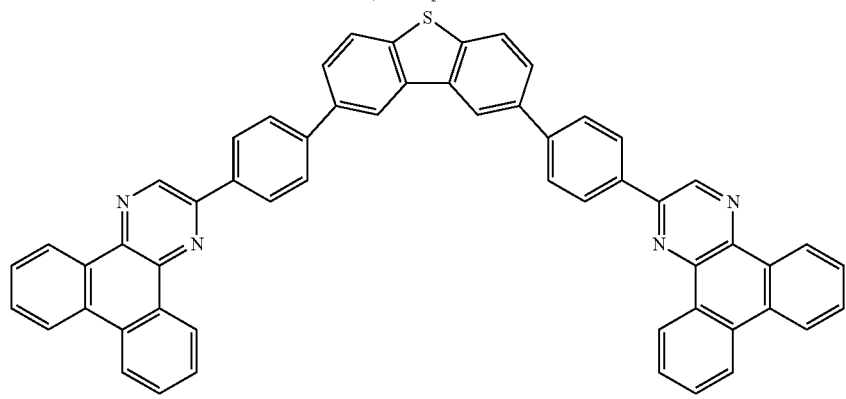

(107)
2,8pDBqP2DBt

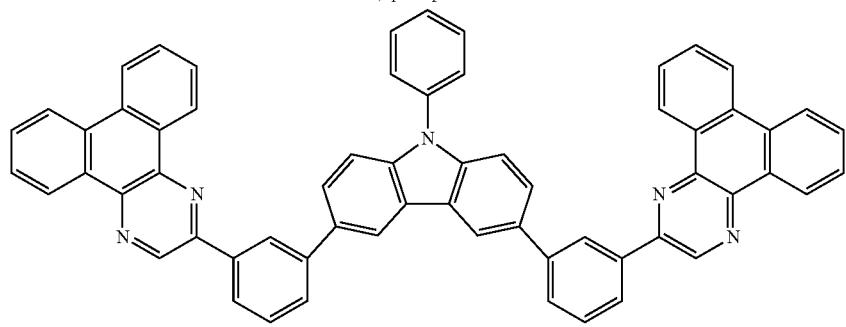

(100)
mDBqP2PC

Methods of manufacturing Light-emitting elements 1 to 6 of this example will be described below.

(Light-Emitting Element 1)

First, over a substrate 1100, an indium oxide-tin oxide containing silicon or silicon oxide (ITO—$SiO_2$, hereinafter abbreviated to ITSO) was deposited by a sputtering method, whereby a first electrode 1101 was formed. Note that the composition ratio of $In_2O_3$ to $SnO_2$ and $SiO_2$ in the target used was 85:10:5 [wt %]. The thickness of the first electrode 1101 was 110 nm and the electrode area was 2 mm×2 mm. Here, the first electrode 1101 is an electrode that functions as an anode of the light-emitting element.

Next, in pretreatment for forming the light-emitting element over the substrate 1100, UV ozone treatment was performed for 370 seconds after washing of a surface of the substrate with water and baking at 200° C. for 1 hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in a vacuum evaporation apparatus so that the surface on which the first electrode 1101 was formed faced downward. The pressure in the vacuum evaporation apparatus was reduced to about $10^{-4}$ Pa. After that, over the first electrode 1101, 4,4',4''-(benzene-1,3,5-triyl)tri(dibenzothiophene) (abbreviation: DBT3P-II) and molybdenum oxide were co-deposited by a co-evaporation method, whereby a hole-injection layer 1111 was formed. The thickness of the hole-injection layer 1111 was set to 20 nm, and the weight ratio of DBT3P-II to molybdenum oxide was adjusted to 2:1 (=DBT3P-II:molybdenum oxide). Note that the co-evaporation method refers to an evaporation method in which evaporation is carried out from a plurality of evaporation sources at the same time in one treatment chamber.

Next, on the hole-injection layer 1111, 4-phenyl-4'-(9-phenylfluoren-9-yl)triphenylamine (abbreviation: BPAFLP) was deposited to a thickness of 20 nm, whereby a hole-transport layer 1112 was formed.

Next, 2,2'-(dibenzothiophene-2,8-diyl)di(dibenzo[f,h]quinoxaline) (abbreviation: 2,8DBq2DBt) synthesized in Example 1, N-(1,1'-biphenyl-4-yl)-9,9-dimethyl-N-[4-(9-phenyl-9H-carbazol-3-yl)phenyl]-9H-fluoren-2-amine (abbreviation: PCBBiF), and (acetylacetonato)bis(4,6-diphenylpyrimidinato)iridium(III) (abbreviation: Ir(dppm)$_2$(acac)) were co-deposited by evaporation, whereby a first light-emitting layer 1113a was formed over the hole-transport layer 1112. Here, the weight ratio of 2,8DBq2DBt to PCBBiF and Ir(dppm)$_2$(acac) was adjusted to 0.7:0.3:0.05 (=2,8DBq2DBt:PCBBiF:Ir(dppm)$_2$(acac)). The thickness of the first light-emitting layer 1113a was set to 20 nm.

Next, 2,8DBq2DBt, PCBBiF, and Ir(dppm)$_2$(acac) were co-deposited by evaporation over the first light-emitting layer 1113a, whereby the second light-emitting layer 1113b was formed. Here, the weight ratio of 2,8DBq2DBt to PCBBiF and Ir(dppm)$_2$(acac) was adjusted to 0.8:0.2:0.05 (=2,8DBq2DBt:PCBBiF:Ir(dppm)$_2$(acac)). The thickness of the second light-emitting layer 1113b was set to 20 nm.

Note that in the first light-emitting layer 1113a and the second light-emitting layer 1113b, 2,8DBq2DBt has an electron-transport property and serves as a host material; PCBBiF has a hole-transport property and serves as an assist material; and Ir(dppm)$_2$(acac) converts triplet excitation energy into light emission and serves as a guest material.

Next, 2,8DBq2DBt was deposited by evaporation to a thickness of 20 nm on the second light-emitting layer 1113b, whereby a first electron-transport layer 1114a was formed.

Then, bathophenanthroline (abbreviation: BPhen) was deposited by evaporation to a thickness of 10 nm on the first electron-transport layer 1114a, whereby a second electron-transport layer 1114b was formed.

Next, lithium fluoride (LiF) was deposited by evaporation to a thickness of 1 nm on the second electron-transport layer 1114b, whereby an electron-injection layer 1115 was formed.

Then, aluminum was deposited by evaporation to a thickness of 200 nm over the electron-injection layer 1115, whereby a second electrode 1103 serving as a cathode was formed. Thus, Light-emitting element 1 of this example was fabricated.

Note that in all the above evaporation steps, evaporation was performed by a resistance heating method.

(Light-Emitting Element 2)

In Light-emitting element 2, materials of the first light-emitting layer 1113a, the second light-emitting layer 1113b, and the first electron-transport layer 1114a are different from those in Light-emitting element 1. Components of Light-emitting element 2 which are different from those of Light-emitting element 1 are described below.

Over the hole-transport layer 1112, 2,2'-[(dibenzofuran-2,8-diyl)di(3,1-phenylene)]di(dibenzo[f,h]quinoxaline) (abbreviation: 2,8DBqP2DBf) synthesized in Example 2, PCBBiF, and (acetylacetonato)bis(6-tert-butyl-4-phenylpyrimidinato)iridium(III) (abbreviation: Ir(tBuppm)$_2$(acac)) were co-deposited by evaporation, whereby the first light-emitting layer 1113a was formed. Here, the weight ratio of 2,8DBqP2DBf to PCBBiF and Ir(tBuppm)$_2$(acac) was adjusted to 0.7:0.3:0.05 (=2,8DBqP2DBf:PCBBiF:Ir(tBuppm)$_2$(acac)). The thickness of the first light-emitting layer 1113a was set to 20 nm.

Next, 2,8DBqP2DBf, PCBBiF, and Ir(tBuppm)$_2$(acac) were co-deposited by evaporation over the first light-emitting layer 1113a, whereby the second light-emitting layer 1113b was formed. Here, the weight ratio of 2,8DBqP2DBf to PCBBiF and Ir(tBuppm)$_2$(acac) was adjusted to 0.8:0.2:0.05 (=2,8DBqP2DBf:PCBBiF:Ir(tBuppm)$_2$(acac)). The thickness of the second light-emitting layer 1113b was set to 20 nm.

Note that in the first light-emitting layer 1113a and the second light-emitting layer 1113b, 2,8DBqP2DBf has an electron-transport property and serves as a host material; PCBBiF has a hole-transport property and serves as an assist material; and Ir(tBuppm)$_2$(acac) converts triplet excitation energy into light emission and serves as a guest material.

Next, 2,8DBqP2DBf was deposited by evaporation to a thickness of 15 nm on the second light-emitting layer 1113b, whereby the first electron-transport layer 1114a was formed.

(Light-Emitting Element 3)

In Light-emitting element 3, materials of the first light-emitting layer 1113a, the second light-emitting layer 1113b, and the first electron-transport layer 1114a are different from those in Light-emitting element 1. Components of Light-emitting element 3 which are different from those of Light-emitting element 1 are described below.

Over the hole-transport layer 1112, 2,2'-[(dibenzothiophene-2,8-diyl)di(3,1-phenylene)]di(dibenzo[f,h]quinoline) (abbreviation: 2,8DBQuP2DBt) synthesized in Example 3 and tris(2-phenylpyridinato-N,C$^{2'}$)iridium(III) (abbreviation: Ir(ppy)$_3$) were co-deposited by evaporation, whereby the first light-emitting layer 1113a was formed. Here, the weight ratio of 2,8DBQuP2DBt to Ir(ppy)$_3$ was adjusted to 1:0.08 (=2,8DBQuP2DBt:Ir(ppy)$_3$). The thickness of the first light-emitting layer 1113a was set to 20 nm.

Next, 2,8DBQuP2DBt and Ir(ppy)$_3$ were co-deposited by evaporation over the first light-emitting layer 1113a, whereby the second light-emitting layer 1113b was formed. Here, the weight ratio of 2,8DBQuP2DBt to Ir(ppy)$_3$ was adjusted to 1:0.04 (=2,8DBQuP2DBt:Ir(ppy)$_3$). The thickness of the second light-emitting layer 1113b was set to 20 nm.

Note that in the first light-emitting layer 1113a and the second light-emitting layer 1113b, 2,8DBQuP2DBt has an electron-transport property and serves as a host material; and Ir(ppy)$_3$ converts triplet excitation energy into light emission and serves as a guest material.

Next, 2,8DBQuP2DBt was deposited by evaporation to a thickness of 15 nm on the second light-emitting layer 1113b, whereby the first electron-transport layer 1114a was formed.

(Light-Emitting Element 4)

In Light-emitting element 4, materials of the first light-emitting layer 1113a, the second light-emitting layer 1113b, and the first electron-transport layer 1114a are different from those in Light-emitting element 1. Components of Light-emitting element 4 which are different from those of Light-emitting element 1 are described below.

Over the hole-transport layer 1112, 2,2'-[(dibenzothiophene-2,8-diyl)di(3,1-phenylene)]di(dibenzo[f,h]quinoxaline) (abbreviation: 2,8mDBqP2DBT) synthesized in Example 4, PCBBiF, and Ir(tBuppm)$_2$(acac) were co-deposited by evaporation, whereby a first light-emitting layer 1113a was formed. Here, the weight ratio of 2,8mDBqP2DBT to PCBBiF and Ir(tBuppm)$_2$(acac) was adjusted to 0.7:0.3:0.05 (=2,8mDBqP2DBT:PCBBiF:Ir(tBuppm)$_2$(acac)). The thickness of the first light-emitting layer 1113a was set to 20 nm.

Next, 2,8mDBqP2DBT, PCBBiF, and Ir(tBuppm)$_2$(acac) were co-deposited by evaporation over the first light-emitting layer 1113a, whereby the second light-emitting layer 1113b was formed. Here, the weight ratio of 2,8mDBqP2DBT to PCBBiF and Ir(tBuppm)$_2$(acac) was adjusted to 0.8:0.2:0.05 (=2,8mDBqP2DBT:PCBBiF:Ir(tBuppm)$_2$(acac)). The thickness of the second light-emitting layer 1113b was set to 20 nm.

Note that in the first light-emitting layer 1113a and the second light-emitting layer 1113b, 2,8mDBqP2DBT has an electron-transport property and serves as a host material; PCBBiF has a hole-transport property and serves as an assist material; and Ir(tBuppm)$_2$(acac) converts triplet excitation energy into light emission and serves as a guest material.

Next, 2,8mDBqP2DBT was deposited by evaporation to a thickness of 15 nm on the second light-emitting layer 1113b, whereby the first electron-transport layer 1114a was formed.

(Light-Emitting Element 5)

In Light-emitting element 5, the thickness of the second electron-transport layer and materials of the first light-emitting layer 1113a, the second light-emitting layer 1113b, and the first electron-transport layer 1114a are different from those in Light-emitting element 1. Components of Light-emitting element 5 which are different from those of Light-emitting element 1 are described below.

Over the hole-transport layer 1112, 2,2'-[(dibenzothiophene-2,8-diyl)di(4,1-phenylene)]di(dibenzo[f,h]quinoxaline) (abbreviation: 2,8pDBqP2DBt) synthesized in Example 5, PCBBiF, and Ir(dppm)$_2$(acac) were co-deposited by evaporation, whereby the first light-emitting layer 1113a was formed. Here, the weight ratio of 2,8pDBqP2DBt to PCBBiF and Ir(dppm)$_2$(acac) was adjusted to 0.7:0.3: 0.05 (=2,8pDBqP2DBt:PCBBiF:Ir(dppm)$_2$(acac)). The thickness of the first light-emitting layer 1113a was set to 20 nm.

Next, 2,8pDBqP2DBt, PCBBiF, and Ir(dppm)$_2$(acac) were co-deposited by evaporation over the first light-emitting layer 1113a, whereby the second light-emitting layer 1113b was formed. Here, the weight ratio of 2,8pDBqP2DBt to PCBBiF and Ir(dppm)$_2$(acac) was adjusted to 0.8:0.2: 0.05 (=2,8pDBqP2DBt:PCBBiF:Ir(dppm)$_2$(acac)). The thickness of the second light-emitting layer 1113b was set to 20 nm.

Note that in the first light-emitting layer 1113a and the second light-emitting layer 1113b, 2,8pDBqP2DBt has an electron-transport property and serves as a host material; PCBBiF has a hole-transport property and serves as an assist material; and Ir(dppm)$_2$(acac) converts triplet excitation energy into light emission and serves as a guest material.

Next, 2,8pDBqP2DBt was deposited by evaporation to a thickness of 20 nm on the second light-emitting layer 1113b, whereby the first electron-transport layer 1114a was formed.

Next, BPhen was deposited by evaporation to a thickness of 15 nm on the first electron-transport layer 1114a, whereby the second electron-transport layer 1114b was formed.

(Light-Emitting Element 6)

In Light-emitting element 6, materials of the first light-emitting layer 1113a, the second light-emitting layer 1113b, and the first electron-transport layer 1114a are different from those in Light-emitting element 1. Components of Light-emitting element 6 which are different from those of Light-emitting element 1 are described below.

Over the hole-transport layer 1112, 2,7-di[3-(2-dibenzo[f,h]quinoxalinyl)phenyl]-9-phenyl-9H-carbazole (abbreviation: mDBqP2PC) synthesized in Example 6, PCBBiF, and Ir(dppm)$_2$(acac) were co-deposited by evaporation, whereby the first light-emitting layer 1113a was formed. Here, the weight ratio of mDBqP2PC to PCBBiF and Ir(dppm)$_2$(acac) was adjusted to 0.7:0.3:0.05 (=mDBqP2PC:PCBBiF:Ir(dppm)$_2$(acac)). The thickness of the first light-emitting layer 1113a was set to 20 nm.

Next, mDBqP2PC, PCBBiF, and Ir(dppm)$_2$(acac) were co-deposited by evaporation over the first light-emitting layer 1113a, whereby the second light-emitting layer 1113b was formed. Here, the weight ratio of mDBqP2PC to PCBBiF and Ir(dppm)$_2$(acac) was adjusted to 0.8:0.2: 0.05 (=mDBqP2PC:PCBBiF:Ir(dppm)$_2$(acac)). The thickness of the second light-emitting layer 1113b was set to 20 nm.

Note that in the first light-emitting layer 1113a and the second light-emitting layer 1113b, mDBqP2PC has an electron-transport property and serves as a host material; PCBBiF has a hole-transport property and serves as an assist material; and Ir(dppm)$_2$(acac) converts triplet excitation energy into light emission and serves as a guest material.

Next, mDBqP2PC was deposited by evaporation to a thickness of 20 nm on the second light-emitting layer 1113b, whereby the first electron-transport layer 1114a was formed.

Table 1 shows element structures of Light-emitting elements 1 to 6 obtained as described above.

TABLE 1

| | First electrode | Hole-injection layer | Hole-transport layer | First light-emitting layer | Second light-emitting layer | First electron-transport layer | Second electron-transport layer | Electron injection layer | Second electrode |
|---|---|---|---|---|---|---|---|---|---|
| Light-emitting element 1 | ITSO 110 nm | DBT3P-II:MoOx (=2:1) 20 nm | BPAFLP 20 nm | v.i. | v.i. | 2,8DBq2DBt 20 nm | Bphen 10 nm | LiF 1 nm | Al 200 nm |

TABLE 1-continued

| | | | | | | | | | | |
|---|---|---|---|---|---|---|---|---|---|---|
| Light-emitting element 2 | ITSO 110 nm | DBT3P-II:MoOx (=2:1) 20 nm | BPAFLP 20 nm | v.i. | v.i. | 2,8DBqP2DBf 15 nm | Bphen 10 nm | LiF 1 nm | Al 200 nm | |
| Light-emitting element 3 | ITSO 110 nm | DBT3P-II:MoOx (=2:1) 20 nm | BPAFLP 20 nm | v.i. | v.i. | 2,8DBQuP2DBt 15 nm | Bphen 10 nm | LiF 1 nm | Al 200 nm | |
| Light-emitting element 4 | ITSO 110 nm | DBT3P-II:MoOx (=2:1) 20 nm | BPAFLP 20 nm | v.i. | v.i. | 2,8mDBqP2DBT 15 nm | Bphen 10 nm | LiF 1 nm | Al 200 nm | |
| Light-emitting element 5 | ITSO 110 nm | DBT3P-II:MoOx (=2:1) 20 nm | BPAFLP 20 nm | v.i. | v.i. | 2,8pDBqP2DBt 20 nm | Bphen 15 nm | LiF 1 nm | Al 200 nm | |
| Light-emitting element 6 | ITSO 110 nm | DBT3P-II:MoOx (=2:1) 20 nm | BPAFLP 20 nm | v.i. | v.i. | mDBqP2PC 20 nm | Bphen 10 nm | LiF 1 nm | Al 200 nm | |

| | First light-emitting layer | Second light-emitting layer |
|---|---|---|
| Light-emitting element 1 | 2,8DBq2DBt:PCBBiF:Ir(dppm)$_2$(acac) (=0.7:0.3:0.05) 20 nm | 2,8DBq2DBt:PCBBiF:Ir(dppm)$_2$(acac) (=0.8:0.2:0.05) 20 nm |
| Light-emitting element 2 | 2,8DBqP2DBf:PCBBiF:Ir(tBuppm)$_2$(acac) (=0.7:0.3:0.05) 20 nm | 2,8DBqP2DBf:PCBBiF:Ir(tBuppm)$_2$(acac) (=0.8:0.2:0.05) 20 nm |
| Light-emitting element 3 | 2,8DBQuP2DBt:Ir(ppy)$_3$ (=1:0.08) 20 nm | 2,8DBQuP2DBt:Ir(ppy)$_3$ (=1:0.04) 20 nm |
| Light-emitting element 4 | 2,8mDBqP2DBT:PCBBiF:Ir(tBuppm)2(acac) (=0.7:0.3:0.05) 20 nm | 2,8mDBqP2DBT:PCBBiF:Ir(tBuppm)$_2$(acac) (=0.8:0.2:0.05) 20 nm |
| Light-emitting element 5 | 2,8pDBqP2DBt:PCBBiF:Ir(dppm)$_2$(acac) (=0.7:0.3:0.05) 20 nm | 2,8pDBqP2DBt:PCBBiF:Ir(dppm)$_2$(acac) (=0.8:0.2:0.05) 20 nm |
| Light-emitting element 6 | mDBqP2PC:PCBBiF:Ir(dppm)$_2$(acac) (=0.7:0.3:0.05) 20 nm | mDBqP2PC:PCBBiF:Ir(dppm)$_2$(acac) (=0.8:0.2:0.05) 20 nm |

In a glove box containing a nitrogen atmosphere, Light-emitting elements 1 to 6 were each sealed with a glass substrate so as not to be exposed to the air (specifically, a sealant was applied onto an outer edge of the element and heat treatment was performed at 80° C. for 1 hour at the time of sealing). Then, operation characteristics of the light-emitting elements were measured. Note that the measurements were carried out at room temperature (in the atmosphere kept at 25° C.).

FIG. 26, FIG. 32, FIG. 38, FIG. 44, FIG. 50, and FIG. 56 show current density-luminance characteristics of Light-emitting element 1, Light-emitting element 2, Light-emitting element 3, Light-emitting element 4, Light-emitting element 5, and Light-emitting element 6, respectively. In each of FIG. 26, FIG. 32, FIG. 38, FIG. 44, FIG. 50, and FIG. 56, the horizontal axis represents current density (mA/cm$^2$) and the vertical axis represents luminance (cd/m$^2$). FIG. 27, FIG. 33, FIG. 39, FIG. 45, FIG. 51, and FIG. 57 show voltage-luminance characteristics of Light-emitting element 1, Light-emitting element 2, Light-emitting element 3, Light-emitting element 4, Light-emitting element 5, and Light-emitting element 6, respectively. In each of FIG. 27, FIG. 33, FIG. 39, FIG. 45, FIG. 51, and FIG. 57, the horizontal axis represents voltage (V) and the vertical axis represents luminance (cd/m$^2$). FIG. 28, FIG. 34, FIG. 40, FIG. 46, FIG. 52, and FIG. 58 show luminance-current efficiency characteristics of Light-emitting element 1, Light-emitting element 2, Light-emitting element 3, Light-emitting element 4, Light-emitting element 5, and Light-emitting element 6, respectively. In each of FIG. 28, FIG. 34, FIG. 40, FIG. 46, FIG. 52, and FIG. 58, the horizontal axis represents luminance (cd/m$^2$) and the vertical axis represents current efficiency (cd/A). FIG. 29, FIG. 35, FIG. 41, FIG. 47, FIG. 53, and FIG. 59 show voltage-current characteristics of Light-emitting element 1, Light-emitting element 2, Light-emitting element 3, Light-emitting element 4, Light-emitting element 5, and Light-emitting element 6, respectively. In each of FIG. 29, FIG. 35, FIG. 41, FIG. 47, FIG. 53, and FIG. 59, the horizontal axis represents voltage (V) and the vertical axis represents current (mA).

Table 2 shows voltage (V), current density (mA/cm$^2$), CIE chromaticity coordinates (x, y), current efficiency (cd/A), and external quantum efficiency (%) of each light-emitting element at a luminance of 500 cd/m$^2$ to 1000 cd/m$^2$.

TABLE 2

| | Voltage (V) | Current density (mA/cm$^2$) | chromaticity coordinates (x, y) | | Luminance (cd/m$^2$) | current efficiency (cd/A) | External quantum efficiency (%) |
|---|---|---|---|---|---|---|---|
| Light-emitting element 1 | 2.7 | 0.9 | 0.55 | 0.45 | 688 | 77 | 28 |

TABLE 2-continued

| | Voltage (V) | Current density (mA/cm²) | chromaticity coordinates (x, y) | | Luminance (cd/m²) | current efficiency (cd/A) | External quantum efficiency (%) |
|---|---|---|---|---|---|---|---|
| Light-emitting element 2 | 2.8 | 1.0 | 0.42 | 0.57 | 980 | 99 | 26 |
| Light-emitting element 3 | 3.2 | 1.3 | 0.36 | 0.61 | 868 | 67 | 13 |
| Light-emitting element 4 | 2.7 | 0.7 | 0.41 | 0.58 | 725 | 100 | 26 |
| Light-emitting element 5 | 3.0 | 1.7 | 0.57 | 0.43 | 730 | 43 | 18 |
| Light-emitting element 6 | 2.8 | 0.8 | 0.56 | 0.44 | 645 | 76 | 28 |

Figure 30:
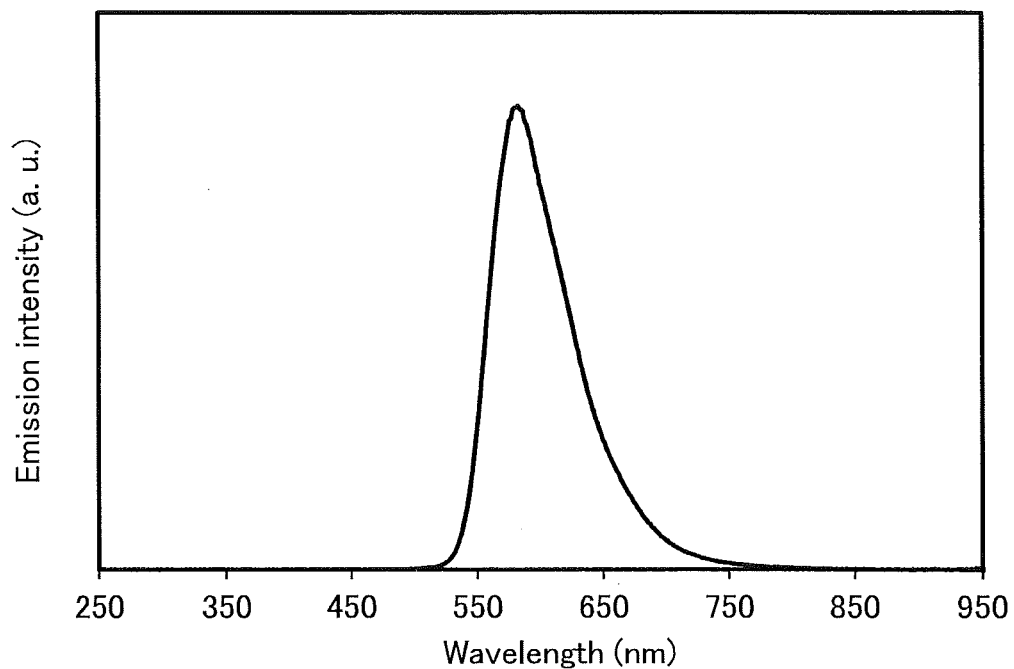
FIG. 30 shows an emission spectrum of Light-emitting element 1 of Example.
Figure 36:
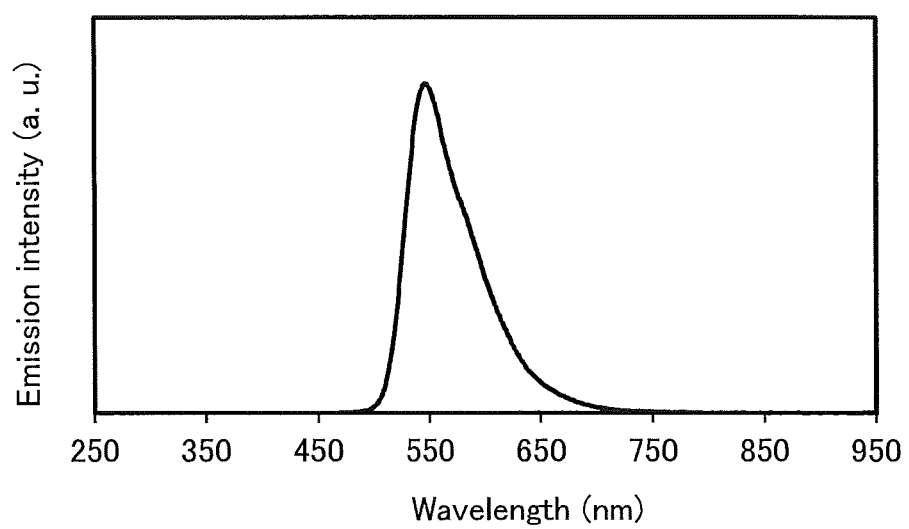
FIG. 36 shows an emission spectrum of Light-emitting element 2 of Example.
Figure 42:
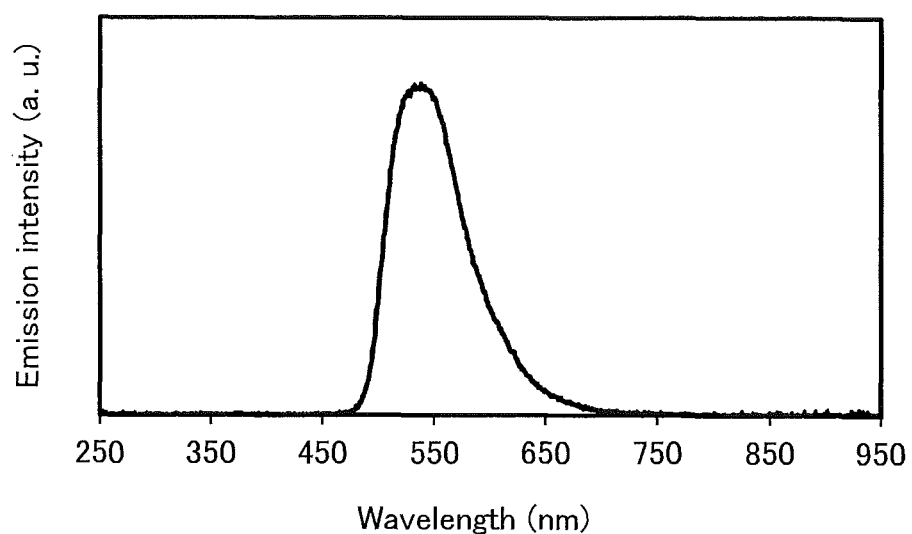
FIG. 42 shows an emission spectrum of Light-emitting element 3 of Example.
Figure 48:
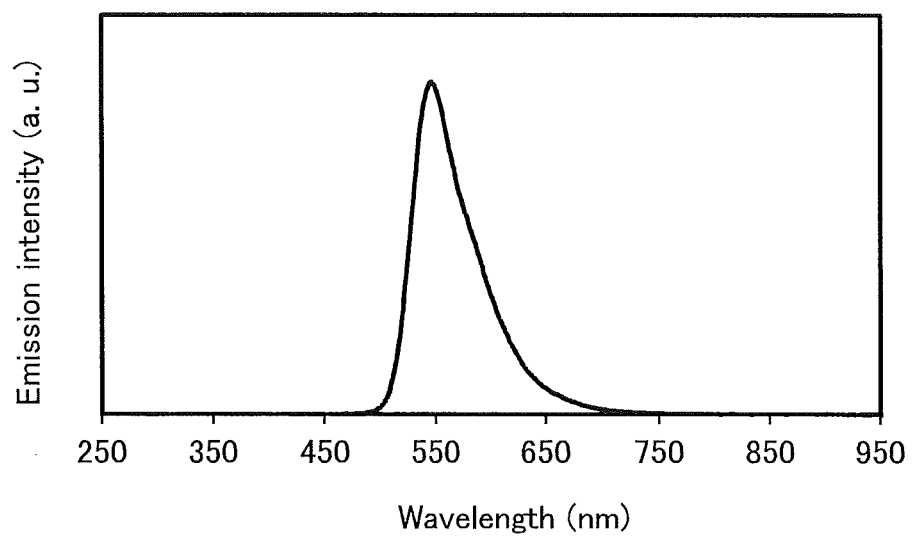
FIG. 48 shows an emission spectrum of Light-emitting element 4 of Example.
Figure 54:
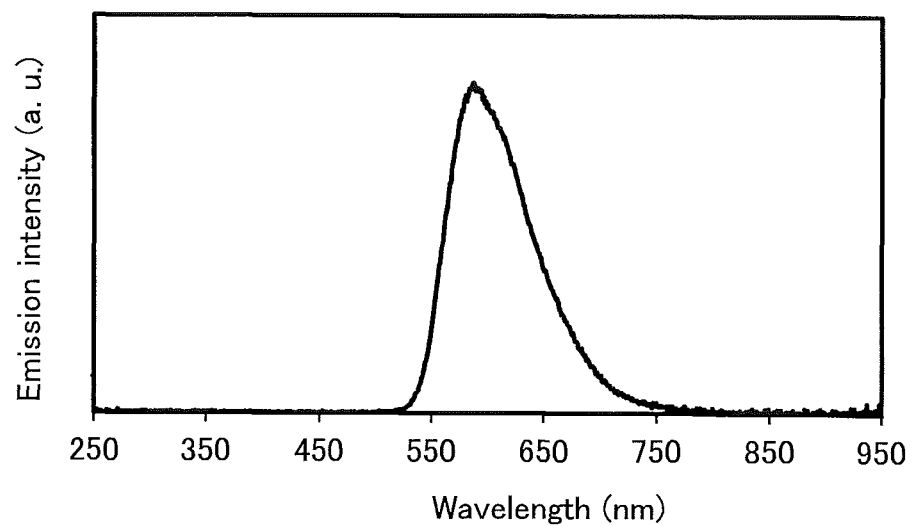
FIG. 54 shows an emission spectrum of Light-emitting element 5 of Example.
Figure 60:
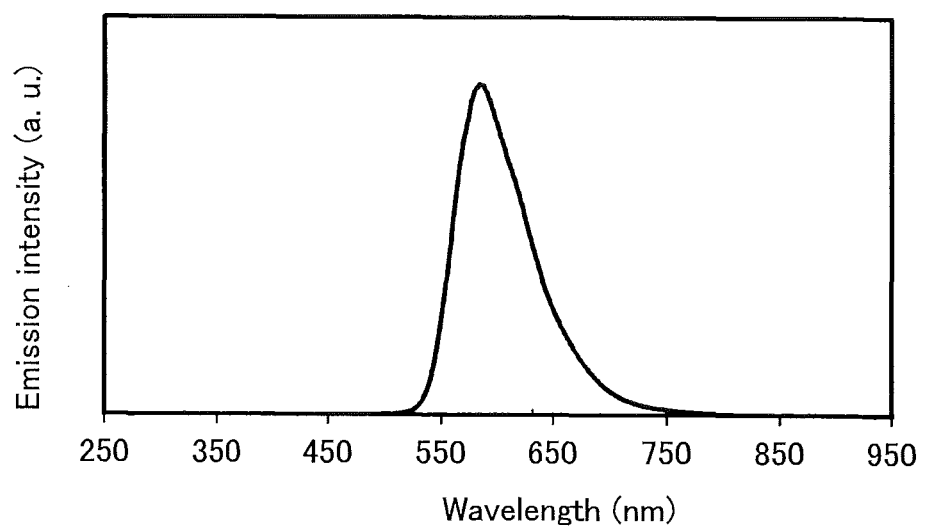
FIG. 60 shows an emission spectrum of Light-emitting element 6 of Example.

FIG. 30, FIG. 36, FIG. 42, FIG. 48, FIG. 54, and FIG. 60 show emission spectra of Light-emitting elements 1, 2, 3, 4, 5, and 6, respectively, at a current density of 2.5 mA/cm². As shown in FIG. 30, the emission spectrum of Light-emitting element 1 has a peak at 583 nm. As shown in FIG. 36, the emission spectrum of Light-emitting element 2 has a peak at 546 nm. As shown in FIG. 42, the emission spectrum of Light-emitting element 3 has a peak at 538 nm. As shown in FIG. 48, the emission spectrum of Light-emitting element 4 has a peak at 546 nm. As shown in FIG. 54, the emission spectrum of Light-emitting element 5 has a peak at 587 nm. As shown in FIG. 60, the emission spectrum of Light-emitting element 6 has a peak at 583 nm.

Next, a reliability test was performed on each of Light-emitting elements 1 to 6. FIG. 31, FIG. 37, FIG. 43, FIG. 49, FIG. 55, and FIG. 61 show results of the reliability tests.

Figure 31:
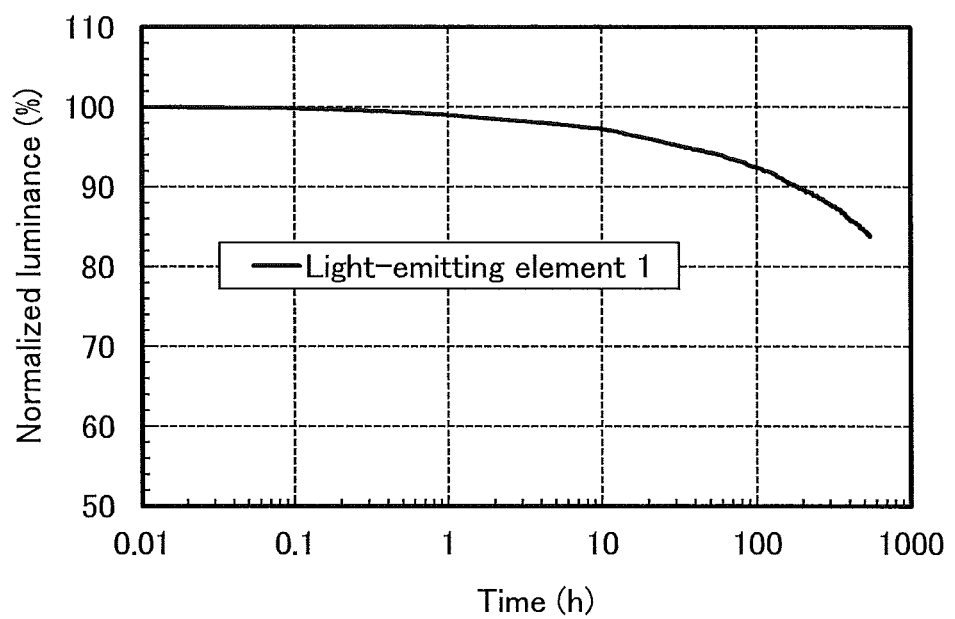
FIG. 31 shows results of a reliability test of Light-emitting element 1 of Example.
Figure 32:
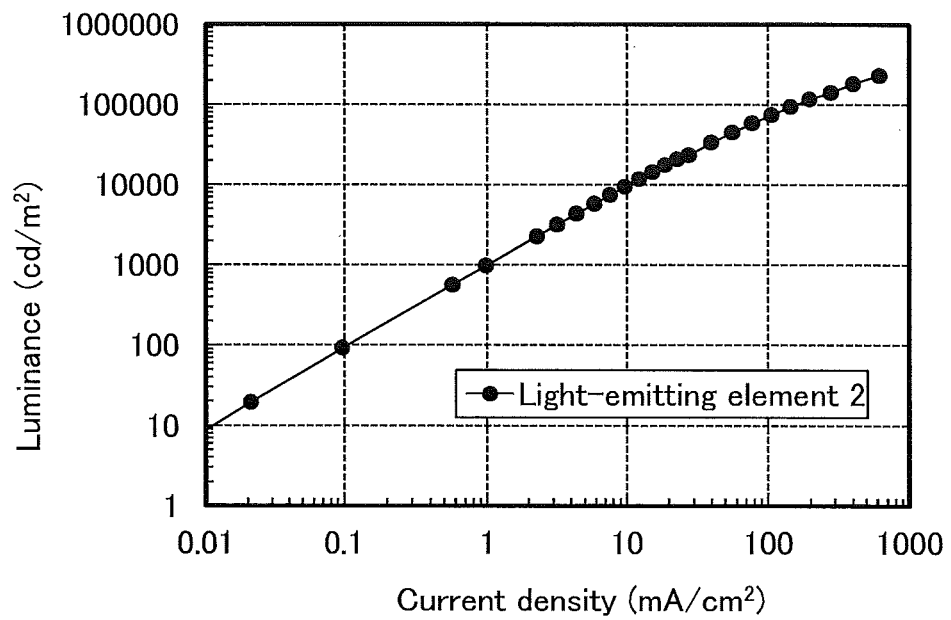
FIG. 32 shows current density-luminance characteristics of Light-emitting element 2 of Example.
Figure 33:
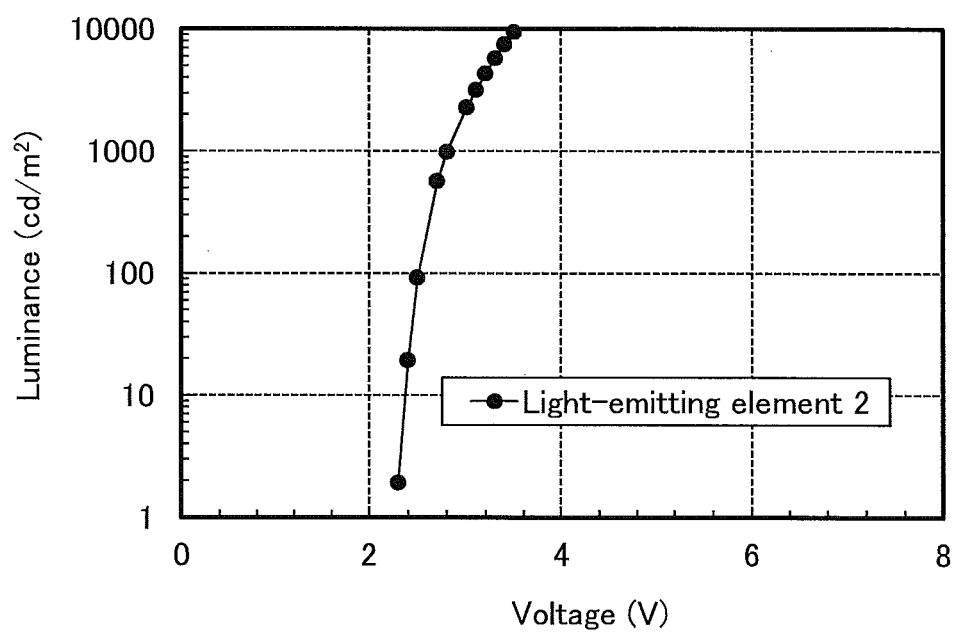
FIG. 33 shows voltage-luminance characteristics of Light-emitting element 2 of Example.
Figure 34:
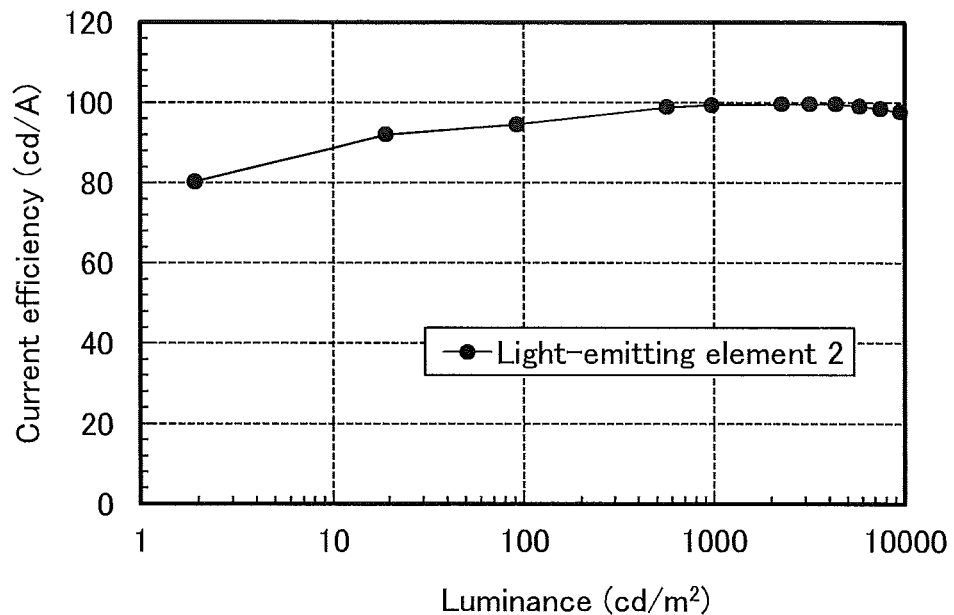
FIG. 34 shows luminance-current efficiency characteristics of Light-emitting element 2 of Example.
Figure 35:
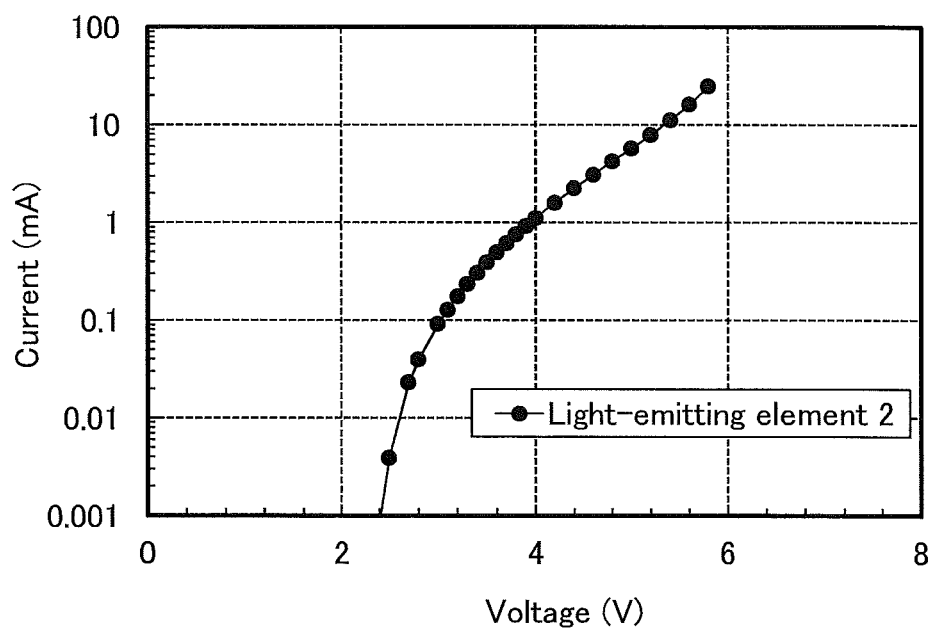
FIG. 35 shows voltage-current characteristics of Light-emitting element 2 of Example.
Figure 37:
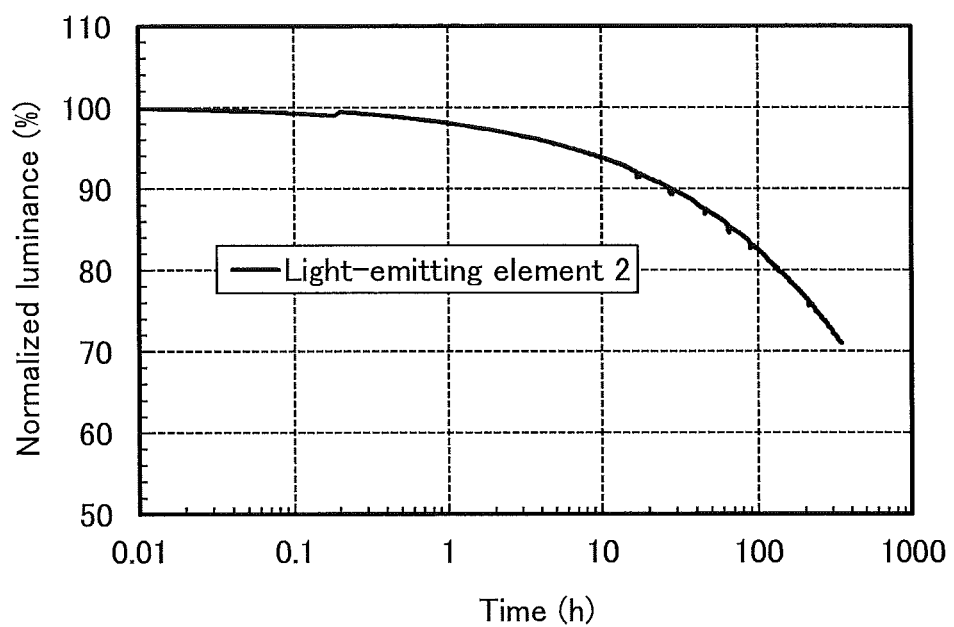
FIG. 37 shows results of a reliability test of Light-emitting element 2 of Example.
Figure 38:
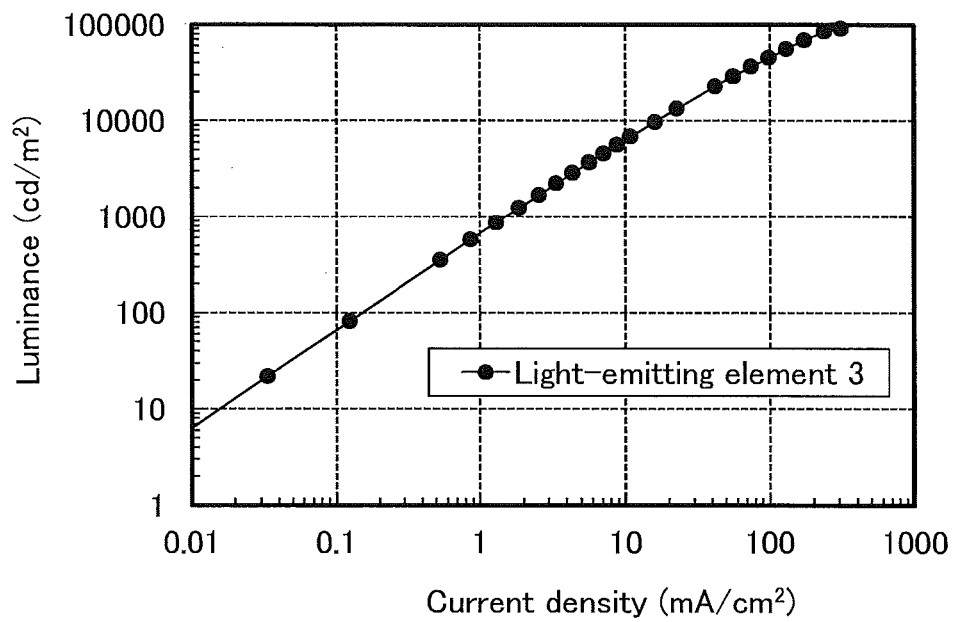
FIG. 38 shows current-luminance density characteristics of Light-emitting element 3 of Example.
Figure 39:
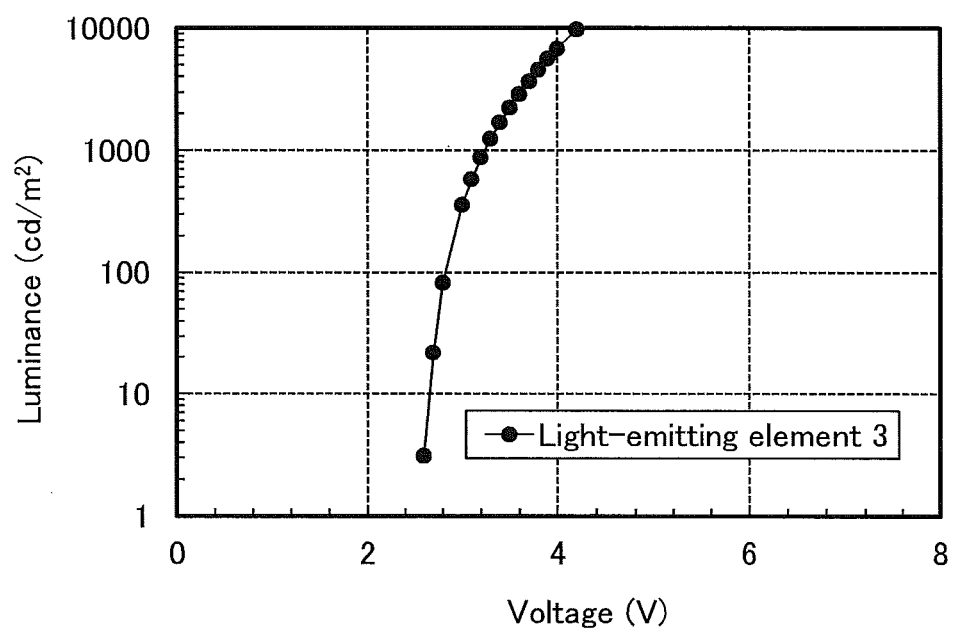
FIG. 39 shows voltage-luminance characteristics of Light-emitting element 3 of Example.
Figure 40:
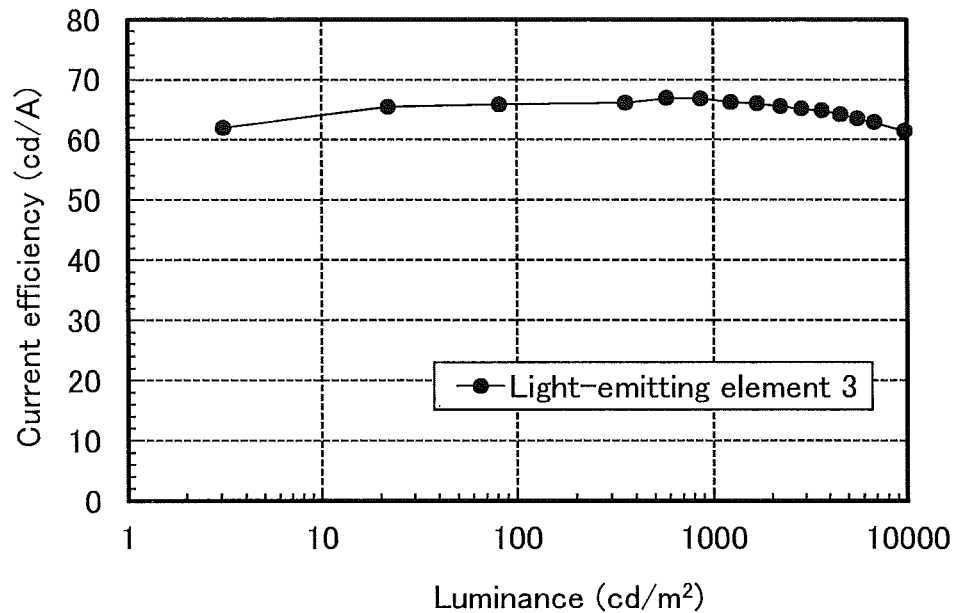
FIG. 40 shows luminance-current efficiency-characteristics of Light-emitting element 3 of Example.
Figure 41:
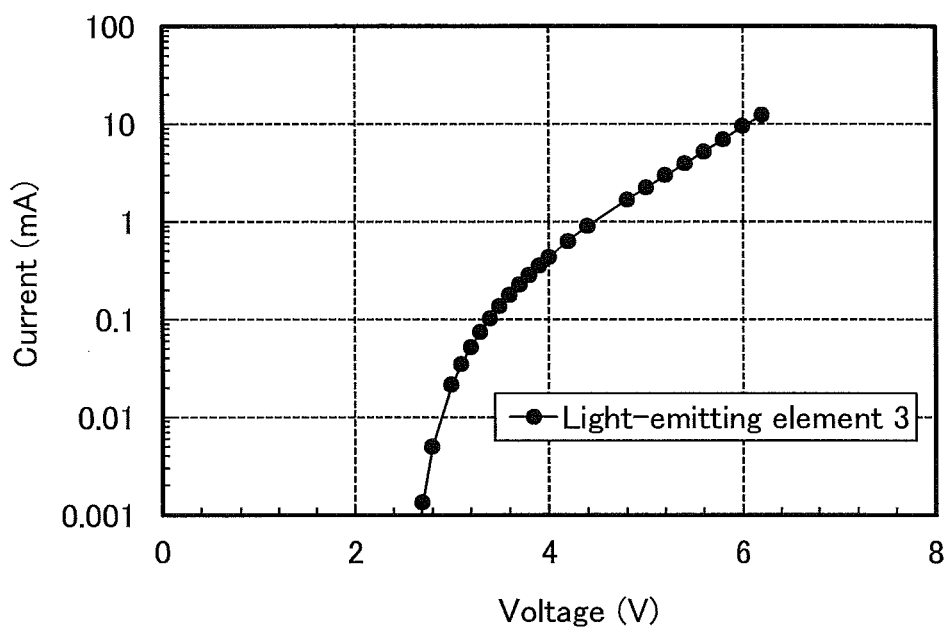
FIG. 41 shows current-voltage characteristics of Light-emitting element 3 of Example.
Figure 43:
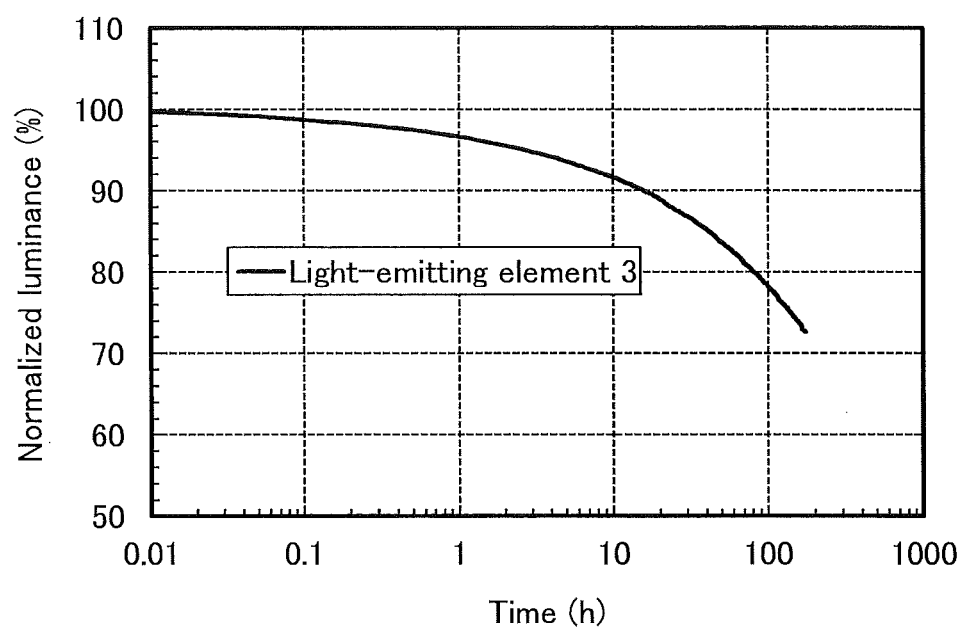
FIG. 43 shows results of a reliability test of Light-emitting element 3 of Example.
Figure 44:
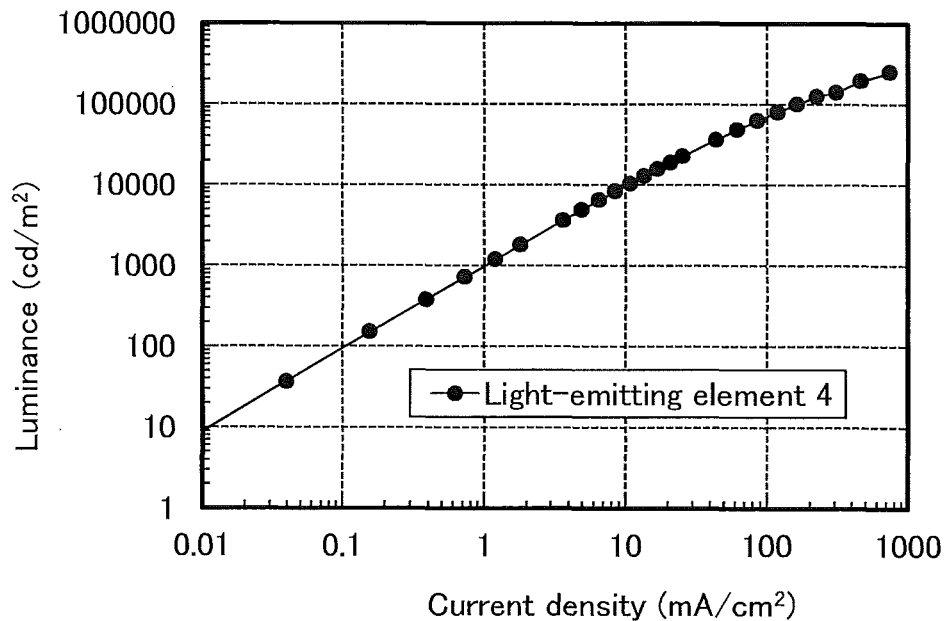
FIG. 44 shows current density-luminance characteristics of Light-emitting element 4 of Example.
Figure 45:
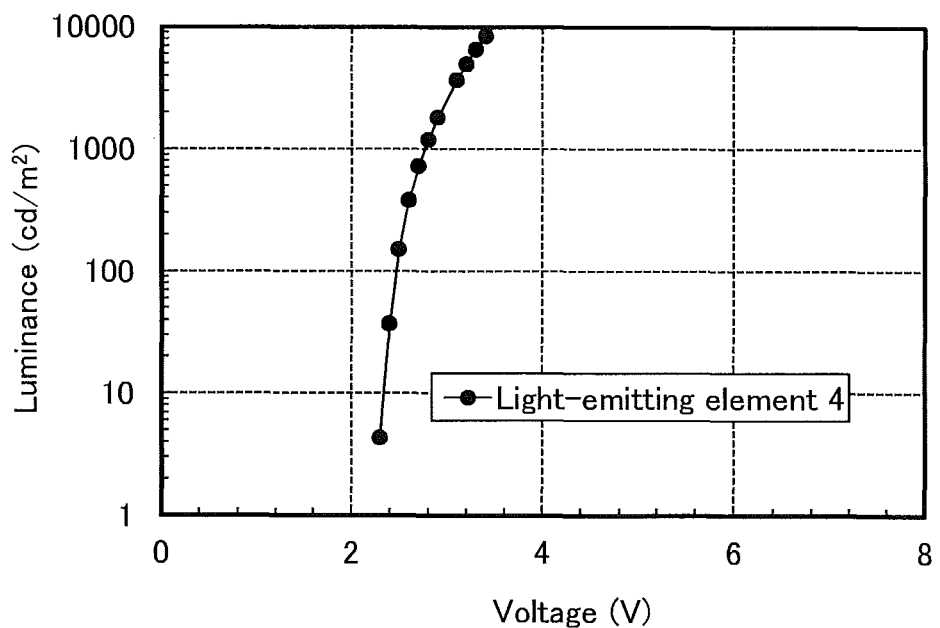
FIG. 45 shows voltage-luminance characteristics of Light-emitting element 4 of Example.
Figure 46:
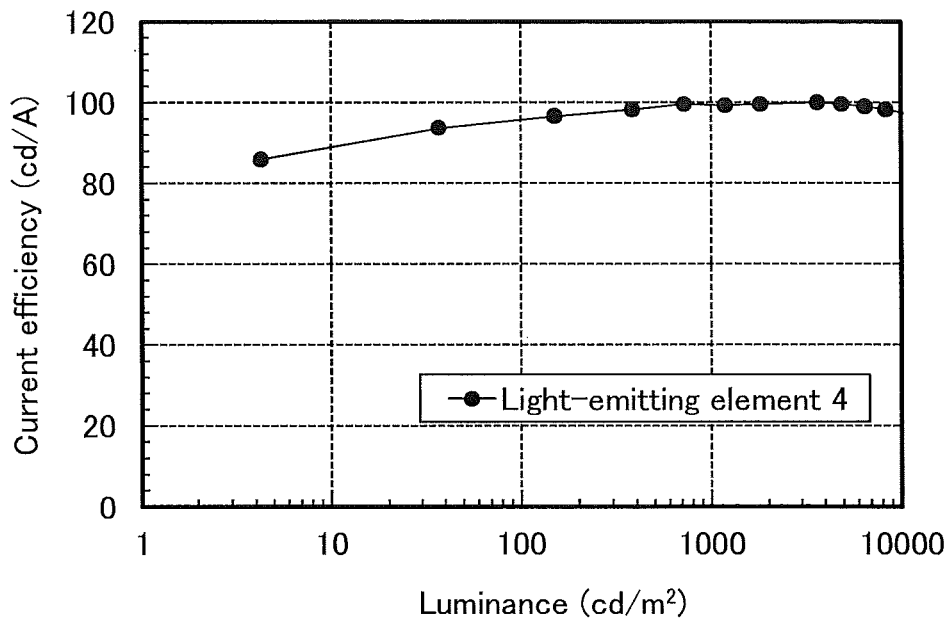
FIG. 46 shows luminance-current efficiency characteristics of Light-emitting element 4 of Example.
Figure 47:
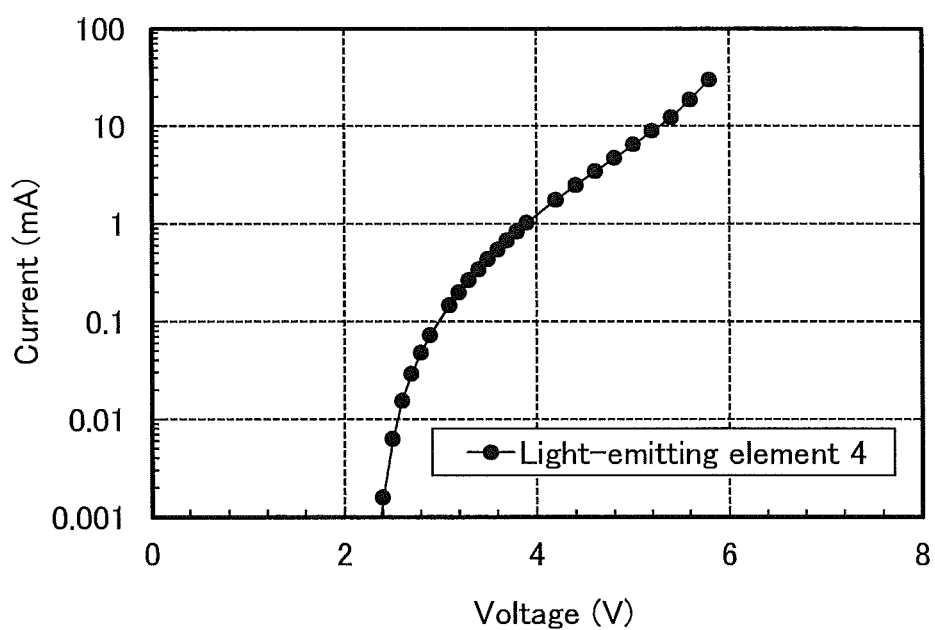
FIG. 47 shows voltage-current characteristics of Light-emitting element 4 of Example.
Figure 49:
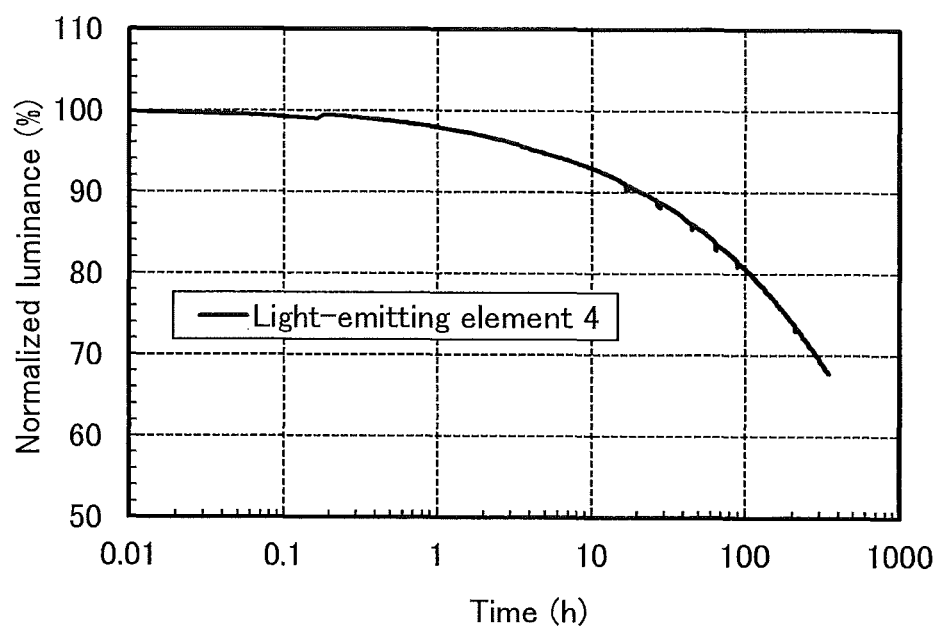
FIG. 49 shows results of a reliability test of Light-emitting element 4 of Example.
Figure 50:
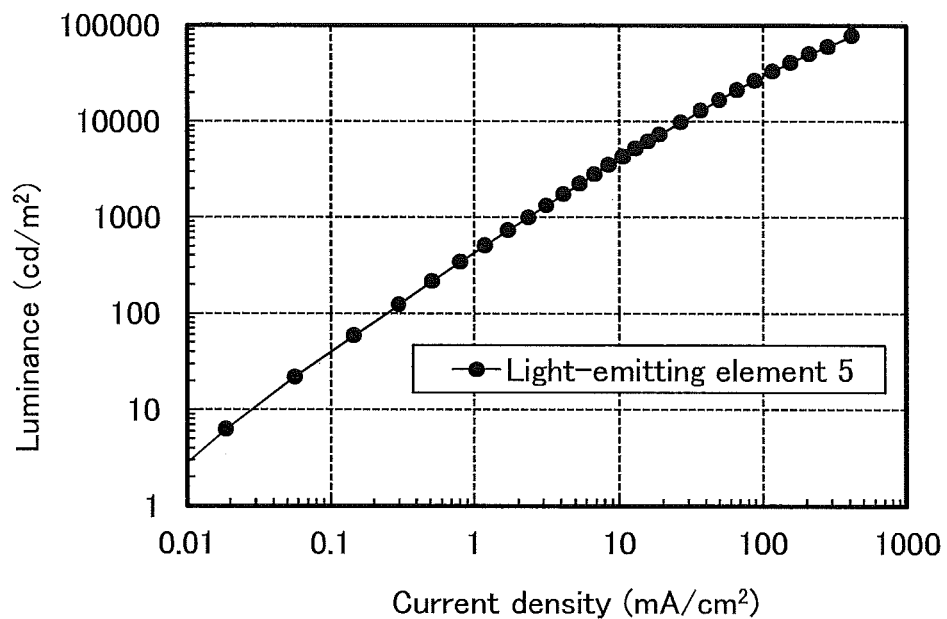
FIG. 50 shows current density-luminance characteristics of Light-emitting element 5 of Example.
Figure 51:
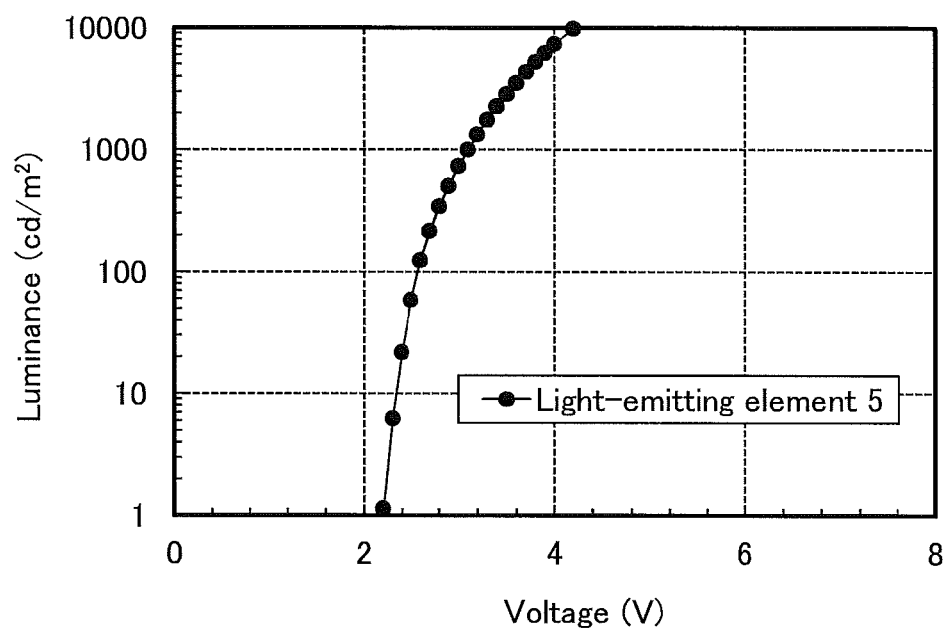
FIG. 51 shows voltage-luminance characteristics of Light-emitting element 5 of Example.
Figure 52:
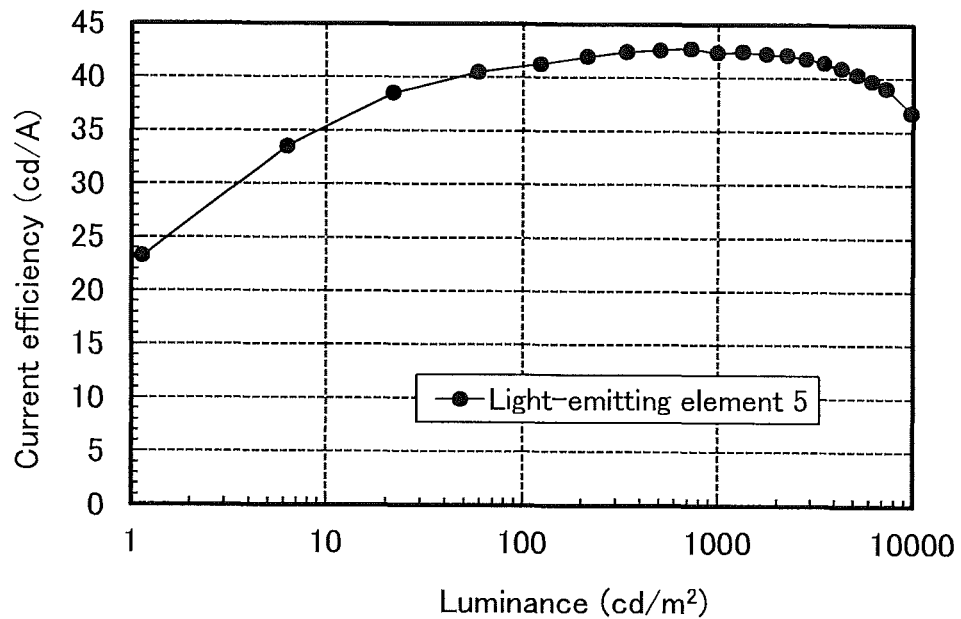
FIG. 52 shows luminance-current efficiency characteristics of Light-emitting element 5 of Example.
Figure 53:
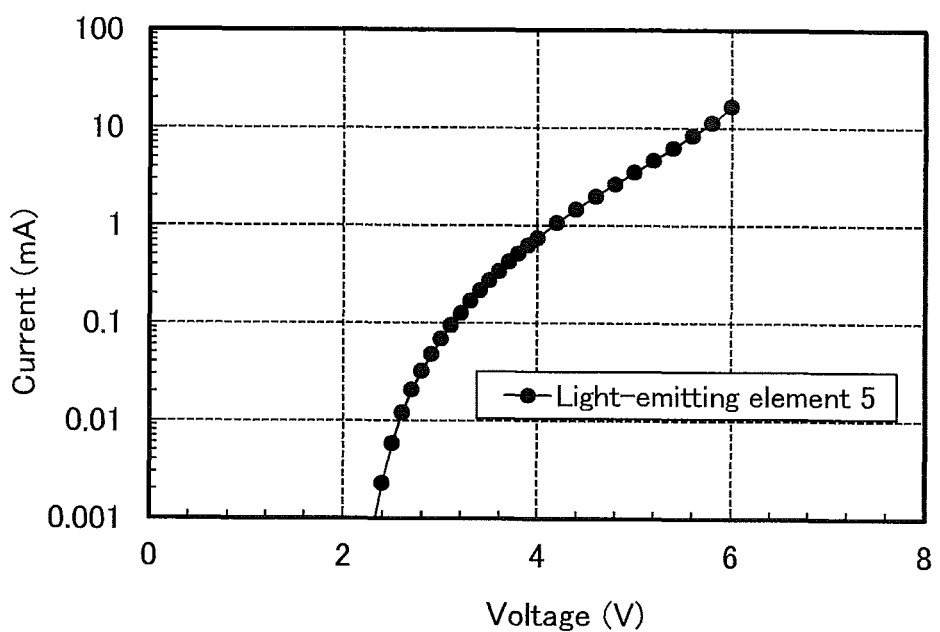
FIG. 53 shows voltage-current characteristics of Light-emitting element 5 of Example.
Figure 55:
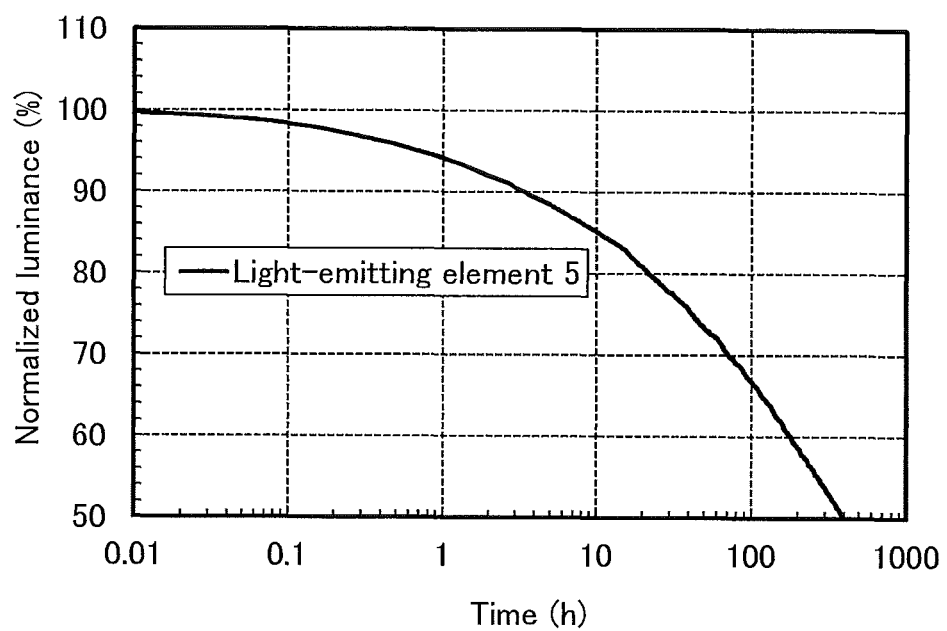
FIG. 55 shows results of a reliability test of Light-emitting element 5 of Example.
Figure 56:
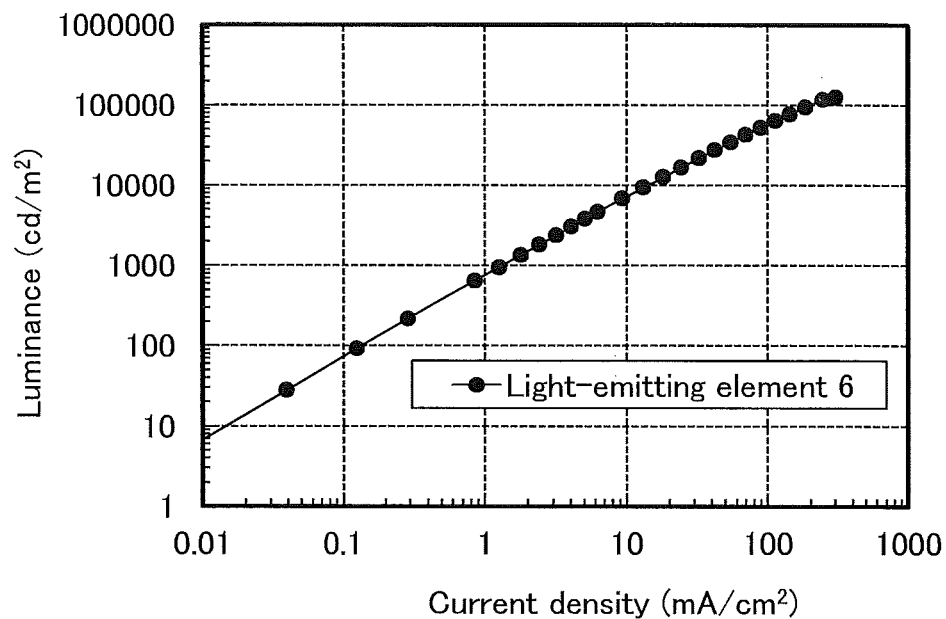
FIG. 56 shows current density-luminance characteristics of Light-emitting element 6 of Example.
Figure 57:
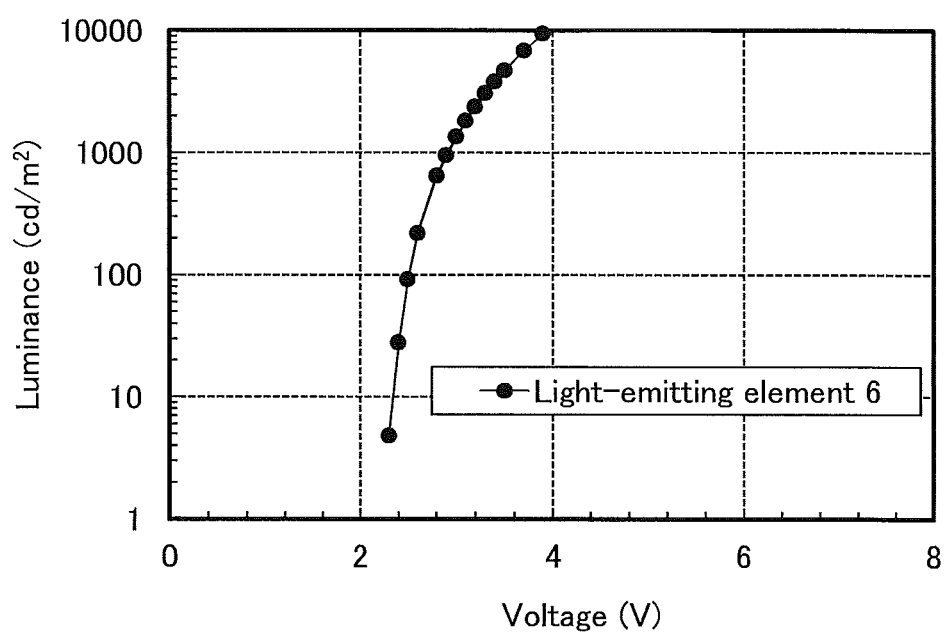
FIG. 57 shows voltage-luminance characteristics of Light-emitting element 6 of Example.
Figure 58:
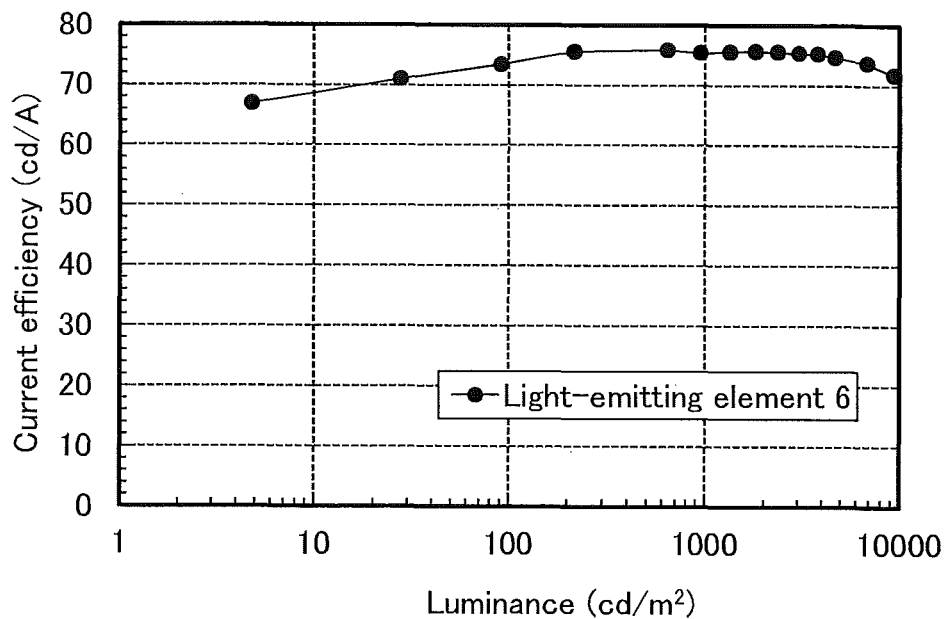
FIG. 58 shows luminance-current efficiency characteristics of Light-emitting element 6 of Example.
Figure 59:
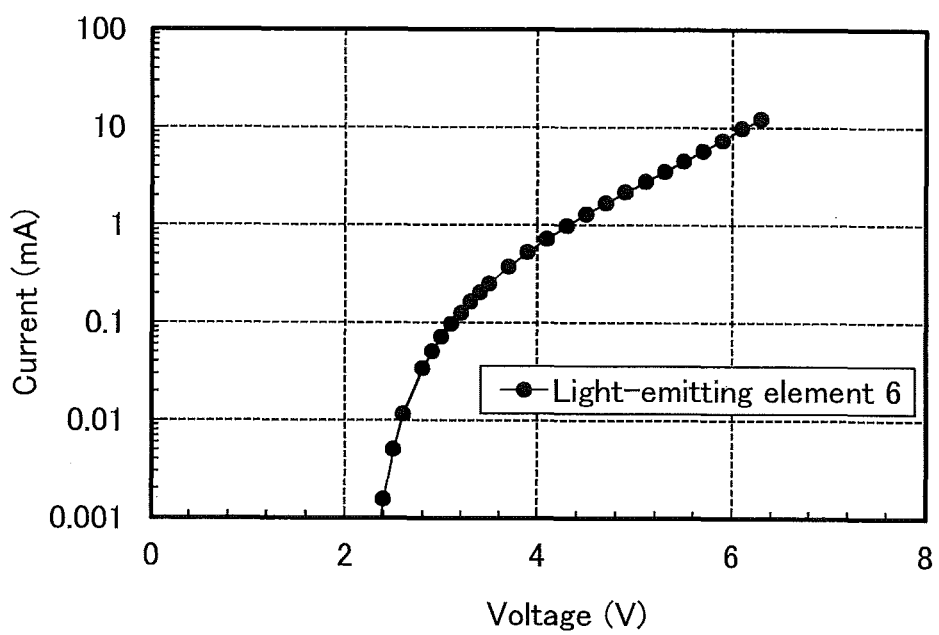
FIG. 59 shows voltage-current characteristics of Light-emitting element 6 of Example.
Figure 61:
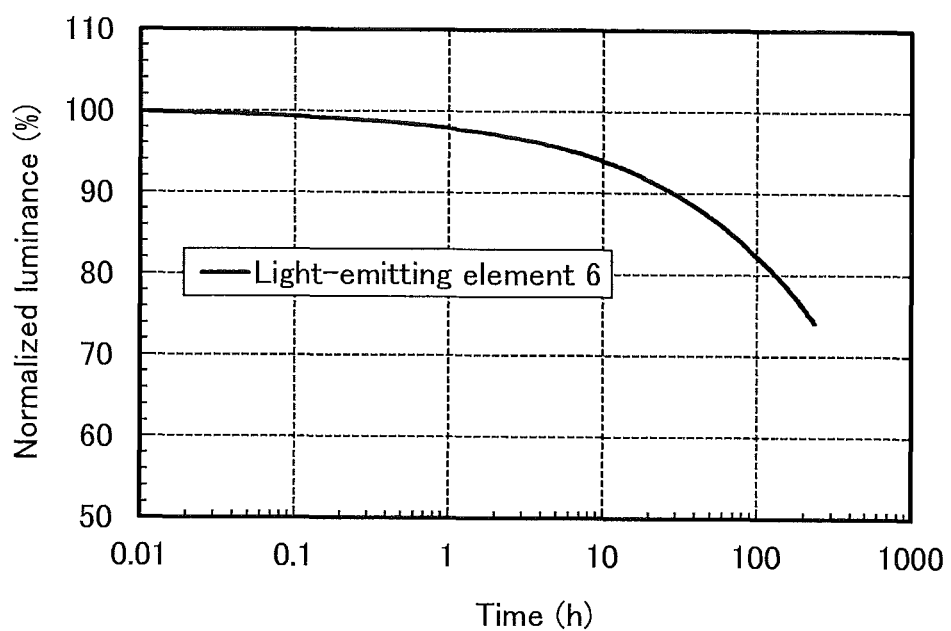
FIG. 61 shows results of a reliability test of Light-emitting element 6 of Example.

In the reliability test, each of Light-emitting elements 1 to 6 was driven under the conditions where the initial luminance was 5000 cd/m² and the current density was constant. In FIG. 31, FIG. 37, FIG. 43, FIG. 49, FIG. 55, and FIG. 61, the horizontal axis represents driving time (h) of the element, and the vertical axis represents normalized luminance (%) with the initial luminance of 100%. FIG. 31 shows that the normalized luminance of Light-emitting element 1 after 546 hours is 83%. FIG. 37 shows that the normalized luminance of Light-emitting element 2 after 346 hours is 70%. FIG. 43 shows that the normalized luminance of Light-emitting element 3 after 174 hours is 72%. FIG. 49 shows that the normalized luminance of Light-emitting element 4 after 346 hours is 67%. FIG. 55 shows that the normalized luminance of Light-emitting element 5 after 388 hours is 50%. FIG. 61 shows that the normalized luminance of Light-emitting element 6 after 236 hours is 74%.

The results of FIG. 31, FIG. 37, FIG. 43, FIG. 49, FIG. 55, and FIG. 61 indicate that Light-emitting elements 1 to 6, each of which is one embodiment of the present invention, have excellent element characteristics (voltage-luminance characteristics, luminance-current efficiency characteristics, and voltage-current characteristics).

Note that the structure described in this example can be combined as appropriate with any of the structures described in the embodiments or the other examples.

This application is based on Japanese Patent Application serial no. 2013-179360 filed with Japan Patent Office on Aug. 30, 2013, the entire contents of which are hereby incorporated by reference.

What is claimed is:

1. A compound represented by a formula (G1):

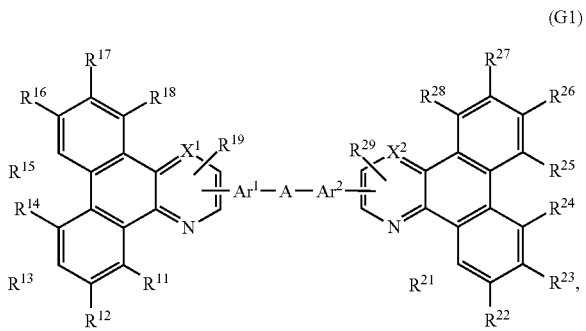

(G1)

wherein:

A represents a substituted or unsubstituted dibenzofuran-diyl group, a substituted or unsubstituted dibenzothiophene-diyl group, a substituted or unsubstituted N-aryl-9H-carbazole-diyl group, a substituted or unsubstituted N-alkyl-9H-carbazole-diyl group, or N-cycloalkyl-9H-carbazole-diyl group;

$Ar^1$ represents a substituted or unsubstituted arylene group;

$Ar^2$ represents a single-bond, or a substituted or unsubstituted arylene group;

$R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms;

$X^1$ and $X^2$ each independently represent a carbon atom or a nitrogen atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms.

2. The compound according to claim 1:
wherein:
the compound is represented by a formula (G2):

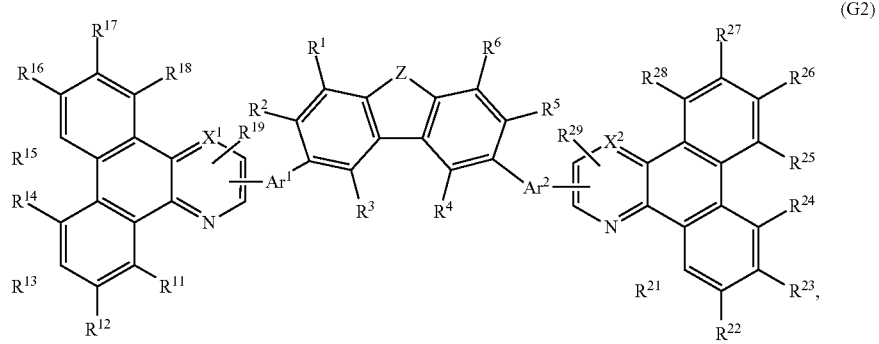

(G2)

R¹ to R⁶ each independently represent hydrogen, an alkyl group having 1 to 6 carbon atoms, a cycloalkyl group having 3 to 6 carbon atoms, or a substituted or unsubstituted aryl group having 6 to 13 carbon atoms, and Z represents an oxygen atom, a sulfur atom, or a nitrogen atom which is bonded to an alkyl group having 1 to 6 carbon atoms, a cycloalkyl group having 3 to 6 carbon atoms, or a substituted or unsubstituted aryl group having 6 to 13 carbon atoms.

3. The compound according to claim 1, wherein Ar² represents a single-bond or a substituted or unsubstituted phenylene group.

4. The compound according to claim 2, wherein the compound is represented by any one of formulae (100), (101), (102), (107), and (183):

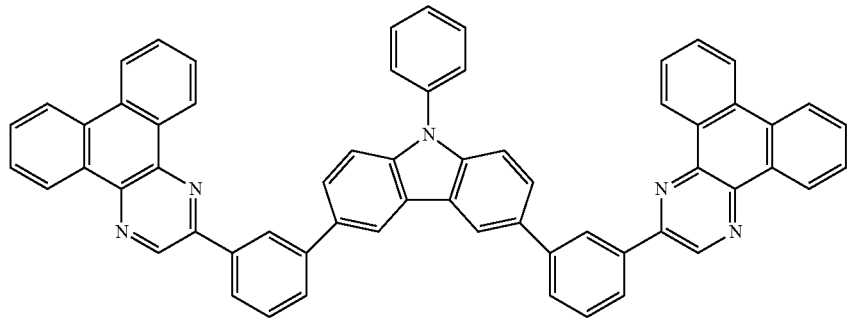

(100)

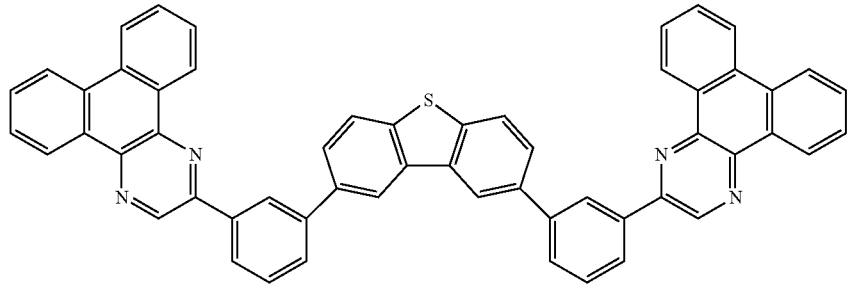

(101)

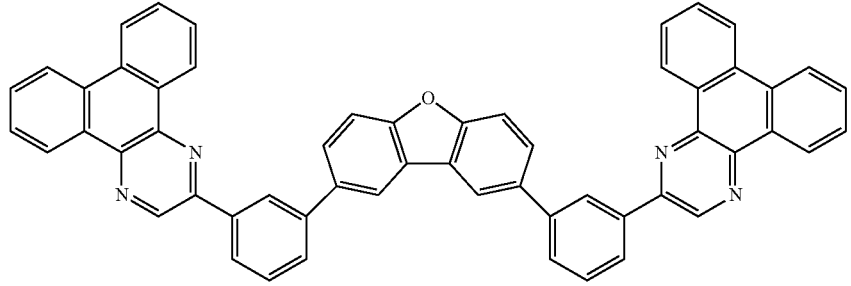

(102)

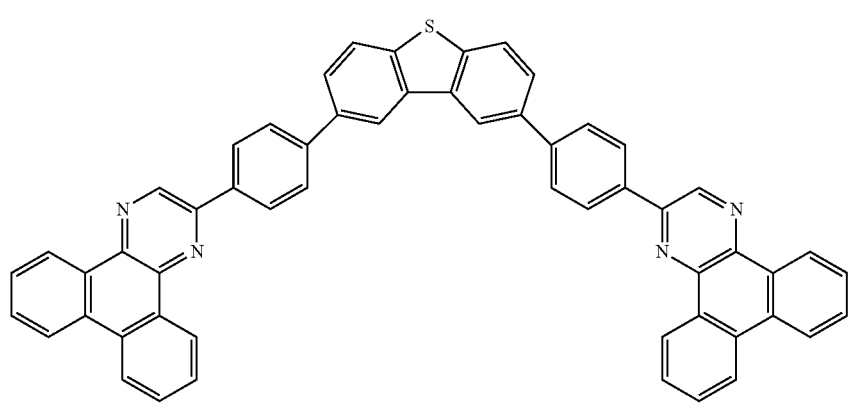

(107)

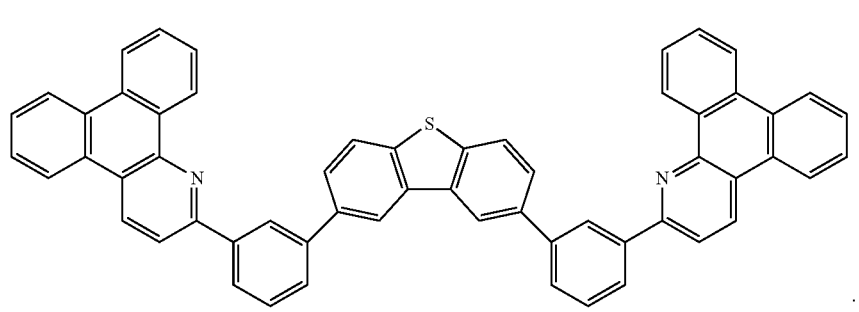

(183)

5. A light-emitting device comprising:
a light-emitting layer between a pair of electrodes, the light-emitting layer comprising a light-emitting substance and a first compound; and
a layer over and in contact with the light-emitting layer, the layer comprising a second compound,
wherein:
at least one of the first compound and the second compound is represented by a formula (G1):

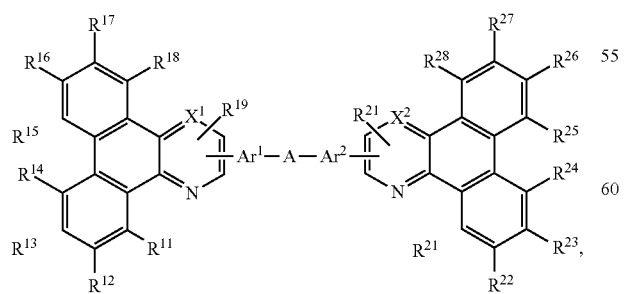

(G1)

A represents a substituted or unsubstituted dibenzofuran-diyl group, a substituted or unsubstituted dibenzothiophene-diyl group, a substituted or unsubstituted N-aryl-9H-carbazole-diyl group, a substituted or unsubstituted N-alkyl-9H-carbazole-diyl group, or N-cycloalkyl-9H-carbazole-diyl group;

$Ar^1$ represents a substituted or unsubstituted arylene group;

$Ar^2$ represents a single-bond, or a substituted or unsubstituted arylene group;

$R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms;

$X^1$ and $X^2$ each independently represent a carbon atom or a nitrogen atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms when each of $X^1$ and $X^2$ is the carbon atom.

6. The light-emitting device according to claim 5:
wherein:
at least one of the first compound and the second compound is represented by a formula (G2):

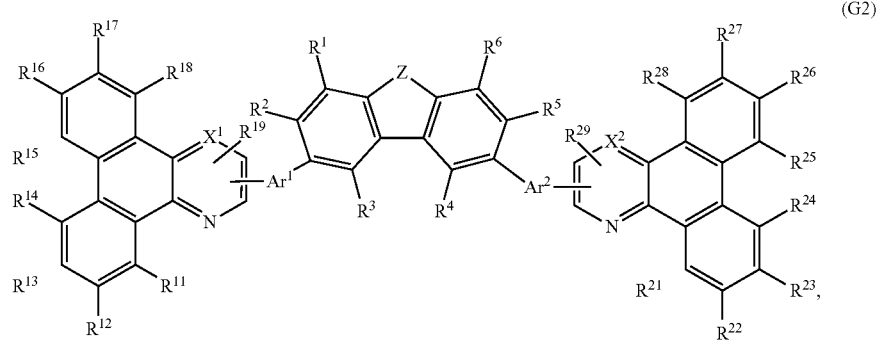

(G2)

R¹ to R⁶ each independently represent hydrogen, an alkyl group having 1 to 6 carbon atoms, a cycloalkyl group having 3 to 6 carbon atoms, or a substituted or unsubstituted aryl group having 6 to 13 carbon atoms, and Z represents an oxygen atom, a sulfur atom, or a nitrogen atom which is bonded to an alkyl group having 1 to 6 carbon atoms, a cycloalkyl group having 3 to 6 carbon atoms, or a substituted or unsubstituted aryl group having 6 to 13 carbon atoms.

7. The light-emitting device according to claim 5, wherein Ar² represents a single-bond or a substituted or unsubstituted phenylene group.

8. The light-emitting device according to claim 6, wherein at least one of the first compound and the second compound is represented by any one of formulae (100), (101), (102), (107), and (183):

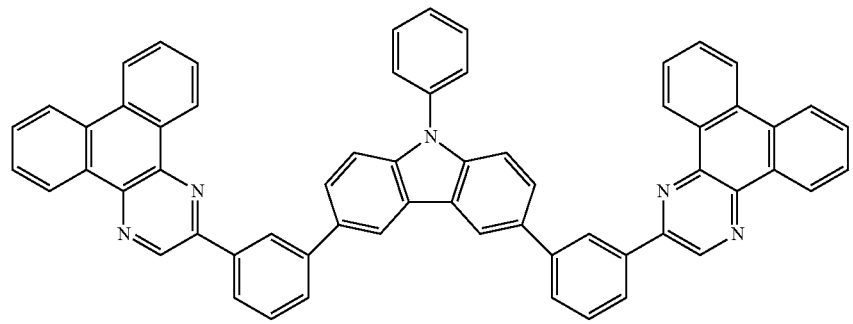

(100)

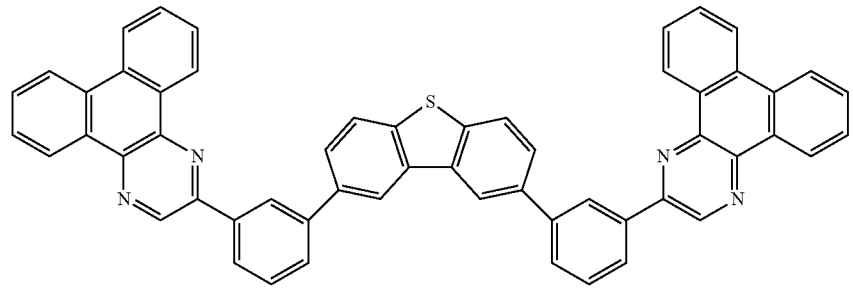

(101)

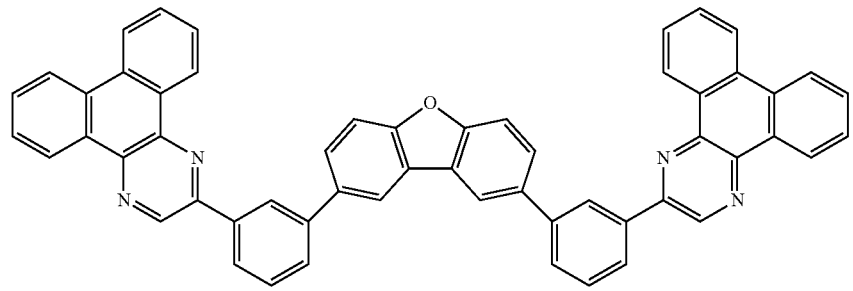

(102)

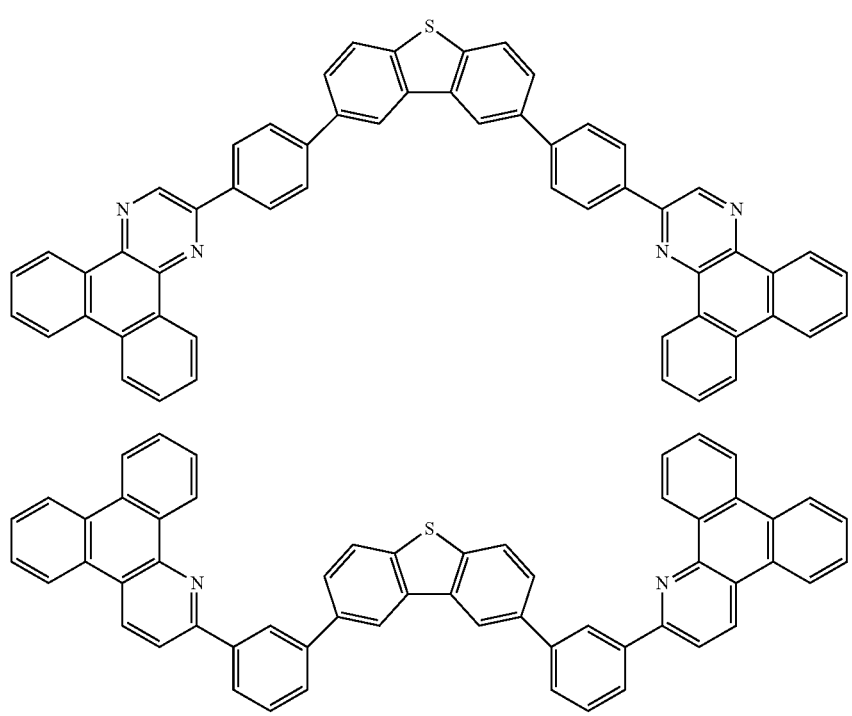

(107)

(183)

9. The light-emitting device according to claim 5, wherein the light-emitting substance is a phosphorescent compound.

10. The light-emitting device according to claim 5, wherein the layer is an electron-transport layer.

11. An electronic device comprising the light-emitting device according to claim 5.

12. A lighting device comprising the light-emitting device according to claim 5.

13. A light-emitting device comprising:
- a first light-emitting layer between a pair of electrodes, the first light-emitting layer comprising a first light-emitting substance, a first compound, and a second compound;
- a second light-emitting layer over and in contact with the first light-emitting layer, the second light-emitting layer comprising a second light-emitting substance, a third compound, and a fourth compound; and
- a layer over and in contact with the second light-emitting layer, the layer comprising a fifth compound,
- wherein:
- at least one of the first compound, the third compound, and the fifth compound is represented by a formula (G1):

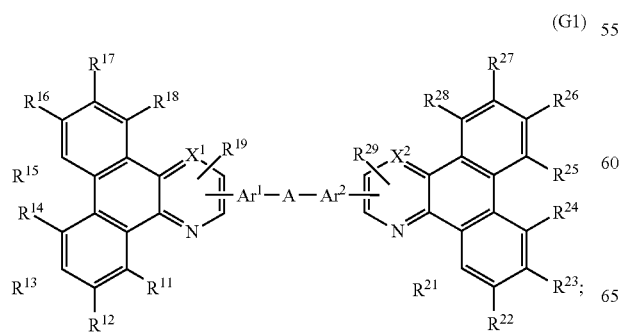

(G1)

A represents a substituted or unsubstituted dibenzofuran-diyl group, a substituted or unsubstituted dibenzothiophene-diyl group, a substituted or unsubstituted N-aryl-9H-carbazole-diyl group, a substituted or unsubstituted N-alkyl-9H-carbazole-diyl group, or N-cycloalkyl-9H-carbazole-diyl group;

$Ar^1$ represents a substituted or unsubstituted arylene group;

$Ar^2$ represents a single-bond, or a substituted or unsubstituted arylene group;

$R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms;

$X^1$ and $X^2$ each independently represent a carbon atom or a nitrogen atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms when each of $X^1$ and $X^2$ is the carbon atom.

14. The light-emitting device according to claim 13:
wherein:
at least one of the first compound, the third compound, and the fifth compound is represented by a formula (G2):

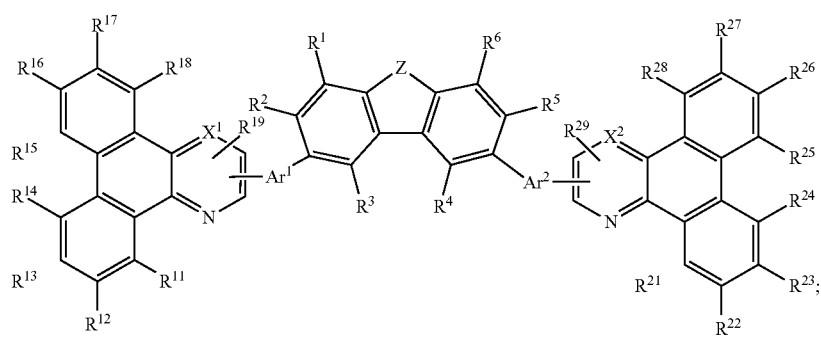

(G2)

R¹ to R⁶ each independently represent hydrogen, an alkyl group having 1 to 6 carbon atoms, a cycloalkyl group having 3 to 6 carbon atoms, or a substituted or unsubstituted aryl group having 6 to 13 carbon atoms, and Z represents an oxygen atom, a sulfur atom, or a nitrogen atom which is bonded to an alkyl group having 1 to 6 carbon atoms, a cycloalkyl group having 3 to 6 carbon atoms, or a substituted or unsubstituted aryl group having 6 to 13 carbon atoms.

15. The light-emitting device according to claim 13, wherein the second compound and the fourth compound has a hole-transport property.

16. The light-emitting device according to claim 13, wherein at least one of a combination of the first compound and the second compound and a combination of the third compound and the fourth compound is configured to form an exciplex.

17. The light-emitting device according to claim 13, wherein:

the first light-emitting substance, the first compound, and the second compound are the same as the second light-emitting substance, the third compound, and the fourth compound, respectively, and the first compound and the third compound are the same as the fifth compound.

18. The light-emitting device according to claim 13, wherein Ar² represents a single-bond or a substituted or unsubstituted phenylene group.

19. The light-emitting device according to claim 13, wherein at least one of the first compound, the third compound, and the fifth compound is represented by any one of formulae (100), (101), (102), (107), and (183):

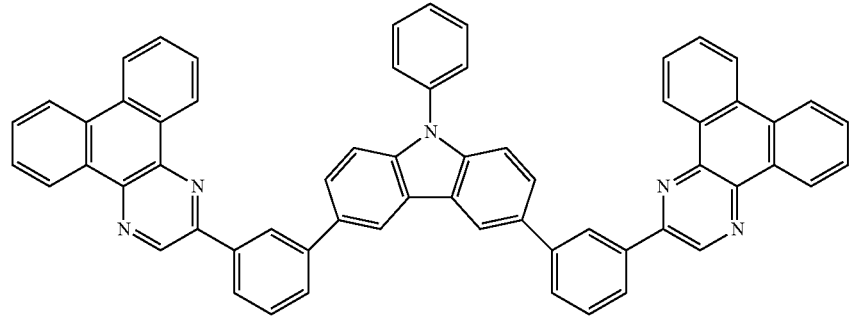

(100)

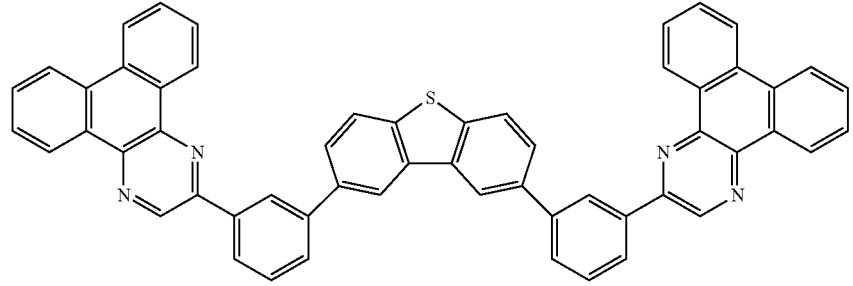

(101)

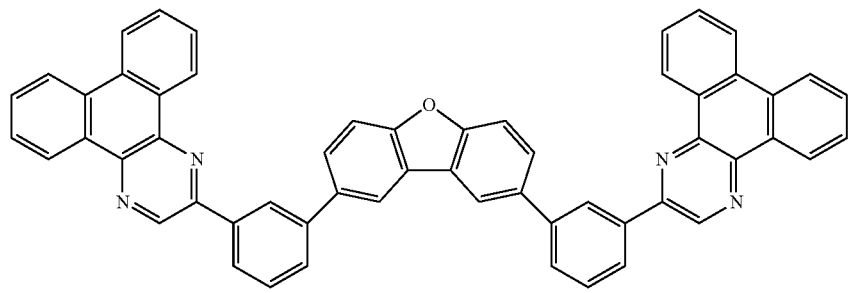
(102)

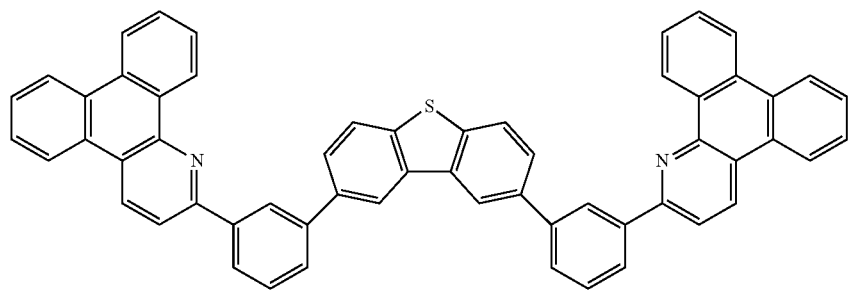
(107)

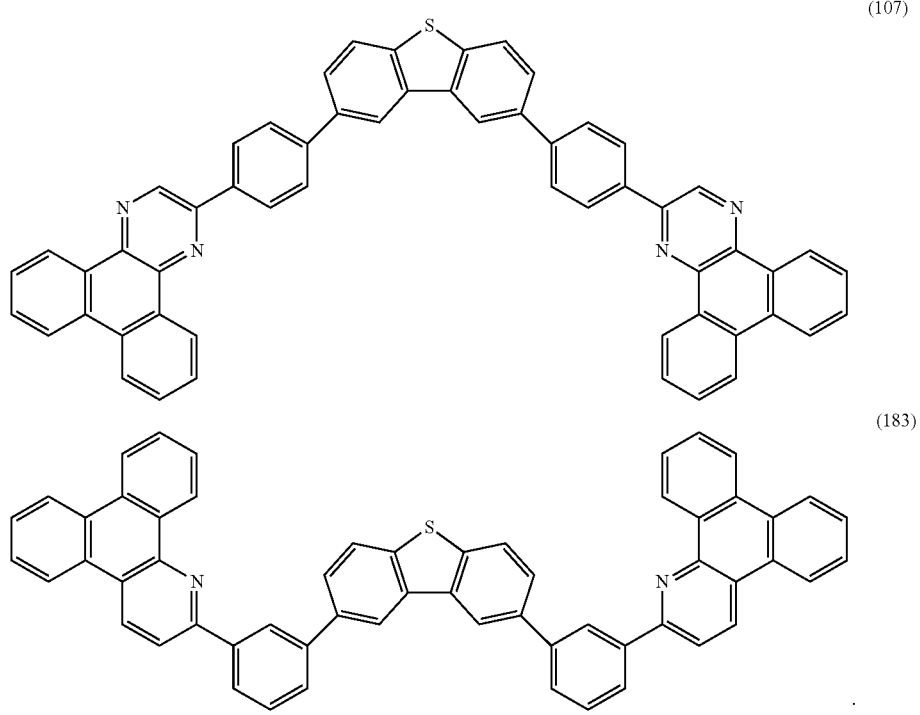
(183)

20. The light-emitting device according to claim 13, wherein at least one of the first light-emitting substance and the second light-emitting substance is a phosphorescent compound.

21. The light-emitting device according to claim 13, wherein the layer is an electron-transport layer.

22. An electronic device comprising the light-emitting device according to claim 13.

23. A lighting device comprising the light-emitting device according to claim 13.

24. A compound represented by a formula (G1):

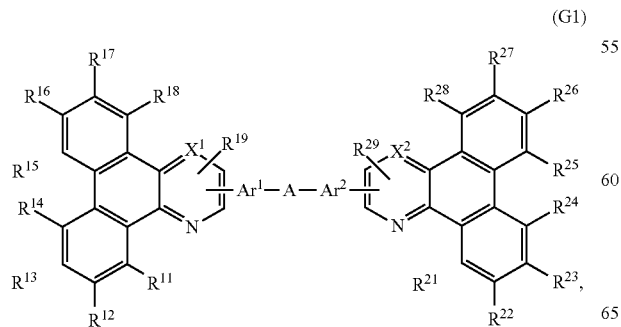
(G1)

wherein:

A represents a substituted or unsubstituted dibenzofuran-diyl group, a substituted or unsubstituted dibenzothiophene-diyl group, a substituted or unsubstituted N-aryl-9H-carbazole-diyl group, a substituted or unsubstituted N-alkyl-9H-carbazole-diyl group, or N-cycloalkyl-9H-carbazole-diyl group;

$Ar^1$ and $Ar^2$ each independently represents a single-bond, or a substituted or unsubstituted arylene group;

$R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms; and $X^1$ and $X^2$ a nitrogen atom, A is bonded to 2-position or 6-position of a dibenzo [f, h] quinoxaline skeleton thorough $Ar^1$, and A is bonded to 2-position or 6-position of a dibenzo [f, h] quinoxaline skeleton thorough $Ar^2$.

25. The compound according to claim 24, wherein the compound is represented by a formulae (105):

(105)

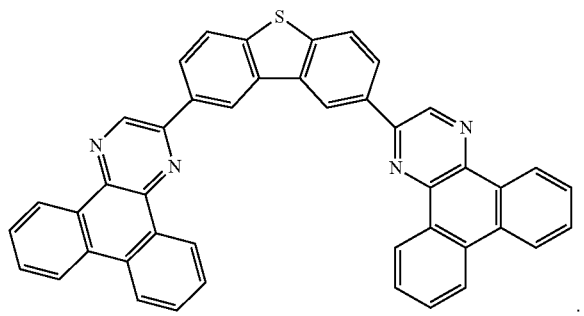

(101)

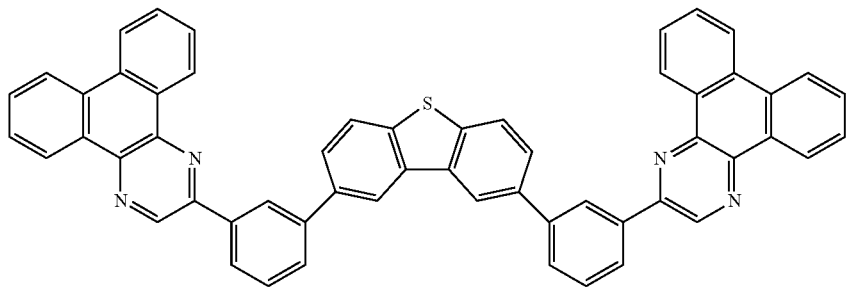

26. A compound represented by a formula (G1):

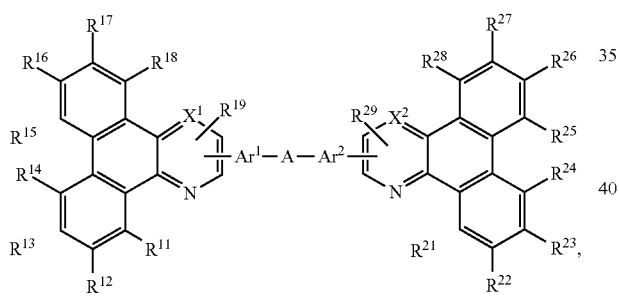

(G1)

wherein:
A represents a substituted or unsubstituted dibenzofuran-diyl group, a substituted or unsubstituted dibenzothiophene-diyl group, a substituted or unsubstituted N-aryl-9H-carbazole-diyl group, a substituted or unsubstituted N-alkyl-9H-carbazole-diyl group, or N-cycloalkyl-9H-carbazole-diyl group;

$Ar^1$ and $Ar^2$ each independently represents a single-bond, or a substituted or unsubstituted arylene group;

$R^{11}$ to $R^{19}$ and $R^{21}$ to $R^{29}$ each independently represent hydrogen, an alkyl group having 1 to 6 carbon atoms, a cycloalkyl group having 3 to 6 carbon atoms, or a substituted or unsubstituted aryl group having 6 to 13 carbon atoms;

$X^1$ and $X^2$ represent a carbon atom; and the carbon atom is bonded to hydrogen, an alkyl group having 1 to 6 carbon atoms, a cycloalkyl group having 3 to 6 carbon atoms, or a substituted or unsubstituted aryl group having 6 to 13 carbon atoms, A is bonded to 2-position of a dibenzo [f, h] quinoline skeleton thorough $Ar^1$, and A is bonded to 2-position a dibenzo [f, h] quinoline skeleton thorough $Ar^2$.

* * * * *